US012268734B2

(12) United States Patent
Potter et al.

(10) Patent No.: US 12,268,734 B2
(45) Date of Patent: Apr. 8, 2025

(54) *MYCOPLASMA* VACCINES AND USES THEREOF

(71) Applicants: University of Saskatchewan, Saskatoon (CA); Kenya Agriculture and Livestock Research Organization (KALRO), Nairobi (KE); International Livestock Research Institute (ILRI), Nairobi (KE)

(72) Inventors: Andrew Potter, Saskatoon (CA); Volker Gerdts, Saskatoon (CA); Jose Perez-Casal, Saskatoon (CA); Yejun Wang, Saskatoon (CA); Hezron Wesonga, Nairobi (KE); Reuben Soi, Nairobi (KE); Jan Naessens, Nairobi (KE); Joerg Jores, Nairobi (KE)

(73) Assignees: University of Saskatchewan, Saskatoon (CA); International Liverstock Research Institute (ILRI), Nairobi (KE); Kenya Agriculture and Livestock Research Organization (KALRO), Nairobi (KE)

( * ) Notice: Subject to any disclaimer, the term of this patent is extended or adjusted under 35 U.S.C. 154(b) by 562 days.

(21) Appl. No.: 17/156,477

(22) Filed: Jan. 22, 2021

(65) Prior Publication Data

US 2021/0244807 A1 Aug. 12, 2021

Related U.S. Application Data

(63) Continuation of application No. 15/746,770, filed as application No. PCT/CA2016/050864 on Jul. 22, 2016, now abandoned.

(60) Provisional application No. 62/195,581, filed on Jul. 22, 2015, provisional application No. 62/195,602, filed on Jul. 22, 2015.

(51) Int. Cl.

| | |
|---|---|
| ***A61K 39/02*** | (2006.01) |
| ***A61K 39/00*** | (2006.01) |
| ***A61P 31/04*** | (2006.01) |
| ***C07K 14/30*** | (2006.01) |
| ***C12N 15/62*** | (2006.01) |

(52) U.S. Cl.

CPC .......... *A61K 39/0241* (2013.01); *A61P 31/04* (2018.01); *C07K 14/30* (2013.01); *C12N 15/62* (2013.01); *A61K 2039/55516* (2013.01); *A61K 2039/55561* (2013.01); *A61K 2039/55566* (2013.01); *C07K 2319/00* (2013.01)

(58) Field of Classification Search

CPC .................................................. A61K 39/0241

See application file for complete search history.

(56) References Cited

U.S. PATENT DOCUMENTS

| | | | |
|---|---|---|---|
| 3,770,380 | A | 11/1973 | Smith |
| 3,876,504 | A | 4/1975 | Koffler |
| 4,011,308 | A | 3/1977 | Giaever |
| 4,016,043 | A | 4/1977 | Schuurs |
| 4,310,550 | A | 1/1982 | Wolff, III |
| 4,338,397 | A | 7/1982 | Gilbert |
| 4,372,745 | A | 2/1983 | Mandle |
| 4,425,437 | A | 1/1984 | Riggs |
| 4,431,739 | A | 2/1984 | Riggs |
| 4,708,871 | A | 11/1987 | Geysen |
| 4,722,890 | A | 2/1988 | Sanders |
| 4,744,984 | A | 5/1988 | Ragland |
| 4,816,567 | A | 3/1989 | Cabilly |
| 4,957,739 | A | 9/1990 | Berget |
| 5,053,451 | A | 10/1991 | Allcock |
| 5,055,400 | A | 10/1991 | Lo |
| 5,149,543 | A | 9/1992 | Cohen |
| 5,151,267 | A | 9/1992 | Babiuk |
| 5,238,823 | A | 8/1993 | Potter |
| 5,273,889 | A | 12/1993 | Potter |
| 5,308,701 | A | 5/1994 | Cohen et al. |
| 5,422,110 | A | 6/1995 | Potter |
| 5,476,657 | A | 12/1995 | Potter |
| 5,494,673 | A | 2/1996 | Andrianov |
| 5,494,682 | A | 2/1996 | Cohen |
| 5,529,777 | A | 6/1996 | Andrianov |
| 5,562,909 | A | 10/1996 | Allcock |
| 5,708,155 | A | 1/1998 | Potter |
| 5,723,129 | A | 3/1998 | Potter |
| 5,807,757 | A | 9/1998 | Andrianov |
| 5,837,268 | A | 11/1998 | Potter |
| 5,855,895 | A | 1/1999 | Andrianov |
| 5,951,988 | A | 9/1999 | Littel-Van |

(Continued)

FOREIGN PATENT DOCUMENTS

| | | | |
|---|---|---|---|
| GB | 2276169 | A | 9/1994 |
| WO | 199308290 | A1 | 4/1993 |

(Continued)

OTHER PUBLICATIONS

Bowie et al. (Science, 1990, 247:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000,10:398-400) (Year: 2000).*
Lanao et al., Mycoplasma Infections. [Updated Aug. 8, 2022]. In: StatPearls [Internet]. Treasure Island (FL): StatPearls Publishing; Jan. 2023-. Available from: https://www.ncbi.nlm.nih.gov/books/NBK536927/) (Year: 2022).*

(Continued)

*Primary Examiner* — Brian Gangle
*Assistant Examiner* — Lakia J Jackson-Tongue
(74) *Attorney, Agent, or Firm* — MORRISON & FOERSTER LLP

(57) ABSTRACT

Immunogenic proteins comprising *Mycoplasma mycoides* subsp. *mycoides* and *M. mycoides* subsp. *capri* proteins, encoding polynucleotides, a method for producing said proteins, and use of compositions to prevent *M. mycoides* subsp. *mycoides* infections are disclosed.

18 Claims, 77 Drawing Sheets

Specification includes a Sequence Listing.

(56) References Cited

U.S. PATENT DOCUMENTS

| | | | |
|---|---|---|---|
| 5,969,126 | A | 10/1999 | Potter |
| 5,985,354 | A | 11/1999 | Mathiowitz |
| 6,015,563 | A | 1/2000 | Andrianov |
| 6,022,960 | A | 2/2000 | Potter |
| 6,100,066 | A | 8/2000 | Potter |
| 6,194,388 | B1 | 2/2001 | Krieg |
| 6,207,171 | B1 | 3/2001 | Payne |
| 6,207,646 | B1 | 3/2001 | Krieg |
| 6,214,806 | B1 | 4/2001 | Krieg |
| 6,218,371 | B1 | 4/2001 | Krieg |
| 6,239,116 | B1 | 5/2001 | Krieg |
| 6,261,573 | B1 | 7/2001 | Loebelenz |
| 6,339,068 | B1 | 1/2002 | Krieg |
| 6,521,746 | B1 | 2/2003 | Potter |
| 6,797,272 | B1 | 9/2004 | Potter |
| 7,279,163 | B1 | 10/2007 | Holt |
| 9,061,001 | B2 | 6/2015 | Van Drunen Littel-van Den Hurk |
| 2003/0139364 | A1 | 7/2003 | Krieg |
| 2017/0290341 | A1 | 10/2017 | Cordova-Kreylos |
| 2019/0030153 | A1 | 1/2019 | Potter |

FOREIGN PATENT DOCUMENTS

| | | | |
|---|---|---|---|
| WO | 200122990 | A2 | 4/2001 |
| WO | 200122990 | A3 | 10/2001 |
| WO | 2003015711 | A2 | 2/2003 |
| WO | 2003015711 | A3 | 6/2004 |
| WO | 2004101795 | A1 | 11/2004 |
| WO | WO2004101795 | * | 11/2004 |
| WO | 2006005943 | A1 | 1/2006 |
| WO | 2010043039 | A1 | 4/2010 |
| WO | 2014121433 | A1 | 8/2014 |

OTHER PUBLICATIONS

Altschul, S.F. et al. (1990). "Basic Local Alignment Search Tool," J. Mol. Biol. 215:403-410.
Andrianov, A.K. et al. (2004, e-pub. Dec. 17, 2003). "Poly(dichlorophosphazene) as a Precursor for Biologically Active Polyphosphazenes: Synthesis, Characterization, and Stabilization," Macromolecules 37(2):414-420.
Andrianov, A.K. et al. (Sep. Oct. 2004). "Synthesis and Biologically Relevant Properties of Polyphosphazene Polyacids," Biomacromolecules 5(5):1999-2006.
Babiuk, L.A. et al. (Jul. 1987). "Protection of Cattle From Bovine Herpesvirus Type I (BHV-1) Infection by Immunization With Individual Viral Glycoproteins," Virology 159(1):57-66.
Bowie, J.U. et al. (Mar. 1990). "Deciphering The Message In Protein Sequences; Tolerance to Amino Acid Substitutions," Science 247(4948):1306-1310.
Campbell, A.D. et al. (Jun. 1953). "Studies on Contagious Pleuropneumonia of Cattle," Australian Veterinary Journal 29(6):154-163.
Churchward, C.P et al. (Sep. 14, 2012, e-pub. Mar. 13, 2012). "A Simplified PCR Method for Genotyping *Mycoplasma mycoides* Subspecies *Mycoides* Small Colony: The Aetiologic Agent of Contagious Bovine Pleuropneumonia,". Vet Microbiol. 159(1-2):257-259.
Cumber, A.J. et al. (Jul. 1992). "Comparative Stabilitles In Vitro and In Vivo of a Recombinant Mouse Antibody FvCys Fragment and a bisFvCys Conjugate," J Immunology 149(1):120-126.
Daleel, E.E. (Sep. 1972). "Report: Contagious Bovine Pleuropneumonia (CBPP) T-1 Broth Vaccine Safety Trials in Sudanese Cattle," Bulletin of Epizootic Diseases in Africa 20(3):199-202.
Didieu, L. et al. (2010). "Comparative Analysis of Four Lipoproteins From *Mycoplasma mycoides* subsp. *Mycoides* Small Colony Identifies LppA as a Major T-Cell Antigen," Comp. Immunol. Microbial. Infect. Dis. 33:279-290.
Dreyer, K. et al. (1999). "Primary Isolate Neutralization by HIV Type 1-Infected Patient Sera in the Era of Highly Active Antiretroviral Therapy," AIDS Res Hum Retroviruses 15(17):1563-1571.
Egwu, G.O. et al. (1996). "Contagious Bovine Pleuropneumonia: An Update," Veterinary Bulletin 66:875-888, 66 pages.
Ehrlich, P.H. et al. (Aug. 19, 1980). "Isolation of an Active Heavy-Chain Variable Domain From a Homogeneous Rabbit Antibody by Cathepsin B Digestion of the Aminoethylated Heavy Chain," Biochem 19(17):4091-4096.
Felgner, P.L. (Sep. 1990). "Particulate Systems and Polymers for In Vitro and In Vivo Delivery of Polynucleotides," Adv. Drug Deliv. Rev. 5(3):163-187.
Final Office Action, mailed Jul. 24, 2020, for U.S. Appl. No. 15/746,770, filed Jan. 22, 2018, 50 pages.
Gall, D. (1966). "The Adjuvant Activity of Aliphatic Nitrogenous Bases," Immunology 11:369-386.
Gantelius, J. et al. (Jul. 2010, e-pub. Mar. 25, 2010). "A Lateral Flow Protein Microarray for Rapid Determination of Contagious Bovine Pleuropneumonia Status in Bovine Serum," J. Microbiol. Methods 82:11-18.
Geysen, H.M. et al. (Jul. 1984). "Use of Peptide Synthesis to Probe Viral Antigens for Epitopes to a Resolution of a Single Amino Acid," Proc. Natl. Acad. Scl. USA 81:3998-4002.
Geysen, H.M. et al. (Jul. 1986). "A Priori Delineation of a Peptide Which Mimics a Discontinuous Antigenic Determinant," Molec. Immunol. 23(7):709-715.
Gourlay, R.N. (1964). "Antigenicity of Mycoplasma mycoides. I. Examination of Body Fluids From Cases of Contagious Bovine Pleuropneumonia," Research in Veterinary Science 5:473-482.
Graham, F.L. et al.(1973) "A New Technique for the Assay of Infectivity of Human Adenovirus 5 DNA," Virology 52:456-467.
Gupta, P.K. et al. (Jul. 1, 2005). "Immunogenic and Antigenic Properties of Recombinant Soluble Glycoprotein of Rabies Virus," Vet. Microbiol. 108(3-4):207-214.
Hackland, A.F. et al. (1994). "Coat Protein-Mediated Resistance in Transgenic Plants," Arch. Virol. 139(1-2):1-22.
Hamsten, C. et al. (2008). "Expression and immunogenicity of Six Putative Variable Surface Proteins in *Mycoplasma mycoides* subsp. *Mycoides* SC," Microbiology 154:539-549.
Hamsten, C. et al. (2009). "Recombinant Surface Proteomics as a Tool to Analyze Humoral Immune Responses in Bovines Infected by *Mycoplasma mycoides* subsp. *Mycoides* Small Colony Type," Mol.Cell.Proteomics 8:2544-2554.
Hamsten, C. et al. (May 2010). "Protein-Specific Analysis of Humoral Immune Responses in a Clinical Trial for Vaccines Against Contagious Bovine Pleuropneumonia," Clin. Vaccine Immunol. 17(5):853-861.
He, Y. et al. (2010). "Methodology Report: Vaxign: The FirstWeb-Based Vaccine Design Program for Reverse Vaccinology and Applications for Vaccine Development," J. Biomed. Biotechnol. 2010:297505, 15 pages.
Hedlin, P.D. et al. (Jan. 22, 2010, e-pub. Nov. 17, 2009). "Design and Delivery of a Cryptic PrPC Epitope for Induction of PrPSc-Specific Antibody Response," Vaccine 28(4):981-988.
Highlander, S.K. et al. (1989). "DNA Sequence of the Pasteurella haemolytica Leukotoxin Gene Cluster," DNA 8(1):15-28.
Hopp, T.P. et al. (Jun. 1981). "Prediction of Protein Antigenic Determinants From Amino Acid Sequences," Proc. Natl. Acad. Sci. USA 78(6):3824-3828.
Hudson, J.R. et al. (Oct. 1963). "Contagious Bovine Pleuropneumonia: A Comparison of the Efficacy of Two Types of Vaccine," Australian Veterinary Journal 39(10):373-385.
Huston, J.S. et al. (Aug. 1988). "Protein Engineering of Antibody Binding Sites: Recovery of Specific Activity in an Anti-Digoxin Single-chain Fv Analogue Produced in *Escherichia coli*," Proc. Natl. Acad. Sci. USA 85:5879-5883.
Inbar, D. et al. (Sep. 1972). "Localization of Antibody-Combining Sites Withing the Variable Portions of Heavy and Light Chains," Proc. Natl. Acad. Sci. USA 69(9):2659-2662.
International Preliminary Report on Patentability, issued Jan. 23, 2018, for PCT Application No. PCT/CA2016/050864, filed Jul. 22, 2016, 15 pages.
International Search Report, mailed Feb. 24, 2016, for PCT Application No. PCT/CA2016/050864, filed Jul. 22, 2016, 11 pages.
Jores, J. et al. (2009). "Analysis of the Immunoproteome of *Mycoplasma mycoides* subsp. *mycoides* Small Colony Type Reveals Immuno-

(56) References Cited

OTHER PUBLICATIONS genic Homologues to Other Known Virulence Traits in Related *Mycoplasma* Species," Vet. Immunol. Immunopathol. 131:238-245.
Juncker, A.S. et al. (2003). "Prediction of Lipoprotein Signal Peptides in Gram-Negative Bacteria," Protein Sci. 12:1652-1664.
Karst, O. (Jan. 1971). "A Comparison of 2 Vaccines Against Contagious Bovine Pleuropneumonia," Research in Veterinary Science 12(1):18-22.
Krogh, A. et al. (2001). "Predicting Transmembrane Protein Topology With a Hidden Markov Model: Application to Complete Genomes," J. Molec. Biol. 305:567-580.
Kyte, J. et al. (1982). "A Simple Method for Displaying the Hydropathic Character of Protein," Journal of Molecular Biology 157:105-132.
Limpens, J. et al. (Nov. 1989). "Synergistic effects of Locally Administered Cytostatic Drugs and a Surfactant on the Development of Delayed-Type Hypersensitivity to Keyhole Limpet Haemocyanin in Mice," Clin. Exp. Immunol. 78(2):256 262.
Lo, R.Y. (Apr. 1990). "Molecular Characterization of Cytotoxins Produced by Haemophilus, Actinobacillus, Pasteurella," Can. J Vet. Res. 54:S33-S35.
Lo, R.Y. et al. (Dec. 1985). "Cloning and Expression of the Leukotoxin Gene of *Pasteurella haemolytica* A1 in *Escherichia coli* K-12,"Infect. Immun. 50(3):667-671.
Lo, R.Y.C. et al. (Sep. 1987). "Nucleotide Sequence of the Leukotoxin Genes of *Pasteurella haemolytica* A1," Infect. Immun. 55(9):1987-1996.
Manso-Silvan, L. et al. (2009). "*Mycoplasma leachii* sp. nov. as a New Species Designation for *Mycoplasma* sp. Bovine Group 7 of Leach, and Reclassification of *Mycoplasma mycoides* subsp. *mycoides* LC as a Serovar of *Mycoplasma mycoides* subsp. *Capri*," International Journal of Systematic and Evolutionary Microbiology 59:1353-1358.
March, J.B. (Oct. 22, 2004). "Improved Formulations for Existing CBPP Vaccines—Recommendations for Change," Vaccine 22(31-32):4358-4364.
Masiga, W.N. et al. (Sep. 1995). "Overview and Epidemiology of contagious Bovine Pleuropneumonia in Africa," Reviews of Science and Technology Office of International Epizootics 14(3):611-620.
Miltiadou. D.R. et al. (Oct. 9, 2009). "Identification of Genes Coding for B Cell Antigens of *Mycoplasma mycoides* subsp. *mycoides* Small Colony (MmmSC) by Using Phage Display," BMC Microbiol. 9:215, 8 pages.
Montefiori, D.C. et al. (Feb. 1988). "Evaluation of Antiviral Drugs and neutralizing Antibodies to Human Immunodeficiency Virus by a Rapid and Sensitive Microtiter Infection Assay," J. Clin. Microbiol. 26(2)231-235.
Morris, G.E. (1996). Epitope Mapping Protocols in Methods in Molecular Biology, vol. 66 (Humana Press, Totowa, New Jersey), 12 pages, preface and index only.
Mulongo, M. et al. (May 2015, e-pub. Mar. 2, 2015). "Vaccination of Cattle With the N Terminus of LppQ of *Mycoplasma mycoides* subsp. *mycoides* Results in Type III Immune Complex Disease Upon Experimental Infection," Infect. Immun. 83(5):1992-2000, 32 pages.
Mulongo, M.M. et al. (Oct. 17, 2013, e-pub. Sep. 11, 2013). "Cattle Immunized Against the Pathogenic L-α-glycerol-3-phosphate Oxidase of *Mycoplasma mycoides* subs. *mycoides* Fail to Generate Neutralizing Antibodies and Succumb to Disease on Challenge," Vaccine 31(44):5020-5025.
Mutwiri, G. et al. (Jan. 26, 2007, e-pub. Oct. 17, 2006). "Poly[di(sodium carboxylatoethylphenoxy) phosphazene] (PCEP) is a Potent Enhancer of Mixed Th1/Th2 Immune Responses in Mice Immunized With Influenza Virus Antigens," Vaccine 25(7):1204-1213.
Naseem, S. et al. (May 19, 2010). "Phage Display-Based Identification and Potential Diagnostic Application of Novel Antigens From *Mycoplasma mycoides* subsp. *mycoides* Small Colony Type," Vet. Microbiol. 142(3-4):285-292.
NCBI Accession No. AE015450.2—"Mycoplasma gallisepticum str. R(low), complete Genome," 464 pages.
NCBI Accession No. AJ515918.1—"*Mycoplasma mycoides* Subsp. *mycoides* SC Putative lppD Gene for Lipoprotein," 3 pages.
NCBI Accession No. BX293980.2—"*Mycoplasma mycoides* Subsp. *mycoides* SC str. PG1, Complete Genome," 376 pages.
NCBI Accession No. CP001621.1, "*Mycoplasma mycoides* Subsp. *Capri* Str. GM12 Transgenic Clone tetM-lacZ, Complete Genome," 153 pages.
NCBI Accession No. CP001668.1—"*Mycoplasma mycoides* Subsp. *capri* str. GM12 Transgenic Clone Deltatypeilires, Complete Genome," 242 pages.
NCBI Accession No. CP001872.1—"Mycoplasma gallisepticum str. R(high), Complete Genome," 246 pages.
NCBI Accession No. CP002027.1—"Synthetic Mycoplasma mycoides JCVI-syn1.0 Clone sMmYCp235-1, Complete Sequence," 365 pages.
NCBI Accession No. CP002107.1—"*Mycoplasma mycoides* Subsp. *mycoides* SC str. Gladysdale MU Clone SC5, Complete Genome," 285 pages.
NCBI Accession No. CP010267.1—"*Mycoplasma mycoides* Subsp. *mycoides* strain izsam_mm5713, Complete Genome," 293 pages.
NCBI Accession No. FM864216.2—"Mycoplasma conjunctivae HRC/581T Complete Genome," 430 pages.
NCBI Accession No. FQ377874.1—"*Mycoplasma mycoides* Subsp. *capri* LC str. 95010 Chromosome, Complete Sequence," 317 pages.
NCBI Accession No. FR668087.1—"Mycoplasma leachil 99/014/6 Complete Genome," 370 pages.
NCBI Accession No. JQ307942—"*Mycoplasma mycoides* Subsp. *mycoides* SC strain 138/5 Chromosomal Replication Initiator Protein DnaA (dnaA) and DnaN (dnaN) Genes, Partial cds," 2 pages.
NCBI Accession No. JQ308103—"*Mycoplasma mycoides* Subsp. *mycoides* SC strain Tan8 Hypothetical Protein Gene, Partial cds," 1 page.
NCBI Accession No. NC_005364.2—"*Mycoplasma mycoides* Subsp. *mycoides* SC str. PG1 Chromosome, Complete Genome," 1 page.
NCBI Accession No. NC_015431.1—"*Mycoplasma mycoides* Subsp. *capri* LC str. 95010 chromosome, complete sequence," 2 pages.
NCBI Accession No. NC_021025.1—"*Mycoplasma mycoides* Subsp. *mycoides* SC str. Gladysdale MU clone SC5, complete genome," 2 pages.
NCBI Accession No. NZ_CP001621.1, "*Mycoplasma mycoides* Subsp. *Capri* Str. GM12 Transgenic Clone tetM-lacZ, Complete Genome," 2 pages.
NCBI Accession No. NZ_CP012387.1—"*Mycoplasma mycoides* Subsp. *capri* strain GM12 Clone YCpMmyc1.1-deltagif, Complete Genome," 2 pages.
NCBI Accession No. NZ_LAEW01000001.1—"*Mycoplasma mycoides* Subsp. *mycoides* Strain B237 gajB237.contig.0_1, Whole Genome Shotgun Sequence," 2 pages.
Nicholas, R. et al. (Aug. 2000). "Contagious Bovine Pleuropneumonia: A Review of Recent Developments," Veterinary Bulletin 70(8):827-838.
Nkando, I. et al. (Oct. 2012, e-pub. Oct. 2, 2011). "Efficacy of Two Vaccine Formulations Against Contagious Bovine Pleuropneumonia (CBPP) in Kenyan Indigenous Cattle," Research in Veterinary Science 93(2):568-573.
Nkando, I.G. et al. (Dec. 2010, e-pub. Jun. 20, 2010). "Assessing the Effectiveness of Intubation as a Challenge Model in Contagious Bovine Pleuropneumonia Vaccine Experiments," Tropical Animal Health and Production 42:1743-1747.
Non-Final Office Action, mailed Oct. 9, 2019, for U.S. Appl. No. 15/746,770, filed Jan. 22, 2018, 8 pages.
Pack, P. et al. (Feb. 18, 1992). "Miniantibodies: Use of Amphipathic Helices to Produce Functional, Flexibly Linked Dimeric FV Fragments with High Avidity in *Escherichia coli*," Biochem. 31(6):1579-1584.
Perez-Casal, J. et al. (Nov. 15, 2015, e-pub. Sep. 9, 2015). "Analysis of Immune Responses to Recombinant Proteins From Strains of *Mycoplasma mycoides* subsp. *mycoides*, the Causative Agent of Contagious Bovine Pleuropneumonia," Vet. Immunol. Immunopathol. 168:103-110.
Porta, C. et al. (Jun. 1996). "Use of Viral Replicons for the Expression of Genes in Plants," Mol. Biotech. 5:209-221.

(56) References Cited

OTHER PUBLICATIONS

Provost, A. et al. (1987). "Contagious Bovine Pleuropneumonia," Reviews of Science and Technology Office of International Epizootics 6(3):625-679.
Reichmann, L. et al. (Mar. 1988). "Reshaping Human Antibodies for Therapy," Nature 332:323-327.
Restriction Requirement, dated Apr. 22, 2019, for U.S. Appl. No. 15/746,770, filed Jan. 22, 2018, 41 pages.
Revell, S.G. (Nov. 1973). "Local Reactions Following C.B.P.P. Vaccination in Zambia," Tropical Animal Health and Production 5(4):246-252.
Schijns, V.E. et al. (Aug. 2000). "Immunological Concepts of Vaccine Adjuvant Activity," Curr. Opi. Immunol. 12(4):456-463.
Selby, M.J. et al. (Jun. 1993). "Expression, Identification and Subcellular Localization of the Proteins Encoded by the Hepatitis C Viral Genome," J. Gen. Virol. 74(Pt. 6):1103-1113.
Smith, R.H. et al. (Jun. 1986). "Cyclophosphamide and Dimethyl Dioctadecyl Ammonium Bromide Immunopotentiate the Delayed-Type Hypersensitivity Response to Inactivated Enveloped Viruses," Immunology 58(2):245 250.
Smith, T.F. et al. (1981). "Comparison of Biosequences," Advances in Appl. Math. 2:482-489.
Snippe, H. et al. (1982). "Adjuvanticity of Dimethyl Dioctadecyl Ammonium Bromide in Guinea Pigs. I. Skin Test Reactions," Int. Arch. Allergy Appl. Immunol. 68(3):201 208.
Strathdee, C.A. et al. (Dec. 1987). "Extensive Homology Between the Leukotoxin of Pasteurella haemolytica A1 and the Alpha-Memolysin of *Escherichia coli*," Infect. Immun. 55(12):3233-3236.
Summers, M.D. et al. (May 1987). "A Manual of Methods for Baculovirus Vectors and Insect Cell Culture Procedures," Texas Agricultural Experiment Station Bulletin No. 1555, 60 pages.
Thiaucourt, F. et al. (2000). "Contagious Bovine Pleuropneumonia. A Reassessment of the Efficacy of Vaccines Used in Africa," Annals of the New York Academy of Science 916:71-80.
Thiaucourt, F. et al. (2011). "Mycoplasma mycoides, from "mycoides Small Colony" to "capri". A Microevolutionary Prespective," BMC Genomics 12(114):1-19.
Tomei, L. et al. (Jul. 1993). "NS3 is a Serine Protease Required for Processing of Hepatitis C Virus Polyprotein," J Virol. 67(7):4017-4026.
Tulasne, J.J. et al. (Dec. 1996). "Contagious Bovine Pleuropneumonia Vaccines: The Current Situation and the Need for Improvement," Reviews of Science and Technology Office of International Epizootics 15(4):1373-1396.
Van Dalen, F. et al. (Jul. 1988). "Preparation and Characterization of Liposomes With Incorporated Neisseria gonorrhoeae Protein IB and Amphiphilic Adjuvants," J. Controlled Release 7(2):123 132.
Van Hoogevest, P. et al. (2014). "The Use of Natural and Synthetic Phospholipids as Pharmaceutical Excipients," Eur. J. Lipid Sci. Technol. 116:1088-1107.
Verhoeyen, M. et al. (Mar. 25, 1988). "Reshaping Human Antibodies: Grafting an Antilysozyme Activity," Science 239(4857):1534-1536.
Welch, R.A. (1991). "Pore-Forming Cytolysins of Gram-Negative Bacteria," Mol. Microbiol. 2:521-528.
Westberg, J. et al. (Feb. 2004). "The Genome Sequence of *Mycoplasma mycoides* subsp. *mycoides* SC Type Strain PG1T, the Causative Agent of Contagious Bovine Pleuropneumonia (CBPP)," Genome Res. 14(2):221-227.
Windsor, R.S. (2000). "The Eradication of Contagious Bovine Pleuropneumonia From South Western Africa. A Plan for Action," Annals of the New York Academy of Science 916:326-332.
Winter, G. et al. (Jan. 24, 1991). "Man-Made Antibodies," Nature 349(6307):293-299.
Wise, K.S. et al. (Aug. 2012). "Complete Genome Sequences of Mycoplasma leachil strain PG50T and the Pathogenic *Mycoplasma mycoides* subsp. *mycoides* Small Colony Biotype Strain Gladysdale," J. Bacteriol. 194(16):4448-4449.
Written Opinion of the International Searching Authority, mailed Feb. 24, 2016, for PCT Application No. PCT/CA2016/050864, filed Jul. 22, 2016, 14 pages.
Yu. N.Y. et al. (Jan. 2011, e-pub. Nov. 10, 2010). "PSORTdb—An Expanded, Auto-Updated, User-Friendly Protein Subcellular Localization Database for Bacteria and Archaea," Nucleic Acids Res. 39:D241-244.
Yu, N.Y. et al. (Jul. 1, 2010, e-pub. May 13, 2010). "PSORTb 3.0: Improved Protein Subcellular Localization Prediction With Refined Localization Subcategories and Predictive Capabilities for All Prokaryotes," Bioinformatics 26(13):1608-1615.
Ziola, B. et al. (Mar. 12, 1987), "In vitro Proliferation of Lymphocytes From Cyclophosphamide-Pretreated Mice Immunized With Antigen Mixed With Dimethyl Dioctadecyl Ammonium Bromide," J. Immunol. Methods 97(2):159-164.

* cited by examiner

FIG. 2A
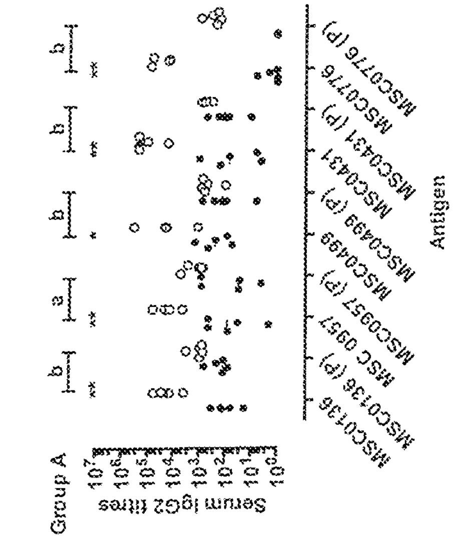
FIG. 2B
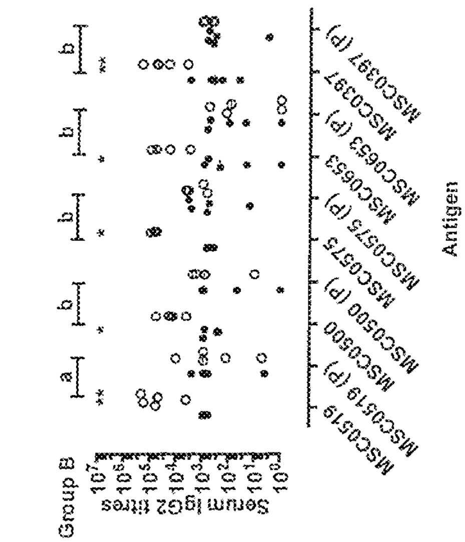
FIG. 2C
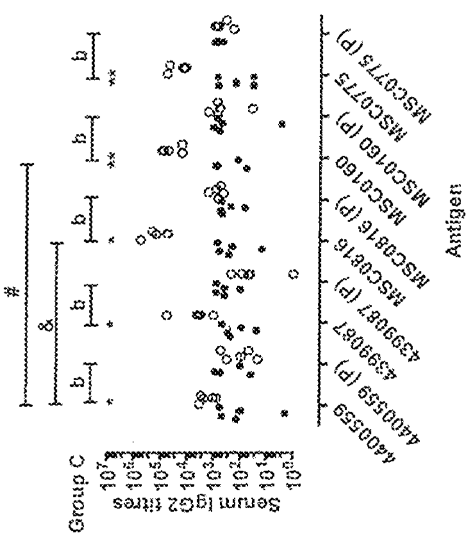
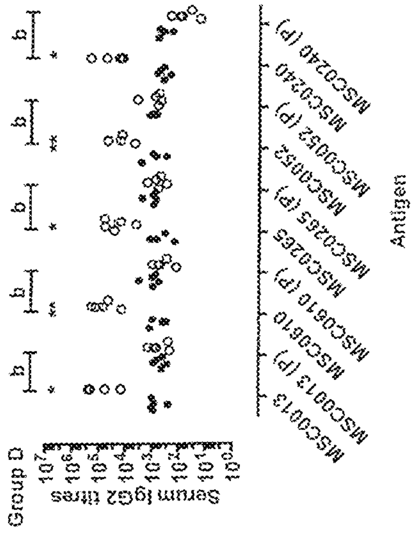
FIG. 2D
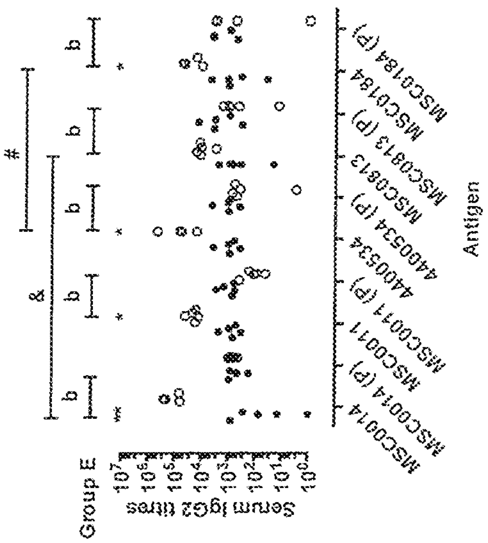
FIG. 2E Group G
Serum IgG1 titres
Antigen
MSC0782
MSC0782 (P)
MSC0401
MSC0401 (P)
MMSA0038
MMSA0038 (P)
MSC1058
MSC1058 (P)
MSC0790
MSC0790 (P)

Group H
MSC0453
MSC0453 (P)
MSC0798
MSC0798 (P)
MMSA0108
MMSA0108 (P)
MSC0266
MSC0266 (P)
MSC0456
MSC0456 (P)

Group I
4400602
4400602 (P)
4400291
4400291 (P)
4400300
4400300 (P)
4400620
4400620 (P)
MSC1005
MSC1005 (P)

Group J
4400616
4400616 (P)
4400615
4400615 (P)
MMSA0415
MMSA0415 (P)
MSC0927
MSC0927 (P)
MSC0804
MSC0804 (P)

Group K
4400622
4400622 (P)
4400371
4400371 (P)
4400226
4400226 (P)
4400021
4400021 (P)
MSC0163
MSC0163 (P)

FIG. 4C
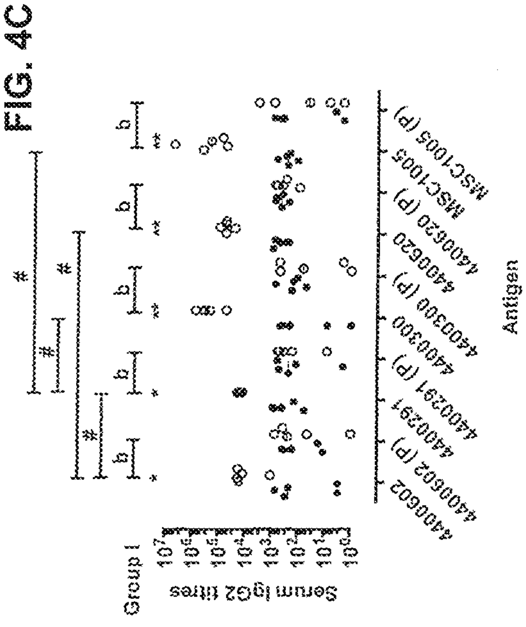
FIG. 4B
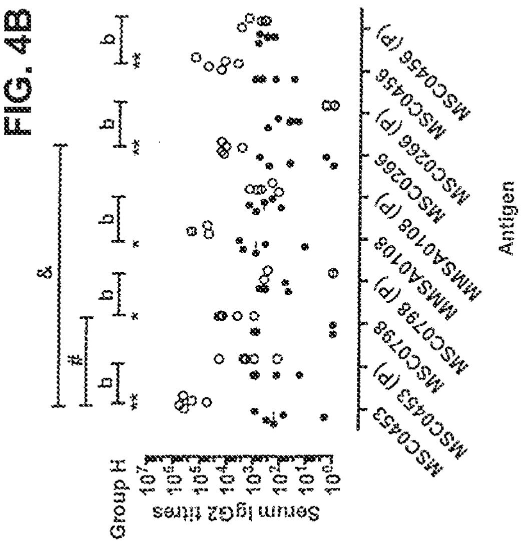
FIG. 4A
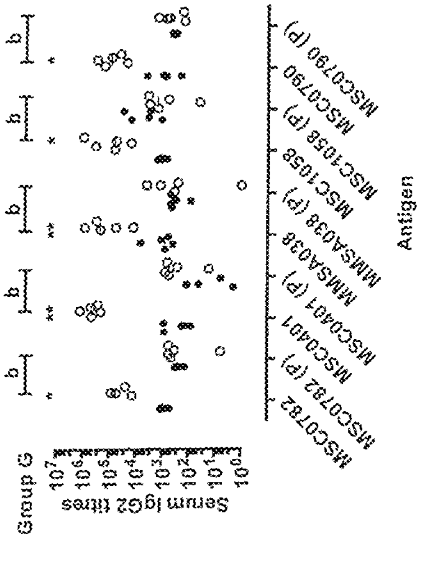
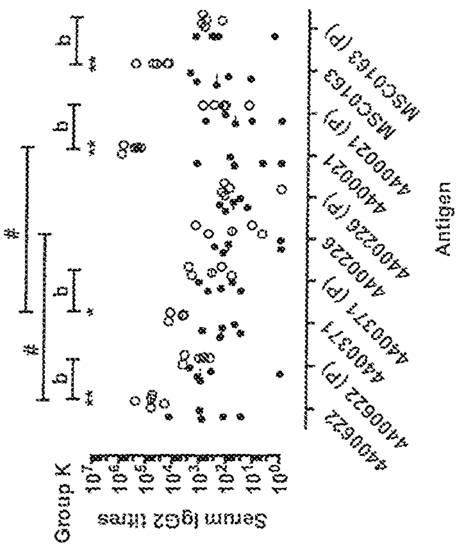
FIG. 4E
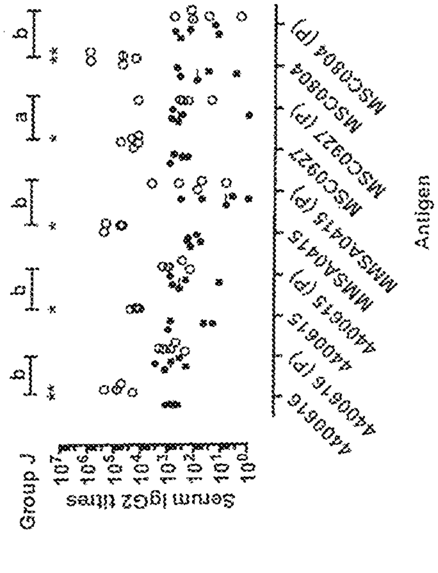
FIG. 4D FIG. 6B
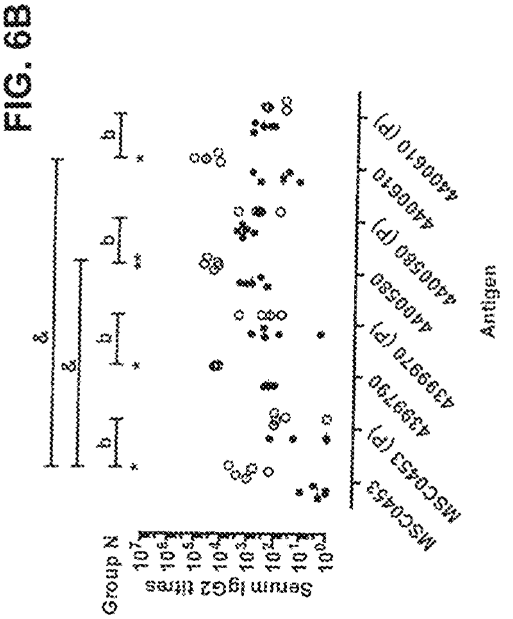
FIG. 6A
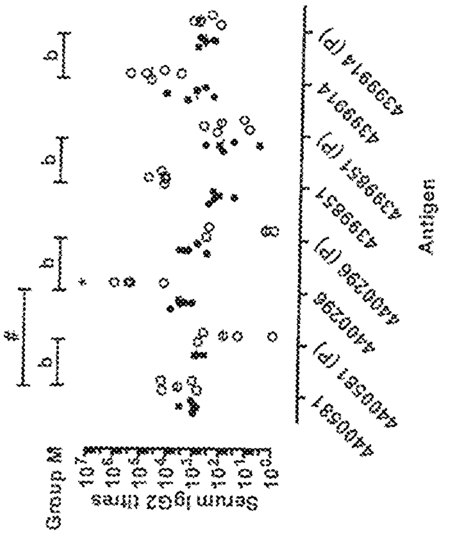
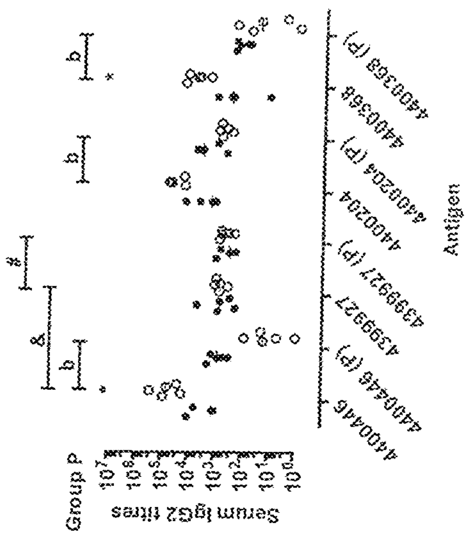
FIG. 6D
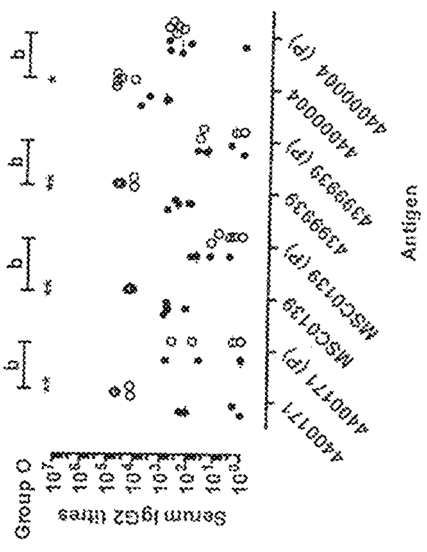
FIG. 6C Group G
Stimulation Index
300
200
100
30
20
10
0
ConA
MSC 0782
MSC 0401
MMS A0381
MSC 1058
MSC 0790
Recall antigens Group H
MSC 0453
MSC 0798
MMS A0108
MSC 0266
MSC 0456

Group I
4400602
4400291
4400300
4400620
MSC 1005

Group J
4400616
4400615
MMS A0415
MSC 0957
MSC 0804

Group K
4400622
4400371
4400226
4400021
MSC 0163

FIG. 9A
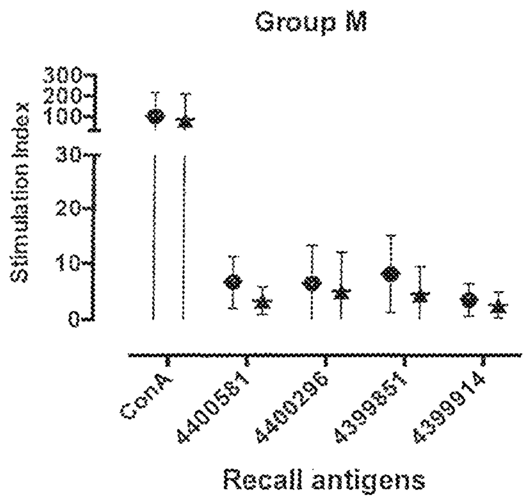
FIG. 9B
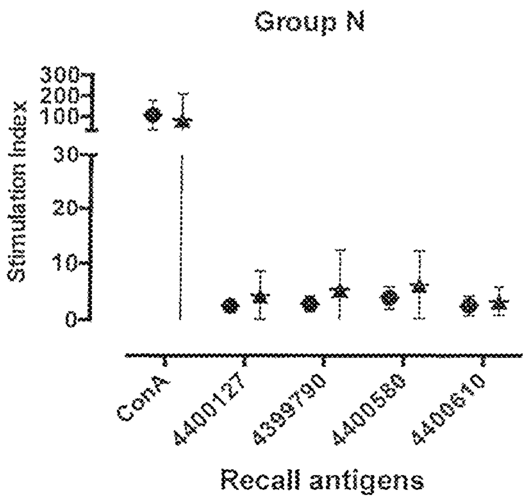
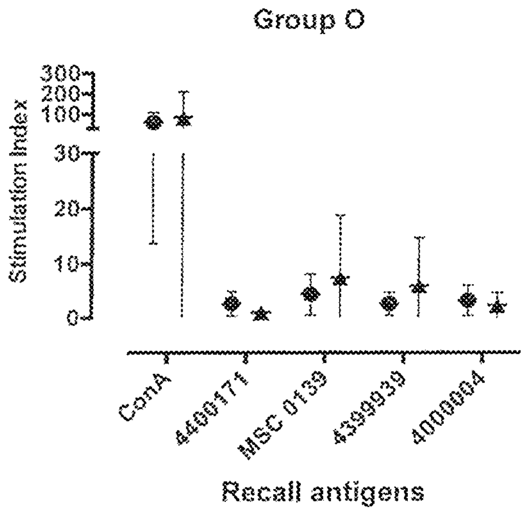
FIG. 9C
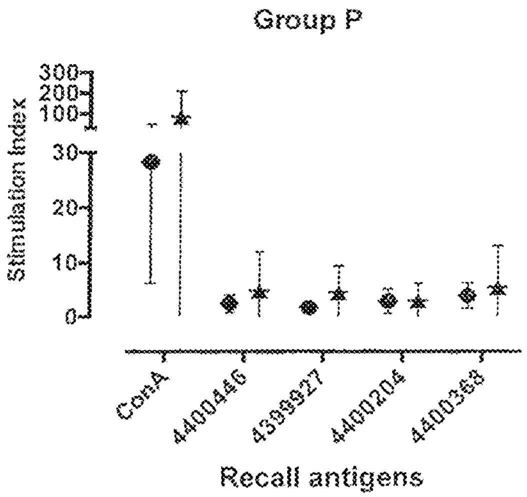
FIG. 9D

FIG. 11A

MSC_0136 Optimized DNA sequence (SEQ ID NO:1)

```
1     AAAAACGAAAACCATTTCAACATCAACTACAAAATGAAAATGGAAATGAA
51    AACCCAGAAAACGGAACAACCGCACAAATATAAAGAAGGCGATCGTACCG
101   AAATTGTGCAGATCGGCTTTTACAAACGCGGTAACGAAATCACGATCAAA
151   CAAATCCCGTACTACGTTAAAAAAGTCCCGGATAAACTGCCGGACGAAAT
201   CCAGTCCCTGTATCGTGCATTTGCTCATCGCTACAAAGATCAAAACCACC
251   CGACCGTCACGGGCTTCGAAAAATGGGACACCAGCAAAATCAAAAACATG
301   TCTTATGTGTTTTACGATAACCAGCTGATCGATGCGGACCTGTCAGAATG
351   GAAAACCTCGAATGTTACGAACATGGACGGCATGTTCAAAAACGCCATCA
401   AATTCAACAACAAAGAAAAACCGCTGAAATGGAACACCGAAAAAGTCGAA
451   AGTATGGAATCCATGTTTGATGGCGCAGAATCTTTTAAACAGAACCTGAA
501   AGATTGGAAAGTGGACAAAGTTACCAAAAACAAAAACTTCTCACGTGCTT
551   CGGGTATTTTCGAACATATCGATAAAAAACCGTCATGGAAAATCACCGAA
601   CACAACGACCCGATTATCAAAAAACCGGAATCGACGGAACCGAAAGTGAT
651   TATCCATCCGAGCCCGTCTCGCCCGAAACAGACCATTCCGCTGACGAAAC
701   TGATCAATCCGATTATCAAAAGCACCCCGAACTCTAATCAAAACCTGGGC
751   ATCCCGAAAACGAACCTGAGCACCACGCCGCAGCAAAGTAAAAAACTGTC
801   CACCCCGGCAATTGTTGGCATCGTGGTTGGTAGTCAGGTCGTGCTGACGT
851   CCCTGGCAGCAGGTATTCCGTACCTGATCAAACGTTTCAAAAAA
```

FIG. 11B

MSC_0136 Protein sequence (SEQ ID NO:2)

```
1     KNENHFNINYKMKMEMKTQKTEQPHKYKEGDRTEIVQIGFYKRGNEITIK
51    QIPYYVKKVPDKLPDEIQSLYRAFAHRYKDQNHPTVTGFEKWDTSKIKNM
101   SYVFYDNQLIDADLSEWKTSNVTNMDGMFKNAIKFNNKEKPLKWNTEKVE
151   SMESMFDGAESFKQNLKDWKVDKVTKNKNFSRASGIFEHIDKKPSWKITE
201   HNDPIIKKPESTEPKVIIHPSPSRPKQTIPLTKLINPIIKSTPNSNQNLG
251   IPKTNLSTTPQQSKKLSTPAIVGIVVGSQVVLTSLAAGIPYLIKRFKK
```

FIG. 12A

MSC_0957 Optimized DNA sequence (SEQ ID NO:3)

```
1     TGCAGTACCACGATTACCCATACGATCAAAACGTCCTTTAACGATAACGT
51    TAAAGTCGAAAAATTCACCTGGGACGGCAATAAATATACCTCCAAAGAAC
101   AGTCAACGAACATTCAAGATATCACCAATAGCCTGAACGGTACCACGAAT
151   GCATACTCTAAAACCATTACGGACGTGCTGAACCTGTTTACCCGTAATAT
201   CCAGGAAGTTCGCAACCTGAAAGAAAGCTATGACCTGTTTCGTGGCAAAG
251   CAGAAAATACGTCGGTGGTTGGCTATTACACCGGTGCTAACAGTCAGCGC
301   CAAAAAATCTCCCAGCAAGATTTCTACAAAAAACTGGATGACAGTGACAC
351   CCACATCAGCTCTCTGAAAGGTCTGCTGCAGCTGCGTGAATTCGTTAACG
401   ATAACAAAAACAAAACCACGGTCGAACCGTGGAAAAATAGCCTGAAAACG
451   GATGCGGACGAAGTTAAAAAATGGTCTGATGAATTCACCAAAAATCTGGA
501   CAACATTGTCAACAGTTCCATCGATAACAAAATCAAAAACATCAAACTGG
551   TGTCTAAAGTTAGTAAAACGTCATCGAGCTTTGCCACCTTCGAACAGGAC
601   GTGAAAACCAGCCCGACGGGCTCTAGTATTAACCTGACGGAACGCAACAA
651   TGAAACCGTCGTGGGCGATATCAAAAACCTGAAAGACCATAATCCGTATG
701   TCTTTGGTACCAGTCCGGTGAATGATCCGTTCGGCATGAACGTGATTGGT
751   GAAAATAAAGATCCGGACATTAAAAACCTGAAACCGACCATCAAATATTC
801   CACCGAAAAACTGACGAAAAAAGATGACTCATACATTAATCTGTCGAACA
851   ATGGTAACAACAACAACCAGTTCGTTTACAACATCAACCAAAAATGGGAA
901   CTGTCCTCAGCACATAATTTCTATTACATGAGCAAAGATCCGGAAACGCT
951   GGAACTGCAGATTACCCACAGCATCGAAAACAAATCTTTTACCTTCTACG
1001  TCCAATTTGGCGGTCTGCGTAAAATTTATACCCCGATCGTGGAATCTTAC
1051  ACCCCGAAAAATACGAACTCAGCGGATAAACGTTATTCGTTTGTGGGCTG
1101  GGCCTTCAATTCGTACCGCTTTAGCGATGACTTCTCTAAGGGTAACTCGA
1151  GCCCGTACAAATTCAAAGATATTAGTCTGAAAATCTCCCAGAACGCTTTC
1201  ACCACGAATACCGGCAGCGTTAACGGTAAA
```

FIG. 12B

MSC_0957 Protein sequence (SEQ ID NO:4)

```
1     CSTTITHTIKTSFNDNVKVEKFTWDGNKYTSKEQSTNIQDITNSLNGTTN
51    AYSKTITDVLNLFTRNIQEVRNLKESYDLFRGKAENTSVVGYYTGANSQR
101   QKISQQDFYKKLDDSDTHISSLKGLLQLREFVNDNKNKTTVEPWKNSLKT
151   DADEVKKWSDEFTKNLDNIVNSSIDNKIKNIKLVSKVSKTSSSFATFEQD
201   VKTSPTGSSINLTERNNETVVGDIKNLKDHNPYVFGTSPVNDPFGMNVIG
251   ENKDPDIKNLKPTIKYSTEKLTKKDDSYINLSNNGNNNNQFVYNINQKWE
301   LSSAHNFYYMSKDPETLELQITHSIENKSFTFYVQFGGLRKIYTPIVESY
351   TPKNTNSADKRYSFVGWAFNSYRFSDDFSKGNSSPYKFKDISLKISQNAF
401   TTNTGSVNGK
```

FIG. 13A

MSC_0499 Optimized DNA sequence (SEQ ID NO:5)

```
1     TGCACCACGAAAAACGATAAATTCAACAAACCGTTCATCACCGACGAACTGGCGCAGAAA
61    ATTATCTCAGGTCTGAAACTGTCGGATGACTTTAATTTCACCACGGGCGAACGTTTCAGT
121   AAACTGGATTACAAATCCCTGATTCTGGACATGATCAACGAAATCATCTCCAAAAACAAA
181   TACACCGATAACTGGAACAACCTGAGCAAAAAATTTGGTCTGGAAATTGAACAGGCGAAA
241   GAATTCGGCAACAAAAAAGCCGAAAACGTTCTGAAAAACCTGAGCACCATCAAACTGTTC
301   GCAGATTATACGTCTAAACGCGCTTTTGAAGAAGATTTCGACAGTGTGGATCTGAGTTAT
361   TCCGAAAATTACCCGCTGAATCCGTATAACCTGGAAAGCAAAAACGGTCAGAAAGATAAA
421   ACCGTTTACGCGATCTACTACAAAAACAACAACGGCGGTAGCTCTAGTGGTTCCTCATCG
481   AATGGCGGTGGCACCAACGGTGAAGCAACGTGGCTGCGTTGGCAGACCACGGGTGAATTT
541   GATAATATTGACAACCCGATCCCGTCAACCCCGCAACTGCCGAATATCTCGCTGCTGACC
601   GATACGAGCTCTAAAAACTTCCGCATTGCCAAACTGTCCAAACCGAAAGATCAGGAATAT
661   ATCACCAATACGGCAAGTGTTAAAGAAGACGGTAAAGCTACCAATAACGGCAATAACGAA
721   TTTGTCGAATGGTACAAAAACAGTTCCGACAAATTCGAAACCGATGGTCAGGGCATCATG
781   CAATACCGTTTCATGTACCATTTCAAAACGAAAATCGAAGCGAAACTGTTTAATGATCTG
841   CTGGGTCACGCCTATATTGACAGCAACCTGTTCGTGGATAAAAACGACAACAAATCAGCA
901   TCGAACAAGAAAATTATCCTGAACAACGTCAGTAAACTGATTTCCGATATCCAGAGCAAT
961   TATTCTCAAGTGGACAAAACCATTAGTAACGTGAAAATGGTTTGGGCATTTAGCCTGGAT
1021  AAACAGAAAGTCTCTGAAGTGAACGGTGCTATCAATCAATATGTCAACCCGGATGGCAGC
1081  CTGACCAATGAAGACAACAAGAAAACCCTGAAAAACGTGTTCGATAAAATCAAATACAAA
1141  GCGACCAACGAATCAAAACAGGGTACGGATTCGCTGCTGAGCATTTCTGGTTTCAACGGC
1201  TTCGTTAAAAACAAAGATAACAACATCGAAAGTCTGTCCGGCGACCTGAAACTGACCGAA
1261  GAAGCGAAAAAAGCGGTCGCCCGCGTGAATGTTCCGTCTCTGCTGACGAATAACAATAAC
1321  GGCTTTGCCAGTGAAAACTCCAATAACGTGGATTATGTCTTTGTGCTGCCGATTTACCTG
1381  AATGACCTGTTTAGCTCGAACGACATGCAGATCAAACGTGAAACCGAAAGCTCTGGTGGC
1441  GCCGGTTCAAATGGCTCGAACTATGAACTGAATGTTCTGGAAAACACCTGGGTCAACCTG
1501  AATGACAAATTTAGCCTGGATAATCGCTACTTCGACAACCTGACGATCAAAAAAGTGGAA
1561  TCTCAAAATAACGGTGAAGCACTGGTGGCTAACAACAACGATAAATGGTACGTTAGCCTG
1621  AAAAACGGCAATGACAACAAAAAAGTTGAAGTCACCTACAGCGATGACAGCAAGAAAATT
1681  ATCACGCTGAAAAAAGTTGATAAAAACAACATCAAAACCCTGGACTTCACGTACAAACTG
1741  TCACAGTCGGATTTCAACAAACAGCTGTTCAAACAAAACCCGACCGCAAACATCACGTAT
1801  GATATCAACCTGAAAAACTACGATAACATCAAAGACAAACAGAACGATGCTTATATCTGG
1861  AAAAACGATCCGAAAAAATCTAACGATATCCAAGACCTGTCCGCGGCCAAAAAACAGGTG
1921  CTGCTGGATCAACTGGAAGCGATCACCGCCAAAAATCCGGACGTTCAGAACGCAGCTAAA
1981  ACCGAACTGTATTCGGCATATCTGTACACGGATGGTATCTACTACAAATCACTGTTCGAC
2041  GAAATCAGCAAATACATCGAATCTGAAAAACCGACCCTGGAT
```

FIG. 13B

MSC_0499 Protein sequence (SEQ ID NO:6)

```
1     CTTKNDKFNKPFITDELAQKIISGLKLSDDFNFTTGERFSKLDYKSLILDMINEIISKNK
61    YTDNWNNLSKKFGLEIEQAKEFGNKKAENVLKNLSTIKLFADYTSKRAFEEDFDSVDLSY
121   SENYPLNPYNLESKNGQKDKTVYAIYYKNNNGGSSSGSSSNGGGTNGEATWLRWQTTGEF
181   DNIDNPIPSTPQLPNISLLTDTSSKNFRIAKLSKPKDQEYITNTASVKEDGKATNNGNNE
241   FVEWYKNSSDKFETDGQGIMQYRFMYHFKTKIEAKLFNDLLGHAYIDSNLFVDKNDNKSA
301   SNKKIILNNVSKLISDIQSNYSQVDKTISNVKMVWAFSLDKQKVSEVNGAINQYVNPDGS
361   LTNEDNKKTLKNVFDKIKYKATNESKQGTDSLLSISGFNGFVKNKDNNIESLSGDLKLTE
421   EAKKAVARVNVPSLLTNNNNGFASENSNNVDYVFVLPIYLNDLFSSNDMQIKRETESSGG
481   AGSNGSNYELNVLENTWVNLNDKFSLDNRYFDNLTIKKVESQNNGEALVANNNDKWYVSL
541   KNGNDNKKVEVTYSDDSKKIITLKKVDKNNIKTLDFTYKLSQSDFNKQLFKQNPTANITY
601   DINLKNYDNIKDKQNDAYIWKNDPKKSNDIQDLSAAKKQVLLDQLEAITAKNPDVQNAAK
661   TELYSAYLYTDGIYYKSLFDEISKYIESEKPTLD
```

FIG. 14A

MSC_0431 Optimized DNA sequence (SEQ ID NO:7)

```
1      TGCGCAAACATCGAAATGTCAAAAAACAAAAAAGATAAAGACAAAGATCT
51     GAAATCGGACAAAAACAAAGATCAGAACAACAAATTCGACAAAAGCAAAG
101    ATAAAAACCAAAACTCTAAACCGAACAACAACGATCAGAATAGTAAATCC
151    AACCAAGACAAAACCTCACCGAAAGATAATCCGTCGACGCAGTCAGAATC
201    GGAAAAACAGGAAAACTCCAAACAATATGACCTGGATAAACTGATCACGA
251    ACAAATTCATCAGCATCGACGGCTCTGGTACCGGCGATGGTAAACTGGCT
301    AAACTGCCGCAGAACCTGCAAGAATATCTGGATCTGATCAAAAAACAGAA
351    CCCGAAATTCACCCTGACGCTGAATAACGTCAGTTTCAATGTGGAAGAAA
401    ATGATAACTCCGGCTACAAAAAAGTCAGCGTGTCTACGAAGGGTAACTCT
451    AAAAACCCGGTTATCGTCTACTTCTACAAAGACCGTCATGATACCGTTTA
501    TGAAGGCGAGAAAAAAGAAGTGGTTAAAGAAATCGGTTGGAGTAAATCCA
551    CCTACAGTACGGACATCCTGCACTTCGATGAACAGACGAAAGAAGTCCCG
601    GAAAACCTGCCGCCGTTTATCACCAGCCTGGAAGGCGCGTTCCGCAACAA
651    CATCCAAGAAACCATCAAAAACCTGGACAAATGGGATACGAGCAACATCG
701    AATTCATGAACGAAACCTTCTACGAAGCGAAAAATTTTAACCAGGATATC
751    TCTGGTTGGAAAACCAATAACGTTAGTAACATGGATTCCATGTTTTATGG
801    CGCCAGCTCTTTCGACCGTAATCTGAGCGGTTGGAACGTGGATAAAGTTA
851    TTACCTACATCGAATTCAACAAAGATTCAAAAATCTCGGAACGTAACAAA
901    CCGAAATTCAAAGAACTGAAACGCATTCATCAGGGCCAAGGTGCAACCAA
951    AATCCTGCACAATCGCGGCTTTCTGAATAAAATGAACCTG
```

FIG. 14B

MSC_0431 Protein sequence (SEQ ID NO:8)

```
1      CANIEMSKNKKDKDKDLKSDKNKDQNNKFDKSKDKNQNSKPNNNDQNSKS
51     NQDKTSPKDNPSTQSESEKQENSKQYDLDKLITNKFISIDGSGTGDGKLA
101    KLPQNLQEYLDLIKKQNPKFTLTLNNVSFNVEENDNSGYKKVSVSTKGNS
151    KNPVIVYFYKDRHDTVYEGEKKEVVKEIGWSKSTYSTDILHFDEQTKEVP
201    ENLPPFITSLEGAFRNNIQETIKNLDKWDTSNIEFMNETFYEAKNFNQDI
251    SGWKTNNVSNMDSMFYGASSFDRNLSGWNVDKVITYIEFNKDSKISERNK
301    PKFKELKRIHQGQGATKILHNRGFLNKMNL
```

FIG. 15A

MSC_0776 Optimized DNA Sequence (SEQ ID NO:9)

```
1     TGTAAAACGACGCAAAATCAACAGGGCATCTATAAAATTGTGGACTTCGAAAAAGAAAAT
61    CAAATCAACATTCTGAGCGAAATCAACCAGTTTTTCGAAAAACATGATTTCAACGAACAG
121   CTGGTTCAATTCGTCAACAAAGATAGCCACAATTATATTACCCTGGACTCTCTGATGAAA
181   AACAATTATGCGGCCAAATACGTGAAATTTGATAAAGACAAATTCAAACAGATCATCAAA
241   AAAGAATTCAACCTGAGTGATGCATACCTGAATAAACTGGAAATCGAAGTTGACTATACC
301   AACATTGATCGCGACTACTCCAACAATTTTGATATTGTCTTCCCGATTCGTATCAAACGC
361   CAGCTGGAAAATCATAAAAAAGCGAGCTATCAACCGGGCCTGTTTACGGAACAGATTATC
421   AAATTCCGCCTGAAAAACGTGAAAAGCTCTCCGTCGGAAGCATTTTTCGCTGAAGAACTG
481   AAAGATGTTTTCAACAAACTGAAAGAACTGAAATACGATAACTTCACCGCGCGTCTGAAA
541   ACGAACATCAGTAACGAACTGAAAAAACAGATCGATCAATGGAACATCAACGAACTGGAC
601   AGTACCCAACTGTCCAACATCTTCGAAATCAACATCTCCGAATTCGATCAGCTGAAAACC
661   AACAATCCGAATTTTGTGTTCAAAAGTACGATCTTTGGTGTTGATTTCTCCGACAAAAAC
721   CTGGCGCTGAATGAAGGCTATCTGAAAGTGCGTTTTGCCGTTAAAGAAGGTTTCGATAGT
781   AAAGACAAAACCAAACAGATCAACCTGATCAACAAAGAAATCAACGAACTGATCGTGAAA
841   AAAGAAAACCTGGAAAAAACCAACAACTCAGATTCGAACAAAACGGAAATCGACAAACTG
901   ATCCAGATCATCAAACAAAAAAGCGCGCAGCTGACCAAAATTAAACAAAAAGCCCTGCCG
961   GCGGAAGCCGGCATCACGAAACTGATCAAATTCAAATTCGATTGGAACGACCAGTTTTGG
1021  AAAAACATCAAACTGAACGAAGTGATCAAAATCGATACCATCAAATATGGTATCAGCAAT
1081  ACCGATTTCCTGTCTCTGACGAAAGACAACCTGATTGTTAAAATCCTGAACAAAGATGTG
1141  CGTAACGTTGACATTAAGAAAATTGAAAAAACCAACGATTTCCGCAACGCGAAACTGGTC
1201  CTGGATGTGCTGCTGAAAGACAACAAAAAACTGGAACTGAACAAGAAAATTGGCGTGGGT
1261  AAATATAGCCTGCTGTACGAAAATGATTTCATCAAAAACAACATCCAGGCCCCGTATTTC
1321  ACCACGGAACGTCTGACCCAAGAAAACCTGCAGTCTGTTAATAAAGATTTCTTTCGCCAG
1381  TTTGACTCAGAACTGTTCTCGGGCGGTTATGCAAGTTCCCGTGGCTTTTACGCTCCGAAA
1441  ATTACCACGCCGATCTTCATGCACATTGGTGAAGATTATATTGCGAATGACTTTCAGGCC
1501  GTGCTGATGCCGTATGATGGCGAAATTATCGCAGCTTACGAACTGAGCACCAACGTCCCG
1561  TTCGCAGGCGTGGGTACGGTGGTTGTCGTGAAAATTAAAGTTTCTGATCTGGACTGGACC
1621  CCGAAAGAAAAAGAAATCTATCTGAACAACAACAAAGATCATATCTACATGTCATTTCTG
1681  CACCTGGACGCATCGCGCACGCTGAATAACCAGAAACTGGGTTGGTCAGCTGAAAAAGTT
1741  GTCCTGAATAACAATCGTACCATTCAAGTGGTTAAATCGCTGACGCCGGAAAAACCGCAG
1801  AAAGTCGCCAAAAATACCATTATCGGCTATCTGGGTAACAATGCAAGTAACGGCGGTTGG
1861  ATGTCCCATGCTCACGTTAACCTGTACACCAATCGCCCGTCATATCTGTCGGAAAACTAC
1921  TTTAGCACGAAATCTAATCAAGGCCTGAGCGAAGATCGTATCAAACAGTACCATCAAAAC
1981  ATCAACGGTAAAGAAACCTGGCGTCAGTTTGGCAATATTGGTCTGCACCAGTCTCCGCAA
2041  CGTCCGCCGTACACCATCAACGAAGTTGATCAAATTACGGGCGTCGAAAAACTGGACGAA
2101  AACAAAAAGAAAATTGTCGTGAAAAACGAACAGGCGCTGTTTCTGCCGAACCTGAGCATG
2161  TCTCTGTTCGAAAAACGCCTGGGTTATGCCAACCCGAATCTGGTCTACCGTCTGCGCGAT
2221  AATAAAACCGTGAGTTTTTCCGTTAAAGAAGTCAACAAACTGACG
```

FIG. 15B

MSC_0776 Protein sequence (SEQ ID NO:10)

```
1     CKTTQNQQGIYKIVDFEKENQINILSEINQFFEKHDFNEQLVQFVNKDSHNYITLDSLMK
61    NNYAAKYVKFDKDKFKQIIKKEFNLSDAYLNKLEIEVDYTNIDRDYSNNFDIVFPIRIKR
121   QLENHKKASYQPGLFTEQIIKFRLKNVKSSPSEAFFAEELKDVFNKLKELKYDNFTARLK
181   TNISNELKKQIDQWNINELDSTQLSNIFEINISEFDQLKTNNPNFVFKSTIFGVDFSDKN
241   LALNEGYLKVRFAVKEGFDSKDKTKQINLINKEINELIVKKENLEKTNNSDSNKTEIDKL
301   IQIIKQKSAQLTKIKQKALPAEAGITKLIKFKFDWNDQFWKNIKLNEVIKIDTIKYGISN
361   TDFLSLTKDNLIVKILNKDVRNVDIKKIEKTNDFRNAKLVLDVLLKDNKKLELNKKIGVG
421   KYSLLYENDFIKNNIQAPYFTTERLTQENLQSVNKDFFRQFDSELFSGGYASSRGFYAPK
481   ITTPIFMHIGEDYIANDFQAVLMPYDGEIIAAYELSTNVPFAGVGTVVVVKIKVSDLDWT
541   PKEKEIYLNNNKDHIYMSFLHLDASRTLNNQKLGWSAEKVVLNNNRTIQVVKSLTPEKPQ
601   KVAKNTIIGYLGNNASNGGWMSHAHVNLYTNRPSYLSENYFSTKSNQGLSEDRIKQYHQN
661   INGKETWRQFGNIGLHQSPQRPPYTINEVDQITGVEKLDENKKKIVVKNEQALFLPNLSM
721   SLFEKRLGYANPNLVYRLRDNKTVSFSVKEVNKLT
```

FIG. 16A

YP_004400559.1 optimized DNA sequence (SEQ ID NO:11)

```
1       ATGAGCAACAACAACAAAAAAGAAGAAAAGCAATCAAAGGAAATGAATAA
51      AAATCAAACCTCTAACTCCACGAGCACCAATATGAACAACACGCAGGGCA
101     GCAATAGCTCTACCACGACCAACATTACCTCTAACCCGATCAATAGTGTC
151     ACGTCCATGGCGACCCAACCGAAAAACGAAACCTTTTTCAATAAGGAACC
201     GCTGATCTTTTCAGAACTGGATTATGTGTCGGAATACTTCAAGCGTAAGG
251     AACATATTGCGCGCACCAGCGAACTGATCCTGGAAAACTCTGAAGGCATT
301     AAACGTCGTATGCAGAATAGTACGGTTGAAACGACCCACCGTGATTCCCT
351     GGCCGAAACCCAAGACCTGATTCTGGAAAACAGCAACGGTGTGGTTAACT
401     TCAAGAAG
```

FIG. 16B

YP_004400559.1 protein sequence (SEQ ID NO:12)

```
1       MSNNNKKEEKQSKEMNKNQTSNSTSTNMNNTQGSNSSTTTNITSNPINSV
51      TSMATQPKNETFFNKEPLIFSELDYVSEYFKRKEHIARTSELILENSEGI
101     KRRMQNSTVETTHRDSLAETQDLILENSNGVVNFKK
```

FIG. 17A

YP_004399807.1 Optimized DNA sequence (SEQ ID NO:13)

```
1       ATGAGCAGCAAAGTTCAGGTTATCAACAAGTTCGATGACATTACGTCCAT
51      TAAAAACACGGGTGCGTTCAAAAACAATCAGGCATTCATTTCCCGTTCAG
101     AACTGAAAGAAATCGTCAGCTCTAACAATACCACGATTTCTAATACCACG
151     AGTTCCACCGCAGTGATGACCTCGACGAGCACCACGTCTATCGGCACCCA
201     GACGAACAATAACAATGACCTGAAGAACGCGAGTGAACGCCTGAAAGCCC
251     TGGCGGCCAACAACTTCACCAAGAACAAGAAGCAGGCATGGGATTCCCTG
301     CAAAACGCTTCAATGACCTTCTATAAAAAGGTGCAGCCGACCGCGGTCAA
351     TGTGCTGGGTTACGAACAAATTACCAAAGACAACGTTGAAAAACTGGATA
401     AGGAACTGAAAACCGTTTTTCTGGTCTTCAAGGACAATACCAAAGAAACG
451     GAAAAGCTGGAAGTGGAACTGCTGCCGGAAATTAACAATGGCAACAAAGT
501     TATCGACAATGGTAACCTGTATCTGGATCTGCTGGAAAAACCGGAAAATC
551     TGAAGCTGGCGAACCAGAAAAGCATTATCGAAGTGCTGCGTCCGGAAATT
601     ACCAAAATCAAGGTGGTTCTGCAAAATACCAAAAACAATAACTCCACGAA
651     CAAAGAAGATATCAAGAACACCGAAGTTTTCAACCTGCTGATTAAACAGC
701     TGAGCATCTATCTGGCAAATGCTGTCAAATACTTTAACTCTGAAAGTGGC
751     ATTATCACCACGAATCCGACCTTCTCGTATAAAACGCGCAGCAATCAAAT
801     CTACGACTACATCGTTAAGAACAAGAAGGATGAACTGTACAAGAAGCTGG
851     AAACCGCGTTTACGTCAGAATTCAACAAGATCAACTTCATCGATATCTTC
901     AAAGACTTCCAGTTCGATGAAAACAACAGTAACGATAACAAAAAGATTAT
951     CACCAAGATTATCAAATCATCGACGAATAGCTCTGCCAGTTCCTCAAACT
1001    CGAGCACCACGACCACGACCGAACTGTCTAGTACGACCACGCGT
```

FIG. 17B

YP_004399807.1 Protein sequence (SEQ ID NO:14)

```
1       MSSKVQVINKFDDITSIKNTGAFKNNQAFISRSELKEIVSSNNTTISNTT
51      SSTAVMTSTSTTSIGTQTNNNNDLKNASERLKALAANNFTKNKKQAWDSL
101     QNASMTFYKKVQPTAVNVLGYEQITKDNVEKLDKELKTVFLVFKDNTKET
151     EKLEVELLPEINNGNKVIDNGNLYLDLLEKPENLKLANQKSIIEVLRPEI
201     TKIKVVLQNTKNNNSTNKEDIKNTEVFNLLIKQLSIYLANAVKYFNSESG
251     IITTNPTFSYKTRSNQIYDYIVKNKKDELYKKLETAFTSEFNKINFIDIF
301     KDFQFDENNSNDNKKIITKIIKSSTNSSASSSNSSTTTTTELSSTTTR
```

FIG. 18A

MSC_0816 Optimized DNA sequence (SEQ ID NO:15)

```
1       GCAAACAAAAACTCTGTCGAAAACAACATCTATATCAGTAAACAGATTCAACGCAAACCG
61      CATAAAATCGAAGGCGATAAACTGATTGAAATCGGTTATTACTGGGATTCTCACGACCGT
121     CAGGTGCGCATTATGCGTATCCCGCCGACCGTGAAAGTTATCGCGGCCCAGCTGCCGCCG
181     ATTATCACGAGTCTGAAAGGCGCATTTCAAGCTCGCATTAACGACGTTATCTGGCATGTC
241     CCGTGGGATACCAAAAACATCACGAACATGAACAGCATGTTCTACAACAATATTTGGTTC
301     AACAGCTCTAGTATCCTGGAATGGGATACCTCCAATGTTACGGACATGGGTGAAATGTTT
361     GGCCGTACCGGTAGCTTCAACCAGGATCTGTCCAAATGGGACGTCTCAAAAGTGAAAAAC
421     TTCAAGAAAATGTTCTACAACGCGAAAAAATACAACAACAACGATAAACCGCTGAAATGG
481     AACGACAAACTGAAATCTGCAGTCAATATGGAAGATATGTTTCAAGGCGCTAGTGACTTC
541     AAACATAGTCTGTCCGATTGGAAACTGGAAACCGAAATCAACAACAAAAACTTCGGTCTG
601     CTGGAAGATCGCCACCCGAAATGGAAAGAAAAACTGATTAAACCGTCCTCACCGATCTCG
661     AGCTCTAATTCCCTGAGTTCCAATAACATCAATGATCGCTCAGATGACAACCAGATTAAT
721     CGTAACTCATCGACCCCGACGAATAGCAACACCATCTCTACGAATCCGAGTAACGATCTG
781     AGCTCTAATACCACGAATAACGAAAACATTTCGGAAAGTTCCATGAGCAATAACATGCTG
841     GAAATTCCGATCAATAGCGAAAACAAACCGGAAAACCCGAAAAACAACGAAAACATCAAC
901     TACAAAATCCTGCCGAAAGTGGACAAAACCAAAAAACAGAGCGAAGCGAAAAACAAAATC
961     CCGGTTGAAAAAGGCGAACTGTCGAAAGATGAAAATCAAACCACGAAAACCAGCAACGCC
1021    ATCAAAGACAAAGAAAACTCATCGATCAAATCAGATTCGCTGTACAAAATTCCGCCGAAA
1081    CCGAACACCATTATCAGCAAACTGAGCTCTCCGAATGCGGGCATTATCACGGGTGCCGTG
1141    TTTCGT
```

FIG. 18B

MSC_0816 Protein sequence (SEQ ID NO:16)

```
1       ANKNSVENNIYISKQIQRKPHKIEGDKLIEIGYYWDSHDRQVRIMRIPPTVKVIAAQLPP
61      IITSLKGAFQARINDVIWHVPWDTKNITNMNSMFYNNIWFNSSSILEWDTSNVTDMGEMF
121     GRTGSFNQDLSKWDVSKVKNFKKMFYNAKKYNNNDKPLKWNDKLKSAVNMEDMFQGASDF
181     KHSLSDWKLETEINNKNFGLLEDRHPKWKEKLIKPSSPISSSNSLSSNNINDRSDDNQIN
241     RNSSTPTNSNTISTNPSNDLSSNTTNNENISESSMSNNMLEIPINSENKPENPKNNENIN
301     YKILPKVDKTKKQSEAKNKIPVEKGELSKDENQTTKTSNAIKDKENSSIKSDSLYKIPPK
361     PNTIISKLSSPNAGIITGAVFR
```

FIG. 19A

MSC_0160 Optimized DNA sequence (SEQ ID NO:17)

```
1     ATGGCGAAAGAACAGTTTGATCGTAGCCTGCCGCATGTGAACATTGGCACCATCGGTCAT
61    GTTGACCACGGCAAAACCACGCTGACCGCGGCCATTACGAAAGTTCTGTCTGAACAGGGT
121   AACGCAGAATTCAAAGATTACGCAAACATCGACAATGCTCCGGAAGAACGTGAACGCGGC
181   ATTACCATCAACACGGCGCATGTGGAATATAAAACCGCGAATCGCCATTACGCCCACGTC
241   GATTGCCCGGGTCACGCAGACTACGTGAAAAACATGATTACGGGTGCAGCTCAGATGGAT
301   GGCGCTATCCTGGTGGTTGCAGCAACCGACGGTCCGATGCCGCAGACGCGTGAACACATT
361   CTGCTGTCCCGCCAAGTGGGTGTTCCGAAAATCGTCGTGTTTCTGAACAAATGTGATATG
421   GTTGAAGATGACGAAATGATTGATCTGGTGGAAATGGAAATCCGTGACCTGCTGACCGAA
481   TATGATTTCGACGGCGAAGGTGCCCCGGTTATTCGTGGCAGCGCACTGGGTGCTCTGAAC
541   GGTGATTCTAAATGGACCGGCGCGATTAATGAACTGATGGCAGCTGTGGATGAATACATC
601   CCGACCCCGCAGCGTGATGCCGACAAAACGTTTCTGATGCCGGTGGAAGATGTTTTCACC
661   ATCACGGGTCGTGGTACCGTTGCAACGGGTCGTGTCGAACGCGGCACCGTCAAAGTGAAC
721   GAAGAAGTTGAAATTATCGGCCTGAAAGAAGAACCGACCAAAACGGTTGTCACGGGTCTG
781   GAAATGTTTCGTAAACTGCTGGATTTCGCGGTGGCCGGTGACAATGTTGGTGCACTGCTG
841   CGTGGTGTCGATCGTCATTCAGTGGAACGCGGTCAGGTTCTGGCCAAACCGGGCACCATT
901   AAACCGCACACGGTCCTGAAAGCGTCGGTGTATGCCCTGACCCAGGAAGAAGGCGGTCGT
961   CATAAACCGTTTTTCAACAAATATCGTCCGCAATTTTACTTCCGCACCACGGATGTCACC
1021  GGTGAAGTGACGCTGCCGGAAGGCACCGATATGGTTATGCCGGGTGACAATGTCGAAATG
1081  GAAATTCAACTGATCAAACCGGTTGCAGTCGAAGAAGGTACCAAATTTAGTATTCGTGAA
1141  GGCGGTCGTACCATCGGTGCTGGTACGGTGATTTCCATCGAAAAA
```

FIG. 19B

MSC_0160 Protein sequence (SEQ ID NO:18)

```
1     MAKEQFDRSLPHVNIGTIGHVDHGKTTLTAAITKVLSEQGNAEFKDYANIDNAPEERERG
61    ITINTAHVEYKTANRHYAHVDCPGHADYVKNMITGAAQMDGAILVVAATDGPMPQTREHI
121   LLSRQVGVPKIVVFLNKCDMVEDDEMIDLVEMEIRDLLTEYDFDGEGAPVIRGSALGALN
181   GDSKWTGAINELMAAVDEYIPTPQRDADKTFLMPVEDVFTITGRGTVATGRVERGTVKVN
241   EEVEIIGLKEEPTKTVVTGLEMFRKLLDFAVAGDNVGALLRGVDRHSVERGQVLAKPGTI
301   KPHTVLKASVYALTQEEGGRHKPFFNKYRPQFYFRTTDVTGEVTLPEGTDMVMPGDNVEM
361   EIQLIKPVAVEEGTKFSIREGGRTIGAGTVISIEK
```

FIG. 20A

MSC_0775 Optimized DNA sequence (SEQ ID NO:19)

```
1     TGTAAAAACCCGCTGTTCAATCAATCACTGAGCGAAAAAATCTACCTGAACTACAATCTG
61    CAAACGGAAAAAGACAAACAAGAATTTGAAAACTATAATCAGATTAACATGCTGAGCGAA
121   ATCAATCAATACTTCACCAAACATGATCACAACAAAGACCTGGTGAAATTTACCACGGAT
181   GGCGCGTCCGGTGACACCGTTGAATTCAACAACATCATGAAAAACAACTATGCCTCAAAA
241   TACATCAAATTCGATCAGGACAAATTCAAAGAAATCATCAAAAAAGAATTCAATCTGTCA
301   GATTCGTTCCTGAAACGTCTGGAATTCGAAGTCGACTACAACAACATCTCGCGCGATTAC
361   GGCAACAATTTTGACGTTATTTTCCCGATCCGTGTTAAACTGCCGCTGGTCAGCCATAAC
421   AATTTCAAATATCAGCAAGGCCTGTTTATTGAACAGACCTTTAAATTCCGCATCAAAAAC
481   GTCAAAGCGAGCGGTTCTGAAAAAATCGATGTGTCTAAAATCAAAGACATCTACAACGAA
541   CTGGTGAAACTGAAAGATAAAAACAACTTCACGGCCAGTGTGAAAACCGTTACGGAAGAA
601   ACCAAAAAACTGGTTGATGAATGGGGTATTCATGAACTGAACAGCACGCAACTGAGCTCT
661   ATCTTCGATATCAAAACCGAAGAATTCGATAACCTGATCAAAGACAAAAAAGAAGTGGAA
721   CACAAAGTTACCATCACGGATGTGGACCTGAGTGATCCGTCCCTGGCGATTAACGAAGGC
781   CTGCTGAAACTGCGTCTGGGCGTTAAAATCAAGGGTAAAGAAACCGAAACGGGTGTCAAC
841   GTGTGGATCAAATTCAACTTCGATCAGAAAGACACCTTTTGGAAAGAACTGAAAATCAGT
901   GAATCCATCAAAGTCAACACGGTGAAATTCAGTGAAACCAATACGGATTTTACCAAACTG
961   ATGAACGACAACCTGATCATCAAATCAAAATCGAAATTCATCAAAAACATCAAACTGAGT
1021  TCCATCGATAAAACCACGGACTATCGTAATTCCGGCGTCCTGCTGGAAGTGCTGACCAAC
1081  GAATCAAAAGATAACGTGATCAAACTGCATAAAAAACCGGGCGTTGGTAAATATACCGAT
1141  CTGTACTCCGCAGACTTCACGAAAAACAATATCCACGCGCCGAATTTTGCCACCGAAAAA
1201  CTGACGCAGGAAAACCTGAAATCTATCAACAAAGATTTCTTTCGCCAATTTGACTCAGAA
1261  CTGTTCTCGGGCGGTTATGCTCGTTCACGCGGCTTCTACTCGGAAAAAGTGAAAAGCCCG
1321  AAATTCATGCATATCGGTGAAGATTACATCGCAAACGACTTTCAGGCTGTTCTGATGCCG
1381  TATGATGGTGAAATTATCGCGGCCTACGAACTGAGCACCAATGTGCCGTTCGCAGGCGTT
1441  GGTACGGTTCTGGTCGCTAAAGTGCCGATCACCAGCCTGCCGTGGTCTCCGAAACAGAAA
1501  GAAATCGAACTGAACGATAACAAAACGCATATCTACATCAGCTTTCTGCACCTGGATGCC
1561  CAACGCACCCTGAACAATGACAAACTGGGCTGGGTGGCAGAAACCGCTAAACTGAAAAAA
1621  GATAAAACGGTTAAAGTGGTTAAAAGTGTCACCCCGTCCACGCCGAAAAAAGTCAGCAAA
1681  GGTACCGTGATCGGCTATCTGGGTGATCACTCATCGAACGGCGGTTGGATGTCTCATGCA
1741  CACATTAATCTGTACACGAACCGTCCGAATTATCTGAGTGAAAACTACTTTAGCTCTAAA
1801  ACCATTCGTGCGCAGCTGGATGACAAACGCGCCAAAGGCTATAAAAGTTCCGTGTCTAAC
1861  AATGATTTCAGTGCCATTGGCAATATCGGTGTTGAACGCAAAATTGATACGAAAATCTAT
1921  CAGGTCGACCCGAAAACCGGCATTGAAGATAAACAAAAAGCAATTTCGGACGAAATCCCG
1981  CTGTACTTCAACGGCCTGAGCATGCTGGGTTTTGAAAAAACCAAAGGTTATGCTAACCCG
2041  AATCTGATGTACAAACTGCGTGATGAACGCACCGTGAGCTTTTCTGTTAAAGAAGTCAAT
2101  AAACTG
```

FIG. 20B

MSC_0775 Protein sequence (SEQ ID NO:20)

```
1     CKNPLFNQSLSEKIYLNYNLQTEKDKQEFENYNQINMLSEINQYFTKHDHNKDLVKFTTD
61    GASGDTVEFNNIMKNNYASKYIKFDQDKFKEIIKKEFNLSDSFLKRLEFEVDYNNISRDY
121   GNNFDVIFPIRVKLPLVSHNNFKYQQGLFIEQTFKFRIKNVKASGSEKIDVSKIKDIYNE
181   LVKLKDKNNFTASVKTVTEETKKLVDEWGIHELNSTQLSSIFDIKTEEFDNLIKDKKEVE
241   HKVTITDVDLSDPSLAINEGLLKLRLGVKIKGKETETGVNVWIKFNFDQKDTFWKELKIS
301   ESIKVNTVKFSETNTDFTKLMNDNLIIKSKSKFIKNIKLSSIDKTTDYRNSGVLLEVLTN
361   ESKDNVIKLHKKPGVGKYTDLYSADFTKNNIHAPNFATEKLTQENLKSINKDFFRQFDSE
421   LFSGGYARSRGFYSEKVKSPKFMHIGEDYIANDFQAVLMPYDGEIIAAYELSTNVPFAGV
481   GTVLVAKVPITSLPWSPKQKEIELNDNKTHIYISFLHLDAQRTLNNDKLGWVAETAKLKK
541   DKTVKVVKSVTPSTPKKVSKGTVIGYLGDHSSNGGWMSHAHINLYTNRPNYLSENYFSSK
601   TIRAQLDDKRAKGYKSSVSNNDFSAIGNIGVERKIDTKIYQVDPKTGIEDKQKAISDEIP
661   LYFNGLSMLGFEKTKGYANPNLMYKLRDERTVSFSVKEVNKL
```

FIG. 21A

YP_004400127.1 optimized DNA sequence (SEQ ID NO:21)

```
1     ATGAAGACGGACAACACGAACCAAAAAATCAAGGAAAAGGACAACGAAAC
51    GGGTAGTAAAGACAAGGACAAACCGAATAATAACCTGAACAGCTCTGAAC
101   AGGATCTGCCGAAAGACCAACCGATTACCAAAAAGGAAAAAGATGAAAAG
151   ACGGACAGCTTTGCGGATAAACTGAAAAAGGATCTGAAAAAGATCCTGGA
201   CAAGAAGGAAGATCTGAAGATCCGTGAATACAGCACCAAACTGATCTCTA
251   AATACTTCCAGAAAAGTTCCGAAAAACAACTGCTGAAAGATTGGTTCGAC
301   CTGGAAAAGAAAATTAAAAAATGGTTCGACGAATCTGAACTGAACGAAAT
351   CAAAAAGGAAATCACCATCCTGTTTTCAGAATCGCTGGATAACAATAGTA
401   ACAATCAGGAATCCCGCAAACTGAAGGATCTGCTGGACAAAGTGACGAAG
451   GATAACAAAGAAGGCATTCTGGAAGAAGTTAAAAACCTGTTTGGTCAGAA
501   GATCTCAAAAGAACTGGAAGAAAAACTGAAGTCGGAAACCGATGGCATCA
551   ACAATCTGCTGTCAAAAAAGCAATACGAAACCATCAAGACGAAGCTGTTC
601   GATATCGTGGATAAAACGGCCGAACTGGAAAAGAACATCAAA
```

FIG 21B

YP_004400127.1 Protein sequence (SEQ ID NO:22)

```
1     MKTDNTNQKIKEKDNETGSKDKDKPNNNLNSSEQDLPKDQPITKKEKDEK
51    TDSFADKLKKDLKKILDKKEDLKIREYSTKLISKYFQKSSEKQLLKDWFD
101   LEKKIKKWFDESELNEIKKEITILFSESLDNNSNNQESRKLKDLLDKVTK
151   DNKEGILEEVKNLFGQKISKELEEKLKSETDGINNLLSKKQYETIKTKLF
201   DIVDKTAELEKNIK
```

YP_004399790.1 Optimized DNA sequence (SEQ ID NO:23)

```
1     ATGAAAAAACTGCTGGCGATTCTGGGCACGATGGCTATCTCCTCCACCGG
51    CGCTTCCCTGGTTATTGCTTGCGACAACCCGACGAAAAACGATAGCAAAA
101   AGCCGGAAACCAAACCGGAAACCCCGACGAATTCCGGCTCAAACGAAACG
151   TCCAATCAGGGCTCAAACGAAGGTTCGAATAAAGAAAAGGATAATTCGGA
201   ACCGAGCAAGCCGACCAAACCGGTGAAGCCGGCATCAGGCACCGCTTCTC
251   TGGTTAGCAAAACGGATATCTCAGCATGGAGCAGCATTTTTATGGACTCG
301   ATCACCGGTGAAGATATTCAAGACCATTCTGTGGAAGAAAAAGAAAAGGC
351   GGATAAAGCCAAGAACAAAGAATTCGTGGAAGTTCTGGACGAAATCAACA
401   AACTGACCCCGACGCTGGAAAATGAACTGAAACAGCTGGCACAAAAGTTC
451   AAGGAAATCAAGGAAAAACTGGCTAAGGAAAAGGAACTGAAGGATCAGAA
501   GAACAACAAGGAATTCGTCGAAGTGCTGGATGAAATTAACAAACTGAGTG
551   TGACCTTTGAAAAGGAACTGAAAGCCCTGTTCAAAAAGATTGGTGAAAAC
601   GAACTGGAAAAGGAACGTCTGTACAAGGAATTCACCACGAGTTCCTCAAA
651   TGCGACCAAATATTACTTCGAAGCCCTGGATACGAAAAAGGAAGTTAGCG
701   AATGGAATTTTGAACGTGGCCGCCTGGTCGAACTGATTTCGAGCATCGAC
751   CGCCAGGTGAAGGAACTGAAATCTAGTGGCAAGGATATCAAAAGCGTTAT
801   CGACACCGTCAAATCTAACCTGGAAAACTACAAGAACAGTATCAAGGAAC
851   ATAAGAACTCCAAGGTTTTCTGGAAGTACGAAATGTGGACCCACTGGCTG
901   GAAGATGTCCTGACGAATCTGAAAAACCAGAATCAA
```

B

YP_004399790.1 Protein sequence (SEQ ID NO:24)

```
1     MKKLLAILGTMAISSTGASLVIACDNPTKNDSKKPETKPETPTNSGSNET
51    SNQGSNEGSNKEKDNSEPSKPTKPVKPASGTASLVSKTDISAWSSIFMDS
101   ITGEDIQDHSVEEKEKADKAKNKEFVEVLDEINKLTPTLENELKQLAQKF
151   KEIKEKLAKEKELKDQKNNKEFVEVLDEINKLSVTFEKELKALFKKIGEN
201   ELEKERLYKEFTTSSSNATKYYFEALDTKKEVSEWNFERGRLVELISSID
251   RQVKELKSSGKDIKSVIDTVKSNLENYKNSIKEHKNSKVFWKYEMWTHWL
301   EDVLTNLKNQNQ
```

FIG. 23A

YP_004400580.1 optimized DNA sequence (SEQ ID NO:25)

```
1      ATGAAGAAGCTGCTGATTGGTTTTAGTAGTATTTTTGCGTTCCTGACCGT
51     CTCGTGTTCCATTAGTACCCCGAAGATTAACCCGACGATCAACAAGAACG
101    AAAACAAGCTGTACAAGAATAAATACGTGAGCGAACTGCTGAACCTGTAT
151    CTGTCAGACTCGAAACTGCGTGATAGTTACATCAATGACCAGGAAAACGT
201    TAGCGATTCTAAATTTTCCGAACTGAAGTATGGCCTGACCTTTTACCCGA
251    TTTTCATCCATCGTTCACTGGATTATCATATTGGTCAGCACTACCGCGTT
301    ATTATCCAAAAGTCGAAAAATGCTCTGGAACAGACGCTGAAAAACGATTG
351    GTATTGGGTCCTGGACAACATCACCAACTTCAAGTACAACTTCAACCCGT
401    ATGGCGATCTGTACAACGATTTCGACAAGGATGAAAACCTGTTTAACCAG
451    CTGGAAAAAGACCTGGGTTCTCTGATTAGCTCTGTCAAGAACAAGAACGT
501    GCAAAAGATCATCAAGATCAACCTGGATGAAGTGGTTAACGAAAAGATCA
551    AAGATGACTATCTGAAAAAGGAAGCCCTGTACCTGATCTTCGATAACAAC
601    AAGGCAATCAAGATCTGGAAGTACGAAAACCAGAATAAAACCGAATTCCT
651    GATGACCACGGACCTGTTTATCTTCAAAGACACGAACAACCTGGAAAACC
701    AAATCAAGGAACTGGAAAACACCATCTTCGAAAAGCGTAAGGTCGAATAC
751    AACAACAACCTGGAAAACATCAACAAGAACATCGAAGCTACCAAAAAGCG
801    CAAGGAAAAAGCGCAGCAAGAAATCCAGGATCTGAAGGAAAAGATCAAAA
851    AGCTGGAAAAGACGAACACCACGACCACGACCCCGCTGGCACTGACCAGT
901    TCCGCCATTCTGCTGAGCGCACCGAAAAACGATAAAAAGAAAGAACCGAC
951    GCTGGAAGAACTGAAGAAAGATCTGGAAAAGAAAGAAAAACAGAGCCAGC
1001   AATTCGACGAAAACGTTAAGAAATACGAAAAGAACATCGAAGATCTGCCG
1051   CAGAAGTCTAACGACAAGAAGTTCCTGGAATTCCACGCAACCGATCAATA
1101   CAACGAACGCCTGAAAGAAAGTCTGAATGAAATCAACAAAGACGGC
```

FIG. 23B

YP_004400580.1 Protein sequence (SEQ ID NO:26)

```
1      MKKLLIGFSSIFAFLTVSCSISTPKINPTINKNENKLYKNKYVSELLNLY
51     LSDSKLRDSYINDQENVSDSKFSELKYGLTFYPIFIHRSLDYHIGQHYRV
101    IIQKSKNALEQTLKNDWYWVLDNITNFKYNFNPYGDLYNDFDKDENLFNQ
151    LEKDLGSLISSVKNKNVQKIIKINLDEVVNEKIKDDYLKKEALYLIFDNN
201    KAIKIWKYENQNKTEFLMTTDLFIFKDTNNLENQIKELENTIFEKRKVEY
251    NNNLENINKNIEATKKRKEKAQQEIQDLKEKIKKLEKTNTTTTPLALTS
301    SAILLSAPKNDKKKEPTLEELKKDLEKKEKQSQQFDENVKKYEKNIEDLP
351    QKSNDKKFLEFHATDQYNERLKESLNEINKDG
```

FIG. 24A

YP_004400610.1 Optimized DNA sequence (SEQ ID NO:27)

```
1     ATGGGTGACCGTGCCCCGAGTGCGAAATCTGCGGAAAAGGTGGAAAACAA
51    GGAAAAAACGAAGCCGAGCGAAGCGCCGAAGAAAGGTGAAAAGAGTGAAG
101   AAAAGGAAAACGAAAAGGATAAGGAACTGAAGGCAGTGTTTTCAAAAGTT
151   GAGGGTCAGAACATTGGCAACTTCCAACCGAACAACAAGAACATCGTTAG
201   CCAGGGTGATATCAAAAAGGAACTGGCGAATAAACTGGGTGTCAGCGAAT
251   CTGACCTGCAAGGCCTGAAGCTGAACTATGATGACAAATCCGGTGAAGTC
301   ACCCTGCCGAAGTTCAACAACAAGAACCTGAAGTTCAAGTTCACCACGTT
351   CTACCAGCTGGGCAAAATTAAGACGTCAAAAATCGATAACGTGCTGTTTC
401   TGTCGCAACTGGACATTAAAAAGGAACTGGCCAACAAACTGAAGGTTAAA
451   GAAAGCGATCTGCAAGAACTGAAAACCGACTCTACGAACGGCATCGGTGC
501   CGGCAGTGTCCGTTCCAAAACCTTCGTGGGCATTCTGGAATTTAAATTCG
551   AAATCGATGAAAATAAA
```

FIG. 24B

YP_004400610.1 Protein sequence (SEQ ID NO:28)

```
1     MGDRAPSAKSAEKVENKEKTKPSEAPKKGEKSEEKENEKDKELKAVFSKV
51    EGQNIGNFQPNNKNIVSQGDIKKELANKLGVSESDLQGLKLNYDDKSGEV
101   TLPKFNNKNLKFKFTTFYQLGKIKTSKIDNVLFLSQLDIKKELANKLKVK
151   ESDLQELKTDSTNGIGAGSVRSKTFVGILEFKFEIDENK
```

FIG. 25A

YP_004400127.1-YP_004399790.1 fusion DNA (SEQ ID NO:50)

```
1     CATATGAAAACGGACAATACCAACCAAAAAATCAAAGAAAAAGACAACGA
51    AACGGGCAGTAAAGACAAAGACAAACCGAACAATAACCTGAATAGCTCTG
101   AACAGGATCTGCCGAAAGACCAACCGATCACCAAGAAAGAAAAAGATGAA
151   AAAACGGACAGCTTTGCAGATAAACTGAAGAAAGATCTGAAGAAAATTCT
201   GGACAAGAAAGAAGATCTGAAAATCCGTGAATACAGTACCAAACTGATCT
251   CCAAATACTTCCAGAAAAGTTCCGAAAAACAACTGCTGAAAGATTGGTTC
301   GACCTGGAAAAGAAAATTAAAAAATGGTTCGACGAAAGCGAACTGAACGA
351   AATTAAGAAAGAAATCACCATCCTGTTTTCCGAATCACTGGATAACAATT
401   CAAACAATCAGGAATCGCGCAAACTGAAAGATCTGCTGGACAAAGTTACC
451   AAAGATAACAAAGAAGGCATCCTGGAAGAAGTCAAAAACCTGTTTGGTCA
501   GAAAATCTCAAAAGAACTGGAAGAAAAACTGAAATCGGAAACCGATGGCA
551   TCAACAATCTGCTGAGCAAAAAACAATACGAAACCATCAAAACGAAACTG
601   TTCGATATTGTGGACAAAACGGCCGAACTGGAGAAAAACATCAAAGGCGG
651   TGGCGGTGGCGGTATGAAAAAACTGCTGGCAATCCTGGGCACCATGGCTA
701   TTTCATCGACGGGTGCGAGTCTGGTTATTGCCTGCGACAATCCGACCAAA
751   AACGATTCCAAAAAACCGGAAACGAAACCGGAAACCCCGACGAATTCGGG
801   TAGCAACGAAACCTCGAATCAGGGCAGCAACGAAGGTTCTAACAAAGAAA
851   AAGATAACTCTGAACCGAGTAAACCGACGAAACCGGTGAAACCGGCAAGC
901   GGCACCGCTTCCCTGGTTTCAAAAACGGACATTAGCGCGTGGAGCTCTAT
951   TTTTATGGATTCTATCACCGGTGAAGATATTCAAGACCATTCTGTGGAAG
1001  AAAAAGAAAAAGCGGACAAAGCCAAAAATAAAGAATTCGTGGAAGTTCTG
1051  GATGAAATCAACAAACTGACCCCGACGCTGGAAAATGAACTGAAACAGCT
1101  GGCACAAAAATTCAAAGAAATCAAAGAAAAACTGGCTAAAGAAAAAGAAC
1151  TGAAAGACCAGAAAAACAACAAAGAATTCGTCGAAGTGCTGGACGAAATT
1201  AACAAACTGAGTGTCACCTTTGAAAAAGAACTGAAAGCCCTGTTCAAGAA
1251  AATTGGCGAAAACGAACTGGAAAAAGAACGTCTGTACAAAGAATTCACCA
1301  CGAGTTCCTCAAATGCGACCAAATATTACTTCGAAGCCCTGGATACCAAG
1351  AAAGAAGTGAGCGAATGGAACTTTGAACGTGGCCGCCTGGTCGAACTGAT
1401  TTCGAGCATCGATCGCCAGGTGAAAGAACTGAAATCTAGTGGTAAAGACA
1451  TCAAAAGCGTTATCGATACCGTCAAATCTAACCTGGAAAATTACAAAAAC
1501  AGTATCAAAGAACACAAAAATTCCAAAGTTTTCTGGAAATACGAAATGTG
1551  GACGCACTGGCTGGAAGATGTTCTGACCAACCTGAAAAATCAAAATCAAT
1601  AAGGATCC
```

FIG. 25B

YP_004400127.1-YP_004399790.1 fusion protein (SEQ ID NO:51)

```
1     MKTDNTNQKIKEKDNETGSKDKDKPNNNLNSSEQDLPKDQPITKKEKDEK
51    TDSFADKLKKDLKKILDKKEDLKIREYSTKLISKYFQKSSEKQLLKDWFD
101   LEKKIKKWFDESELNEIKKEITILFSESLDNNSNNQESRKLKDLLDKVTK
151   DNKEGILEEVKNLFGQKISKELEEKLKSETDGINNLLSKKQYETIKTKLF
201   DIVDKTAELEKNIKGGGGGGMKKLLAILGTMAISSTGASLVIACDNPTKN
251   DSKKPETKPETPTNSGSNETSNQGSNEGSNKEKDNSEPSKPTKPVKPASG
301   TASLVSKTDISAWSSIFMDSITGEDIQDHSVEEKEKADKAKNKEFVEVLD
351   EINKLTPTLENELKQLAQKFKEIKEKLAKEKELKDQKNNKEFVEVLDEIN
401   KLSVTFEKELKALFKKIGENELEKERLYKEFTTSSSNATKYYFEALDTKK
451   EVSEWNFERGRLVELISSIDRQVKELKSSGKDIKSVIDTVKSNLENYKNS
501   IKEHKNSKVFWKYEMWTHWLEDVLTNLKNQNQ
```

FIG. 26A

YP_004400610.1-YP_004400580.1 fusion DNA (SEQ ID NO:52)

```
1     CATATGGGCGACCGTGCCCCGTCCGCAAAATCCGCAGAAAAAGTGGAAAA
51    TAAAGAAAAAACCAAACCGAGTGAAGCCCCGAAGAAGGGCGAAAAGAGTG
101   AAGAAAAGGAAAACGAAAAGGATAAAGAACTGAAAGCCGTCTTTTCCAAA
151   GTGGAAGGCCAGAATATTGGTAACTTCCAACCGAACAACAAAAACATCGT
201   CTCCCAGGGCGATATTAAGAAAGAACTGGCAAACAAACTGGGCGTGTCAG
251   AATCGGACCTGCAAGGTCTGAAACTGAATTATGATGACAAAAGCGGCGAA
301   GTGACGCTGCCGAAATTCAACAACAAAAACCTGAAATTCAAATTCACCAC
351   GTTCTACCAGCTGGGTAAAATCAAAACCAGTAAAATCGATAACGTTCTGT
401   TTCTGTCCCAACTGGACATTAAGAAAGAACTGGCTAACAAACTGAAAGTC
451   AAAGAATCAGATCTGCAGGAACTGAAAACGGACTCGACCAACGGTATCGG
501   CGCGGGTAGCGTGCGTTCTAAAACCTTCGTTGGTATTCTGGAATTCAAAT
551   TCGAAATCGATGAAAACAAAGGCGGTGGCGGTGGCAGCATTTCTACGCCG
601   AAAATTAACCCGACCATCAACAAAAACGAAAACAAACTGTACAAAAACAA
651   ATACGTCTCAGAACTGCTGAACCTGTATCTGAGTGACTCCAAACTGCGCG
701   ATAGCTACATCAATGACCAGGAAAACGTTTCAGATTCGAAATTCTCTGAA
751   CTGAAATATGGCCTGACCTTTTACCCGATTTTCATCCATCGTTCACTGGA
801   TTATCATATTGGTCAGCACTACCGCGTGATTATCCAAAAATCGAAAAATG
851   CGCTGGAACAGACGCTGAAAAACGATTGGTATTGGGTTCTGGACAACATC
901   ACCAACTTCAAATACAACTTCAACCCGTATGGCGATCTGTACAACGATTT
951   CGACAAAGATGAAAACCTGTTTAACCAGCTGGAAAAAGACCTGGGTAGTC
1001  TGATCAGCTCTGTTAAAAACAAAAACGTCCAAAAAATCATCAAAATCAAC
1051  CTGGATGAAGTGGTTAACGAAAAAATCAAAGATGACTACCTGAAGAAAGA
1101  AGCGCTGTACCTGATCTTCGATAACAACAAAGCAATCAAAATCTGGAAAT
1151  ACGAAAACCAGAACAAAACCGAATTCCTGATGACCACGGACCTGTTTATC
1201  TTCAAAGACACGAACAATCTGGAAAATCAGATTAAAGAACTGGAAAACAC
1251  CATCTTCGAAAAACGTAAAGTGGAATACAACAACAACCTGGAAAACATCA
1301  ACAAAAACATCGAAGCTACCAAAAAACGCAAAGAAAAAGCGCAGCAAGAA
1351  ATCCAGGATCTGAAAGAAAAAATCAAAAAACTGGAAAAAACGAATACCAC
1401  CACCACCACCCCGCTGGCCCTGACCAGTTCCGCCATTCTGCTGTCTGCAC
1451  CGAAAAACGATAAAAAGAAAGAACCGACGCTGGAAGAACTGAAGAAAGAT
1501  CTGGAAAAGAAAGAAAAACAGAGCCAGCAATTTGACGAAAACGTTAAAAA
1551  ATACGAGAAAAACATCGAAGATCTGCCGCAGAAATCTAACGACAAAAAAT
1601  TCCTGGAATTCCACGCGACCGATCAATACAATGAACGTCTGA
```

FIG. 26B

YP_004400610.1-YP_004400580.1 fusion protein (SEQ ID NO:53)

```
1     MGDRAPSAKSAEKVENKEKTKPSEAPKKGEKSEEKENEKDKELKAVFSKV
51    EGQNIGNFQPNNKNIVSQGDIKKELANKLGVSESDLQGLKLNYDDKSGEV
101   TLPKFNNKNLKFKFTTFYQLGKIKTSKIDNVLFLSQLDIKKELANKLKVK
151   ESDLQELKTDSTNGIGAGSVRSKTFVGILEFKFEIDENKGGGGGSISTPK
201   INPTINKNENKLYKNKYVSELLNLYLSDSKLRDSYINDQENVSDSKFSEL
251   KYGLTFYPIFIHRSLDYHIGQHYRVIIQKSKNALEQTLKNDWYWVLDNIT
301   NFKYNFNPYGDLYNDFDKDENLFNQLEKDLGSLISSVKNKNVQKIIKINL
351   DEVVNEKIKDDYLKKEALYLIFDNNKAIKIWKYENQNKTEFLMTTDLFIF
401   KDTNNLENQIKELENTIFEKRKVEYNNNLENINKNIEATKKRKEKAQQEI
451   QDLKEKIKKLEKTNTTTTTPLALTSSAILLSAPKNDKKKEPTLEELKKDL
501   EKKEKQSQQFDENVKKYEKNIEDLPQKSNDKKFLEFHATDQYNERLKESL
551   NEINKDG
```

FIG. 27A pAA352-YP_004400127.1-YP_004399790.1 fusion DNA (SEQ ID NO:54)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA

FIG. 27A (continued)

2501 TCGAAGAAATCATCGGTCAAAATGGCGAGCGGATCACCTCAAAGCAAGTT
2551 GATGATCTTATCGCAAAAGGTAACGGCAAAATTACCCAAGATGAGCTATC
2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCATGAAAACGGACAATACCAACC
2801 AAAAAATCAAAGAAAAAGACAACGAAACGGGCAGTAAAGACAAAGACAAA
2851 CCGAACAATAACCTGAATAGCTCTGAACAGGATCTGCCGAAAGACCAACC
2901 GATCACCAAGAAAGAAAAAGATGAAAAAACGGACAGCTTTGCAGATAAAC
2951 TGAAGAAAGATCTGAAGAAAATTCTGGACAAGAAAGAAGATCTGAAAATC
3001 CGTGAATACAGTACCAAACTGATCTCCAAATACTTCCAGAAAAGTTCCGA
3051 AAAACAACTGCTGAAAGATTGGTTCGACCTGGAAAAGAAAATTAAAAAAT
3101 GGTTCGACGAAAGCGAACTGAACGAAATTAAGAAAGAAATCACCATCCTG
3151 TTTTCCGAATCACTGGATAACAATTCAAACAATCAGGAATCGCGCAAACT
3201 GAAAGATCTGCTGGACAAAGTTACCAAAGATAACAAAGAAGGCATCCTGG
3251 AAGAAGTCAAAAACCTGTTTGGTCAGAAAATCTCAAAAGAACTGGAAGAA
3301 AAACTGAAATCGGAAACCGATGGCATCAACAATCTGCTGAGCAAAAAACA
3351 ATACGAAACCATCAAAACGAAACTGTTCGATATTGTGGACAAAACGGCCG
3401 AACTGGAGAAAAACATCAAAGGCGGTGGCGGTGGCGGTATGAAAAAACTG
3451 CTGGCAATCCTGGGCACCATGGCTATTTCATCGACGGGTGCGAGTCTGGT
3501 TATTGCCTGCGACAATCCGACCAAAAACGATTCCAAAAAACCGGAAACGA
3551 AACCGGAAACCCCGACGAATTCGGGTAGCAACGAAACCTCGAATCAGGGC
3601 AGCAACGAAGGTTCTAACAAAGAAAAAGATAACTCTGAACCGAGTAAACC
3651 GACGAAACCGGTGAAACCGGCAAGCGGCACCGCTTCCCTGGTTTCAAAAA
3701 CGGACATTAGCGCGTGGAGCTCTATTTTTATGGATTCTATCACCGGTGAA
3751 GATATTCAAGACCATTCTGTGGAAGAAAAAGAAAAAGCGGACAAAGCCAA
3801 AAATAAAGAATTCGTGGAAGTTCTGGATGAAATCAACAAACTGACCCCGA
3851 CGCTGGAAAATGAACTGAAACAGCTGGCACAAAAATTCAAAGAAATCAAA
3901 GAAAAACTGGCTAAAGAAAAAGAACTGAAAGACCAGAAAAACAACAAAGA
3951 ATTCGTCGAAGTGCTGGACGAAATTAACAAACTGAGTGTCACCTTTGAAA
4001 AAGAACTGAAAGCCCTGTTCAAGAAAATTGGCGAAAACGAACTGGAAAAA
4051 GAACGTCTGTACAAAGAATTCACCACGAGTTCCTCAAATGCGACCAAATA
4101 TTACTTCGAAGCCCTGGATACCAAGAAAGAAGTGAGCGAATGGAACTTTG
4151 AACGTGGCCGCCTGGTCGAACTGATTTCGAGCATCGATCGCCAGGTGAAA
4201 GAACTGAAATCTAGTGGTAAAGACATCAAAAGCGTTATCGATACCGTCAA
4251 ATCTAACCTGGAAAATTACAAAAACAGTATCAAAGAACACAAAAATTCCA
4301 AAGTTTTCTGGAAATACGAAATGTGGACGCACTGGCTGGAAGATGTTCTG
4351 ACCAACCTGAAAAATCAAAATCAATAA

FIG. 27B

LtkA-YP_004400127.1-YP_004399790.1 fusion protein (SEQ ID NO:55)

```
1     MATVIDLSFPKTGAKKIILYIPQNYQYDTEQGNGLQDLVKAAEELGIEVQ
51    REERNNIATAQTSLGTIQTAIGLTERGIVLSAPQIDKLLQKTKAGQALGS
101   AESIVQNANKAKTVLSGIQSILGSVLAGMDLDEALQNNSNQHALAKAGLE
151   LTNSLIENIANSVKTLDEFGEQISQFGSKLQNIKGLGTLGDKLKNIGGLD
201   KAGLGLDVISGLLSGATAALVLADKNASTAKKVGAGFELANQVVGNITKA
251   VSSYILAQRVAAGLSSTGPVAALIASTVSLAISPLAFAGIADKFNHAKSL
301   ESYAERFKKLGYDGDNLLAEYQRGTGTIDASVTAINTALAAIAGGVSAAA
351   AGSVIASPIALLVSGITGVISTILQYSKQAMFEHVANKIHNKIVEWEKNN
401   HGKNYFENGYDARYLANLQDNMKFLLNLNKELQAERVIAITQQQWDNNIG
451   DLAGISRLGEKVLSGKAYVDAFEEGKHIKADKLVQLDSANGIIDVSNSGK
501   AKTQHILFRTPLLTPGTEHRERVQTGKYEYITKLNINRVDSWKITDGAAS
551   STFDLTNVVQRIGIELDNAGNVTKTKETKIIAKLGEGDDNVFVGSGTTEI
601   DGGEGYDRVHYSRGNYGALTIDATKETEQGSYTVNRFVETGKALHEVTST
651   HTALVGNREEKIEYRHSNNQHHAGYYTKDTLKAVEEIIGTSHNDIFKGSK
701   FNDAFNGGDGVDTIDGNDGNDRLFGGKGDDILDGGNGDDFIDGGKGNDLL
751   HGGKGDDIFVHRKGDGNDIITDSDGNDKLSFSDSNLKDLTFEKVKHNLVI
801   TNSKKEKVTIQNWFREADFAKEVPNYKATKDEKIEEIIGQNGERITSKQV
851   DDLIAKGNGKITQDELSKVVDNYELLKHSKNVTNSLDKLISSVSAFTSSN
901   DSRNVLVAPTSMLDQSLSSLQFARGSMKTDNTNQKIKEKDNETGSKDKDK
951   PNNNLNSSEQDLPKDQPITKKEKDEKTDSFADKLKKDLKKILDKKEDLKI
1001  REYSTKLISKYFQKSSEKQLLKDWFDLEKKIKKWFDESELNEIKKEITIL
1051  FSESLDNNSNNQESRKLKDLLDKVTKDNKEGILEEVKNLFGQKISKELEE
1101  KLKSETDGINNLLSKKQYETIKTKLFDIVDKTAELEKNIKGGGGGGMKKL
1151  LAILGTMAISSTGASLVIACDNPTKNDSKKPETKPETPTNSGSNETSNQG
1201  SNEGSNKEKDNSEPSKPTKPVKPASGTASLVSKTDISAWSSIFMDSITGE
1251  DIQDHSVEEKEKADKAKNKEFVEVLDEINKLTPTLENELKQLAQKFKEIK
1301  EKLAKEKELKDQKNNKEFVEVLDEINKLSVTFEKELKALFKKIGENELEK
1351  ERLYKEFTTSSSNATKYYFEALDTKKEVSEWNFERGRLVELISSIDRQVK
1401  ELKSSGKDIKSVIDTVKSNLENYKNSIKEHKNSKVFWKYEMWTHWLEDVL
1451  TNLKNQNQ
```

FIG. 28A pAA352-YP_004400610.1-YP_004400580.1 fusion DNA (SEQ ID NO:56)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
```

FIG. 28A (continued)

2551 GATGATCTTATCGCAAAAGGTAACGGCAAAATTACCCAAGATGAGCTATC
2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCATGGGCGACCGTGCCCCGTCCG
2801 CAAAATCCGCAGAAAAAGTGGAAAATAAAGAAAAAACCAAACCGAGTGAA
2851 GCCCCGAAGAAGGGCGAAAAGAGTGAAGAAAAGGAAAACGAAAAGGATAA
2901 AGAACTGAAAGCCGTCTTTTCCAAAGTGGAAGGCCAGAATATTGGTAACT
2951 TCCAACCGAACAACAAAAACATCGTCTCCCAGGGCGATATTAAGAAAGAA
3001 CTGGCAAACAAACTGGGCGTGTCAGAATCGGACCTGCAAGGTCTGAAACT
3051 GAATTATGATGACAAAAGCGGCGAAGTGACGCTGCCGAAATTCAACAACA
3101 AAAACCTGAAATTCAAATTCACCACGTTCTACCAGCTGGGTAAAATCAAA
3151 ACCAGTAAAATCGATAACGTTCTGTTTCTGTCCCAACTGGACATTAAGAA
3201 AGAACTGGCTAACAAACTGAAAGTCAAAGAATCAGATCTGCAGGAACTGA
3251 AAACGGACTCGACCAACGGTATCGGCGCGGGTAGCGTGCGTTCTAAAACC
3301 TTCGTTGGTATTCTGGAATTCAAATTCGAAATCGATGAAAACAAAGGCGG
3351 TGGCGGTGGCAGCATTTCTACGCCGAAAATTAACCCGACCATCAACAAAA
3401 ACGAAAACAAACTGTACAAAAACAAATACGTCTCAGAACTGCTGAACCTG
3451 TATCTGAGTGACTCCAAACTGCGCGATAGCTACATCAATGACCAGGAAAA
3501 CGTTTCAGATTCGAAATTCTCTGAACTGAAATATGGCCTGACCTTTTACC
3551 CGATTTTCATCCATCGTTCACTGGATTATCATATTGGTCAGCACTACCGC
3601 GTGATTATCCAAAAATCGAAAAATGCGCTGGAACAGACGCTGAAAAACGA
3651 TTGGTATTGGGTTCTGGACAACATCACCAACTTCAAATACAACTTCAACC
3701 CGTATGGCGATCTGTACAACGATTTCGACAAAGATGAAAACCTGTTTAAC
3751 CAGCTGGAAAAAGACCTGGGTAGTCTGATCAGCTCTGTTAAAAACAAAAA
3801 CGTCCAAAAAATCATCAAAATCAACCTGGATGAAGTGGTTAACGAAAAAA
3851 TCAAAGATGACTACCTGAAGAAAGAAGCGCTGTACCTGATCTTCGATAAC
3901 AACAAAGCAATCAAAATCTGGAAATACGAAAACCAGAACAAAACCGAATT
3951 CCTGATGACCACGGACCTGTTTATCTTCAAAGACACGAACAATCTGGAAA
4001 ATCAGATTAAAGAACTGGAAAACACCATCTTCGAAAAACGTAAAGTGGAA
4051 TACAACAACAACCTGGAAAACATCAACAAAAACATCGAAGCTACCAAAAA
4101 ACGCAAAGAAAAAGCGCAGCAAGAAATCCAGGATCTGAAAGAAAAAATCA
4151 AAAAACTGGAAAAAAACGAATACCACCACCACCACCCCGCTGGCCCTGACC
4201 AGTTCCGCCATTCTGCTGTCTGCACCGAAAAACGATAAAAAGAAAGAACC
4251 GACGCTGGAAGAACTGAAGAAAGATCTGGAAAAGAAAGAAAAACAGAGCC
4301 AGCAATTTGACGAAAACGTTAAAAAATACGAGAAAAACATCGAAGATCTG
4351 CCGCAGAAATCTAACGACAAAAAATTCCTGGAATTCCACGCGACCGATCA
4401 ATACAATGAACGTCTGA

FIG. 28B

LtkA-YP_004400610.1-YP_004400580.1 fusion protein (SEQ ID NO:57)

```
1     MATVIDLSFPKTGAKKIILYIPQNYQYDTEQGNGLQDLVKAAEELGIEVQ
51    REERNNIATAQTSLGTIQTAIGLTERGIVLSAPQIDKLLQKTKAGQALGS
101   AESIVQNANKAKTVLSGIQSILGSVLAGMDLDEALQNNSNQHALAKAGLE
151   LTNSLIENIANSVKTLDEFGEQISQFGSKLQNIKGLGTLGDKLKNIGGLD
201   KAGLGLDVISGLLSGATAALVLADKNASTAKKVGAGFELANQVVGNITKA
251   VSSYILAQRVAAGLSSTGPVAALIASTVSLAISPLAFAGIADKFNHAKSL
301   ESYAERFKKLGYDGDNLLAEYQRGTGTIDASVTAINTALAAIAGGVSAAA
351   AGSVIASPIALLVSGITGVISTILQYSKQAMFEHVANKIHNKIVEWEKNN
401   HGKNYFENGYDARYLANLQDNMKFLLNLNKELQAERVIAITQQQWDNNIG
451   DLAGISRLGEKVLSGKAYVDAFEEGKHIKADKLVQLDSANGIIDVSNSGK
501   AKTQHILFRTPLLTPGTEHRERVQTGKYEYITKLNINRVDSWKITDGAAS
551   STFDLTNVVQRIGIELDNAGNVTKTKETKIIAKLGEGDDNVFVGSGTTEI
601   DGGEGYDRVHYSRGNYGALTIDATKETEQGSYTVNRFVETGKALHEVTST
651   HTALVGNREEKIEYRHSNNQHHAGYYTKDTLKAVEEIIGTSHNDIFKGSK
701   FNDAFNGGDGVDTIDGNDGNDRLFGGKGDDILDGGNGDDFIDGGKGNDLL
751   HGGKGDDIFVHRKGDGNDIITDSDGNDKLSFSDSNLKDLTFEKVKHNLVI
801   TNSKKEKVTIQNWFREADFAKEVPNYKATKDEKIEEIIGQNGERITSKQV
851   DDLIAKGNGKITQDELSKVVDNYELLKHSKNVTNSLDKLISSVSAFTSSN
901   DSRNVLVAPTSMLDQSLSSLQFARGSMGDRAPSAKSAEKVENKEKTKPSE
951   APKKGEKSEEKENEKDKELKAVFSKVEGQNIGNFQPNNKNIVSQGDIKKE
1001  LANKLGVSESDLQGLKLNYDDKSGEVTLPKFNNKNLKFKFTTFYQLGKIK
1051  TSKIDNVLFLSQLDIKKELANKLKVKESDLQELKTDSTNGIGAGSVRSKT
1101  FVGILEFKFEIDENKGGGGGSISTPKINPTINKNENKLYKNKYVSELLNL
1151  YLSDSKLRDSYINDQENVSDSKFSELKYGLTFYPIFIHRSLDYHIGQHYR
1201  VIIQKSKNALEQTLKNDWYWVLDNITNFKYNFNPYGDLYNDFDKDENLFN
1251  QLEKDLGSLISSVKNKNVQKIIKINLDEVVNEKIKDDYLKKEALYLIFDN
1301  NKAIKIWKYENQNKTEFLMTTDLFIFKDTNNLENQIKELENTIFEKRKVE
1351  YNNNLENINKNIEATKKRKEKAQQEIQDLKEKIKKLEKTNTTTTTPLALT
1401  SSAILLSAPKNDKKKEPTLEELKKDLEKKEKQSQQFDENVKKYEKNIEDL
1451  PQKSNDKKFLEFHATDQYNERLKESLNEINKDG
```

FIG. 29A pAA352-MSC_0160 fusion DNA (SEQ ID NO:58)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
```

FIG. 29A (continued)

```
2551  GATGATCTTATCGCAAAAGGTAACGGCAAAATTACCCAAGATGAGCTATC
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCGCGAAAGAACAGTTTGATCGTA
2801  GCCTGCCGCATGTGAACATTGGCACCATCGGTCATGTTGACCACGGCAAA
2851  ACCACGCTGACCGCGGCCATTACGAAAGTTCTGTCTGAACAGGGTAACGC
2901  AGAATTCAAAGATTACGCAAACATCGACAATGCTCCGGAAGAACGTGAAC
2951  GCGGCATTACCATCAACACGGCGCATGTGGAATATAAAACCGCGAATCGC
3001  CATTACGCCCACGTCGATTGCCCGGGTCACGCAGACTACGTGAAAAACAT
3051  GATTACGGGTGCAGCTCAGATGGATGGCGCTATCCTGGTGGTTGCAGCAA
3101  CCGACGGTCCGATGCCGCAGACGCGTGAACACATTCTGCTGTCCCGCCAA
3151  GTGGGTGTTCCGAAAATCGTCGTGTTTCTGAACAAATGTGATATGGTTGA
3201  AGATGACGAAATGATTGATCTGGTGGAAATGGAAATCCGTGACCTGCTGA
3251  CCGAATATGATTTCGACGGCGAAGGTGCCCCGGTTATTCGTGGCAGCGCA
3301  CTGGGTGCTCTGAACGGTGATTCTAAATGGACCGGCGCGATTAATGAACT
3351  GATGGCAGCTGTGGATGAATACATCCCGACCCCGCAGCGTGATGCCGACA
3401  AAACGTTTCTGATGCCGGTGGAAGATGTTTTCACCATCACGGGTCGTGGT
3405  ACCGTTGCAACGGGTCGTGTCGAACGCGGCACCGTCAAAGTGAACGAAGA
3501  AGTTGAAATTATCGGCCTGAAAGAAGAACCGACCAAAACGGTTGTCACGG
3551  GTCTGGAAATGTTTCGTAAACTGCTGGATTTCGCGGTGGCCGGTGACAAT
3601  GTTGGTGCACTGCTGCGTGGTGTCGATCGTCATTCAGTGGAACGCGGTCA
3651  GGTTCTGGCCAAACCGGGCACCATTAAACCGCACACGGTCCTGAAAGCGT
3701  CGGTGTATGCCCTGACCCAGGAAGAAGGCGGTCGTCATAAACCGTTTTTC
3751  AACAAATATCGTCCGCAATTTTACTTCCGCACCACGGATGTCACCGGTGA
3801  AGTGACGCTGCCGGAAGGCACCGATATGGTTATGCCGGGTGACAATGTCG
3851  AAATGGAAATTCAACTGATCAAACCGGTTGCAGTCGAAGAAGGTACCAAA
3901  TTTAGTATTCGTGAAGGCGGTCGTACCATCGGTGCTGGTACGGTGATTTC
3951  CATCGAAAAATAA
```

FIG. 29B

LtkA-MSC_0160 fusion protein (SEQ ID NO:59)

1 MATVIDLSFPKTGAKKIILYIPQNYQYDTEQGNGLQDLVKAAEELGIEVQ

51 REERNNIATAQTSLGTIQTAIGLTERGIVLSAPQIDKLLQKTKAGQALGS

101 AESIVQNANKAKTVLSGIQSILGSVLAGMDLDEALQNNSNQHALAKAGLE

151 LTNSLIENIANSVKTLDEFGEQISQFGSKLQNIKGLGTLGDKLKNIGGLD

201 KAGLGLDVISGLLSGATAALVLADKNASTAKKVGAGFELANQVVGNITKA

251 VSSYILAQRVAAGLSSTGPVAALIASTVSLAISPLAFAGIADKFNHAKSL

301 ESYAERFKKLGYDGDNLLAEYQRGTGTIDASVTAINTALAAIAGGVSAAA

351 AGSVIASPIALLVSGITGVISTILQYSKQAMFEHVANKIHNKIVEWEKNN

401 HGKNYFENGYDARYLANLQDNMKFLLNLNKELQAERVIAITQQQWDNNIG

451 DLAGISRLGEKVLSGKAYVDAFEEGKHIKADKLVQLDSANGIIDVSNSGK

501 AKTQHILFRTPLLTPGTEHRERVQTGKYEYITKLNINRVDSWKITDGAAS

551 STFDLTNVVQRIGIELDNAGNVTKTKETKIIAKLGEGDDNVFVGSGTTEI

601 DGGEGYDRVHYSRGNYGALTIDATKETEQGSYTVNRFVETGKALHEVTST

651 HTALVGNREEKIEYRHSNNQHHAGYYTKDTLKAVEEIIGTSHNDIFKGSK

701 FNDAFNGGDGVDTIDGNDGNDRLFGGKGDDILDGGNGDDFIDGGKGNDLL

751 HGGKGDDIFVHRKGDGNDIITDSDGNDKLSFSDSNLKDLTFEKVKHNLVI

801 TNSKKEKVTIQNWFREADFAKEVPNYKATKDEKIEEIIGQNGERITSKQV

851 DDLIAKGNGKITQDELSKVVDNYELLKHSKNVTNSLDKLISSVSAFTSSN

901 DSRNVLVAPTSMLDQSLSSLQFARGSAKEQFDRSLPHVNIGTIGHVDHGK

951 TTLTAAITKVLSEQGNAEFKDYANIDNAPEERERGITINTAHVEYKTANR

1001 HYAHVDCPGHADYVKNMITGAAQMDGAILVVAATDGPMPQTREHILLSRQ

1051 VGVPKIVVFLNKCDMVEDDEMIDLVEMEIRDLLTEYDFDGEGAPVIRGSA

1101 LGALNGDSKWTGAINELMAAVDEYIPTPQRDADKTFLMPVEDVFTITGRG

1151 TVATGRVERGTVKVNEEVEIIGLKEEPTKTVVTGLEMFRKLLDFAVAGDN

1201 VGALLRGVDRHSVERGQVLAKPGTIKPHTVLKASVYALTQEEGGRHKPFF

1251 NKYRPQFYFRTTDVTGEVTLPEGTDMVMPGDNVEMEIQLIKPVAVEEGTK

1301 FSIREGGRTIGAGTVISIEK

FIG. 30A pAA352-MSC_0136 fusion DNA (SEQ ID NO:60)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA
2501 TCGAAGAAATCATCGGTCAAAATGGCGAGCGGATCACCTCAAAGCAAGTT

FIG. 30A (continued)

```
2551  GATGATCTTATCGCAAAAGGTAACGGCAAAATTACCCAAGATGAGCTATC
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCAAAAACGAAAACCATTTCAACA
2801  TCAACTACAAAATGAAAATGGAAATGAAAACCCAGAAAACGGAACAACCG
2851  CACAAATATAAAGAAGGCGATCGTACCGAAATTGTGCAGATCGGCTTTTA
2901  CAAACGCGGTAACGAAATCACGATCAAACAAATCCCGTACTACGTTAAAA
2951  AAGTCCCGGATAAACTGCCGGACGAAATCCAGTCCCTGTATCGTGCATTT
3001  GCTCATCGCTACAAAGATCAAAACCACCCGACCGTCACGGGCTTCGAAAA
3051  ATGGGACACCAGCAAAATCAAAAACATGTCTTATGTGTTTTACGATAACC
3101  AGCTGATCGATGCGGACCTGTCAGAATGGAAAACCTCGAATGTTACGAAC
3151  ATGGACGGCATGTTCAAAAACGCCATCAAATTCAACAACAAAGAAAAACC
3201  GCTGAAATGGAACACCGAAAAAGTCGAAAGTATGGAATCCATGTTTGATG
3251  GCGCAGAATCTTTTAAACAGAACCTGAAAGATTGGAAAGTGGACAAAGTT
3301  ACCAAAAACAAAAACTTCTCACGTGCTTCGGGTATTTTCGAACATATCGA
3351  TAAAAAACCGTCATGGAAAATCACCGAACACAACGACCCGATTATCAAAA
3401  AACCGGAATCGACGGAACCGAAAGTGATTATCCATCCGAGCCCGTCTCGC
3451  CCGAAACAGACCATTCCGCTGACGAAACTGATCAATCCGATTATCAAAAG
3501  CACCCCGAACTCTAATCAAAACCTGGGCATCCCGAAAACGAACCTGAGCA
3551  CCACGCCGCAGCAAAGTAAAAAACTGTCCACCCCGGCAATTGTTGGCATC
3601  GTGGTTGGTAGTCAGGTCGTGCTGACGTCCCTGGCAGCAGGTATTCCGTA
3651  CCTGATCAAACGTTTCAAAAAATAA
```

FIG. 30B

LtkA-MSC_0136 fusion protein (SEQ ID NO:61)

1 MATVIDLSFPKTGAKKIILYIPQNYQYDTEQGNGLQDLVKAAEELGIEVQ

51 REERNNIATAQTSLGTIQTAIGLTERGIVLSAPQIDKLLQKTKAGQALGS

101 AESIVQNANKAKTVLSGIQSILGSVLAGMDLDEALQNNSNQHALAKAGLE

151 LTNSLIENIANSVKTLDEFGEQISQFGSKLQNIKGLGTLGDKLKNIGGLD

201 KAGLGLDVISGLLSGATAALVLADKNASTAKKVGAGFELANQVVGNITKA

251 VSSYILAQRVAAGLSSTGPVAALIASTVSLAISPLAFAGIADKFNHAKSL

301 ESYAERFKKLGYDGDNLLAEYQRGTGTIDASVTAINTALAAIAGGVSAAA

351 AGSVIASPIALLVSGITGVISTILQYSKQAMFEHVANKIHNKIVEWEKNN

401 HGKNYFENGYDARYLANLQDNMKFLLNLNKELQAERVIAITQQQWDNNIG

451 DLAGISRLGEKVLSGKAYVDAFEEGKHIKADKLVQLDSANGIIDVSNSGK

501 AKTQHILFRTPLLTPGTEHRERVQTGKYEYITKLNINRVDSWKITDGAAS

551 STFDLTNVVQRIGIELDNAGNVTKTKETKIIAKLGEGDDNVFVGSGTTEI

601 DGGEGYDRVHYSRGNYGALTIDATKETEQGSYTVNRFVETGKALHEVTST

651 HTALVGNREEKIEYRHSNNQHHAGYYTKDTLKAVEEIIGTSHNDIFKGSK

701 FNDAFNGGDGVDTIDGNDGNDRLFGGKGDDILDGGNGDDFIDGGKGNDLL

751 HGGKGDDIFVHRKGDGNDIITDSDGNDKLSFSDSNLKDLTFEKVKHNLVI

801 TNSKKEKVTIQNWFREADFAKEVPNYKATKDEKIEEIIGQNGERITSKQV

851 DDLIAKGNGKITQDELSKVVDNYELLKHSKNVTNSLDKLISSVSAFTSSN

901 DSRNVLVAPTSMLDQSLSSLQFARGSKNENHFNINYKMKMEMKTQKTEQP

951 HKYKEGDRTEIVQIGFYKRGNEITIKQIPYYVKKVPDKLPDEIQSLYRAF

1001 AHRYKDQNHPTVTGFEKWDTSKIKNMSYVFYDNQLIDADLSEWKTSNVTN

1051 MDGMFKNAIKFNNKEKPLKWNTEKVESMESMFDGAESFKQNLKDWKVDKV

1101 TKNKNFSRASGIFEHIDKKPSWKITEHNDPIIKKPESTEPKVIIHPSPSR

1151 PKQTIPLTKLINPIIKSTPNSNQNLGIPKTNLSTTPQQSKKLSTPAIVGI

1201 VVGSQVVLTSLAAGIPYLIKRFKK

FIG. 31A pAA352-MSC_0431 fusion DNA (SEQ ID NO:62)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA
2501 TCGAAGAAATCATCGGTCAAAATGGCGAGCGGATCACCTCAAAGCAAGTT

FIG. 31A (continued)

2551 GATGATCTTATCGCAAAAGGTAACGGCAAAATTACCCAAGATGAGCTATC
2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCTGCGCAAACATCGAAATGTCAA
2801 AAAACAAAAAAGATAAAGACAAAGATCTGAAATCGGACAAAAACAAAGAT
2851 CAGAACAACAAATTCGACAAAAGCAAAGATAAAAACCAAAACTCTAAACC
2901 GAACAACAACGATCAGAATAGTAAATCCAACCAAGACAAAACCTCACCGA
2951 AAGATAATCCGTCGACGCAGTCAGAATCGGAAAAACAGGAAAACTCCAAA
3001 CAATATGACCTGGATAAACTGATCACGAACAAATTCATCAGCATCGACGG
3051 CTCTGGTACCGGCGATGGTAAACTGGCTAAACTGCCGCAGAACCTGCAAG
3101 AATATCTGGATCTGATCAAAAAACAGAACCCGAAATTCACCCTGACGCTG
3151 AATAACGTCAGTTTCAATGTGGAAGAAAATGATAACTCCGGCTACAAAAA
3201 AGTCAGCGTGTCTACGAAGGGTAACTCTAAAAACCCGGTTATCGTCTACT
3251 TCTACAAAGACCGTCATGATACCGTTTATGAAGGCGAGAAAAAAGAAGTG
3301 GTTAAAGAAATCGGTTGGAGTAAATCCACCTACAGTACGGACATCCTGCA
3351 CTTCGATGAACAGACGAAAGAAGTCCCGGAAAACCTGCCGCCGTTTATCA
3401 CCAGCCTGGAAGGCGCGTTCCGCAACAACATCCAAGAAACCATCAAAAAC
3451 CTGGACAAATGGGATACGAGCAACATCGAATTCATGAACGAAACCTTCTA
3501 CGAAGCGAAAAATTTTAACCAGGATATCTCTGGTTGGAAAACCAATAACG
3551 TTAGTAACATGGATTCCATGTTTTATGGCGCCAGCTCTTTCGACCGTAAT
3601 CTGAGCGGTTGGAACGTGGATAAAGTTATTACCTACATCGAATTCAACAA
3651 AGATTCAAAAATCTCGGAACGTAACAAACCGAAATTCAAAGAACTGAAAC
3701 GCATTCATCAGGGCCAAGGTGCAACCAAAATCCTGCACAATCGCGGCTTT
3751 CTGAATAAAATGAACCTGTAA

FIG. 31B

LtkA-MSC_0431 fusion protein (SEQ ID NO:63)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSCANIEMSKNKKDKDKDLKSDKNKD
951 QNNKFDKSKDKNQNSKPNNNDQNSKSNQDKTSPKDNPSTQSESEKQENSK
1001 QYDLDKLITNKFISIDGSGTGDGKLAKLPQNLQEYLDLIKKQNPKFTLTL
1051 NNVSFNVEENDNSGYKKVSVSTKGNSKNPVIVYFYKDRHDTVYEGEKKEV
1101 VKEIGWSKSTYSTDILHFDEQTKEVPENLPPFITSLEGAFRNNIQETIKN
1151 LDKWDTSNIEFMNETFYEAKNFNQDISGWKTNNVSNMDSMFYGASSFDRN
1201 LSGWNVDKVITYIEFNKDSKISERNKPKFKELKRIHQGQGATKILHNRGF
1251 LNKMNL

FIG. 32A pAA352-MSC_0499 fusion DNA (SEQ ID NO:64)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
```

FIG. 32A (continued)

2551 GATGATCTTATCGCAAAAGGTAACGGCAAAATTACCCAAGATGAGCTATC
2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCTGCACCACGAAAAACGATAAAT
2801 TCAACAAACCGTTCATCACCGACGAACTGGCGCAGAAAATTATCTCAGGT
2851 CTGAAACTGTCGGATGACTTTAATTTCACCACGGGCGAACGTTTCAGTAA
2901 ACTGGATTACAAATCCCTGATTCTGGACATGATCAACGAAATCATCTCCA
2951 AAAACAAATACACCGATAACTGGAACAACCTGAGCAAAAAATTTGGTCTG
3001 GAAATTGAACAGGCGAAAGAATTCGGCAACAAAAAAGCCGAAAACGTTCT
3051 GAAAAACCTGAGCACCATCAAACTGTTCGCAGATTATACGTCTAAACGCG
3101 CTTTTGAAGAAGATTTCGACAGTGTGGATCTGAGTTATTCCGAAAATTAC
3151 CCGCTGAATCCGTATAACCTGGAAAGCAAAAACGGTCAGAAAGATAAAAC
3201 CGTTTACGCGATCTACTACAAAAACAACAACGGCGGTAGCTCTAGTGGTT
3251 CCTCATCGAATGGCGGTGGCACCAACGGTGAAGCAACGTGGCTGCGTTGG
3301 CAGACCACGGGTGAATTTGATAATATTGACAACCCGATCCCGTCAACCCC
3351 GCAACTGCCGAATATCTCGCTGCTGACCGATACGAGCTCTAAAAACTTCC
3401 GCATTGCCAAACTGTCCAAACCGAAAGATCAGGAATATATCACCAATACG
3451 GCAAGTGTTAAAGAAGACGGTAAAGCTACCAATAACGGCAATAACGAATT
3501 TGTCGAATGGTACAAAAACAGTTCCGACAAATTCGAAACCGATGGTCAGG
3551 GCATCATGCAATACCGTTTCATGTACCATTTCAAAACGAAAATCGAAGCG
3601 AAACTGTTTAATGATCTGCTGGGTCACGCCTATATTGACAGCAACCTGTT
3651 CGTGGATAAAAACGACAACAAATCAGCATCGAACAAGAAAATTATCCTGA
3701 ACAACGTCAGTAAACTGATTTCCGATATCCAGAGCAATTATTCTCAAGTG
3751 GACAAAACCATTAGTAACGTGAAAATGGTTTGGGCATTTAGCCTGGATAA
3801 ACAGAAAGTCTCTGAAGTGAACGGTGCTATCAATCAATATGTCAACCCGG
3851 ATGGCAGCCTGACCAATGAAGACAACAAGAAAACCCTGAAAAACGTGTTC
3901 GATAAAATCAAATACAAAGCGACCAACGAATCAAAACAGGGTACGGATTC
3951 GCTGCTGAGCATTTCTGGTTTCAACGGCTTCGTTAAAAACAAAGATAACA
4001 ACATCGAAAGTCTGTCCGGCGACCTGAAACTGACCGAAGAAGCGAAAAAA
4051 GCGGTCGCCCGCGTGAATGTTCCGTCTCTGCTGACGAATAACAATAACGG
4101 CTTTGCCAGTGAAAACTCCAATAACGTGGATTATGTCTTTGTGCTGCCGA
4151 TTTACCTGAATGACCTGTTTAGCTCGAACGACATGCAGATCAAACGTGAA
4201 ACCGAAAGCTCTGGTGGCGCCGGTTCAAATGGCTCGAACTATGAACTGAA
4251 TGTTCTGGAAAACACCTGGGTCAACCTGAATGACAAATTTAGCCTGGATA
4301 ATCGCTACTTCGACAACCTGACGATCAAAAAAGTGGAATCTCAAAATAAC
4351 GGTGAAGCACTGGTGGCTAACAACAACGATAAATGGTACGTTAGCCTGAA
4401 AAACGGCAATGACAACAAAAAAGTTGAAGTCACCTACAGCGATGACAGCA
4451 AGAAAATTATCACGCTGAAAAAAGTTGATAAAAACAACATCAAAACCCTG
4501 GACTTCACGTACAAACTGTCACAGTCGGATTTCAACAAACAGCTGTTCAA
4551 ACAAAACCCGACCGCAAACATCACGTATGATATCAACCTGAAAAACTACG
4601 ATAACATCAAAGACAAACAGAACGATGCTTATATCTGGAAAAACGATCCG
4651 AAAAAATCTAACGATATCCAAGACCTGTCCGCGGCCAAAAAACAGGTGCT
4701 GCTGGATCAACTGGAAGCGATCACCGCCAAAAATCCGGACGTTCAGAACG
4751 CAGCTAAAACCGAACTGTATTCGGCATATCTGTACACGGATGGTATCTAC
4801 TACAAATCACTGTTCGACGAAATCAGCAAATACATCGAATCTGAAAAACC
4851 GACCCTGGATTAA

FIG. 32B

LtkA-MSC_0499 fusion protein (SEQ ID NO:65)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSCTTKNDKFNKPFITDELAQKIISG
951 LKLSDDFNFTTGERFSKLDYKSLILDMINEIISKNKYTDNWNNLSKKFGL
1001 EIEQAKEFGNKKAENVLKNLSTIKLFADYTSKRAFEEDFDSVDLSYSENY
1051 PLNPYNLESKNGQKDKTVYAIYYKNNNGGSSSGSSSNGGGTNGEATWLRW
1101 QTTGEFDNIDNPIPSTPQLPNISLLTDTSSKNFRIAKLSKPKDQEYITNT
1151 ASVKEDGKATNNGNNEFVEWYKNSSDKFETDGQGIMQYRFMYHFKTKIEA
1201 KLFNDLLGHAYIDSNLFVDKNDNKSASNKKIILNNVSKLISDIQSNYSQV
1251 DKTISNVKMVWAFSLDKQKVSEVNGAINQYVNPDGSLTNEDNKKTLKNVF
1301 DKIKYKATNESKQGTDSLLSISGFNGFVKNKDNNIESLSGDLKLTEEAKK
1351 AVARVNVPSLLTNNNNGFASENSNNVDYVFVLPIYLNDLFSSNDMQIKRE
1401 TESSGGAGSNGSNYELNVLENTWVNLNDKFSLDNRYFDNLTIKKVESQNN
1451 GEALVANNNDKWYVSLKNGNDNKKVEVTYSDDSKKIITLKKVDKNNIKTL
1501 DFTYKLSQSDFNKQLFKQNPTANITYDINLKNYDNIKDKQNDAYIWKNDP
1551 KKSNDIQDLSAAKKQVLLDQLEAITAKNPDVQNAAKTELYSAYLYTDGIY
1601 YKSLFDEISKYIESEKPTLD

FIG. 33A pAA352-MSC_0775 fusion DNA (SEQ ID NO:66)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
```

FIG. 33A (continued)

2551 GATGATCTTATCGCAAAAGGTAACGGCAAAATTACCCAAGATGAGCTATC
2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCCAAACGGAAAAAGACAAACAAG
2801 AATTTGAAAACTATAATCAGATTAACATGCTGAGCGAAATCAATCAATAC
2851 TTCACCAAACATGATCACAACAAAGACCTGGTGAAATTTACCACGGATGG
2901 CGCGTCCGGTGACACCGTTGAATTCAACAACATCATGAAAAACAACTATG
2951 CCTCAAAATACATCAAATTCGATCAGGACAAATTCAAAGAAATCATCAAA
3001 AAAGAATTCAATCTGTCAGATTCGTTCCTGAAACGTCTGGAATTCGAAGT
3051 CGACTACAACAACATCTCGCGCGATTACGGCAACAATTTTGACGTTATTT
3101 TCCCGATCCGTGTTAAACTGCCGCTGGTCAGCCATAACAATTTCAAATAT
3151 CAGCAAGGCCTGTTTATTGAACAGACCTTTAAATTCCGCATCAAAAACGT
3201 CAAAGCGAGCGGTTCTGAAAAAATCGATGTGTCTAAAATCAAAGACATCT
3251 ACAACGAACTGGTGAAACTGAAAGATAAAAACAACTTCACGGCCAGTGTG
3301 AAAACCGTTACGGAAGAAACCAAAAAACTGGTTGATGAATGGGGTATTCA
3351 TGAACTGAACAGCACGCAACTGAGCTCTATCTTCGATATCAAAACCGAAG
3401 AATTCGATAACCTGATCAAAGACAAAAAAGAAGTGGAACACAAAGTTACC
3451 ATCACGGATGTGGACCTGAGTGATCCGTCCCTGGCGATTAACGAAGGCCT
3501 GCTGAAACTGCGTCTGGGCGTTAAAATCAAGGGTAAAGAAACCGAAACGG
3551 GTGTCAACGTGTGGATCAAATTCAACTTCGATCAGAAAGACACCTTTTGG
3601 AAAGAACTGAAAATCAGTGAATCCATCAAAGTCAACACGGTGAAATTCAG
3651 TGAAACCAATACGGATTTTACCAAACTGATGAACGACAACCTGATCATCA
3701 AATCAAAATCGAAATTCATCAAAAACATCAAACTGAGTTCCATCGATAAA
3751 ACCACGGACTATCGTAATTCCGGCGTCCTGCTGGAAGTGCTGACCAACGA
3801 ATCAAAAGATAACGTGATCAAACTGCATAAAAAACCGGGCGTTGGTAAAT
3851 ATACCGATCTGTACTCCGCAGACTTCACGAAAAACAATATCCACGCGCCG
3901 AATTTTGCCACCGAAAAACTGACGCAGGAAAACCTGAAATCTATCAACAA
3951 AGATTTCTTTCGCCAATTTGACTCAGAACTGTTCTCGGGCGGTTATGCTC
4001 GTTCACGCGGCTTCTACTCGGAAAAAGTGAAAAGCCCGAAATTCATGCAT
4051 ATCGGTGAAGATTACATCGCAAACGACTTTCAGGCTGTTCTGATGCCGTA
4101 TGATGGTGAAATTATCGCGGCCTACGAACTGAGCACCAATGTGCCGTTCG
4151 CAGGCGTTGGTACGGTTCTGGTCGCTAAAGTGCCGATCACCAGCCTGCCG
4201 TGGTCTCCGAAACAGAAAGAAATCGAACTGAACGATAACAAAACGCATAT
4251 CTACATCAGCTTTCTGCACCTGGATGCCCAACGCACCCTGAACAATGACA
4301 AACTGGGCTGGGTGGCAGAAACCGCTAAACTGAAAAAAGATAAAACGGTT
4351 AAAGTGGTTAAAAGTGTCACCCCGTCCACGCCGAAAAAAGTCAGCAAAGG
4401 TACCGTGATCGGCTATCTGGGTGATCACTCATCGAACGGCGGTTGGATGT
4451 CTCATGCACACATTAATCTGTACACGAACCGTCCGAATTATCTGAGTGAA
4501 AACTACTTTAGCTCTAAAACCATTCGTGCGCAGCTGGATGACAAACGCGC
4551 CAAAGGCTATAAAAGTTCCGTGTCTAACAATGATTTCAGTGCCATTGGCA
4601 ATATCGGTGTTGAACGCAAAATTGATACGAAAATCTATCAGGTCGACCCG
4651 AAAACCGGCATTGAAGATAAACAAAAAGCAATTTCGGACGAAATCCCGCT
4701 GTACTTCAACGGCCTGAGCATGCTGGGTTTTGAAAAAACCAAAGGTTATG
4751 CTAACCCGAATCTGATGTACAAACTGCGTGATGAACGCACCGTGAGCTTT
4801 TCTGTTAAAGAAGTCAATAAACTGTAA

FIG. 33B

LtkA-MSC_0775 fusion protein (SEQ ID NO:67)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSQTEKDKQEFENYNQINMLSEINQY
951 FTKHDHNKDLVKFTTDGASGDTVEFNNIMKNNYASKYIKFDQDKFKEIIK
1001 KEFNLSDSFLKRLEFEVDYNNISRDYGNNFDVIFPIRVKLPLVSHNNFKY
1051 QQGLFIEQTFKFRIKNVKASGSEKIDVSKIKDIYNELVKLKDKNNFTASV
1101 KTVTEETKKLVDEWGIHELNSTQLSSIFDIKTEEFDNLIKDKKEVEHKVT
1151 ITDVDLSDPSLAINEGLLKLRLGVKIKGKETETGVNVWIKFNFDQKDTFW
1201 KELKISESIKVNTVKFSETNTDFTKLMNDNLIIKSKSKFIKNIKLSSIDK
1251 TTDYRNSGVLLEVLTNESKDNVIKLHKKPGVGKYTDLYSADFTKNNIHAP
1301 NFATEKLTQENLKSINKDFFRQFDSELFSGGYARSRGFYSEKVKSPKFMH
1351 IGEDYIANDFQAVLMPYDGEIIAAYELSTNVPFAGVGTVLVAKVPITSLP
1401 WSPKQKEIELNDNKTHIYISFLHLDAQRTLNNDKLGWVAETAKLKKDKTV
1451 KVVKSVTPSTPKKVSKGTVIGYLGDHSSNGGWMSHAHINLYTNRPNYLSE
1501 NYFSSKTIRAQLDDKRAKGYKSSVSNNDFSAIGNIGVERKIDTKIYQVDP
1551 KTGIEDKQKAISDEIPLYFNGLSMLGFEKTKGYANPNLMYKLRDERTVSF
1601 SVKEVNKL

FIG. 34A pAA352-MSC_0776 fusion DNA (SEQ ID NO:68)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
2551  GATGATCTTATCGCAAAAGGTAACGGCAAAATTACCCAAGATGAGCTATC
```

FIG. 34A (continued)

2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCTGTAAAACGACGCAAAATCAAC
2801 AGGGCATCTATAAAATTGTGGACTTCGAAAAAGAAAATCAAATCAACATT
2851 CTGAGCGAAATCAACCAGTTTTTCGAAAAACATGATTTCAACGAACAGCT
2901 GGTTCAATTCGTCAACAAAGATAGCCACAATTATATTACCCTGGACTCTC
2951 TGATGAAAAACAATTATGCGGCCAAATACGTGAAATTTGATAAAGACAAA
3001 TTCAAACAGATCATCAAAAAAGAATTCAACCTGAGTGATGCATACCTGAA
3051 TAAACTGGAAATCGAAGTTGACTATACCAACATTGATCGCGACTACTCCA
3101 ACAATTTTGATATTGTCTTCCCGATTCGTATCAAACGCCAGCTGGAAAAT
3151 CATAAAAAAGCGAGCTATCAACCGGGCCTGTTTACGGAACAGATTATCAA
3201 ATTCCGCCTGAAAAACGTGAAAAGCTCTCCGTCGGAAGCATTTTTCGCTG
3251 AAGAACTGAAAGATGTTTTCAACAAACTGAAAGAACTGAAATACGATAAC
3301 TTCACCGCGCGTCTGAAAACGAACATCAGTAACGAACTGAAAAAACAGAT
3351 CGATCAATGGAACATCAACGAACTGGACAGTACCCAACTGTCCAACATCT
3401 TCGAAATCAACATCTCCGAATTCGATCAGCTGAAAACCAACAATCCGAAT
3451 TTTGTGTTCAAAAGTACGATCTTTGGTGTTGATTTCTCCGACAAAAACCT
3501 GGCGCTGAATGAAGGCTATCTGAAAGTGCGTTTTGCCGTTAAAGAAGGTT
3551 TCGATAGTAAAGACAAAACCAAACAGATCAACCTGATCAACAAAGAAATC
3601 AACGAACTGATCGTGAAAAAAGAAAACCTGGAAAAAACCAACAACTCAGA
3651 TTCGAACAAAACGGAAATCGACAAACTGATCCAGATCATCAAACAAAAAA
3701 GCGCGCAGCTGACCAAAATTAAACAAAAAGCCCTGCCGGCGGAAGCCGGC
3751 ATCACGAAACTGATCAAATTCAAATTCGATTGGAACGACCAGTTTTGGAA
3801 AAACATCAAACTGAACGAAGTGATCAAAATCGATACCATCAAATATGGTA
3851 TCAGCAATACCGATTTCCTGTCTCTGACGAAAGACAACCTGATTGTTAAA
3901 ATCCTGAACAAAGATGTGCGTAACGTTGACATTAAGAAAATTGAAAAAAC
3951 CAACGATTTCCGCAACGCGAAACTGGTCCTGGATGTGCTGCTGAAAGACA
4001 ACAAAAAACTGGAACTGAACAAGAAAATTGGCGTGGGTAAATATAGCCTG
4051 CTGTACGAAAATGATTTCATCAAAAACAACATCCAGGCCCCGTATTTCAC
4101 CACGGAACGTCTGACCCAAGAAAACCTGCAGTCTGTTAATAAAGATTTCT
4151 TTCGCCAGTTTGACTCAGAACTGTTCTCGGGCGGTTATGCAAGTTCCCGT
4201 GGCTTTTACGCTCCGAAAATTACCACGCCGATCTTCATGCACATTGGTGA
4251 AGATTATATTGCGAATGACTTTCAGGCCGTGCTGATGCCGTATGATGGCG
4301 AAATTATCGCAGCTTACGAACTGAGCACCAACGTCCCGTTCGCAGGCGTG
4351 GGTACGGTGGTTGTCGTGAAAATTAAAGTTTCTGATCTGGACTGGACCCC
4401 GAAAGAAAAAGAAATCTATCTGAACAACAACAAAGATCATATCTACATGT
4451 CATTTCTGCACCTGGACGCATCGCGCACGCTGAATAACCAGAAACTGGGT
4501 TGGTCAGCTGAAAAAGTTGTCCTGAATAACAATCGTACCATTCAAGTGGT
4551 TAAATCGCTGACGCCGGAAAAACCGCAGAAAGTCGCCAAAAATACCATTA
4601 TCGGCTATCTGGGTAACAATGCAAGTAACGGCGGTTGGATGTCCCATGCT
4651 CACGTTAACCTGTACACCAATCGCCCGTCATATCTGTCGGAAAACTACTT
4701 TAGCACGAAATCTAATCAAGGCCTGAGCGAAGATCGTATCAAACAGTACC
4751 ATCAAAACATCAACGGTAAAGAAACCTGGCGTCAGTTTGGCAATATTGGT
4801 CTGCACCAGTCTCCGCAACGTCCGCCGTACACCATCAACGAAGTTGATCA
4851 AATTACGGGCGTCGAAAAACTGGACGAAAACAAAAAGAAAATTGTCGTGA
4901 AAAACGAACAGGCGCTGTTTCTGCCGAACCTGAGCATGTCTCTGTTCGAA
4951 AAACGCCTGGGTTATGCCAACCCGAATCTGGTCTACCGTCTGCGCGATAA
5001 TAAAACCGTGAGTTTTTCCGTTAAAGAAGTCAACAAACTGACGTAA

FIG. 34B

LtkA-MSC_0776 fusion protein (SEQ ID NO:69)

| | |
|---|---|
| 1 | **MATVIDLSFPKTGAKKIILYIPQNYQYDTEQGNGLQDLVKAAEELGIEVQ** |
| 51 | **REERNNIATAQTSLGTIQTAIGLTERGIVLSAPQIDKLLQKTKAGQALGS** |
| 101 | **AESIVQNANKAKTVLSGIQSILGSVLAGMDLDEALQNNSNQHALAKAGLE** |
| 151 | **LTNSLIENIANSVKTLDEFGEQISQFGSKLQNIKGLGTLGDKLKNIGGLD** |
| 201 | **KAGLGLDVISGLLSGATAALVLADKNASTAKKVGAGFELANQVVGNITKA** |
| 251 | **VSSYILAQRVAAGLSSTGPVAALIASTVSLAISPLAFAGIADKFNHAKSL** |
| 301 | **ESYAERFKKLGYDGDNLLAEYQRGTGTIDASVTAINTALAAIAGGVSAAA** |
| 351 | **AGSVIASPIALLVSGITGVISTILQYSKQAMFEHVANKIHNKIVEWEKNN** |
| 401 | **HGKNYFENGYDARYLANLQDNMKFLLNLNKELQAERVIAITQQQWDNNIG** |
| 451 | **DLAGISRLGEKVLSGKAYVDAFEEGKHIKADKLVQLDSANGIIDVSNSGK** |
| 501 | **AKTQHILFRTPLLTPGTEHRERVQTGKYEYITKLNINRVDSWKITDGAAS** |
| 551 | **STFDLTNVVQRIGIELDNAGNVTKTKETKIIAKLGEGDDNVFVGSGTTEI** |
| 601 | **DGGEGYDRVHYSRGNYGALTIDATKETEQGSYTVNRFVETGKALHEVTST** |
| 651 | **HTALVGNREEKIEYRHSNNQHHAGYYTKDTLKAVEEIIGTSHNDIFKGSK** |
| 701 | **FNDAFNGGDGVDTIDGNDGNDRLFGGKGDDILDGGNGDDFIDGGKGNDLL** |
| 751 | **HGGKGDDIFVHRKGDGNDIITDSDGNDKLSFSDSNLKDLTFEKVKHNLVI** |
| 801 | **TNSKKEKVTIQNWFREADFAKEVPNYKATKDEKIEEIIGQNGERITSKQV** |
| 851 | **DDLIAKGNGKITQDELSKVVDNYELLKHSKNVTNSLDKLISSVSAFTSSN** |
| 901 | **DSRNVLVAPTSMLDQSLSSLQFARGS**CKTTQNQQGIYKIVDFEKENQINI |
| 951 | LSEINQFFEKHDFNEQLVQFVNKDSHNYITLDSLMKNNYAAKYVKFDKDK |
| 1001 | FKQIIKKEFNLSDAYLNKLEIEVDYTNIDRDYSNNFDIVFPIRIKRQLEN |
| 1051 | HKKASYQPGLFTEQIIKFRLKNVKSSPSEAFFAEELKDVFNKLKELKYDN |
| 1101 | FTARLKTNISNELKKQIDQWNINELDSTQLSNIFEINISEFDQLKTNNPN |
| 1151 | FVFKSTIFGVDFSDKNLALNEGYLKVRFAVKEGFDSKDKTKQINLINKEI |
| 1201 | NELIVKKENLEKTNNSDSNKTEIDKLIQIIKQKSAQLTKIKQKALPAEAG |
| 1251 | ITKLIKFKFDWNDQFWKNIKLNEVIKIDTIKYGISNTDFLSLTKDNLIVK |
| 1301 | ILNKDVRNVDIKKIEKTNDFRNAKLVLDVLLKDNKKLELNKKIGVGKYSL |
| 1351 | LYENDFIKNNIQAPYFTTERLTQENLQSVNKDFFRQFDSELFSGGYASSR |
| 1401 | GFYAPKITTPIFMHIGEDYIANDFQAVLMPYDGEIIAAYELSTNVPFAGV |
| 1451 | GTVVVVKIKVSDLDWTPKEKEIYLNNNKDHIYMSFLHLDASRTLNNQKLG |
| 1501 | WSAEKVVLNNNRTIQVVKSLTPEKPQKVAKNTIIGYLGNNASNGGWMSHA |
| 1551 | HVNLYTNRPSYLSENYFSTKSNQGLSEDRIKQYHQNINGKETWRQFGNIG |
| 1601 | LHQSPQRPPYTINEVDQITGVEKLDENKKKIVVKNEQALFLPNLSMSLFE |
| 1651 | KRLGYANPNLVYRLRDNKTVSFSVKEVNKLT |

FIG. 35A pAA352-MSC_0816 fusion DNA (SEQ ID NO:70)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA
2501 TCGAAGAAATCATCGGTCAAAATGGCGAGCGGATCACCTCAAAGCAAGTT

FIG. 35A (continued)

```
2551  GATGATCTTATCGCAAAAGGTAACGGCAAAATTACCCAAGATGAGCTATC
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCGCAAACAAAAACTCTGTCGAAA
2801  ACAACATCTATATCAGTAAACAGATTCAACGCAAACCGCATAAAATCGAA
2851  GGCGATAAACTGATTGAAATCGGTTATTACTGGGATTCTCACGACCGTCA
2901  GGTGCGCATTATGCGTATCCCGCCGACCGTGAAAGTTATCGCGGCCCAGC
2951  TGCCGCCGATTATCACGAGTCTGAAAGGCGCATTTCAAGCTCGCATTAAC
3001  GACGTTATCTGGCATGTCCCGTGGGATACCAAAAACATCACGAACATGAA
3051  CAGCATGTTCTACAACAATATTTGGTTCAACAGCTCTAGTATCCTGGAAT
3101  GGGATACCTCCAATGTTACGGACATGGGTGAAATGTTTGGCCGTACCGGT
3151  AGCTTCAACCAGGATCTGTCCAAATGGGACGTCTCAAAAGTGAAAAACTT
3201  CAAGAAAATGTTCTACAACGCGAAAAAATACAACAACAACGATAAACCGC
3251  TGAAATGGAACGACAAACTGAAATCTGCAGTCAATATGGAAGATATGTTT
3301  CAAGGCGCTAGTGACTTCAAACATAGTCTGTCCGATTGGAAACTGGAAAC
3351  CGAAATCAACAACAAAAACTTCGGTCTGCTGGAAGATCGCCACCCGAAAT
3401  GGAAAGAAAAACTGATTAAACCGTCCTCACCGATCTCGAGCTCTAATTCC
3451  CTGAGTTCCAATAACATCAATGATCGCTCAGATGACAACCAGATTAATCG
3501  TAACTCATCGACCCCGACGAATAGCAACACCATCTCTACGAATCCGAGTA
3551  ACGATCTGAGCTCTAATACCACGAATAACGAAAACATTTCGGAAAGTTCC
3601  ATGAGCAATAACATGCTGGAAATTCCGATCAATAGCGAAAACAAACCGGA
3651  AAACCCGAAAAACAACGAAAACATCAACTACAAAATCCTGCCGAAAGTGG
3701  ACAAAACCAAAAAACAGAGCGAAGCGAAAAACAAAATCCCGGTTGAAAAA
3751  GGCGAACTGTCGAAAGATGAAAATCAAACCACGAAAACCAGCAACGCCAT
3801  CAAAGACAAAGAAAACTCATCGATCAAATCAGATTCGCTGTACAAAATTC
3851  CGCCGAAACCGAACACCATTATCAGCAAACTGAGCTCTCCGAATGCGGGC
3901  ATTATCACGGGTGCCGTGTTTCGTTAA
```

FIG. 35B

LtkA-MSC_0816 fusion protein (SEQ ID NO:71)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSANKNSVENNIYISKQIQRKPHKIE
951 GDKLIEIGYYWDSHDRQVRIMRIPPTVKVIAAQLPPIITSLKGAFQARIN
1001 DVIWHVPWDTKNITNMNSMFYNNIWFNSSSILEWDTSNVTDMGEMFGRTG
1051 SFNQDLSKWDVSKVKNFKKMFYNAKKYNNNDKPLKWNDKLKSAVNMEDMF
1101 QGASDFKHSLSDWKLETEINNKNFGLLEDRHPKWKEKLIKPSSPISSSNS
1151 LSSNNINDRSDDNQINRNSSTPTNSNTISTNPSNDLSSNTTNNENISESS
1201 MSNNMLEIPINSENKPENPKNNENINYKILPKVDKTKKQSEAKNKIPVEK
1251 GELSKDENQTTKTSNAIKDKENSSIKSDSLYKIPPKPNTIISKLSSPNAG
1301 IITGAVFR

FIG. 36A pAA352-MSC_0957 fusion DNA (SEQ ID NO:72)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA
2501 TCGAAGAAATCATCGGTCAAAATGGCGAGCGGATCACCTCAAAGCAAGTT
2551 GATGATCTTATCGCAAAAGGTAACGGCAAAATTACCCAAGATGAGCTATC

FIG. 36A (continued)

```
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCTGCAGTACCACGATTACCCATA
2801  CGATCAAAACGTCCTTTAACGATAACGTTAAAGTCGAAAAATTCACCTGG
2851  GACGGCAATAAATATACCTCCAAAGAACAGTCAACGAACATTCAAGATAT
2901  CACCAATAGCCTGAACGGTACCACGAATGCATACTCTAAAACCATTACGG
2951  ACGTGCTGAACCTGTTTACCCGTAATATCCAGGAAGTTCGCAACCTGAAA
3001  GAAAGCTATGACCTGTTTCGTGGCAAAGCAGAAAATACGTCGGTGGTTGG
3051  CTATTACACCGGTGCTAACAGTCAGCGCCAAAAAATCTCCCAGCAAGATT
3101  TCTACAAAAAACTGGATGACAGTGACACCCACATCAGCTCTCTGAAAGGT
3151  CTGCTGCAGCTGCGTGAATTCGTTAACGATAACAAAAACAAAACCACGGT
3201  CGAACCGTGGAAAAATAGCCTGAAAACGGATGCGGACGAAGTTAAAAAAT
3251  GGTCTGATGAATTCACCAAAAATCTGGACAACATTGTCAACAGTTCCATC
3301  GATAACAAAATCAAAAACATCAAACTGGTGTCTAAAGTTAGTAAAACGTC
3351  ATCGAGCTTTGCCACCTTCGAACAGGACGTGAAAACCAGCCCGACGGCT
3401  CTAGTATTAACCTGACGGAACGCAACAATGAAACCGTCGTGGGCGATATC
3451  AAAAACCTGAAAGACCATAATCCGTATGTCTTTGGTACCAGTCCGGTGAA
3501  TGATCCGTTCGGCATGAACGTGATTGGTGAAAATAAAGATCCGGACATTA
3551  AAAACCTGAAACCGACCATCAAATATTCCACCGAAAAACTGACGAAAAAA
3601  GATGACTCATACATTAATCTGTCGAACAATGGTAACAACAACAACCAGTT
3651  CGTTTACAACATCAACCAAAAATGGGAACTGTCCTCAGCACATAATTTCT
3701  ATTACATGAGCAAAGATCCGGAAACGCTGGAACTGCAGATTACCCACAGC
3751  ATCGAAAACAAATCTTTTACCTTCTACGTCCAATTTGGCGGTCTGCGTAA
3801  AATTTATACCCCGATCGTGGAATCTTACACCCCGAAAAATACGAACTCAG
3851  CGGATAAACGTTATTCGTTTGTGGGCTGGGCCTTCAATTCGTACCGCTTT
3901  AGCGATGACTTCTCTAAGGGTAACTCGAGCCCGTACAAATTCAAAGATAT
3951  TAGTCTGAAAATCTCCCAGAACGCTTTCACCACGAATACCGGCAGCGTTA
4001  ACGGTAAATAA
```

FIG. 36B

LtkA-MSC_0957 fusion protein (SEQ ID NO:73)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSCSTTITHTIKTSFNDNVKVEKFTW
951 DGNKYTSKEQSTNIQDITNSLNGTTNAYSKTITDVLNLFTRNIQEVRNLK
1001 ESYDLFRGKAENTSVVGYYTGANSQRQKISQQDFYKKLDDSDTHISSLKG
1051 LLQLREFVNDNKNKTTVEPWKNSLKTDADEVKKWSDEFTKNLDNIVNSSI
1101 DNKIKNIKLVSKVSKTSSSFATFEQDVKTSPTGSSINLTERNNETVVGDI
1151 KNLKDHNPYVFGTSPVNDPFGMNVIGENKDPDIKNLKPTIKYSTEKLTKK
1201 DDSYINLSNNGNNNNQFVYNINQKWELSSAHNFYYMSKDPETLELQITHS
1251 IENKSFTFYVQFGGLRKIYTPIVESYTPKNTNSADKRYSFVGWAFNSYRF
1301 SDDFSKGNSSPYKFKDISLKISQNAFTTNTGSVNGK

FIG. 37A pAA352-MSC_0446-MSC_0177 fusion DNA (SEQ ID NO:74)

1 ATGGCTACTGTTATAGATCTAAGCTTCCCAAAAACTGGGGCAAAAAAAAT
51 TATCCTCTATATTCCCCAAAATTACCAATATGATACTGAACAAGGTAATG
101 GTTTACAGGATTTAGTCAAAGCGGCCGAAGAGTTGGGGATTGAGGTACAA
151 AGAGAAGAACGCAATAATATTGCAACAGCTCAAACCAGTTTAGGCACGAT
201 TCAAACCGCTATTGGCTTAACTGAGCGTGGCATTGTGTTATCCGCTCCAC
251 AAATTGATAAATTGCTACAGAAAACTAAAGCAGGCCAAGCATTAGGTTCT
301 GCCGAAAGCATTGTACAAAATGCAAATAAAGCCAAAACTGTATTATCTGG
351 CATTCAATCTATTTTAGGCTCAGTATTGGCTGGAATGGATTTAGATGAGG
401 CCTTACAGAATAACAGCAACCAACATGCTCTTGCTAAAGCTGGCTTGGAG
451 CTAACAAATTCATTAATTGAAAATATTGCTAATTCAGTAAAAACACTTGA
501 CGAATTTGGTGAGCAAATTAGTCAATTTGGTTCAAAACTACAAAATATCA
551 AAGGCTTAGGGACTTTAGGAGACAAACTCAAAAATATCGGTGGACTTGAT
601 AAAGCTGGCCTTGGTTTAGATGTTATCTCAGGGCTATTATCGGGCGCAAC
651 AGCTGCACTTGTACTTGCAGATAAAAATGCTTCAACAGCTAAAAAAGTGG
701 GTGCGGGTTTTGAATTGGCAAACCAAGTTGTTGGTAATATTACCAAAGCC
751 GTTTCTTCTTACATTTTAGCCCAACGTGTTGCAGCAGGTTTATCTTCAAC
801 TGGGCCTGTGGCTGCTTTAATTGCTTCTACTGTTTCTCTTGCGATTAGCC
851 CATTAGCATTTGCCGGTATTGCCGATAAATTTAATCATGCAAAAAGTTTA
901 GAGAGTTATGCCGAACGCTTTAAAAAATTAGGCTATGACGGAGATAATTT
951 ATTAGCAGAATATCAGCGGGGAACAGGGACTATTGATGCATCGGTTACTG
1001 CAATTAATACCGCATTGGCCGCTATTGCTGGTGGTGTGTCTGCTGCTGCA
1051 GCCGGCTCGGTTATTGCTTCACCGATTGCCTTATTAGTATCTGGGATTAC
1101 CGGTGTAATTTCTACGATTCTGCAATATTCTAAACAAGCAATGTTTGAGC
1151 ACGTTGCAAATAAAATTCATAACAAAATTGTAGAATGGGAAAAAAATAAT
1201 CACGGTAAGAACTACTTTGAAAATGGTTACGATGCCCGTTATCTTGCGAA
1251 TTTACAAGATAATATGAAATTCTTACTGAACTTAAACAAAGAGTTACAGG
1301 CAGAACGTGTCATCGCTATTACTCAGCAGCAATGGGATAACAACATTGGT
1351 GATTTAGCTGGTATTAGCCGTTTAGGTGAAAAAGTCCTTAGTGGTAAAGC
1401 CTATGTGGATGCGTTTGAAGAAGGCAAACACATTAAAGCCGATAAATTAG
1451 TACAGTTGGATTCGGCAAACGGTATTATTGATGTGAGTAATTCGGGTAAA
1501 GCGAAAACTCAGCATATCTTATTCAGAACGCCATTATTGACGCCGGGAAC
1551 AGAGCATCGTGAACGCGTACAAACAGGTAAATATGAATATATTACCAAGC
1601 TCAATATTAACCGTGTAGATAGCTGGAAAATTACAGATGGTGCAGCAAGT
1651 TCTACCTTTGATTTAACTAACGTTGTTCAGCGTATTGGTATTGAATTAGA
1701 CAATGCTGGAAATGTAACTAAAACCAAAGAAACAAAAATTATTGCCAAAC
1751 TTGGTGAAGGTGATGACAACGTATTTGTTGGTTCTGGTACGACGGAAATT
1801 GATGGCGGTGAAGGTTACGACCGAGTTCACTATAGCCGTGGAAACTATGG
1851 TGCTTTAACTATTGATGCAACCAAAGAGACCGAGCAAGGTAGTTATACCG
1901 TAAATCGTTTCGTAGAAACCGGTAAAGCACTACACGAAGTGACTTCAACC
1951 CATACCGCATTAGTGGGCAACCGTGAAGAAAAAATAGAATATCGTCATAG
2001 CAATAACCAGCACCATGCCGGTTATTACACCAAAGATACCTTGAAAGCTG
2051 TTGAAGAAATTATCGGTACATCACATAACGATATCTTTAAAGGTAGTAAG
2101 TTCAATGATGCCTTTAACGGTGGTGATGGTGTCGATACTATTGACGGTAA
2151 CGACGGCAATGACCGCTTATTTGGTGGTAAAGGCGATGATATTCTCGATG
2201 GTGGAAATGGTGATGATTTTATCGATGGCGGTAAAGGCAACGACCTATTA
2251 CACGGTGGCAAGGGCGATGATATTTTCGTTCACCGTAAAGGCGATGGTAA
2301 TGATATTATTACCGATTCTGACGGCAATGATAAATTATCATTCTCTGATT
2351 CGAACTTAAAAGATTTAACATTTGAAAAAGTTAAACATAATCTTGTCATC
2401 ACGAATAGCAAAAAAGAGAAAGTGACCATTCAAAACTGGTTCCGAGAGGC
2451 TGATTTTGCTAAAGAAGTGCCTAATTATAAAGCAACTAAAGATGAGAAAA
2501 TCGAAGAAATCATCGGTCAAAATGGCGAGCGGATCACCTCAAAGCAAGTT
2551 GATGATCTTATCGCAAAAGGTAACGGCAAAATTACCCAAGATGAGCTATC

FIG. 37A (continued)

2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCCTGCTGTTCCTGGTGAAGAAAA
2801 CCACCATCAACCAGATTAGCGACAACAACAACAACAGCAGCACCAACAAG
2851 CAGGACAAGAACAAACAAGATCACAGCAACAACGAGAAAATGGGTGAAAA
2901 CACCAAAAACGACAGCGATAAGATCAACACCGAGAAAACCCTGGACAACG
2951 ATCGTATGAACAACCAGAGCGACCAACCGCGTGAGGAAAGCACCCCGCGT
3001 AACAACGATAGCAAAGAGAACGTTTGGAGCCGTGGCATTAAGAAACGTAT
3051 CCTGGAAAGCCTGAACAGCACCAACCTGGACTACCTGAAGACCCTGAGCA
3101 ACAGCCTGATCCAGGAGAAGGAAAAAACCCTGATTAGCAACAACATCGAC
3151 AAGAAAACCCTGGAGTATAAGACCAAACTGACCAAGTTCAGCAGCGAACT
3201 GAAGTTCGATGAGATTAAGAAAGAACTGATCAGCAGCCTGGAGGAAAGCA
3251 TTAAGAAAAACAAGAACAACCAGCACCAACACAAACTGCTGCTGCACCAA
3301 TTCAAGGACCGTCAGCTGGAGAAACAACACATCAGCGAAATTACCAAGCT
3351 GATCATTGACATCTACCGTAGCAACCTGCTGAACGAACTGTATAAAGAGC
3401 TGGATGAAAAAATTCAGAAGGAGAACCGTGAATTCGAGGAAATCTTCAAG
3451 CGTAAGAACAAGAACGAGATCAAGAACAAGCTGTTTGACCTGGTGGATAA
3501 GATCGTTGATCTGCAAGAAGCGCTGAAAAACATGAGCGTGGGTGGCGGTA
3551 TGAGCATTAAAAGCCTGCTGACCATCCTGAGCAGCCTGATGATTAGCGCG
3601 AGCGGTGTTGGCCTGGTGGTTGCGTGCACCAAGACCGACAGCACCCAGGC
3651 GCCGAGCACCAACCAAAACAAAGACAAGGATAAGAAAGATGGTAACGGCA
3701 AGAGCGAGGAAAAACCGAAGGTGATCAGCAAAAGCCAGTGGAGCGACGCG
3751 TTTCGTGATAGCATTACCGGTTGGGACATCGAGAACTACGATTTCAGCAA
3801 ACCGAACAACAACCAGAACCTGCCGAAATTTCCGAAGCAAAACATCGAAG
3851 TGGGCACCTATAGCAAGAAACAAGTTCTGGACAACAGCGCGCTGCACAGC
3901 AGCATTAAGAAAAAGATCGATGAGATCCTGAAGATCGAGGAGAAGAGCCT
3951 GAAGGTGGAGAACGTTTACTTCGACGATGAAAGCGGCAAGGCGATCGTTA
4001 AAAGCACCAAGTTCAGCGACACCCTGAAGGTGACCTTTCTGGTTAAAGAG
4051 AACCTGGAACTGGGCGCGTATACCAAGGACCAGATCCTGGATAACAGCAA
4101 GTTCCACAGCACCATTAAAAAGAAAATTGCGGAGATCCTGAAGGTGGATG
4151 AAAGCACCCTGACCGTGCTGGACGTTTACTATGAAGATAAAACCGGCGGT
4201 GGCGTGGTTAAAAGCACCAAGCTGCCGAACGAGATTAAGTTCATCTTTAG
4251 CGTTAAAGAAAAGTGACCATGGCATCACAGTATCGTGATGACAGAGGCAG
4301 GGAGTGGGACAAAATTGAAATCAAATAATGATTTTATTTTGACTGATAGT
4351 GACCTGTTCGTTGCAACAAATTGATAA

FIG. 37B

LtkA- MSC_0446-MSC_0177 fusion protein (SEQ ID NO:75)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSLLFLVKKTTINQISDNNNNSSTNK
951 QDKNKQDHSNNEKMGENTKNDSDKINTEKTLDNDRMNNQSDQPREESTPR
1001 NNDSKENVWSRGIKKRILESLNSTNLDYLKTLSNSLIQEKEKTLISNNID
1051 KKTLEYKTKLTKFSSELKFDEIKKELISSLEESIKKNKNNQHQHKLLLHQ
1101 FKDRQLEKQHISEITKLIIDIYRSNLLNELYKELDEKIQKENREFEEIFK
1151 RKNKNEIKNKLFDLVDKIVDLQEALKNMSVGGGMSIKSLLTILSSLMISA
1201 SGVGLVVACTKTDSTQAPSTNQNKDKDKKDGNGKSEEKPKVISKSQWSDA
1251 FRDSITGWDIENYDFSKPNNNQNLPKFPKQNIEVGTYSKKQVLDNSALHS
1301 SIKKKIDEILKIEEKSLKVENVYFDDESGKAIVKSTKFSDTLKVTFLVKE
1351 NLELGAYTKDQILDNSKFHSTIKKKIAEILKVDESTLTVLDVYYEDKTGG
1401 GVVKSTKLPNEIKFIFSVKEK

FIG. 38A pAA352-MSC 0922-MSC_1058 fusion DNA (SEQ ID NO:76)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
2551  GATGATCTTATCGCAAAAGGTAACGGCAAAATTACCCAAGATGAGCTATC
```

FIG. 38A (continued)

```
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCAAGAAACTGCTGATCGGCTTCA
2801  GCAGCATTTTCGCGTTTCTGACCGTGAGCTGCAGCACCAGCACCCCGAAG
2851  GTTAACCCGACCATCAACAAGAACGAGAACAAACTGTACAAAAACAAGTA
2901  TGTGAGCAAGCTGCTGAACCTGTACCTGAGCGACAGCAAACTGCGTGATA
2951  GCTATATTAACGACCAGGAGAACGTTAGCGATAGCAAGTTTAGCGAACTG
3001  AAATACGGCCTGACCTTCTATCCGATCTTTATTCACCGTAGCCTGGACTA
3051  CTATGTGGGTCAGCACTACCGTGTTATCATTCAAAAAGCGAAGAACAGCC
3101  TGGAGCAAACCCTGCGTAACGATTGGTACTGGGTGCTGGACAACATCACC
3151  AACTTCAAGTATAACTTTAACCCGTACGGCGATCTGTATAACGAATTCAA
3201  CAAAGACGAGGACCTGTTCAAGCAGGTTGAAAAAGACCTGGGTAGCCTGA
3251  TCAGCAGCATCAAGAACAAGAACGTGCAAAACATCATCCGTGTTAACCTG
3301  AACAACAGCATCAACGAGAAAATTAAGGACGATTACCTGAAGAAAGAAGC
3351  GCTGTATCTGGTGTTCGATAACAACAAAGCGATCAAGATCTGGAAGTACG
3401  AATACAAGAACAAGATCGAGTTCCTGATGACCAGCGACCTGTTCGTTTTT
3451  AAGGACGCGAACAACCTGGAGAACCAGATCGAGCAACTGGAAAACACCAT
3501  TTTCGAAAAACGTAAAAGCGAGTACAACAACAACCTGGAAAGCATCAACA
3551  AAAGCATTGAGACCACCAAGAAACGTAAAGAAAAGACCCAGCAAGAGATC
3601  CAGGAACTGAAAGAGAAGATTGAAAAGCTGGAGAAAGAAACCAACACCAC
3651  CACCACCGCGCCGCTGGCGCTGGCGCTGGATACCCGTACCATTGCGCCGG
3701  GCGTGCTGAAGAACGACAAGAAAAAGGAGCCGACCATTGAGGAACTGAAA
3751  AAGGATCTGGAGAAAAAGGAAAAACAGCTGGAGCAATTCGACGAAAACGT
3801  TAAAAAGTACGAGAAGGACATCGAAGATCTGCCGCAGAAAAGCAACGATA
3851  AAAAGTTCCTGGAATTTCACGCGAAGAACCAATATAACGAGCGTCTGAAA
3901  GAAAGCCTGAACGAGATCAACAAGGACGGCTGGAAAATTGTGCGTTTTAG
3951  CATGCGTGGTATCTACGAGCAGGAAGGTGGCGGTAAAAAGCTGCTGACCA
4001  TTCTGGGCAGCGTGGGTCTGGTTGCGACCACCAGCGCGGCGGTTATTGCG
4051  TGCGGTGATAAGACCAGCCAAAAAACCCCGGACACCAAGCCGACCGAGGA
4101  AACCCGTAAAGAGGACAAAGAGGAACCGAAAAAGGACGATGAAAAAACCA
4151  CCGAGGACAAAAAGAAAGAGGAAGCGTTCAGCAAGGTGGAAAAACAGATC
4201  ATTGGCAACTTTAGCCCGAACAACAACAACGCGGTGCCGCAGAGCAACAT
4251  CAAGAAAAAGCTGGCGGAGCTGCTGAAGGTTCAAGAGAGCGAACTGACCG
4301  ACCTGAACGTGGATTATGAAAACAACACCGGTACCGTTAAAATCAAGGAC
4351  AGCAGCAAAGCGATTGAGTTCAAGTTTAGCGTTAAAGAGAAGAAGATCAA
4401  CAACTGACCATGGCATCACAGTATCGTGATGACAGAGGCAGGGAGTGGGA
4451  CAAAATTGAAATCAAATAATGATTTTATTTTGACTGATAGTGACCTGTTC
4501  GTTGCAACAAATTGATAA
```

FIG. 38B

LtkA-MSC_0922-MSC_1058 fusion protein (SEQ ID NO:77)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSKKLLIGFSSIFAFLTVSCSTSTPK
951 VNPTINKNENKLYKNKYVSKLLNLYLSDSKLRDSYINDQENVSDSKFSEL
1001 KYGLTFYPIFIHRSLDYYVGQHYRVIIQKAKNSLEQTLRNDWYWVLDNIT
1051 NFKYNFNPYGDLYNEFNKDEDLFKQVEKDLGSLISSIKNKNVQNIIRVNL
1101 NNSINEKIKDDYLKKEALYLVFDNNKAIKIWKYEYKNKIEFLMTSDLFVF
1151 KDANNLENQIEQLENTIFEKRKSEYNNNLESINKSIETTKKRKEKTQQEI
1201 QELKEKIEKLEKETNTTTTAPLALALDTRTIAPGVLKNDKKKEPTIEELK
1251 KDLEKKEKQLEQFDENVKKYEKDIEDLPQKSNDKKFLEFHAKNQYNERLK
1301 ESLNEINKDGWKIVRFSMRGIYEQEGGGKKLLTILGSVGLVATTSAAVIA
1351 CGDKTSQKTPDTKPTEETRKEDKEEPKKDDEKTTEDKKKEEAFSKVEKQI
1401 IGNFSPNNNNAVPQSNIKKKLAELLKVQESELTDLNVDYENNTGTVKIKD
1451 SSKAIEFKFSVKEKKINN

FIG. 39A pAA352-YP_004399807.1 fusion DNA sequence (SEQ ID NO:78)

```
1     ATGGCTACTGTTATAGATCTAAGCTTCCCAAAAACTGGGGCAAAAAAAAT
51    TATCCTCTATATTCCCCAAAATTACCAATATGATACTGAACAAGGTAATG
101   GTTTACAGGATTTAGTCAAAGCGGCCGAAGAGTTGGGGATTGAGGTACAA
151   AGAGAAGAACGCAATAATATTGCAACAGCTCAAACCAGTTTAGGCACGAT
201   TCAAACCGCTATTGGCTTAACTGAGCGTGGCATTGTGTTATCCGCTCCAC
251   AAATTGATAAATTGCTACAGAAAACTAAAGCAGGCCAAGCATTAGGTTCT
301   GCCGAAAGCATTGTACAAAATGCAAATAAAGCCAAAACTGTATTATCTGG
351   CATTCAATCTATTTTAGGCTCAGTATTGGCTGGAATGGATTTAGATGAGG
401   CCTTACAGAATAACAGCAACCAACATGCTCTTGCTAAAGCTGGCTTGGAG
451   CTAACAAATTCATTAATTGAAAATATTGCTAATTCAGTAAAAACACTTGA
501   CGAATTTGGTGAGCAAATTAGTCAATTTGGTTCAAAACTACAAAATATCA
551   AAGGCTTAGGGACTTTAGGAGACAAACTCAAAAATATCGGTGGACTTGAT
601   AAAGCTGGCCTTGGTTTAGATGTTATCTCAGGGCTATTATCGGGCGCAAC
651   AGCTGCACTTGTACTTGCAGATAAAAATGCTTCAACAGCTAAAAAAGTGG
701   GTGCGGGTTTTGAATTGGCAAACCAAGTTGTTGGTAATATTACCAAAGCC
751   GTTTCTTCTTACATTTTAGCCCAACGTGTTGCAGCAGGTTTATCTTCAAC
801   TGGGCCTGTGGCTGCTTTAATTGCTTCTACTGTTTCTCTTGCGATTAGCC
851   CATTAGCATTTGCCGGTATTGCCGATAAATTTAATCATGCAAAAAGTTTA
901   GAGAGTTATGCCGAACGCTTTAAAAAATTAGGCTATGACGGAGATAATTT
951   ATTAGCAGAATATCAGCGGGGAACAGGGACTATTGATGCATCGGTTACTG
1001  CAATTAATACCGCATTGGCCGCTATTGCTGGTGGTGTGTCTGCTGCTGCA
1051  GCCGGCTCGGTTATTGCTTCACCGATTGCCTTATTAGTATCTGGGATTAC
1101  CGGTGTAATTTCTACGATTCTGCAATATTCTAAACAAGCAATGTTTGAGC
1151  ACGTTGCAAATAAAATTCATAACAAAATTGTAGAATGGGAAAAAAAATAAT
1201  CACGGTAAGAACTACTTTGAAAATGGTTACGATGCCCGTTATCTTGCGAA
1251  TTTACAAGATAATATGAAATTCTTACTGAACTTAAACAAAGAGTTACAGG
1301  CAGAACGTGTCATCGCTATTACTCAGCAGCAATGGGATAACAACATTGGT
1351  GATTTAGCTGGTATTAGCCGTTTAGGTGAAAAAGTCCTTAGTGGTAAAGC
1401  CTATGTGGATGCGTTTGAAGAAGGCAAACACATTAAAGCCGATAAATTAG
1451  TACAGTTGGATTCGGCAAACGGTATTATTGATGTGAGTAATTCGGGTAAA
1501  GCGAAAACTCAGCATATCTTATTCAGAACGCCATTATTGACGCCGGGAAC
1551  AGAGCATCGTGAACGCGTACAAACAGGTAAATATGAATATATTACCAAGC
1601  TCAATATTAACCGTGTAGATAGCTGGAAAATTACAGATGGTGCAGCAAGT
1651  TCTACCTTTGATTTAACTAACGTTGTTCAGCGTATTGGTATTGAATTAGA
1701  CAATGCTGGAAATGTAACTAAAACCAAAGAAACAAAAATTATTGCCAAAC
1751  TTGGTGAAGGTGATGACAACGTATTTGTTGGTTCTGGTACGACGGAAATT
1801  GATGGCGGTGAAGGTTACGACCGAGTTCACTATAGCCGTGGAAACTATGG
1851  TGCTTTAACTATTGATGCAACCAAAGAGACCGAGCAAGGTAGTTATACCG
1901  TAAATCGTTTCGTAGAAACCGGTAAAGCACTACACGAAGTGACTTCAACC
1951  CATACCGCATTAGTGGGCAACCGTGAAGAAAAAATAGAATATCGTCATAG
2001  CAATAACCAGCACCATGCCGGTTATTACACCAAAGATACCTTGAAAGCTG
2051  TTGAAGAAATTATCGGTACATCACATAACGATATCTTTAAAGGTAGTAAG
2101  TTCAATGATGCCTTTAACGGTGGTGATGGTGTCGATACTATTGACGGTAA
2151  CGACGGCAATGACCGCTTATTTGGTGGTAAAGGCGATGATATTCTCGATG
2201  GTGGAAATGGTGATGATTTTATCGATGGCGGTAAAGGCAACGACCTATTA
2251  CACGGTGGCAAGGGCGATGATATTTTCGTTCACCGTAAAGGCGATGGTAA
2301  TGATATTATTACCGATTCTGACGGCAATGATAAATTATCATTCTCTGATT
2351  CGAACTTAAAAGATTTAACATTTGAAAAAGTTAAACATAATCTTGTCATC
2401  ACGAATAGCAAAAAAGAGAAAGTGACCATTCAAAACTGGTTCCGAGAGGC
2451  TGATTTTGCTAAAGAAGTGCCTAATTATAAAGCAACTAAAGATGAGAAAA
2501  TCGAAGAAATCATCGGTCAAAATGGCGAGCGGATCACCTCAAAGCAAGTT
2551  GATGATCTTATCGCAAAAGGTAACGGCAAAATTACCCAAGATGAGCTATC
```

FIG. 39A (continued)

2601 AAAAGTTGTTGATAACTATGAATTGCTCAAACATAGCAAAAATGTGACAA
2651 ACAGCTTAGATAAGTTAATCTCATCTGTAAGTGCATTTACCTCGTCTAAT
2701 GATTCGAGAAATGTATTAGTGGCTCCAACTTCAATGTTGGATCAAAGTTT
2751 ATCTTCTCTTCAATTTGCTAGGGGATCCAGCAGCAAAGTTCAGGTTATCA
2801 ACAAGTTCGATGACATTACGTCCATTAAAAACACGGGTGCGTTCAAAAAC
2851 AATCAGGCATTCATTTCCCGTTCAGAACTGAAAGAAATCGTCAGCTCTAA
2901 CAATACCACGATTTCTAATACCACGAGTTCCACCGCAGTGATGACCTCGA
2951 CGAGCACCACGTCTATCGGCACCCAGACGAACAATAACAATGACCTGAAG
3001 AACGCGAGTGAACGCCTGAAAGCCCTGGCGGCCAACAACTTCACCAAGAA
3051 CAAGAAGCAGGCATGGGATTCCCTGCAAAACGCTTCAATGACCTTCTATA
3101 AAAAGGTGCAGCCGACCGCGGTCAATGTGCTGGGTTACGAACAAATTACC
3151 AAAGACAACGTTGAAAAACTGGATAAGGAACTGAAAACCGTTTTTCTGGT
3201 CTTCAAGGACAATACCAAAGAAACGGAAAAGCTGGAAGTGGAACTGCTGC
3251 CGGAAATTAACAATGGCAACAAAGTTATCGACAATGGTAACCTGTATCTG
3301 GATCTGCTGGAAAAACCGGAAAATCTGAAGCTGGCGAACCAGAAAAGCAT
3351 TATCGAAGTGCTGCGTCCGGAAATTACCAAAATCAAGGTGGTTCTGCAAA
3401 ATACCAAAAACAATAACTCCACGAACAAAGAAGATATCAAGAACACCGAA
3451 GTTTTCAACCTGCTGATTAAACAGCTGAGCATCTATCTGGCAAATGCTGT
3501 CAAATACTTTAACTCTGAAAGTGGCATTATCACCACGAATCCGACCTTCT
3551 CGTATAAAACGCGCAGCAATCAAATCTACGACTACATCGTTAAGAACAAG
3601 AAGGATGAACTGTACAAGAAGCTGGAAACCGCGTTTACGTCAGAATTCAA
3651 CAAGATCAACTTCATCGATATCTTCAAAGACTTCCAGTTCGATGAAAACA
3701 ACAGTAACGATAACAAAAAGATTATCACCAAGATTATCAAATCATCGACG
3751 AATAGCTCTGCCAGTTCCTCAAACTCGAGCACCACGACCACGACCGAACT
3801 GTCTAGTACGACCACGCGTTAA

FIG. 39B

LtkA-YP_004399807.1 fusion protein (SEQ ID NO:79)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSSSKVQVINKFDDITSIKNTGAFKN
951 NQAFISRSELKEIVSSNNTTISNTTSSTAVMTSTSTTSIGTQTNNNNDLK
1001 NASERLKALAANNFTKNKKQAWDSLQNASMTFYKKVQPTAVNVLGYEQIT
1051 KDNVEKLDKELKTVFLVFKDNTKETEKLEVELLPEINNGNKVIDNGNLYL
1101 DLLEKPENLKLANQKSIIEVLRPEITKIKVVLQNTKNNNSTNKEDIKNTE
1151 VFNLLIKQLSIYLANAVKYFNSESGIITTNPTFSYKTRSNQIYDYIVKNK
1201 KDELYKKLETAFTSEFNKINFIDIFKDFQFDENNSNDNKKIITKIIKSST
1251 NSSASSSNSSTTTTTELSSTTTR

FIG. 40A pAA352-YP_004400559.1 fusion DNA sequence (SEQ ID NO:80)

```
1       ATGGCTACTGTTATAGATCTAAGCTTCCCAAAAACTGGGGCAAAAAAAAT
51      TATCCTCTATATTCCCCAAAATTACCAATATGATACTGAACAAGGTAATG
101     GTTTACAGGATTTAGTCAAAGCGGCCGAAGAGTTGGGGATTGAGGTACAA
151     AGAGAAGAACGCAATAATATTGCAACAGCTCAAACCAGTTTAGGCACGAT
201     TCAAACCGCTATTGGCTTAACTGAGCGTGGCATTGTGTTATCCGCTCCAC
251     AAATTGATAAATTGCTACAGAAAACTAAAGCAGGCCAAGCATTAGGTTCT
301     GCCGAAAGCATTGTACAAAATGCAAATAAAGCCAAAACTGTATTATCTGG
351     CATTCAATCTATTTTAGGCTCAGTATTGGCTGGAATGGATTTAGATGAGG
401     CCTTACAGAATAACAGCAACCAACATGCTCTTGCTAAAGCTGGCTTGGAG
451     CTAACAAATTCATTAATTGAAAATATTGCTAATTCAGTAAAAACACTTGA
501     CGAATTTGGTGAGCAAATTAGTCAATTTGGTTCAAAACTACAAAATATCA
551     AAGGCTTAGGGACTTTAGGAGACAAACTCAAAAATATCGGTGGACTTGAT
601     AAAGCTGGCCTTGGTTTAGATGTTATCTCAGGGCTATTATCGGGCGCAAC
651     AGCTGCACTTGTACTTGCAGATAAAAATGCTTCAACAGCTAAAAAAGTGG
701     GTGCGGGTTTTGAATTGGCAAACCAAGTTGTTGGTAATATTACCAAAGCC
751     GTTTCTTCTTACATTTTAGCCCAACGTGTTGCAGCAGGTTTATCTTCAAC
801     TGGGCCTGTGGCTGCTTTAATTGCTTCTACTGTTTCTCTTGCGATTAGCC
851     CATTAGCATTTGCCGGTATTGCCGATAAATTTAATCATGCAAAAAGTTTA
901     GAGAGTTATGCCGAACGCTTTAAAAAATTAGGCTATGACGGAGATAATTT
951     ATTAGCAGAATATCAGCGGGGAACAGGGACTATTGATGCATCGGTTACTG
1001    CAATTAATACCGCATTGGCCGCTATTGCTGGTGGTGTGTCTGCTGCTGCA
1051    GCCGGCTCGGTTATTGCTTCACCGATTGCCTTATTAGTATCTGGGATTAC
1101    CGGTGTAATTTCTACGATTCTGCAATATTCTAAACAAGCAATGTTTGAGC
1151    ACGTTGCAAATAAAATTCATAACAAAATTGTAGAATGGGAAAAAAATAAT
1201    CACGGTAAGAACTACTTTGAAAATGGTTACGATGCCCGTTATCTTGCGAA
1251    TTTACAAGATAATATGAAATTCTTACTGAACTTAAACAAAGAGTTACAGG
1301    CAGAACGTGTCATCGCTATTACTCAGCAGCAATGGGATAACAACATTGGT
1351    GATTTAGCTGGTATTAGCCGTTTAGGTGAAAAAGTCCTTAGTGGTAAAGC
1401    CTATGTGGATGCGTTTGAAGAAGGCAAACACATTAAAGCCGATAAATTAG
1451    TACAGTTGGATTCGGCAAACGGTATTATTGATGTGAGTAATTCGGGTAAA
1501    GCGAAAACTCAGCATATCTTATTCAGAACGCCATTATTGACGCCGGGAAC
1551    AGAGCATCGTGAACGCGTACAAACAGGTAAATATGAATATATTACCAAGC
1601    TCAATATTAACCGTGTAGATAGCTGGAAAATTACAGATGGTGCAGCAAGT
1651    TCTACCTTTGATTTAACTAACGTTGTTCAGCGTATTGGTATTGAATTAGA
1701    CAATGCTGGAAATGTAACTAAAACCAAAGAAACAAAAATTATTGCCAAAC
1751    TTGGTGAAGGTGATGACAACGTATTTGTTGGTTCTGGTACGACGGAAATT
1801    GATGGCGGTGAAGGTTACGACCGAGTTCACTATAGCCGTGGAAACTATGG
1851    TGCTTTAACTATTGATGCAACCAAAGAGACCGAGCAAGGTAGTTATACCG
1901    TAAATCGTTTCGTAGAAACCGGTAAAGCACTACACGAAGTGACTTCAACC
1951    CATACCGCATTAGTGGGCAACCGTGAAGAAAAAATAGAATATCGTCATAG
2001    CAATAACCAGCACCATGCCGGTTATTACACCAAAGATACCTTGAAAGCTG
2051    TTGAAGAAATTATCGGTACATCACATAACGATATCTTTAAAGGTAGTAAG
2101    TTCAATGATGCCTTTAACGGTGGTGATGGTGTCGATACTATTGACGGTAA
2151    CGACGGCAATGACCGCTTATTTGGTGGTAAAGGCGATGATATTCTCGATG
2201    GTGGAAATGGTGATGATTTTATCGATGGCGGTAAAGGCAACGACCTATTA
2251    CACGGTGGCAAGGGCGATGATATTTTCGTTCACCGTAAAGGCGATGGTAA
2301    TGATATTATTACCGATTCTGACGGCAATGATAAATTATCATTCTCTGATT
2351    CGAACTTAAAAGATTTAACATTTGAAAAAGTTAAACATAATCTTGTCATC
2401    ACGAATAGCAAAAAAGAGAAAGTGACCATTCAAAACTGGTTCCGAGAGGC
2451    TGATTTTGCTAAAGAAGTGCCTAATTATAAAGCAACTAAAGATGAGAAAA
2501    TCGAAGAAATCATCGGTCAAAATGGCGAGCGGATCACCTCAAAGCAAGTT
```

FIG. 40A (continued)

```
2551  GATGATCTTATCGCAAAAGGTAACGGCAAAATTACCCAAGATGAGCTATC
2601  AAAAGTTGTTGATAACTATGAATTGCTCAAACATAGCAAAAATGTGACAA
2651  ACAGCTTAGATAAGTTAATCTCATCTGTAAGTGCATTTACCTCGTCTAAT
2701  GATTCGAGAAATGTATTAGTGGCTCCAACTTCAATGTTGGATCAAAGTTT
2751  ATCTTCTCTTCAATTTGCTAGGGGATCCAGCAACAACAACAAAAAAGAAG
2801  AAAAGCAATCAAAGGAAATGAATAAAAATCAAACCTCTAACTCCACGAGC
2851  ACCAATATGAACAACACGCAGGGCAGCAATAGCTCTACCACGACCAACAT
2901  TACCTCTAACCCGATCAATAGTGTCACGTCCATGGCGACCCAACCGAAAA
2951  ACGAAACCTTTTTCAATAAGGAACCGCTGATCTTTTCAGAACTGGATTAT
3001  GTGTCGGAATACTTCAAGCGTAAGGAACATATTGCGCGCACCAGCGAACT
3051  GATCCTGGAAAACTCTGAAGGCATTAAACGTCGTATGCAGAATAGTACGG
3101  TTGAAACGACCCACCGTGATTCCCTGGCCGAAACCCAAGACCTGATTCTG
3151  GAAAACAGCAACGGTGTGGTTAACTTCAAGAAGTAA
```

FIG. 40B

LtkA-YP_004400559.1 fusion protein (SEQ ID NO:81)

1 MATVIDLSFPKTGAKKIILYIPQNYQYDTEQGNGLQDLVKAAEELGIEVQ
51 REERNNIATAQTSLGTIQTAIGLTERGIVLSAPQIDKLLQKTKAGQALGS
101 AESIVQNANKAKTVLSGIQSILGSVLAGMDLDEALQNNSNQHALAKAGLE
151 LTNSLIENIANSVKTLDEFGEQISQFGSKLQNIKGLGTLGDKLKNIGGLD
201 KAGLGLDVISGLLSGATAALVLADKNASTAKKVGAGFELANQVVGNITKA
251 VSSYILAQRVAAGLSSTGPVAALIASTVSLAISPLAFAGIADKFNHAKSL
301 ESYAERFKKLGYDGDNLLAEYQRGTGTIDASVTAINTALAAIAGGVSAAA
351 AGSVIASPIALLVSGITGVISTILQYSKQAMFEHVANKIHNKIVEWEKNN
401 HGKNYFENGYDARYLANLQDNMKFLLNLNKELQAERVIAITQQQWDNNIG
451 DLAGISRLGEKVLSGKAYVDAFEEGKHIKADKLVQLDSANGIIDVSNSGK
501 AKTQHILFRTPLLTPGTEHRERVQTGKYEYITKLNINRVDSWKITDGAAS
551 STFDLTNVVQRIGIELDNAGNVTKTKETKIIAKLGEGDDNVFVGSGTTEI
601 DGGEGYDRVHYSRGNYGALTIDATKETEQGSYTVNRFVETGKALHEVTST
651 HTALVGNREEKIEYRHSNNQHHAGYYTKDTLKAVEEIIGTSHNDIFKGSK
701 FNDAFNGGDGVDTIDGNDGNDRLFGGKGDDILDGGNGDDFIDGGKGNDLL
751 HGGKGDDIFVHRKGDGNDIITDSDGNDKLSFSDSNLKDLTFEKVKHNLVI
801 TNSKKEKVTIQNWFREADFAKEVPNYKATKDEKIEEIIGQNGERITSKQV
851 DDLIAKGNGKITQDELSKVVDNYELLKHSKNVTNSLDKLISSVSAFTSSN
901 DSRNVLVAPTSMLDQSLSSLQFARGSSNNNKKEEKQSKEMNKNQTSNSTS
951 TNMNNTQGSNSSTTTNITSNPINSVTSMATQPKNETFFNKEPLIFSELDY
1001 VSEYFKRKEHIARTSELILENSEGIKRRMQNSTVETTHRDSLAETQDLIL
1051 ENSNGVVNFKK

FIG. 41

```
atg gct act gtt ata gat cta agc ttc cca aaa act ggg gca aaa aaa
Met Ala Thr Val Ile Asp Leu Ser Phe Pro Lys Thr Gly Ala Lys Lys
1               5                   10                  15

att atc ctc tat att ccc caa aat tac caa tat gat act gaa caa ggt
Ile Ile Leu Tyr Ile Pro Gln Asn Tyr Gln Tyr Asp Thr Glu Gln Gly
            20                  25                  30

aat ggt tta cag gat tta gtc aaa gcg gcc gaa gag ttg ggg att gag
Asn Gly Leu Gln Asp Leu Val Lys Ala Ala Glu Glu Leu Gly Ile Glu
        35                  40                  45

gta caa aga gaa gaa cgc aat aat att gca aca gct caa acc agt tta
Val Gln Arg Glu Glu Arg Asn Asn Ile Ala Thr Ala Gln Thr Ser Leu
    50                  55                  60

ggc acg att caa acc gct att ggc tta act gag cgt ggc att gtg tta
Gly Thr Ile Gln Thr Ala Ile Gly Leu Thr Glu Arg Gly Ile Val Leu
65                  70                  75                  80

tcc gct cca caa att gat aaa ttg cta cag aaa act aaa gca ggc caa
Ser Ala Pro Gln Ile Asp Lys Leu Leu Gln Lys Thr Lys Ala Gly Gln
                85                  90                  95

gca tta ggt tct gcc gaa agc att gta caa aat gca aat aaa gcc aaa
Ala Leu Gly Ser Ala Glu Ser Ile Val Gln Asn Ala Asn Lys Ala Lys
            100                 105                 110

act gta tta tct ggc att caa tct att tta ggc tca gta ttg gct gga
Thr Val Leu Ser Gly Ile Gln Ser Ile Leu Gly Ser Val Leu Ala Gly
        115                 120                 125

atg gat tta gat gag gcc tta cag aat aac agc aac caa cat gct ctt
Met Asp Leu Asp Glu Ala Leu Gln Asn Asn Ser Asn Gln His Ala Leu
    130                 135                 140

gct aaa gct ggc ttg gag cta aca aat tca tta att gaa aat att gct
Ala Lys Ala Gly Leu Glu Leu Thr Asn Ser Leu Ile Glu Asn Ile Ala
145                 150                 155                 160

aat tca gta aaa aca ctt gac gaa ttt ggt gag caa att agt caa ttt
Asn Ser Val Lys Thr Leu Asp Glu Phe Gly Glu Gln Ile Ser Gln Phe
                165                 170                 175

ggt tca aaa cta caa aat atc aaa ggc tta ggg act tta gga gac aaa
Gly Ser Lys Leu Gln Asn Ile Lys Gly Leu Gly Thr Leu Gly Asp Lys
            180                 185                 190
```

FIG. 41 (continued)

```
ctc aaa aat atc ggt gga ctt gat aaa gct ggc ctt ggt tta gat gtt
Leu Lys Asn Ile Gly Gly Leu Asp Lys Ala Gly Leu Gly Leu Asp Val
        195                 200                 205

atc tca ggg cta tta tcg ggc gca aca gct gca ctt gta ctt gca gat
Ile Ser Gly Leu Leu Ser Gly Ala Thr Ala Ala Leu Val Leu Ala Asp
    210                 215                 220

aaa aat gct tca aca gct aaa aaa gtg ggt gcg ggt ttt gaa ttg gca
Lys Asn Ala Ser Thr Ala Lys Lys Val Gly Ala Gly Phe Glu Leu Ala
225                 230                 235                 240

aac caa gtt gtt ggt aat att acc aaa gcc gtt tct tct tac att tta
Asn Gln Val Val Gly Asn Ile Thr Lys Ala Val Ser Ser Tyr Ile Leu
                245                 250                 255

gcc caa cgt gtt gca gca ggt tta tct tca act ggg cct gtg gct gct
Ala Gln Arg Val Ala Ala Gly Leu Ser Ser Thr Gly Pro Val Ala Ala
            260                 265                 270

tta att gct tct act gtt tct ctt gcg att agc cca tta gca ttt gcc
Leu Ile Ala Ser Thr Val Ser Leu Ala Ile Ser Pro Leu Ala Phe Ala
        275                 280                 285

ggt att gcc gat aaa ttt aat cat gca aaa agt tta gag agt tat gcc
Gly Ile Ala Asp Lys Phe Asn His Ala Lys Ser Leu Glu Ser Tyr Ala
    290                 295                 300

gaa cgc ttt aaa aaa tta ggc tat gac gga gat aat tta tta gca gaa
Glu Arg Phe Lys Lys Leu Gly Tyr Asp Gly Asp Asn Leu Leu Ala Glu
305                 310                 315                 320

tat cag cgg gga aca ggg act att gat gca tcg gtt act gca att aat
Tyr Gln Arg Gly Thr Gly Thr Ile Asp Ala Ser Val Thr Ala Ile Asn
                325                 330                 335

acc gca ttg gcc gct att gct ggt ggt gtg tct gct gct gca gcc ggc
Thr Ala Leu Ala Ala Ile Ala Gly Gly Val Ser Ala Ala Ala Ala Gly
            340                 345                 350

tcg gtt att gct tca ccg att gcc tta tta gta tct ggg att acc ggt
Ser Val Ile Ala Ser Pro Ile Ala Leu Leu Val Ser Gly Ile Thr Gly
        355                 360                 365

gta att tct acg att ctg caa tat tct aaa caa gca atg ttt gag cac
Val Ile Ser Thr Ile Leu Gln Tyr Ser Lys Gln Ala Met Phe Glu His
    370                 375                 380
```

FIG. 41 (continued)

```
gtt gca aat aaa att cat aac aaa att gta gaa tgg gaa aaa aat aat
Val Ala Asn Lys Ile His Asn Lys Ile Val Glu Trp Glu Lys Asn Asn
385                 390                 395                 400

cac ggt aag aac tac ttt gaa aat ggt tac gat gcc cgt tat ctt gcg
His Gly Lys Asn Tyr Phe Glu Asn Gly Tyr Asp Ala Arg Tyr Leu Ala
                405                 410                 415

aat tta caa gat aat atg aaa ttc tta ctg aac tta aac aaa gag tta
Asn Leu Gln Asp Asn Met Lys Phe Leu Leu Asn Leu Asn Lys Glu Leu
            420                 425                 430

cag gca gaa cgt gtc atc gct att act cag cag caa tgg gat aac aac
Gln Ala Glu Arg Val Ile Ala Ile Thr Gln Gln Gln Trp Asp Asn Asn
        435                 440                 445

att ggt gat tta gct ggt att agc cgt tta ggt gaa aaa gtc ctt agt
Ile Gly Asp Leu Ala Gly Ile Ser Arg Leu Gly Glu Lys Val Leu Ser
    450                 455                 460

ggt aaa gcc tat gtg gat gcg ttt gaa gaa ggc aaa cac att aaa gcc
Gly Lys Ala Tyr Val Asp Ala Phe Glu Glu Gly Lys His Ile Lys Ala
465                 470                 475                 480

gat aaa tta gta cag ttg gat tcg gca aac ggt att att gat gtg agt
Asp Lys Leu Val Gln Leu Asp Ser Ala Asn Gly Ile Ile Asp Val Ser
                485                 490                 495

aat tcg ggt aaa gcg aaa act cag cat atc tta ttc aga acg cca tta
Asn Ser Gly Lys Ala Lys Thr Gln His Ile Leu Phe Arg Thr Pro Leu
            500                 505                 510

ttg acg ccg gga aca gag cat cgt gaa cgc gta caa aca ggt aaa tat
Leu Thr Pro Gly Thr Glu His Arg Glu Arg Val Gln Thr Gly Lys Tyr
        515                 520                 525

gaa tat att acc aag ctc aat att aac cgt gta gat agc tgg aaa att
Glu Tyr Ile Thr Lys Leu Asn Ile Asn Arg Val Asp Ser Trp Lys Ile
    530                 535                 540

aca gat ggt gca gca agt tct acc ttt gat tta act aac gtt gtt cag
Thr Asp Gly Ala Ala Ser Ser Thr Phe Asp Leu Thr Asn Val Val Gln
545                 550                 555                 560

cgt att ggt att gaa tta gac aat gct gga aat gta act aaa acc aaa
Arg Ile Gly Ile Glu Leu Asp Asn Ala Gly Asn Val Thr Lys Thr Lys
                565                 570                 575
```

FIG. 41 (continued)

```
gaa aca aaa att att gcc aaa ctt ggt gaa ggt gat gac aac gta ttt
Glu Thr Lys Ile Ile Ala Lys Leu Gly Glu Gly Asp Asp Asn Val Phe
            580                 585                 590

gtt ggt tct ggt acg acg gaa att gat ggc ggt gaa ggt tac gac cga
Val Gly Ser Gly Thr Thr Glu Ile Asp Gly Gly Glu Gly Tyr Asp Arg
        595                 600                 605

gtt cac tat agc cgt gga aac tat ggt gct tta act att gat gca acc
Val His Tyr Ser Arg Gly Asn Tyr Gly Ala Leu Thr Ile Asp Ala Thr
    610                 615                 620

aaa gag acc gag caa ggt agt tat acc gta aat cgt ttc gta gaa acc
Lys Glu Thr Glu Gln Gly Ser Tyr Thr Val Asn Arg Phe Val Glu Thr
625                 630                 635                 640

ggt aaa gca cta cac gaa gtg act tca acc cat acc gca tta gtg ggc
Gly Lys Ala Leu His Glu Val Thr Ser Thr His Thr Ala Leu Val Gly
                645                 650                 655

aac cgt gaa gaa aaa ata gaa tat cgt cat agc aat aac cag cac cat
Asn Arg Glu Glu Lys Ile Glu Tyr Arg His Ser Asn Asn Gln His His
            660                 665                 670

gcc ggt tat tac acc aaa gat acc ttg aaa gct gtt gaa gaa att atc
Ala Gly Tyr Tyr Thr Lys Asp Thr Leu Lys Ala Val Glu Glu Ile Ile
        675                 680                 685

ggt aca tca cat aac gat atc ttt aaa ggt agt aag ttc aat gat gcc
Gly Thr Ser His Asn Asp Ile Phe Lys Gly Ser Lys Phe Asn Asp Ala
    690                 695                 700

ttt aac ggt ggt gat ggt gtc gat act att gac ggt aac gac ggc aat
Phe Asn Gly Gly Asp Gly Val Asp Thr Ile Asp Gly Asn Asp Gly Asn
705                 710                 715                 720

gac cgc tta ttt ggt ggt aaa ggc gat gat att ctc gat ggt gga aat
Asp Arg Leu Phe Gly Gly Lys Gly Asp Asp Ile Leu Asp Gly Gly Asn
                725                 730                 735

ggt gat gat ttt atc gat ggc ggt aaa ggc aac gac cta tta cac ggt
Gly Asp Asp Phe Ile Asp Gly Gly Lys Gly Asn Asp Leu Leu His Gly
            740                 745                 750

ggc aag ggc gat gat att ttc gtt cac cgt aaa ggc gat ggt aat gat
Gly Lys Gly Asp Asp Ile Phe Val His Arg Lys Gly Asp Gly Asn Asp
        755                 760                 765
```

FIG. 41 (continued)

```
att att acc gat tct gac ggc aat gat aaa tta tca ttc tct gat tcg
Ile Ile Thr Asp Ser Asp Gly Asn Asp Lys Leu Ser Phe Ser Asp Ser
    770                 775                 780

aac tta aaa gat tta aca ttt gaa aaa gtt aaa cat aat ctt gtc atc
Asn Leu Lys Asp Leu Thr Phe Glu Lys Val Lys His Asn Leu Val Ile
785                 790                 795                 800

acg aat agc aaa aaa gag aaa gtg acc att caa aac tgg ttc cga gag
Thr Asn Ser Lys Lys Glu Lys Val Thr Ile Gln Asn Trp Phe Arg Glu
                805                 810                 815

gct gat ttt gct aaa gaa gtg cct aat tat aaa gca act aaa gat gag
Ala Asp Phe Ala Lys Glu Val Pro Asn Tyr Lys Ala Thr Lys Asp Glu
            820                 825                 830

aaa atc gaa gaa atc atc ggt caa aat ggc gag cgg atc acc tca aag
Lys Ile Glu Glu Ile Ile Gly Gln Asn Gly Glu Arg Ile Thr Ser Lys
        835                 840                 845

caa gtt gat gat ctt atc gca aaa ggt aac ggc aaa att acc caa gat
Gln Val Asp Asp Leu Ile Ala Lys Gly Asn Gly Lys Ile Thr Gln Asp
    850                 855                 860

gag cta tca aaa gtt gtt gat aac tat gaa ttg ctc aaa cat agc aaa
Glu Leu Ser Lys Val Val Asp Asn Tyr Glu Leu Leu Lys His Ser Lys
865                 870                 875                 880

aat gtg aca aac agc tta gat aag tta atc tca tct gta agt gca ttt
Asn Val Thr Asn Ser Leu Asp Lys Leu Ile Ser Ser Val Ser Ala Phe
                885                 890                 895

acc tcg tct aat gat tcg aga aat gta tta gtg gct cca act tca atg
Thr Ser Ser Asn Asp Ser Arg Asn Val Leu Val Ala Pro Thr Ser Met
            900                 905                 910

ttg gat caa agt tta tct tct ctt caa ttt gct agg gga tcc
Leu Asp Gln Ser Leu Ser Ser Leu Gln Phe Ala Arg Gly Ser
        915                 920                 925
```

*MYCOPLASMA* VACCINES AND USES THEREOF

CROSS-REFERENCE TO RELATED APPLICATIONS

This application is a Continuation application of U.S. application Ser. No. 15/746,770, claiming International Filing Date of Jul. 22, 2016, which is a US national phase application under 35 U.S.C. § 371 of International Application No. PCT/CA2016/050864, filed on Jul. 22, 2016, which claims the priority benefit of U.S. Provisional Application No. 62/195,581, filed on Jul. 22, 2015, and U.S. Provisional Application No. 62/195,602, filed on Jul. 22, 2015, the disclosures of each of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 267342002701SEQLIST.TXT, date recorded: Apr. 16, 2021, size: 343 KB).

TECHNICAL FIELD

The present invention pertains generally to immunogenic compositions and methods for treating and/or preventing *Mycoplasma* infection. In particular, the invention relates to the use of multiple *Mycoplasma* antigens in subunit vaccine compositions to elicit immune responses against *Mycoplasma* infections such as contagious bovine pleuropneumonia.

BACKGROUND

*Mycoplasma*, belonging to the class Mollicutes, is a bacterium that lacks a cell wall and causes a number of diseases in humans, livestock, domestic animals and birds. *Mycoplasma* diseases cause serious illness in humans and other animals and also result in severe economic losses to the food industry.

For example, contagious bovine pleuropneumonia (CBPP) is a highly communicable lung disease in cattle caused by *Mycoplasma mycoides* subsp. *mycoides* (Mmm), previously specified as biotype small colony (Mmm SC) (Manso-Silvan et al., *International.fournal of Systematic and Evolutionary Microbiology* (2009) 59 1353-1358). Currently, the disease is a major constraint to cattle production in Africa causing severe socio-economic consequences. For example, CBPP is included in the Office International des Epizooties (O.I.E.) reportable diseases and hence affected countries are excluded from international trade of live animals and embryos.

Many countries have successfully eradicated the disease by employing a combination of test, slaughter and vaccination. Historically CBPP was eradicated by eliminating the whole cattle herd wherever the disease was detected i.e. stamping-out. This strategy, however, does not prove realistic in some countries where it is considered too costly and logistically difficult to apply. Stamping-out is also problematic because CBPP occurs among pastoral communities where movement control is difficult to implement. Therefore, extensive vaccination programs remain the only viable option for CBPP control in Africa (Windsor, R. S., *Annals of the New York Academy of Science*, (2000) 916:326-332, March, J. B., *Vaccine* (2004) 22:4358-4364).

Vaccines against CBPP have included live attenuated strains of Mmm, such as V5, KH3J, T1/44 and its streptomycin-resistant derivative T1/SR. Although these vaccines confer some level of protection, they are constrained by low potency and efficacy (Karst, O., *Research in Veterinary Science* (1971) 12:18-22; Masiga et al., *Reviews of Science and Technology Office of International Epizootics* (1995) 14:611-620; Tulasne et al., *Reviews of Science and Technology Office of International Epizootics* (1996) 15:1373-1396; Nicholas et al., *Veterinary Bulletin* (2000) 70:827-838; Thiaucourt et al., *Annals of the New York Academy of Science* (2000) 916:71-80). Additionally, these vaccines are known to cause severe adverse effects post-vaccination (Daleel, E. E., *Bulletin of Epizootic Diseases in Africa* (1971) 20:199-202; Revell, S. G., *Troppical Animal Health and Production* (1973) 5:246-52; Provost et al., *Reviews of Science and Technology Office of International Epizootics* (1987) 6:625-679) and induce short-term immunity, one year or less (Egwu et al., *Veterinary Bulletin* (1996) 66:875-888. Thus, annual vaccination is necessary to achieve a sufficient level of protection (Thiaucourt et al., *Annals of the New York Academy of Science* (2000) 916:71-80).

A number of recombinant proteins from Mmm have been tested for their capacity to induce protection. It is known that variable surface proteins may enhance colonization of lung and may be differentially expressed between cultured or in vivo organisms. However, a combination of five variable surface proteins from Mmm did not provide protection against CBPP (Hamsten et al., *Clinical and Vaccine Immunology* (2010) 17:853-86). Another membrane protein, trans-membrane L-α-glycerol-3-phosphate oxidase (GlpO) was used to immunize cattle, but no protection was observed (Mulongo et al., *Vaccine* (2013) 31:5020-5025). Similarly, animals immunized against Lipoprotein Q (LppQ) were not protected, but exhibited significantly enhanced post-challenge pathology (Mulongo et al., *Infect. Immun.* (2015) 83:1992-2000).

However, the use of *Mycoplasma* proteins and nucleic acids as described herein in vaccine compositions has not heretofore been suggested. It is clear there remains an urgent need for the development of effective strategies for the treatment and prevention of *Mycoplasma* infection.

SUMMARY OF THE INVENTION

The present invention is based on the discovery of *Mycoplasma* proteins for use in subunit vaccine compositions that stimulate humoral, cellular and/or protective immune responses in animals and humans. A systematic approach was used to identify such proteins. In particular, reverse vaccinology was employed in which *M. mycoides* proteins were prioritized for their likelihood to protect against disease using bioinformatics and reactivity with antisera from infected cattle. The prioritized proteins were then tested for their capacity to induce antibody and proliferation reactions. A multitude of recombinant proteins that were identified as most likely to be immunogenic were used to immunize animals and humoral and cellular immune responses were quantified. Additionally, animals were challenged with the *M. mycoides* proteins to reveal protective antigens against contagious bovine pleuropneumonia (CBPP).

Thus, the *Mycoplasma* compositions described herein are useful for the treatment and/or prevention of various *Mycoplasma* infections, including CBPP. Such compositions can reduce the prevalence of *Mycoplasma* diseases which can lead to life threatening infections in humans and non-human animals and provide safer and more effective subunit vaccines.

Accordingly, the invention is directed to isolated, immunogenic *Mycoplasma* proteins, fusions of one or more of these proteins, or conjugates of these proteins with immunogenic carriers and compositions comprising the same.

In one embodiment, the immunogenic *Mycoplasma* protein is selected from: (a) a fusion protein comprising two or more *M mycoides* proteins selected from *M. mycoides* subsp. *mycoides* (Mmm) and *M. mycoides* subsp. *capri* (Mmc) proteins (b) an Mmm or Mmc protein or fusion protein conjugated with an immunogenic carrier, (c) variants of the proteins of (a) and (b); or (d) a protein corresponding to (a) or (b) from another *Mycoplasma* strain, species or subspecies. In certain embodiments, the Mmm and Mmc protein or fusion protein comprises an Mmm and/or an Mmc protein listed in Table 1 or Table 4, variants thereof, or the corresponding proteins from another *Mycoplasma* strain, species or subspecies.

In additional embodiments, the immunogenic protein or fusion protein comprises (a) a protein comprising the amino acid sequence of SEQ ID NOS:2, 4, 6, 8, 10, 12, 14, 16, 18, 20, 22, 24, 26 or 28; (b) an Mmm protein present in the fusion of SEQ ID NO:75; (c) an Mmm protein present in the fusion of SEQ ID NO:77; (d) variants of (a), (b) and (c); or (e) the corresponding protein from another *Mycoplasma* strain, species or subspecies.

In certain embodiments, the fusion protein is selected from: (a) a protein comprising the amino acid sequence of SEQ ID NO:51, (b) a protein comprising the amino acid sequence of SEQ ID NO:53; (c) a protein comprising amino acids 927-1421 of SEQ ID NO:75; (d) a protein comprising amino acids 927-1468 of SEQ ID NO:77; (e) variants of (a), (b), (c) and (d); or (f) a fusion protein comprising proteins corresponding to (a), (b), (c) and (d) from another *Mycoplasma* strain, species or subspecies.

In additional embodiments, the Mmm or Mmc protein conjugated with a carrier comprises the amino acid sequence of an Mmm or Mmc protein listed in Table 4. In certain embodiments, the carrier is an RTX toxin, such as a detoxified leukotoxin molecule. In certain embodiments, the amino acid sequence of the protein conjugate comprises the amino acid sequence of SEQ ID NOS:55, 57, 59, 61, 63, 65, 67, 69, 71, 73, 75, 77, 79 or 81, or a variant thereof.

In further embodiments, a composition is provided that comprises at least one immunogenic protein as described above, and a pharmaceutically acceptable excipient.

In other embodiments, a composition is provided that comprises at least two immunogenic Mmm and/or Mmc proteins selected from the Mmm and Mmc proteins listed in Tables 1 and 4, immunogenic fragments or variants thereof, or the corresponding *Mycoplasma* proteins from another *Mycoplasma* strain, species or subspecies, and a pharmaceutically acceptable excipient.

In certain embodiments, the *Mycoplasma* proteins of the composition are selected from two or more proteins comprising the amino acid sequences of SEQ ID NOS:2, 4, 6, 8, 10, 12, 14, 16, 18, 20, 22, 24, 26, 28; a protein comprising amino acids 927-1421 of SEQ ID NO:75, a protein comprising amino acids 927-1468 of SEQ ID NO:77; or variants thereof.

In additional embodiments, the composition comprises three to five *Mycoplasma* proteins, such as four or five *Mycoplasma* proteins. In certain embodiments, at least one of the proteins is selected from SEQ ID NOS:2, 4, 6, 8 or 10; or SEQ ID NOS:12, 14, 16, 18 or 20; or SEQ ID NOS:22, 24, 26 or 28.

In further embodiments, the two or more proteins in the composition are provided as a fusion protein.

In yet additional embodiments, the one or more of the proteins comprises an amino acid sequence with at least 90% sequence identity to SEQ ID NOS: 2, 4, 6, 8, 10, 12, 14, 16, 18, 20, 22, 24, 26 or 28.

In additional embodiments, the composition further comprises an immunological adjuvant, such as an adjuvant that comprises (a) a polyphosphazine; (b) a CpG oligonucleotide or a poly(I:C); and (c) a host defense peptide.

In further embodiments, a DNA molecule is provided. The DNA molecule is modified for expression in *E. coli* and is selected from: SEQ ID NOS. 1, 3, 5, 7, 9, 11, 13, 15, 17, 19, 21, 23, 25 or 27; or a DNA sequence that comprises a nucleotide sequence encoding an Mmm protein, wherein the DNA sequence is present in SEQ ID NOS: 50, 52, 54, 56, 58, 60, 62, 64, 66, 68, 70, 72, 74, 76, 78, 80.

In additional embodiments, a recombinant vector is provided. The vector comprises (a) one or more DNA molecules as described above; and (b) control elements that are operably linked to the molecule whereby a coding sequence in the molecule can be transcribed and translated in a host cell.

Also provided is a host cell transformed with the recombinant vector, as well as a method of producing a *Mycoplasma* protein comprising: (a) providing a population of such host cells, and (b) culturing said population of cells under conditions whereby the protein encoded by the DNA molecule present in said recombinant vector is expressed.

In further embodiments, a method of treating or preventing a *Mycoplasma* infection in a vertebrate subject is provided. The method comprises administering a therapeutic amount of any one of the compositions described above, to the subject. In certain embodiments, the subject is a bovine subject and the *Mycoplasma* infection is contagious bovine pleuropneumonia.

In additional embodiments, the invention is directed to a use of an immunogenic composition as described above, for treating or preventing a *Mycoplasma* infection in a vertebrate subject. In certain embodiments, the subject is a bovine subject. In additional embodiments, the *Mycoplasma* infection is contagious bovine pleuropneumonia or an *M. bovis* infection.

These and other embodiments of the subject invention will readily occur to those of skill in the art in view of the disclosure herein.

BRIEF DESCRIPTION OF THE FIGURES

FIGS. 2A-2E show serum IgG2 responses against the recombinant proteins used in trial 1 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group. The protein name followed by (P) indicates the placebo group. The bars across the symbols show the median of the values. Significant differences between the titres in vaccinate and placebo groups are shown by asterisks, *=P<0.05; and **=P<0.01. Significant differences between the day 35 titres of the vaccinated and placebo group for each protein are shown by a=P<0.05, b=P<0.01. Differences between the day 35 IgG2 titres between proteins are shown by #=P<0.05 and &=P<0.01.

FIGS. 4A-4E show serum IgG2 responses against the recombinant proteins used in trial 2 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group. The protein name followed by (P) indicates the placebo group. The bars across the symbols show the median of the values. Significant differences between the titres in the vaccinated and placebo groups are shown by asterisks; *=P<0.05; and **=P<0.01. Significant differences between the day 35 titres of the vaccinated and placebo group for each protein are shown by a=P<0.05, b=P<0.01. Differences between the day 35 IgG2 titres between proteins are shown by #=P<0.05 and &=P<0.01.

FIGS. 6A-6D show serum IgG2 responses against the recombinant proteins used in trial 3 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group. The protein name followed by (P) indicates the placebo group. The bars across the symbols show the median of the values. Significant differences between the titres in the vaccinated and placebo groups are shown by asterisks; *=P<0.05; and **=P<0.01. Significant differences between the day 35 titres of the vaccinated and placebo group for each protein are shown by a=P<0.05, b=P<0.01. Differences between the day 35 IgG2 titres between proteins are shown by #=P<0.05 and &=P<0.01.

FIGS. 9A-9D show PBMC proliferative responses in trial 3 after incubation with the recall antigens as described in the examples The groups are listed on the top of each panel The mean and standard deviation of the stimulation indexes (Si) at day 35 (Two weeks after the boost) for the vaccinated (Black circles) and placebo (Black triangles) groups are shown. The X-axis shows the positive control (ConA) and the recall antigens used in each group. There were no significant differences between the vaccinated and placebo Si for each of the recall antigens and no differences between the Si of any of the antigens in the vaccinated groups.

FIGS. 11A-11B (SEQ ID NOS:1 and 2) show the modified nucleotide sequence of MSC_0136 (SEQ ID NO:1) and the amino acid sequence of the protein antigen MSC_0136 (SEQ ID NO:2) used in the examples. The sequences differ from those reported in NCBI in that the DNA sequence has been modified for expression in *E. coli*; and the protein sequence lacks the first 24 amino acids (the signal sequence).

FIGS. 12A-12B (SEQ ID NOS:3 and 4) show the modified nucleotide sequence of MSC_0957 (SEQ ID NO:3) and the amino acid sequence of the protein antigen MSC_0957 (SEQ ID NO:4) used in the examples. The sequences differ from those reported in NCBT in that the DNA sequence has been modified for expression in *E. coli*; and the protein sequence lacks the first 23 amino acids (the signal sequence).

FIGS. 13A-13B (SEQ ID NOS:5 and 6) show the modified nucleotide sequence of MSC_0499 (SEQ ID NO:5) and amino acid sequence of the protein antigen MSC_0499 (SEQ ID NO:6) used in the examples. The sequences differ from those reported in NCBI in that the DNA sequence has been modified for expression in *E. coli*; and the protein sequence lacks the first 23 amino acids (the signal sequence).

FIGS. 14A-14B (SEQ ID NOS:7 and 8) show the modified nucleotide sequence of MSC_0431 (SEQ ID NO:7) and amino acid sequence of the protein antigen MSC_0431 (SEQ ID NO:8) used in the examples. The sequences differ from those reported in NCBI in that the DNA sequence has been modified for expression in *E. coli*; and the protein sequence lacks the first 26 amino acids (the signal sequence).

FIGS. 15A-15B (SEQ ID NOS:9 and 10) show the modified nucleotide sequence of MSC_0776 (SEQ ID NO:9) and amino acid sequence of the protein antigen MSC_0776 (SEQ ID NO:10) used in the examples. The sequences differ from those reported in NCBI in that the DNA sequence has been modified for expression in *E. coli*; and the protein sequence lacks the first 27 amino acids (the signal sequence).

FIGS. 16A-16B (SEQ ID NOS:11 and 12) show the nucleotide sequence, modified for expression in *E. coli*, of YP_004400559.1 (SEQ ID NO:11) and amino acid sequence of the protein antigen YP_004400559.1 (SEQ ID NO:12) used in the examples. The amino acid sequence differs from that reported in NCBI in that the sequence lacks the first 24 amino acids (the signal sequence) and includes an N-terminal methionine.

FIGS. 17A-17B (SEQ ID NOS:13 and 14) show the nucleotide sequence, modified for expression in *E. coli*, of YP_004399807.1 (SEQ ID NO:13) and amino acid sequence of the protein antigen YP_004399807.1 (SEQ ID NO:14) used in the examples. The amino acid sequence differs from that reported in NCBI in that the sequence lacks the first 24 amino acids (the signal sequence) and includes an N-terminal methionine.

FIGS. 18A-18B (SEQ ID NOS:15 and 16) show the modified nucleotide sequence of MSC_0816 (SEQ ID NO: 15) and amino acid sequence of the protein antigen MSC_0816 (SEQ ID NO:16) used in the examples. The sequences differ from those reported in NCBI in that the DNA sequence has been modified for expression in *E. coli*; and the protein sequence lacks the first 23 amino acids (the signal sequence).

FIGS. 19A-19B (SEQ ID NOS:17 and 18) show the modified nucleotide sequence of MSC_0160 (SEQ ID NO:17) and amino acid sequence of the protein antigen MSC_0160 (SEQ ID NO:18) used in the examples. The DNA sequence differs from that reported in NCBI in that the DNA sequence has been modified for expression in *E. coli.*

FIGS. 20A-20B (SEQ ID NOS:19 and 20) show the modified nucleotide sequence of MSC_0775 (SEQ ID NO:19) and amino acid sequence of the protein antigen MSC_0775 (SEQ ID NO:20) used in the examples. The sequences differ from those reported in NCBI in that the DNA sequence has been modified for expression in *E. coli*; and the protein sequence lacks the first 25 amino acids (the signal sequence).

FIGS. 21A-21B (SEQ ID NOS:21 and 22) show the nucleotide sequence, modified for expression in *E. coli*, of YP_004400127.1 (SEQ ID NO:21) and amino acid sequence of the protein antigen YP_004400127.1 (SEQ ID NO:22) used in the examples. The amino acid sequence differs from that reported in NCBI in that it lacks the first 23 amino acids (the signal sequence) and includes an N-terminal methionine.

FIGS. 22A-22B (SEQ ID NOS:23 and 24) show the nucleotide sequence, modified for expression in *E. coli*, of YP_004399790.1 (SEQ ID NO:23) and amino acid sequence of the protein antigen YP_004399790.1 (SEQ ID NO:24) used in the examples.

FIGS. 23A-23B (SEQ ID NOS:25 and 26) show the nucleotide sequence, modified for expression in *E. coli*, of YP_004400580.1 (SEQ ID NO:25) and amino acid sequence of the protein antigen YP_004400580.1 (SEQ ID NO:26) used in the examples. The amino acid sequence differs from that reported in NCBI in that it lacks 15 amino acids from the C-terminus.

FIGS. 24A-24B (SEQ ID NOS:27 and 28) show the nucleotide sequence, modified for expression in *E. coli*, of YP_004400610.1 (SEQ ID NO:27) and amino acid sequence of the protein antigen YP_004400610.1 (SEQ ID NO:28) used in the examples. The amino acid sequence differs from that reported in NCBI in that the sequence lacks the first 24 amino acids (the signal sequence) and includes an N-terminal methionine.

FIGS. 25A-25B (SEQ ID NOS:50 and 51) show the nucleotide sequence, modified for expression in *E. coli*, of a fusion (SEQ ID NO:50) between YP_004400127.1 and YP_004399790.1 and the amino acid sequence of the protein fusion (SEQ ID NO:51) used in the examples. The YP_004400127.1 sequence occurs at positions 1-214 of the protein and the YP_004399790.1 sequence is present at positions 221-532 of the protein. The two sequences are linked by a $Gly_6$ linker, bolded in the figure.

FIGS. 26A-26B (SEQ ID NOS:52 and 53) show the nucleotide sequence, modified for expression in *E. coli*, of a fusion (SEQ ID NO:52) between sequences derived from YP_004400610.1 and YP_00400580.1 and the amino acid sequence of the protein fusion (SEQ ID NO:53) used in the examples. The YP_004400610.1 sequence occurs at positions 1-189 of the protein and the sequence derived from YP_004399790.1 is present at positions 195-557 of the protein. The YP_00400580.1 sequence in the fusion lacks the first 20 amino acids present in the YP_00400580.1 sequence shown in SEQ ID NO:26. The two sequences are linked by a $Gly_5$ linker, bolded in the figure.

FIGS. 27A-27B (SEQ ID NOS:54 and 55) show the nucleotide sequence, modified for expression in *E. coli*, (SEQ ID NO:54) and amino acid sequence (SEQ ID NO:55) of pAA352-YP 004400127.1-YP 004399790.1 used in the examples. The leukotoxin 352 carrier, (also termed "LKT 352" and "LtxA" herein) occurs at positions 1-926 of the amino acid sequence and is bolded in SEQ ID NO:55, The YP_004400127.1 sequence occurs at positions 927-1140 of SEQ ID NO:55, the YP_004399790.1 sequence is present at positions 1147-1458 of SEQ ID NO:55. The two sequences are linked by a $Gly_6$ linker, bolded in the figure.

FIGS. 28A-28B (SEQ ID NOS:56 and 57) show the nucleotide sequence, modified for expression in *E. coli*, (SEQ ID NO:56) and amino acid sequence (SEQ ID NO:57) of pAA352-YP_004400610.1-YP_00400580.1 used in the examples The leukotoxin 352 carrier, (also termed "LKT 352" and "LtxA" herein) occurs at positions 1-926 of the amino acid sequence and is bolded in SEQ ID NO:57; The YP_004400610.1 sequence occurs at positions 927-1115 of SEQ ID NO:57; the YP_00400580.1 sequence is present at positions 1121-1483 of SEQ ID NO:57. The YP_00400580.1 sequence in the fusion lacks the first 20 amino acids present in the YP_00400580.1 sequence shown in SEQ ID NO:26. The two sequences are linked by a $Gly_5$ linker, bolded in the figure.

FIGS. 29A-29B (SEQ ID NOS:58 and 59) show the nucleotide sequence, modified for expression in *E. coli*, (SEQ ID NO:58) and amino acid sequence (SEQ ID NO:59) of pAA352-MSC_0160 used in the examples. The leukotoxin 352 carrier, (also termed "LKT 352" and "LtxA" herein) occurs at positions 1-926 of the amino acid sequence and is bolded in SEQ ID NO:59; The MSC_0160 sequence occurs at positions 927-1320 of SEQ ID NO:59. The MSC_0160 sequence lacks the N-terminal methionine shown in SEQ ID NO:18.

FIGS. 30A-30B (SEQ ID NOS:60 and 61) show the nucleotide sequence, modified for expression in *E. coli*, (SEQ ID NO:60) and amino acid sequence (SEQ ID NO:61) of pAA352-MSC_0136 used in the examples. The leukotoxin 352 carrier, (also termed "LKT 352" and "LtxA" herein) occurs at positions 1-926 of the amino acid sequence and is bolded in SEQ ID NO:61; the MSC_0136 sequence occurs at positions 927-1224 of SEQ ID NO:61.

FIGS. 31A-31B (SEQ ID NOS:62 and 63) show the nucleotide sequence, modified for expression in *E. coli*, (SEQ ID NO:62) and amino acid sequence (SEQ ID NO:63) of pAA352-MSC_0431 used in the examples. The leukotoxin 352 carrier, (also termed "LKT 352" and "LtxA" herein) occurs at positions 1-926 of the amino acid sequence and is bolded in SEQ ID NO:63; the MSC 0431 sequence occurs at positions 927-1256 of SEQ ID NO:63.

FIGS. 32A-32B (SEQ ID NOS:64 and 65) show the nucleotide sequence, modified for expression in *E. coli*, (SEQ ID NO:64) and amino acid sequence (SEQ ID NO:65) of pAA352-MSC_0499 used in the examples. The leukotoxin 352 carrier, (also termed "LKT 352" and "LtxA" herein) occurs at positions 1-926 of the amino acid sequence and is bolded in SEQ ID NO:65; the MSC_0499 sequence occurs at positions 927-1620 of SEQ ID NO:65.

FIGS. 33A-33B (SEQ ID NOS:66 and 67) show the nucleotide sequence, modified for expression in *E. coli*, (SEQ ID NO:66) and amino acid sequence (SEQ ID NO:67) of pAA352-MSC_0775 used in the examples. The leukotoxin 352 carrier, (also termed "LKT 352" and "LtxA" herein) occurs at positions 1-926 of the amino acid sequence and is bolded in SEQ ID NO 67; the MSC_0775 sequence occurs at positions 927-1608 of SEQ ID NO:67. The MSC_0775 sequence lacks the first 20 amino acids shown in SEQ ID NO:20.

FIGS. 34A-34B (SEQ ID NOS.68 and 69) show the nucleotide sequence, modified for expression in *E. coli*, (SEQ ID NO:68) and amino acid sequence (SEQ ID NO:69) of pAA352-MSC_0776 used in the examples. The leukotoxin 352 carrier, (also termed "LKT 352" and "LtxA" herein) occurs at positions 1-926 of the amino acid sequence and is bolded in SEQ ID NO:69; the MSC_0776 sequence occurs at positions 927-1681 of SEQ ID NO:69.

FIGS. 35A-35B (SEQ ID NOS:70 and 71) show the nucleotide sequence, modified for expression in *E. coli*, (SEQ ID NO:70) and amino acid sequence (SEQ ID NO:71) of pAA352-MSC_0816 used in the examples. The leukotoxin 352 carrier, (also termed "LKT 352" and "LtxA" herein) occurs at positions 1-926 of the amino acid sequence and is bolded in SEQ ID NO:71; the MSC_0816 sequence occurs at positions 927-1308 of SEQ ID NO:71.

FIGS. 36A-36B (SEQ ID NOS:72 and 73) show the nucleotide sequence, modified for expression in *E. coli*, (SEQ ID NO:72) and amino acid sequence (SEQ ID NO:73) of pAA352-MSC_0957 used in the examples. The leukotoxin 352 carrier, (also termed "LKT 352" and "LtxA" herein) occurs at positions 1-926 of the amino acid sequence and is bolded in SEQ ID NO:73; the MSC_0957 sequence occurs at positions 927-1336 of SEQ ID NO:73.

FIGS. 37A-37B (SEQ ID NOS:74 and 75) show the nucleotide sequence, modified for expression in *E. coli*, (SEQ ID NO:74) and amino acid sequence (SEQ ID NO:75) of pAA352-MSC_0466-MSC_0117 used in the examples. The leukotoxin 352 carrier, (also termed "LKT 352" and "LtxA" herein) occurs at positions 1-926 of the amino acid sequence and is bolded in SEQ ID NO:75; The MSC 0466 sequence occurs at positions 927-1180 of SEQ ID NO:75; the MSC 0117 sequence is present at positions 1184-1421 of SEQ ID NO:75. The two sequences are linked by a $Gly_3$ linker, bolded in the figure.

FIGS. 38A-38B (SEQ ID NOS:76 and 77) show the nucleotide sequence, modified for expression in *E. coli*, (SEQ ID NO:76) and amino acid sequence (SEQ ID NO:77) of pAA352-MSC_0922-MSC_1058 used in the examples. The leukotoxin 352 carrier, (also termed "LKT 352" and "LtxA" herein) occurs at positions 1-926 of the amino acid sequence and is bolded in SEQ ID NO:77; The MSC_0922 sequence occurs at positions 927-1325 of SEQ ID NO:77; the MSC_1058 sequence is present at positions 1329-1468 of SEQ ID NO:77. The two sequences are linked by a $Gly_3$ linker, bolded in the figure.

FIGS. 39A-39B (SEQ ID NOS:78 and 79) show the nucleotide sequence, modified for expression in *E. coli*, (SEQ ID NO:78) and amino acid sequence (SEQ ID NO:79) of pAA352-YP_004399807.1 used in the examples. The leukotoxin 352 carrier, (also termed "LKT 352" and "LtxA" herein) occurs at positions 1-926 of the amino acid sequence and is bolded in SEQ ID NO:79; the YP_004399807.1 sequence occurs at positions 927-1273 of SEQ ID NO:79. The YP_004399807.1 sequence lacks the N-terminal methionine shown in SEQ ID NO:14.

FIGS. 40A-40B (SEQ ID NOS:80 and 81) show the nucleotide sequence, modified for expression in *E. coli*, (SEQ ID NO:80) and amino acid sequence (SEQ ID NO:81) of pAA352-YP_00400559.1 used in the examples. The leukotoxin 352 carrier, (also termed "LKT 352" and "LtxA" herein) occurs at positions 1-926 of the amino acid sequence and is bolded in SEQ ID NO:81, the YP_00400559.1 sequence occurs at positions 927-1061 of SEQ ID NO:81. The YP_00400559.1 sequence lacks the N-terminal methionine shown in SEQ ID NO:12.

FIG. 41 (SEQ ID NOS:82 and 83) shows the nucleotide sequence (SEQ ID NO:82) and amino acid sequence (SEQ ID NO:83) of a representative leukotoxin 352 (LKT 352) from plasmid pAA352. The first 10 N-terminal amino acids and last 2 C-terminal amino acids depicted in the figure are flanking sequences from plasmid pAA352. The remaining amino acids are leukotoxin sequences. LKT 352 is a detoxified mutant of leukotoxin.

DETAILED DESCRIPTION OF THE INVENTION

Figures 1A, 1B, 1C, 1D, 1E:
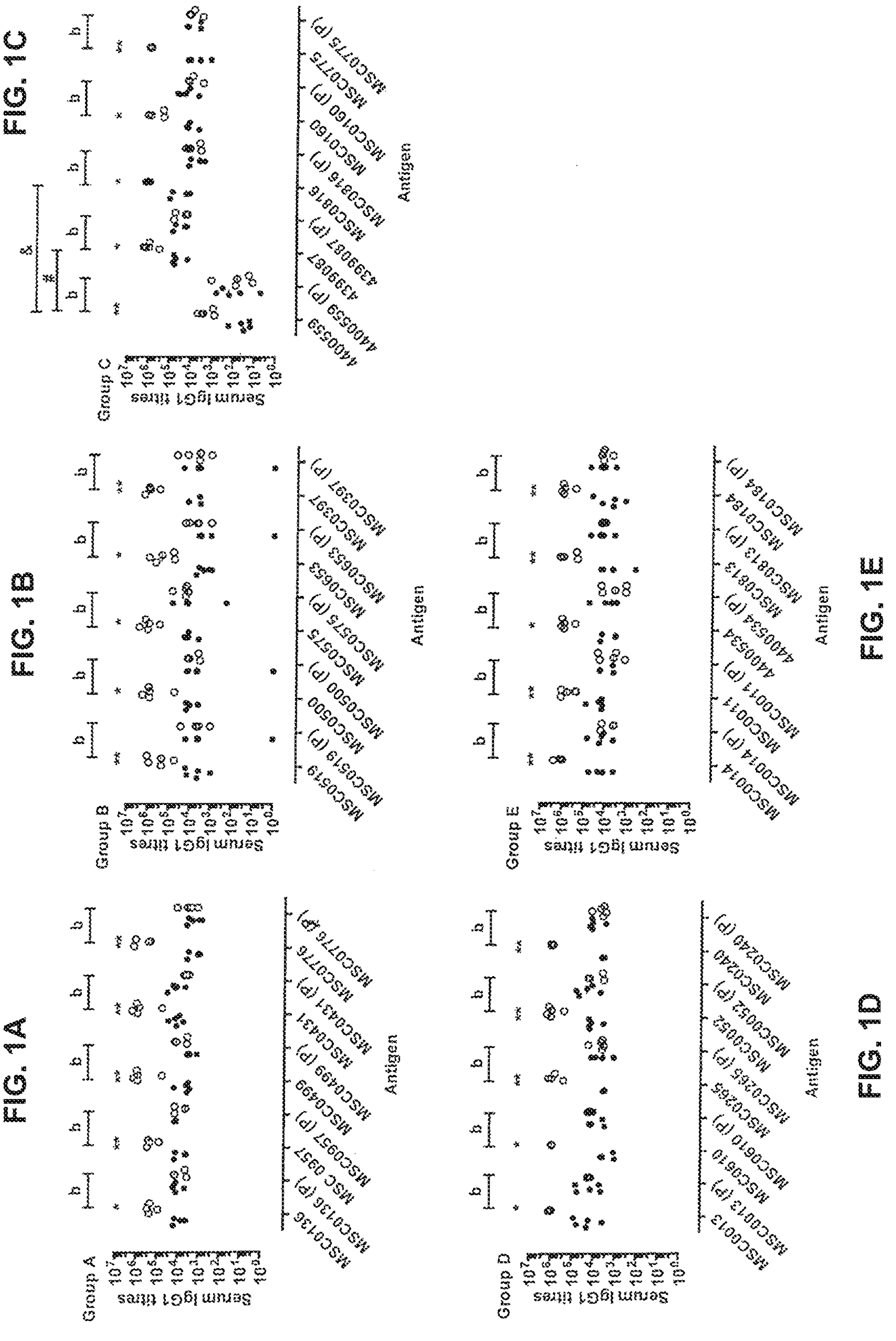
FIGS. 1A-1E show serum IgG1 immune responses to recombinant proteins used in trial 1 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group (names shortened for clarity purposes). The bars across the symbols show the median of the values. Significant differences between the day 0 and day 35 titres for each antigen are shown by asterisks, *=P<0.05; and **=P<0.01. Significant differences between the day 35 titres of the vaccinated and placebo group for each protein are shown by a=P<0.05, b=P<0.01. Differences between the day 35 IgG1 titres between proteins in the same group are shown by #=P<0.05 and &=P<0.01.

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology*, Current Edition, vol. I & II (B. N. Fields and D. M. Knipe, eds.); *Handbook of Experimental Immunology*, Vols.

I-IV (D. M. Weir and C. C. Blackwell eds., Blackwell Scientific Publications); T. E. Creighton, *Proteins: Structures and Molecular Properties* (W. H. Freeman and Company); A. L. Lehninger, *Biochemistry* (Worth Publishers, Inc., current edition); Sambrook, et al., *Molecular Cloning: A Laboratory Manual* (current edition); *Methods in Enzymology* (S. Colowick and N. Kaplan eds, Academic Press, Inc.).

All publications, patents and patent applications cited herein, whether supra or ifra, are hereby incorporated by reference in their entireties.

The following amino acid abbreviations are used throughout the text:

| | | | |
|---|---|---|---|
| Alanine: | Ala (A) | Arginine: | Arg (R) |
| Asparagine: | Asn (N) | Aspartic acid: | Asp (D) |
| Cysteine: | Cys (C) | Glutamine: | Gln (Q) |
| Glutamic acid: | Glu (E) | Glycine: | Gly (G) |
| Histidine: | His (H) | Isoleucine: | Ile (I) |
| Leucine: | Leu (L) | Lysine: | Lys (K) |
| Methionine: | Met (M) | Phenylalanine: | Phe (F) |
| Proline: | Pro (P) | Serine: | Ser (S) |
| Threonine: | Thr (T) | Tryptophan: | Trp (W) |
| Tyrosine: | Tyr (Y) | Valine: | Val (V) |

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an antigen" includes a mixture of two or more such antigens, and the like.

As used herein, the term "*Mycoplasma*" refers to bacteria belonging to the class Mollicutes and the genus *Mycoplasma*. The term intends any species and subspecies of the genus *Mycoplasma*, which is capable of causing disease in an animal or human subject. Such species are described below.

As used herein, the term "*Mycoplasma mycoides*" or "*M. mycoides*" refers to any of the species and subspecies from the *Mycoplasma mycoides* cluster, a group of closely related infectious mycoplasmas. The cluster contains several species and subspecies including *M. mycoides* subsp *mycoides* biotype Small Colony (MmmSC); *M. mycoides* subsp. *mycoides* biotype Large Colony (MmmLC); *M. mycoides* subsp. *capri* (Mmc); *M. capricolum* subsp. *capricolum* (Mcc); *M. capricolum* subsp. *capripneumoniae* (Mccp); and *Mycoplasma* sp. 'bovine group 7' (MBG7).

The term "derived from" is used herein to identify the original source of a molecule but is not meant to limit the method by which the molecule is made which can be, for example, by chemical synthesis or recombinant means.

A "*Mycoplasma* molecule" is a molecule derived from *Mycoplasma*, including, without limitation, polypeptide, protein, antigen, polynucleotide, oligonucleotide, and nucleic acid molecules, as defined herein, from any of the various *Mycoplasma* species and subspecies. The molecule need not be physically derived from the particular bacterium in question, but may be synthetically or recombinantly produced. Nucleic acid and polypeptide sequences for a number of *Mycoplasma* species are known and/or described herein. Representative *Mycoplasma* sequences for use in treating and/or preventing Al *mycoides* infection, such as CBPP, are presented in Tables 1 and 4 and FIGS. 11-40 herein. It is to be understood that while Table 4 and several figures describe *M. mycoides* fusion proteins, as well as conjugates of the fusions, the individual *M. mycoides* proteins in the fusions and the conjugates are also intended The boundaries of the individual *M mycoides* proteins present in the fusions, as well as the *M. mycoides* proteins present in the conjugates, are described above.

Additional representative sequences found in various species are listed in the National Center for Biotechnology Information (NCBI) database. However, a *Mycoplasma* molecule, such as an antigen, as defined herein, is not limited to those shown and described in Tables 1 and 4 and FIGS. 11-40, as various isolates are known and variations in sequences may occur between them.

By "*Mycoplasma* disease" is meant a disease caused in whole or in part by a *Mycoplasma* bacterium. For example, *Mycoplasma* bacteria cause a number of diseases in animals, such as but not limited to pneumonia, e.g., contagious bovine pleuropneumonia, mastitis, arthritis, otitis, keratoconjunctivitis, synovitis, and reproductive disorders. In humans such diseases include pneumonia and other respiratory problems such as tracheobronchitis, bronchiolitis, pharyngitis and croup; pelvic inflammatory disease; and cancer.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

The term "peptide" as used herein refers to a fragment of a polypeptide. Thus, a peptide can include a C-terminal deletion, an N-terminal deletion and/or an internal deletion of the native polypeptide, so long as the entire protein sequence is not present. A peptide will generally include at least about 3-10 contiguous amino acid residues of the full-length molecule, and can include at least about 15-25 contiguous amino acid residues of the full-length molecule, or at least about 20-50 or more contiguous amino acid residues of the full-length molecule, or any integer between 3 amino acids and the number of amino acids in the full-length sequence, provided that the peptide in question retains the ability to elicit the desired biological response.

By "immunogenic" protein, polypeptide or peptide is meant a molecule which includes one or more epitopes and thus can modulate an immune response. Such peptides can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, New Jersey. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g, x-ray crystallography and 2-dimensional nuclear magnetic resonance. See, e.g., *Epitlope Mapping Protocols, supra*. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824-3828 for determining antigenicity profiles, and the Kyte-Doolittle technique, Kyte et al., *J. Mol. Biol.* (1982) 157:105-132 for hydropathy plots.

Immunogenic molecules, for purposes of the present invention, will usually be at least about 5 amino acids in length, such as at least about 10 to about 15 amino acids in length. There is no critical upper limit to the length of the molecule, which can comprise the full-length of the protein sequence, or even a fusion protein comprising two or more epitopes, proteins, antigens, etc..

As used herein, the term "epitope" generally refers to the site on an antigen which is recognized by a T-cell receptor and/or an antibody. Several different epitopes may be carried by a single antigenic molecule. The term "epitope" also includes modified sequences of amino acids which stimulate responses which recognize the whole organism. The epitope can be generated from knowledge of the amino acid and corresponding DNA sequences of the polypeptide, as well as from the nature of particular amino acids (e.g., size, charge, etc.) and the codon dictionary, without undue experimentation. See, e.g., Ivan Roitt, *Essential Immunol*; Janis Kuby, *Immunology.*

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

Thus, an immunological response as used herein may be one that stimulates the production of antibodies. The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells. are activated to, e.g., produce various cytokines, lymphokines and chemokines. Cells activated by an innate immune response include immature and mature Dendritic cells of the monocyte and plasmacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an immunogenic molecule where administration of the composition to a subject results in the development in the subject of a humoral and/or a cellular immune response to the molecule of interest.

An "antigen" refers to a molecule, such as a protein, polypeptide, or fragment thereof, containing one or more epitopes (either linear, conformational or both) that will stimulate a host's immune-system to make a humoral and/or cellular antigen-specific response. The term is used interchangeably with the term "immunogen." Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in DNA immunization applications, is also included in the definition of antigen herein.

By "subunit vaccine" is meant a vaccine composition that includes one or more selected antigens but not all antigens, derived from or homologous to, an antigen from a pathogen of interest. Such a composition is substantially free of intact pathogen cells or pathogenic particles, or the lysate of such cells or particles. Thus, a "subunit vaccine" can be prepared from at least partially purified (preferably substantially purified) immunogenic molecules from the pathogen, or analogs thereof. The method of obtaining an antigen included in the subunit vaccine can thus include standard purification techniques, recombinant production, or synthetic production.

By "carrier" is meant any molecule which when associated with an antigen of interest, imparts enhanced immunogenicity to the antigen.

The term "RTX" toxin, as used herein refers to a protein belonging to the family of molecules characterized by the carboxy-terminus consensus amino acid sequence Gly-Gly-X-Gly-X-Asp (SEQ ID NO:84, Highlander et al., DNA (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). In addition, the term "RTX toxin" refers to a member of the RTX family which is chemically synthesized, isolated from an organism expressing the same, or recombinantly produced. Furthermore, the term intends an immunogenic protein having an amino acid sequence substantially homologous to a contiguous amino acid sequence found in the particular native RTX molecule. Thus, the term includes both full-length and partial sequences, as well as analogues. Although native full-length RTX toxins display cytotoxic activity, the term "RTX toxin" also intends molecules which remain immunogenic yet lack the cytotoxic character of native molecules. In the chimeras produced according to the present invention, a selected RTX polypeptide sequence imparts enhanced immunogenicity to a fused *Mycoplasma* protein or fusion proteins comprising more than one *Mycoplasma* protein or antigen.

The term "leukotoxin polypeptide" or "LKT polypeptide" intends an RTX toxin derived from *P. haemolytica, Actinobacillus pleuropneumoniae*, among others, as defined above. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., DNA (1989) 8:15-28; Welch, *Mol. Microbiol.* (1991) 5:521-528. A selected leukotoxin polypeptide sequence imparts enhanced immunogenicity to a fused *Mycoplasma* protein or fusion proteins comprising more than one *Mycoplasma* protein or antigen.

"Substantially purified" generally refers to isolation of a substance such that the substance comprises the majority percent of the sample in which it resides. Typically in a sample, a substantially purified component comprises 50%, preferably 80%-85%, more preferably 90-95% of the sample. Techniques for purifying molecules of interest are well-known in the art and include, for example, ion-exchange chromatography, affinity chromatography and sedimentation according to density.

By "isolated" is meant that the indicated molecule is separate and discrete from the whole organism with which the molecule is found in nature or is present in the substantial absence of other biological macromolecules of the same type.

An "antibody" intends a molecule that "recognizes," i.e., specifically binds to an epitope of interest present in an antigen. By "specifically binds" is meant that the antibody interacts with the epitope in a "lock and key" type of interaction to form a complex between the antigen and antibody, as opposed to non-specific binding that might occur between the antibody and, for instance, components in a mixture that includes the test substance with which the antibody is reacted. The term "antibody" as used herein includes antibodies obtained from both polyclonal and monoclonal preparations, as well as, the following: hybrid (chimeric) antibody molecules (see, for example, Winter et al., *Nature* (1991).349:293-299; and U.S. Pat. No. 4,816,567); F(ab')2 and F(ab) fragments; Fv molecules (non-covalent heterodimers, see, for example, Inbar et al., *Proc Natl Acad, Sci USA* (1972)_69:2659-2662; and Ehrlich et al, *Biochem* (1980) 19:4091-4096); single-chain Fv molecules (sFv) (see, for example, Huston et al., *Proc Natl Acad Sci USA* (1988) 85:5879-5883); dimeric and trimeric antibody fragment constructs, minibodies (see, e.g., Pack et al., *Biochem* (1992) 31:1579-1584, Cumber et al., *J Immunology* (1992) 149B:120-126); humanized antibody molecules (see, for example, Riechmann et al., *Nature* (1988) 332:323-327; Verhoeyan et al., *Science* (1988)239:1534-1536; and U.K. Patent Publication No. GB 2,276,169, published 21 Sep. 1994); and, any functional fragments obtained from such molecules, wherein such fragments retain immunological binding properties of the parent antibody molecule.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, $F(ab')_2$, Fv, and other fragments, as well as chimeric and humanized homogeneous antibody populations, that exhibit immunological binding properties of the parent monoclonal antibody molecule.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80% -85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, DC, which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, WI) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, CA). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none;

strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning. supra; Nucleic Acid Hybridization, supra.*

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc ), as well as unmodified forms of the polynucleotide or oligonucleotide. In particular, DNA is deoxyribonucleic acid.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vitro or in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. "Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a MI3 origin of replication), at least one multiple cloning site, and a "mammalian" origin of replication (e.g., a SV40 or adenovirus origin of replication).

The term "transfection" is used to refer to the uptake of foreign DNA by a cell. A cell has been "transfected" when exogenous DNA has been introduced inside the cell membrane. A number of transfection techniques are generally known in the art See, e.g., Graham et al. (1973) *Virology,* 52:456, Sambrook et al., *Molecular Cloning, a laboratory manual*, Cold Spring Harbor Laboratories, New York, Davis et al. *Basic Methods in Molecular Biology*, Elsevier. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; non-domestic animals such as elk, deer, mink and feral cats; laboratory animals including rodents such as mice, rats and guinea pigs; birds, including domestic, wild and game birds such as chickens, turkeys and other gallinaceous birds, ducks, geese, pheasant, emu, ostrich and the like. The term does not denote a particular age. Thus, both adult and newborn individuals are intended to be covered.

By "therapeutically effective amount" in the context of the immunogenic compositions described herein is meant an amount of an immunogen which will induce an immunological response, either for antibody production or for treatment or prevention of infection.

As used herein, "treatment" refers to any of (i) the prevention of infection or reinfection, as in a traditional vaccine, or (ii) the reduction or elimination of symptoms from an infected individual. Treatment may be effected prophylactically (prior to infection) or therapeutically (following infection). Additionally, prevention or treatment in the context of the present invention can be a reduction of the amount of bacteria present in the subject of interest.

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based in part on the discovery of immunogenic *Mycoplasma* molecules and formulations comprising combinations of *Mycoplasma* antigens that stimulate an immune response in a subject of interest. These molecules can be provided in an isolated form, as discrete components or as fusion proteins, and may be conjugated to a carrier that enhances immunogenicity of the antigens. The antigens can be incorporated into a pharmaceutical composition, such as a vaccine composition.

In particular, the inventors herein have identified numerous protein antigens in *Mycoplasma mycoides* subsp. *mycoides* (Mmm) and *Mycoplasma mycoides* subsp. *capri* (Mmc) as described in the examples. Immunization of cattle with subunit vaccines comprising several *M. mycoides* antigens elicited significant humoral responses and conferred protection against contagious bovine pleuropneumonia using an Mmm experimental challenge in cattle.

The present invention thus provides immunological compositions and methods for treating and/or preventing *Mycoplasma* disease. Immunization can be achieved by any of the methods known in the art including, but not limited to, use of vaccines containing one or more isolated *Mycoplasma* antigens or fusion proteins comprising multiple antigens, or by passive immunization using antibodies directed against the antigens. Such methods are described in detail below. Moreover, the antigens and antibodies described herein can be used for detecting the presence of *Mycoplasma* bacteria, for example in a biological sample.

The vaccines are useful in vertebrate subjects that are susceptible to *Mycoplasma* infection, including without limitation, animals such as farm animals, including cattle, sheep, pigs, goats and horses; domestic mammals such as dogs and cats, non-domestic animals such as elk, deer, mink and feral cats; humans; avian species, and other species that are raised for meat or egg production such as, but not limited to, chickens, turkeys, geese, ducks, pheasant, emu and ostrich.

In order to further an understanding of the invention, a more detailed discussion is provided below regarding *Mycoplasma* antigens, production thereof, compositions comprising the same, and methods of using such compositions in the treatment or prevention of infection, as well as in the diagnosis of infection.

A. *Mycoplasma* Antigens

Antigens for use in the subject compositions can be derived from any of the several *Mycoplasma* species and subspecies that cause infection, including without limitation, *M. gallisepticum; M. genitalium; M. haemufelis; M. hominis; M. hyopneumoniae; M. laboratorium; M. ovipneumoniae; M. pneumoniae; M. fermentans; M. hyorhinis; M. bovis; M. pulmonis; M. penetrans; M. arthritidis, M. hyponeumoniae; M. agalactiea; M. mycoides; M. arginini; M. adleri; M. agassizii; M.; alkalesens; M. alligatoris; M. amphoriforme; M. anatis; M. anseris; M. auris; M. bovigenitalium; M. bovirhinis; M bovoculi; M. buccale; M. buteonis; M. californicum; M. canadense; M. canis; M. capricolum; M. caviae; M. cavipharyngis; M. citelli; M. cloacale; M. coccoides; M. collis; M columbinasale; M. columbiumm; M. columborale; M. conjunctivae; M. corogypsi; M. coltewii; M. cricetuli; M. crocodyli; M. cynos; M. dispar; M. edwardii; M. elephantis; M. ellvchniae; M. equigenitalium; M. equirhinis; M. falconis; M. fastidiosum; M. faucium; M. felifacium; M. feliminutum; M. flocculare;*

*M. gallinaceum; M. gallinarum; M. gallopavonis; M. gaeteae; M. glycophilium; M. gypis; M. haemocanis; M. haemofelis; M. haemomuris; M. haemosuis; M. hypopharyngis; M. hyosynoviae; M. iguanae; M. imitans; M. indiense; M iners; M. iowae; M. lacutcae; M. lagogenitalium; M. leachii; M. leonicptivi; M. leopharyngis; M. lipofaciens; M. lipophilum; M. lucivorax; M. luminosum; M. maculosum; M. mehileucue; M. meleagridis; M. microti; M. moatsii; M. mobile; M. molare; M. muscosicanis; M. muris; M. mustelae; M. neophronis; M. neurolyticvum; M. opalescens; M. orale; M. ovipneumoniae; M. ovis; M. oxoniensis; M. phocae; M. phocicerebrale; M. phocidae; M. phocirhinis; M. pirum; M. primatum; M. pullorum; M. putrefaciens; M. salivarium; M. simbae; M. spermatophilum; M. spumans; M. sturni; M. sualvi; M. subdolum; M. suis; M. synoviae; M. testudineum; M. testudinis; M. verecunum; M. wenyonii; M. yeatsii.*

The following species use humans as a primary host: *M. amphoriforme; M. buccale; M. faucium; M. fermentans; M. genitalium; M. hominis; M.; lipophiluml M. orale; M. penetrans; M. pirum; M. pneumoniae; M. primatum; M. salivarium; M. spermatophilum* Several species of *Mycoplasma* are frequently detected in different types of cancer cells, including without limitation *M. fermentans; M. genitalium; M. hyorhinis; M.* and *penetrans. M. pneumoniae* is the etiologic agent of primary a typical pneumonia and is also responsible for many respiratory tract infections, such as tracheobronchitis, bronchiolitis, pharyngitis and croup, especially in older children and young adults and in elderly populations. *M. genitalium*, is believed to be involved in pelvic inflammatory diseases.

*M. mycoides* is found in cows and goats, and causes lung disease, such as contagious bovine pleuropneumonia (CBPP). *M. mycoides* is part of the *Mycoplasma mycoides* cluster, a group of closely related infectious mycoplasmas. The cluster comprises several species and subspecies including *M. mycoides* subsp. *mycoides* biotype Small Colony (MmmSC); *M. mycoides* subsp. *mycoides* biotype Large Colony (MmmLC); *M. mycoides* subsp. *capri* (Mmc); *M. capricolum* subsp. *capricolum* (Mcc); *M. capricolum* subsp. *capripneumoniae* (Mccp); and *Mycoplasma* sp. 'bovine group 7' (MBG7).

*M. bovis* is also found in cows and can cause pneumonia, mastitis, and arthritis in cattle. Its etiological role has also been associated with otitis, keratoconjunctivitis, synovitis, and reproductive disorders in cows and bulls. Animals infected with *M. bovis* have depressed immune responses and can exhibit signs of infection such as fever, depression, anorexia, labored breathing, nasal and ocular discharge, coughing, sneezing, gasping, grunting, lameness and swollen joints, mastitis, middle ear infections, abortions, recumbence and death

*M. hyopneumoniae* causes enzootic pneumonia, an economically important and highly prevalent disease in pigs. *M. hyosynoviae* lives in the upper respiratory track of pigs and invades the joints and tendon sheaths of susceptible animals and causes lameness and swelling (arthritis).

*M. ovipneumoniae* causes respiratory infections in sheep and *M. cynos* causes canine infectious respiratory disease (CIRD) in dogs. *M. canis, M. spumans*, and *M. maculosum* can cause mycoplasmosis in dogs and *M. haemofelis* causes infections in cats. *M. gallisepticum* (MG) is an infectious respiratory pathogen of gallinaceous birds such as chicken and turkey.

Although the following discussion is with respect to antigens derived from Mmm and Mmc, the corresponding antigens from any of the above species that cause disease can also be used in immunogenic compositions to treat *Mycoplasma* infection as it is readily apparent from the discussion herein that *Mycoplasma* causes a wide variety of disorders in a number of animals.

Table 1 and Table 4 show antigens for stimulating immune responses against *M. mycoides*, and in particular, against Mmm and Mmc. In the tables, Mmm proteins are indicated as MSC_xxxx and Mmc proteins are indicated as YP_0044xxxxxxxx.1. Table 1 shows individual Mmm and Mmc proteins, while Table 4 shows Mmm and Mmc fusion proteins, as well as conjugates of the fusions and individual Mmm and Mmc proteins with an immunogenic carrier. It is to be understood that when referring to an Mmm or an Mmc protein from Table 4, the individual Mmm and Mmc proteins in the fusions and the conjugates are intended. In this regard, the boundaries of the individual Mmm and Mmc proteins present in the fusions, as well as the Mmm and Mmc proteins present in the conjugates, are described above.

The subject compositions can include one or more of these antigens, such as 2, 3, 4, 5, 6, 7, 8, 9, 10, etc., or antigens from other *Mycoplasma* species and subspecies that correspond to the Mmm and Mmc antigens listed in Tables 1 and 4. Moreover, the antigens present in the compositions can include the full-length amino acid sequences, or fragments or variants of these sequences so long as the antigens stimulate an immunological response, preferably, a protective immune response. Thus, the antigens can be provided with deletions from the N-terminus, including deletions of the native signal sequence, or can include a heterologous signal sequence, no signal sequence at all, or only a portion of the signal sequence. For example, the amino acid sequences for MSC_0136 (SEQ ID NO:2, FIG. 11B); MSC_0957 (SEQ ID NO:4, FIG. 12B); MSC_0499 (SEQ ID NO:6, FIG. 13B); MSC_0431 (SEQ ID NO:8, FIG. 14B), MSC_0776 (SEQ ID NO:10, FIG. 15B), YP_004400559.1 (SEQ ID NO:10, FIG. 16B); YP_004399807.1 (SEQ ID NO:14, FIG. 17B); MSC_0816 (SEQ ID NO:16, FIG. 18B); MSC 0775 (SEQ ID NO:20, FIG. 20B); YP 004400127.1 (SEQ ID NO:22, FIG. 21B) and in the fusion depicted in FIG. 25B (SEQ ID NO:51) and FIG. 27B (SEQ ID NO:55), and YP_004400610.1 (SEQ ID NO:28, FIG. 24B) and the fusion depicted in FIG. 26B (SEQ ID NO:53) and FIG. 28B (SEQ ID NO:57), lack all or a portion of the N-terminal signal sequence. Similarly, the amino acid sequences for YP_00400580.1 in the fusion depicted in FIG. 26B (SEQ ID NO:53) and in FIG. 28B (SEQ ID NO:57); and the MSC_0775 in the fusion depicted in FIG. 33B (SEQ ID NO:67), lack an additional N-terminal truncation of 20 amino acids as compared to the YP_00400580.1 and MSC_0775 sequences shown in SEQ ID NO:26 and SEQ ID NO:20, respectively Additionally, the antigens can include deletions from the C-terminal portion of the molecule, such as deletions of all or a portion of the transmembrane and cytoplasmic domains, if present. For example, YP_004400580.1 (SEQ ID NO:26, FIG. 23B) includes a deletion of approximately 15 amino acids from the C-terminus.

Furthermore, internal deletions can be present so long as the molecule remains immunogenic. Moreover, the molecules optionally include an N-terminal methionine. In this regard, YP_004400559.1 (SEQ ID NO:12, FIG. 16B); YP_004399807.1 (SEQ ID NO:14, FIG. 17B); YP_004400127.1 (SEQ ID NO:22, FIG. 21B); YP_004399790.1 (SEQ ID NO:24, FIG. 22B); YP_004400580.1 (SEQ ID NO:26, FIG. 23B); YP_004400610.1 (SEQ ID NO:28, FIG. 24B) include an N-terminal methionine; while MSC_0136 (SEQ ID NO:2, FIG. 11B); MSC_0957 (SEQ ID NO:4, FIG. 12B); MSC_0499 (SEQ ID NO:6, FIG. 13B); MSC_0431 (SEQ ID NO:8, FIG. 14B); MSC_0776 (SEQ ID NO:10, FIG. 15B); MSC_0816 (SEQ ID NO:16, FIG. 18B); MSC_0160 (SEQ ID NO:18, FIG. 19B); MSC_0775 (SEQ ID NO:20, FIG. 20B); YP_004399790.1 (SEQ ID NO:24, FIG. 22B); YP_004400580.1 (SEQ ID NO:26, FIG. 23B) lack an N-terminal methionine.

As explained above, any of the *M. mycoides* antigens listed in Tables 1 and 4, as well as variants thereof, such as proteins with substantial sequence identity thereto, e.g., sequences that exhibit at least about 50% sequence identity, such as at least about 75% sequence identity, e.g., at least about 80%-85% sequence identity, for example at least about 90% sequence identity, such as at least about 95%-99% sequence identity or more, over a defined length of the molecules, or any integer within these values, will find use herein. Additionally, the corresponding antigens from a different species or subspecies, can be used in combination in the immunogenic compositions described herein, to provide protection against a broad range of *Mycoplasma* bacteria.

The compositions can include *Mycoplasma* antigens from more than one species or subspecies. For instance, the compositions can include one or more Mmm antigens, one or more, Mmc antigens, both Mmm and Mmc antigens, along with one or more *Mycoplasma* antigens from any of the other species/subspecies listed above. Thus, each of the components of a subunit composition or fusion protein can be obtained from the same *Mycoplasma* species, or from different *Mycoplasma* species.

Moreover, if Mmm and/or Mmc antigens are present, they can include various combinations from any of the vaccine groups listed in Table 1, such as from Groups A, B, C, D, E, G, H, I, J, K, M, N, O and/or P. In some embodiments, two or more antigens selected from Group A (SEQ ID NOS:2, 4, 6, 8, 10), Group C (SEQ ID NOS:12, 14, 16, 18, 20) and/or Group N (SEQ ID NOS:22, 24, 26, 28) are present.

The immunogenic compositions can include discrete antigens, i.e., isolated and purified antigens provided separately, or can include fusions of the desired antigens. The fusions will include two or more immunogenic *Mycoplasma* proteins, such as 2, 3, 4, 5, 6, 7, 8, 9, 10, etc., e.g., two or more antigens listed in Tables 1 and 4, or antigens from other *Mycoplasma* species and subspecies that correspond to the Mmm and Mmc antigens listed in Tables 1 and 4. Moreover, as explained above, the antigens present in the fusions can include the full-length amino acid sequences, or fragments or variants of these sequences so long as the antigens stimulate an immunological response, preferably, a protective immune response. In any event, at least one epitope from these antigens will be present. In some embodiments, the fusions will include repeats of desired epitopes. As explained above, the antigens present in fusions can be derived from the same *Mycoplasma* species or subspecies, or from different species or subspecies, to provide increased protection against a broad range of *Mycoplasma* bacteria.

In certain embodiments, the fusions include multiple antigens, such as more than one epitope from a particular *Mycoplasma* antigen, and/or epitopes from more than one *Mycoplasma* antigen. The epitopes can be provided in the full-length antigen sequence, or in a partial sequence that includes the epitope. The epitopes can be from the same *Mycoplasma* species and subspecies, or different *Mycoplasma* species and subspecies. Additionally, the epitopes can be derived from the same *Mycoplasma* protein or from different *Mycoplasma* proteins from the same or different *Mycoplasma* species and subspecies.

More particularly, the fusions (also termed "chimeras" herein) may comprise multiple epitopes, a number of different *Mycoplasma* proteins from the same or different species and subspecies, as well as multiple or tandem repeats of selected *Mycoplasma* sequences, multiple or tandem repeats of selected *Mycoplasma* epitopes, or any combination thereof. Epitopes may be identified using techniques as described above, or fragments of *Mycoplasma* proteins may be tested for immunogenicity and active fragments used in compositions in lieu of the entire polypeptide. Fusions may also include the full-length sequence.

The antigen sequences present in the fusions may be separated by spacers. A selected spacer sequence may encode a wide variety of moieties of one or more amino acids in length. Selected spacer groups may also provide enzyme cleavage sites so that the expressed chimera can be processed by proteolytic enzymes in vivo to yield a number of peptides.

For example, amino acids can be used as spacer sequences. Such spacers will typically include from 1-500 amino acids, such as 1-100 amino acids, e.g., 1-50 amino acids, such as 1-25 amino acids, 1-10 amino acids, 1-3, 1-4, 1-5, 1-6, amino acids, or any integer between 1-500. The spacer amino acids may be the same or different between the various antigens. Particularly preferred amino acids for use as spacers are amino acids with small side groups, such as serine, alanine, glycine and valine, various combinations of amino acids or repeats of the same amino acid. For example, linker sequences including a particular amino acid or combination of amino acids, such as glycine, or glycine-serine, etc. may include 2, 3, 4, 5, 6, 7, 8, 9, 10 . . . 20 . . . 25 . . . 30, etc. of such repeats.

Although particular fusions are exemplified herein which include spacer sequences, it is also to be understood that one or more of the antigens present in the fusion constructs can be directly adjacent to another antigen, without an intervening spacer sequence.

Specific *Mycoplasma* fusion proteins include, but are not limited to, those listed in Table 4. The nucleotide and amino acid sequences of these particular *Mycoplasma* fusion proteins are shown in FIGS. 25A-25B (SEQ ID NOS:50 and 51); FIGS. 26A-26B (SEQ ID NOS:52 and 53); FIGS. 27A-27B (SEQ ID NOS:54 and 55); FIGS. 28A-28B (SEQ ID NOS:56 and 57); FIGS. 37A-37B (SEQ ID NOS:74 and 74); and FIGS. 38A-38B (SEQ ID NOS:76 and 77). However, it is to be understood that fusion proteins for use herein can be derived from any number of *Mycoplasma* antigens.

In order to enhance immunogenicity of the *Mycoplasma* proteins and fusions of multiple antigen molecules, they may be conjugated with a carrier. By "conjugated" is meant that the protein and fusions of interest may be linked to the carrier via non-covalent interactions, such as by electrostatic forces, or by covalent bonds, and the like. Thus, the carrier may be linked to the protein of interest via recombinant production, or the protein may be synthetically or chemically linked to a carrier after or during production. By "carrier" is meant any molecule which when associated with an antigen of interest, imparts immunogenicity to the antigen. Examples of suitable carriers include large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; inactive virus particles; bacterial toxins such as tetanus toxoid, serum albumins, keyhole limpet hemocyanin, thyroglobulin, ovalbumin, sperm whale myoglobin, and other proteins well known to those skilled in the art. Other suitable carriers for the antigens of the present invention include VP6 polypeptides of rotaviruses, or functional fragments thereof, as disclosed in U.S. Pat. No. 5,071,651.

These carriers may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

*Mycoplasma* proteins and multiple antigen fusion molecules can also be conjugated with a member of the RTX family of toxins, such as a *Pasteurella haemolytica* leukotoxin (LKT) polypeptide. See, e.g., International Publication No. WO 93/08290, published 29 Apr. 1993, as well as U.S. Pat. Nos. 5,238,823, 5,273,889, 5,723,129, 5,837,268, 5,422,110,5,708,155, 5,969,126, 6,022,960, 6,521,746 and 6,797,272, all incorporated herein by reference in their entireties.

Leukotoxin polypeptide carriers are derived from proteins belonging to the family of RTX molecules characterized by the carboxy-terminus consensus amino acid sequence Gly-Gly-X-Gly-X-Asp (SEQ ID NO:84, Highlander et al., DNA (1989) 8:15-28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee et al., *Infect. Immun.* (1987) 55:3233-3236; Lo, *Can. J. Vet. Res.* (1990) 54:S33-S35; Welch, *Mol. Microbiol.* (1991) 5:521-528). This family of toxins is known as the "RTX" family of toxins (Lo, *Can. J. Vet. Res.* (1990) 54:S33-S35). The nucleotide sequences and corresponding amino acid sequences for several leukotoxins are known. See, e.g., U.S. Pat. Nos. 4,957,739 and 5,055,400; Lo et al., *Infect. Immun.* (1985) 50:667-67; Lo et al., *Infect. Immun.* (1987) 55:1987-1996; Strathdee et al., *Infect. Immun.* (1987) 55:3233-3236; Highlander et al., *DNA* (1989) 8:15-28; Welch, *Mol. Microbiol.* (1991) 5:521-528. Particular examples of immunogenic leukotoxin polypeptides for use herein include LKT 342, LKT 352, LKT 111, LKT 326 and LKT 101 which are described in greater detail below.

By "LKT 352" is meant a protein derived from the IktA gene present in plasmid pAA352 and described in U.S. Pat. No. 5,476,657, incorporated herein by reference in its entirety. LKT 352, also termed "LtxA" herein, has an N-terminal truncation of the native *P. haemolytica* leukotoxin full-length sequence. Thus, the gene in plasmid pAA352 encodes a truncated leukotoxin, having 914 amino acids which lacks the cytotoxic portion of the molecule. The nucleotide and amino acid sequences of LKT 352 are shown in FIG. 41 (SEQ ID NOS:82 and 83). Note that the amino acid sequence depicted in FIG. 41 includes 10 amino acids from vector pAA352 on the 5'-end and two amino acids from vector pAA352 on the 3'-end. These flanking sequences can be included in the carrier molecule or deleted and the term "LKT 352" refers to both forms.

By "LKT 111" is meant a leukotoxin polypeptide which is derived from the IktA gene present in plasmid pCB111. The plasmid and nucleotide sequence of this gene and the corresponding amino acid sequence are described in U.S. Pat. Nos. 5,723,129 and 5,969,126, incorporated herein by reference in their entireties. The gene encodes a shortened version of leukotoxin which was developed from the recombinant leukotoxin gene present in plasmid pAA352 by removal of an internal DNA fragment of approximately 1300 bp in length. The LKT 111 polypeptide has an estimated molecular weight of 52 kDa (as compared to the 99 kDa LKT 352 polypeptide), retains the ability to act as a carrier molecule, and contains convenient restriction sites for use in producing the fusion proteins of the present invention.

Figures 3A, 3B, 3C, 3D, 3E:
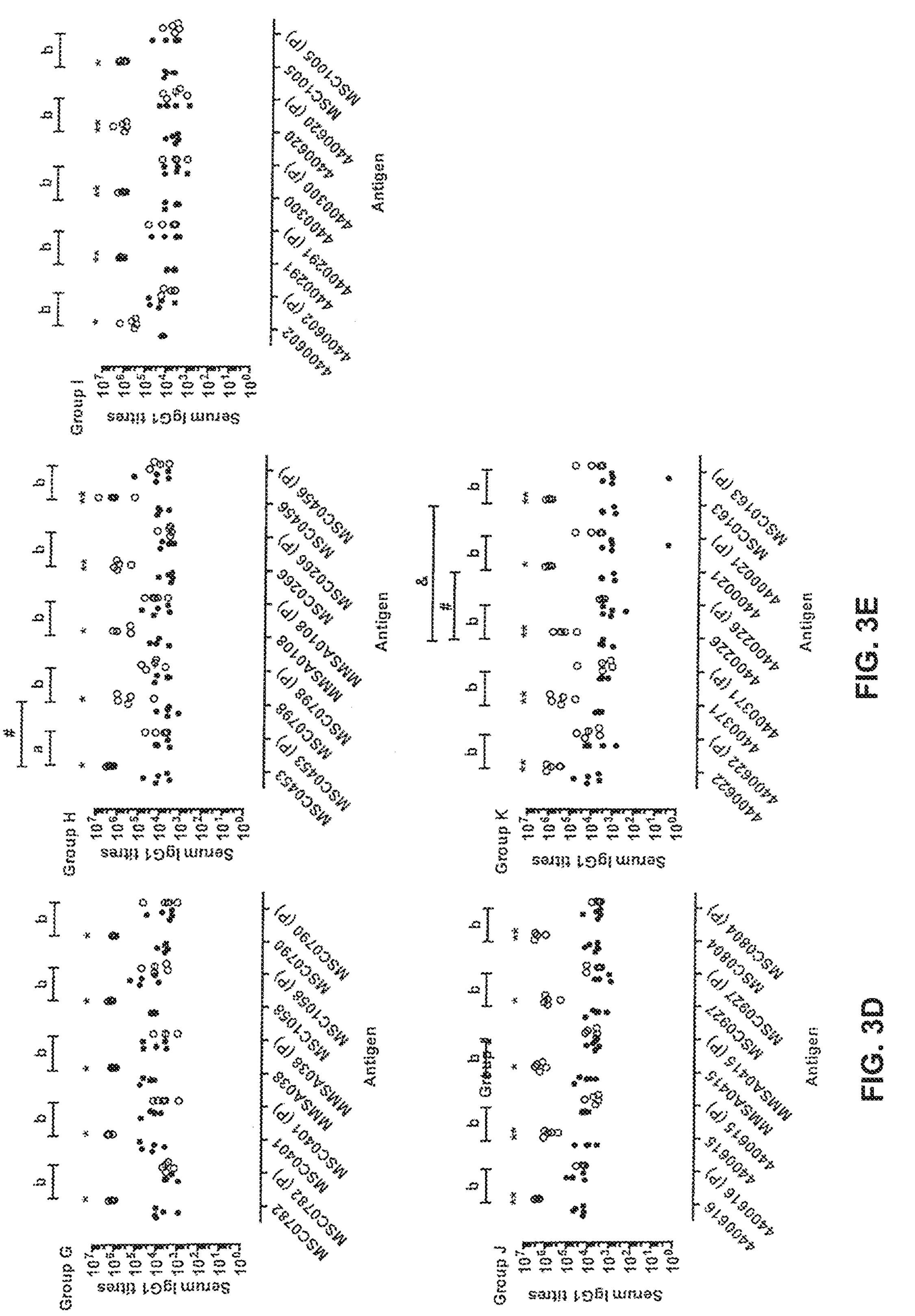
FIGS. 3A-3E show serum IgG1 responses against the recombinant proteins used in trial 2 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group (Names shortened for clarity purposes). The bars across the symbols show the median of the values. Significant differences between the day 0 and day 35 titres for each antigen are shown by asterisks, *=P<0.05; and **=P<0.01. Significant differences between the day 35 titres of the vaccinated and placebo group for each protein are shown by a=P<0.05, b=P<0.01. Differences between the day 35 IgG1 titres between proteins in the same group are shown by #=P<0.05 and &=P<0.01.
Figures 5A, 5B, 5C, 5D:
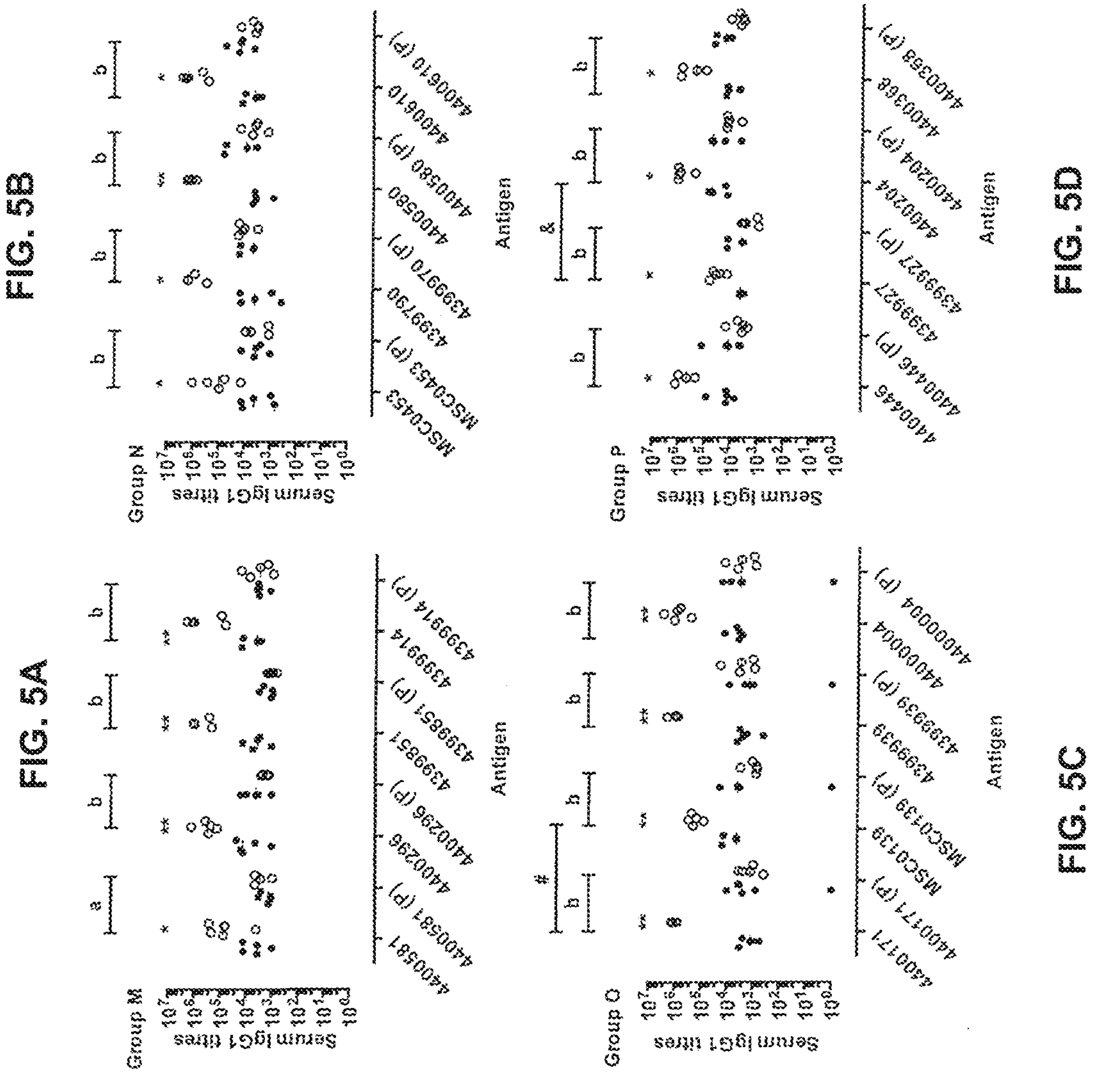
FIGS. 5A-5D show serum IgG1 responses against the recombinant proteins used in trial 3 as described in the examples. For clarity purposes, only the responses at days 0 (Black circles) and 35 (White circles) in the vaccinated and placebo (P) groups are shown. The groups are listed on the side of each panel. The X-axis indicates the recombinant proteins used for each group (Names shortened for clarity purposes). The bars across the symbols show the median of the values. Significant differences between the day 0 and day 35 titres for each antigen are shown by asterisks, *=P<0.05; and **=P<0.01. Significant differences between the day 35 titres of the vaccinated and placebo group for each protein are shown by a=P<0.05, b=P<0.01. Differences between the day 35 IgG1 titres between proteins in the same group are shown by #=P<0.05 and &=P<0.01.
Figure 7:
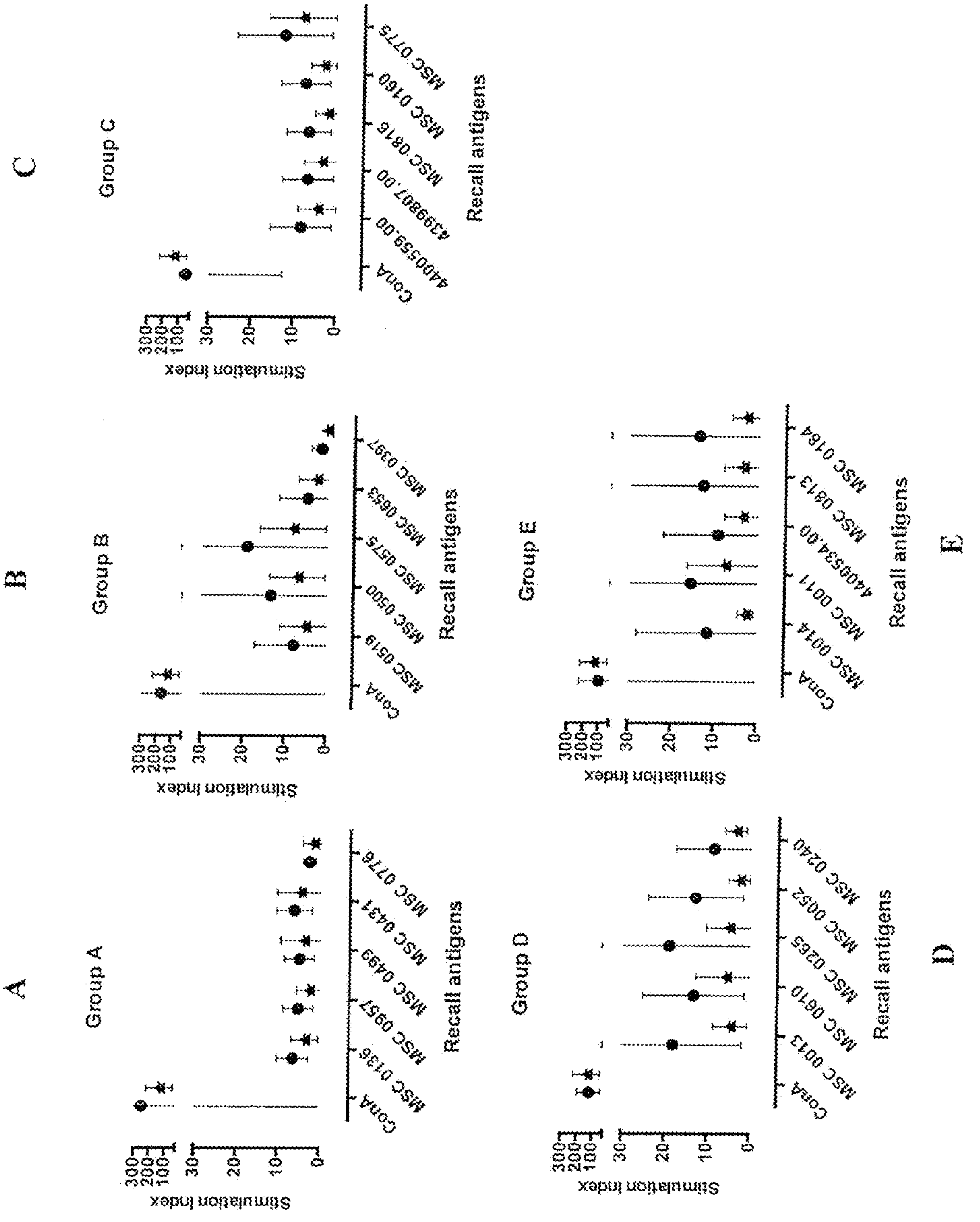
FIGS. 7A-7E show PBMC proliferative responses in trial 1 after incubation with the recall antigens as described in the examples. The groups are listed on the top of each panel. The mean and standard deviation of the stimulation indexes (Si) at day 35 (Two weeks after the boost) for the vaccinated (Black circles) and placebo (Black triangles) groups are shown. The X-axis shows the positive control (ConA) and the recall antigens used in each group. There were no significant differences between the vaccinated and placebo Si for each of the recall antigens and no differences between the Si of any of the antigens in the vaccinated groups.
Figures 8A, 8B, 8C, 8D, 8E:
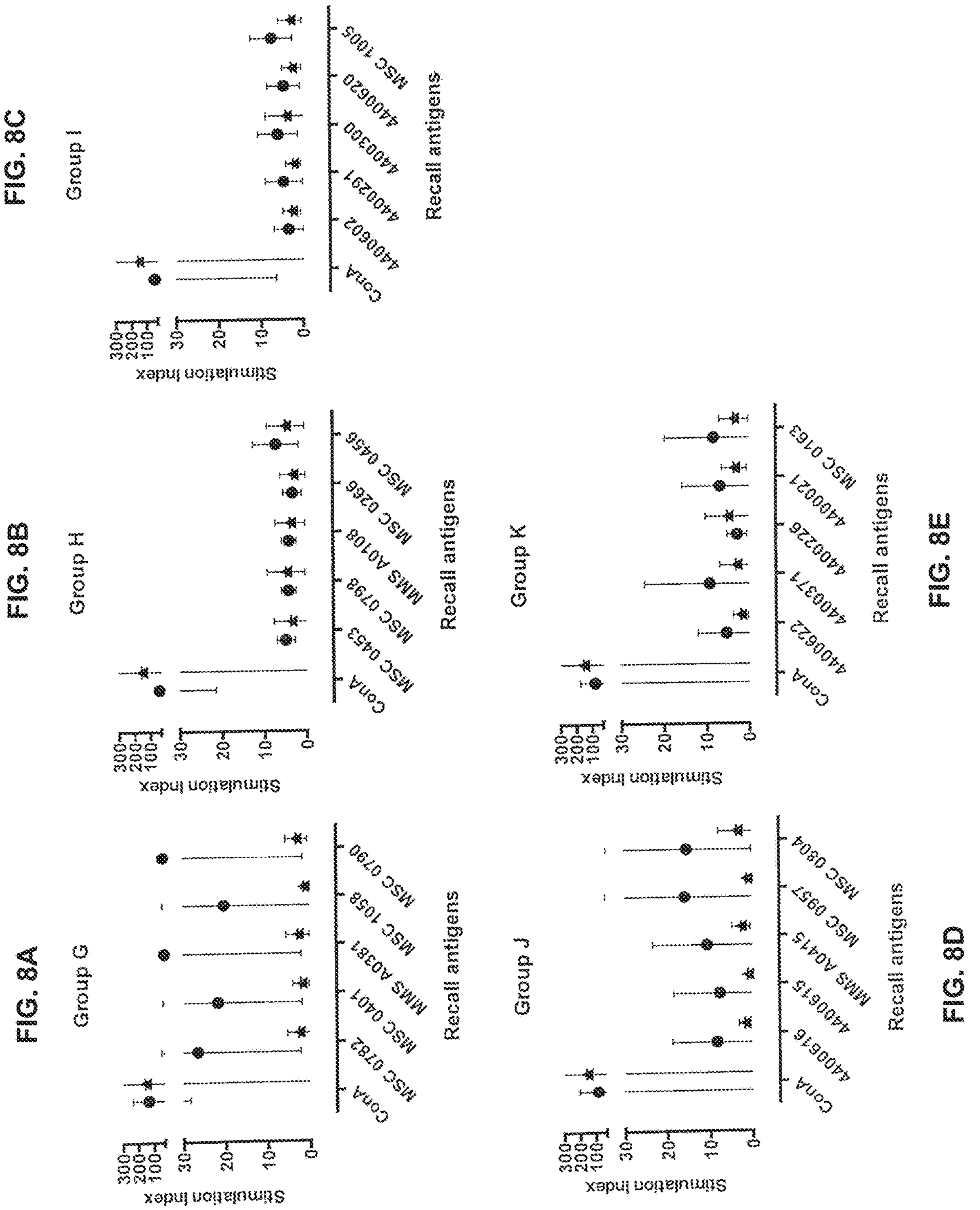
FIGS. 8A-8E show PBMC proliferative responses in trial 2 after incubation with the recall antigens as described in the examples. The groups are listed on the top of each panel. The mean and standard deviation of the stimulation indexes (Si) at day 35 (Two weeks after the boost) for the vaccinated (Black circles) and placebo (Black triangles) groups are shown. The X-axis shows the positive control (ConA) and the recall antigens used in each group. There were no significant differences between the vaccinated and placebo Si for each of the recall antigens and no differences between the Si of any of the antigens in the vaccinated groups.

By "LKT 101" is meant a leukotoxin polypeptide which is derived from the IktA gene present in plasmid pAA101. The plasmid and sequence of LKT 101 is described in U.S. Pat. No. 5,476,657 (see FIG. 3 therein), incorporated herein by reference in its entirety. The LKT 101 polypeptide is expressed from a C-terminally truncated form of the IktA gene which contains the 5' end of the gene up to the unique Pst1 restriction endonuclease site. Thus, LKT 101 includes the first 377 amino acids of native, full-length, *P. haemolytica* leukotoxin.

By "LKT 342" is meant a leukotoxin polypeptide which is derived from the IktA gene present in plasmid pAA342, described in U.S. Pat. No. 5,476,657, incorporated herein in its entirety. LKT 342 has an N-terminal and C-terminal truncation of the native leukotoxin sequence and includes amino acids 38-334 of native leukotoxin.

The various LKT molecules described above are representative and other leukotoxin and RTX molecules that enhance the immunogenicity of the *Mycoplasma* proteins and fusions will also find use herein. Moreover, the carrier molecules need not be physically derived from the sequence present in the corresponding plasmids but may be generated in any manner, including for example, by chemical synthesis or recombinant production, as described below.

Additionally, the *Mycoplasma* proteins and multiple antigen fusion molecules can be fused to either the carboxyl or amino terminals or both of the carrier molecule, or at sites internal to the carrier.

As explained above, carriers can be physically conjugated to the proteins of interest, using standard coupling reactions. Alternatively, chimeric molecules can be prepared recombinantly for use in the present invention, such as by fusing a gene encoding a suitable polypeptide carrier to one or more copies of a gene, or fragment thereof, encoding for selected *Mycoplasma* proteins or *Mycoplasmna* multiple antigen fusion molecules.

Specific leukotoxin/*M. mycoides* conjugates are exemplified herein. However, is to be understood that *Mycoplasma* antigens and fusions of these antigens can be conjugated with any suitable carrier molecule if desired. The nucleotide and amino acid sequences of exemplary conjugates between *M. mycoides* constructs and a leukotoxin carrier are shown in FIGS. 27A-27B (SEQ ID NOS:54 and 55); FIGS. 28A-28B (SEQ ID NOS:56 and 57); FIGS. 29A-29B (SEQ ID NOS:58 and 59); FIGS. 30A-30B (SEQ ID NOS:60 and 61); FIGS. 31A-31B (SEQ ID NOS:62 and 63); FIGS. 32A-32B (SEQ ID NOS:64 and 65); FIGS. 33A-33B (SEQ ID NOS: 66 and 67); FIGS. 34A-34B (SEQ ID NOS:68 and 69); FIGS. 35A-35B (SEQ ID NOS:70 and 71); FIGS. 36A-36B (SEQ ID NOS:72 and 73); FIGS. 37A-37B (SEQ ID NOS: 74 and 75); FIGS. 38A-38B (SEQ ID NOS:76 and 77); FIGS. 39A-39B (SEQ ID NOS:78 and 79); and FIGS. 40A-40B (SEQ ID NOS:80 and 81).

Preferably, the above-described antigens and fusions, are produced recombinantly. A polynucleotide encoding these proteins can be introduced into an expression vector which can be expressed in a suitable expression system. A variety of bacterial, yeast, mammalian and insect expression systems are available in the art and any such expression system can be used. Optionally, a polynucleotide encoding these proteins can be translated in a cell-free translation system. Such methods are well known in the art. The proteins also can be constructed by solid phase protein synthesis.

If desired, the fusion proteins, or the individual components of these proteins, also can contain other amino acid sequences, such as amino acid linkers or signal sequences, either native or heterologous, as well as ligands useful in protein purification, such as glutathione-S-transferase and staphylococcal protein A.

B. *Mycoplasma* Polynucleotides

*Mycoplasma* polynucleotides encoding the *Mycoplasma* antigens, fusions of these antigens or epitopes therefrom, as well as conjugates of these antigens and fusions with carrier molecules, for use in the subject compositions, can be derived from any of the *Mycoplasma* species and subspecies described above. Although the following discussion is with respect to polynucleotides encoding antigens derived from Mmm and Mmc, the corresponding polynucleotides from any of the above species that cause disease can also be used to produce antigens for use in immunogenic compositions to treat *Mycoplasma* infection as it is readily apparent from the discussion herein that *Mycoplasma* causes a wide variety of disorders in a number of animals.

Tables 1 and 4 show polynucleotides encoding antigens, fusions and conjugates for stimulating immune responses against Mmm and Mmc. The polynucleotides described in Tables 1 and 4 have been modified for expression in *E. coli* and thus differ from previously reported and naturally occurring Mmm and Mmc polynucleotide sequences. Additionally, several genomic sequences for various *Mycoplasma* strains, species and subspecies, including Mmm and Mmc are known and reported in the NCBI database, including, but not limited to NCBI accession nos. NC_005364.2; BX293980.2; CP002107.1; CP010267.1; NC_021025.1; NZ_LAEW01000001.1; CP00162.1; CP001668.1; NC_015431.1; FQ377874.1; NZ_CP00162.1; CP002027.1; FR668087.1; FM864216.2; CP001872.1; AE015450.2; NZ_CP012387.1; CP001668.1; NZ_CP00162 1; NC_015431.1; FQ_3777874.1, and sequences from these species and subspecies that correspond to the Mmm and Mmc antigens described herein can be derived therefrom.

The polynucleotide sequences encoding *Mycoplasma* antigens will encode the full-length amino acid sequences, or fragments or variants of these sequences so long as the resulting antigens stimulate an immunological response, preferably, a protective immune response. Thus, the polynucleotides can encode antigens with deletions from the N-terminus, including deletions of the native signal sequence, or antigens with a heterologous signal sequence, no signal sequence at all, or only a portion of the signal sequence. Moreover, the polynucleotides can encode antigens with deletions from the C-terminal portion of the molecule, such as deletions of all or a portion of the transmembrane and cytoplasmic domains, if present, as well as internal deletions, so long as the molecule remains immunogenic. The encoded molecules optionally include an N-terminal methionine. Such molecules are described in detail above.

Preferably, the antigens, fusions and conjugates described above are produced recombinantly using these polynucleotides. Accordingly, once coding sequences for the desired antigens have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used. Optionally, a polynucleotide encoding these proteins can be translated in a cell-free translation system. Such methods are well known in the art.

Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Plant expression systems can also be used to produce the immunogenic proteins. Generally, such systems use virus-based vectors to transfect plant cells with heterologous genes. For a description of such systems see, e.g., Porta et al., *Mol. Biotech.* (1996) 5:209-221; and Hackiand et al., Arch. Virol. (1994) 139:1-22.

Viral systems, such as a vaccinia based infection/transfection system, as described in Tomei et al., *J. Virol*. (1993) 67:4017-4026 and Selby et al., *J. Gen. Virol*. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The coding sequence can be placed under the control of a promoter, ribosome binding site (for bacterial expression) and, optionally, an operator (collectively referred to herein as "control elements"), so that the DNA sequence encoding the desired antigen is transcribed into RNA in the host cell transformed by a vector containing this expression construction. The coding sequence may or may not contain a signal peptide or leader sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic proteins. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli*, *Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa calfornica, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art. If the proteins are not secreted, the cells are then disrupted, using chemical, physical or mechanical means, which lyse the cells yet keep the proteins substantially intact. Following disruption of the cells, cellular debris is removed, generally by centrifugation. Whether produced intracellularly or secreted, the protein can be further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like C. Antibodies The antigens of the present invention can be used to produce antibodies for therapeutic (e.g., passive immunization), diagnostic and purification purposes. These antibodies may be polyclonal or monoclonal antibody preparations, monospecific antisera, or may be hybrid or chimeric antibodies, such as humanized antibodies, altered antibodies, $F(ab')_2$ fragments, F(ab) fragments, Fv fragments, single-domain antibodies, dimeric or trimeric antibody fragment constructs, minibodies, or functional fragments thereof which bind to the antigen in question. Antibodies are produced using techniques well known to those of skill in the art and disclosed in, for example, U.S. Pat. Nos. 4,011,308; 4,722,890; 4,016,043; 3,876,504; 3,770,380; and 4,372,745.

For subjects known to have a *Mycoplasma*-related disease, an anti-*Mycoplasma*-antigen antibody may have therapeutic benefit and can be used to confer passive immunity to the subject in question. Alternatively, antibodies can be used in diagnostic applications, described further below, as well as for purification of the antigen of interest.

D. Compositions

The *Mycoplasma* antigens or antibodies, can be formulated into compositions for delivery to subjects for eliciting an immune response, such as for inhibiting infection. Compositions of the invention may comprise or be co-administered with non-*Mycoplasma* antigens or with a combination of *Mycoplasma* antigens, as described above. Methods of preparing such formulations are described in, e.g., *Remington's Pharmaceutical Sciences*, Mack Publishing Company, Easton, Pennsylvania, 18 Edition, 1990. The compositions of the present invention can be prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the composition may also be added to the formulation. Such adjuvants include any compound or combination of compounds that act to increase an immune response to a *Mycoplasma* antigen or combination of antigens, thus reducing the quantity of antigen necessary in the vaccine, and/or the frequency of injection necessary in order to generate an adequate immune response. Adjuvants may include for example, muramyl dipeptides, AVRIDINE, aqueous adjuvants such as aluminum hydroxide, dimethyldioctadecyl ammonium bromide (DDA), oils, oil-in-water emulsions, water-in-oil emulsions, such as described in U.S. Pat. No. 7,279,163, incorporated herein by reference in its entirety, saponins, cytokines.

Also useful herein is a triple adjuvant formulation as described in, e.g., U.S. Pat. No. 9,061,001, incorporated herein by reference in its entirety. The triple adjuvant formulation includes a host defense peptide, in combination with a polyanionic polymer such as a polyphosphazene, and a nucleic acid sequence possessing immunostimulatory properties (ISS), such as an oligodeoxynucleotide molecule with or without a CpG motif (a cytosine followed by guanosine and linked by a phosphate bond) or the synthetic dsRNA analog poly(1:C).

Examples of host defense peptides for use in the combination adjuvant, as well as individually with the antigen include, without limitation, HH2 (VQLRIRVAVIRA, SEQ ID NO:30); 1002 (VQRWLIVWRIRK, SEQ ID NO:31); 1018 (VRLIVAVRIWRR, SEQ ID NO:32); Indolicidin (ILPWKWPWWPWRR, SEQ ID NO:33); HH111 (ILKWKWPWWPWRR, SEQ ID NO:34), HH113 (ILPWKKPWWPWRR, SEQ ID NO:35), HH970 (ILKWKWPWWKWRR, SEQ ID NO:36); HH1010 (ILRWKWRWWRWRR, SEQ ID NO:37), Nisin Z (Ile-Dhb-Ala-Ile-Dha-Leu-Ala-Abu-Pro-Gly-Ala-Lys-Abu-Gly-Ala-Leu-Met-Gly-Ala-Asn-Met-Lys-Abu-Ala-Abu-Ala-Asn-Ala-Ser-Ile-Asn-Val-Dha-Lys, SEQ ID NO:38); JK1 (VFLRRIRVIVIR; SEQ ID NO:39); JK2 (VFWRRIRVWVIR; SEQ ID NO:40); JK3 (VQLRAIRVRVIR; SEQ ID NO:41); JK4 (VQLRRIRVWVIR; SEQ ID NO:42); JK5 (VQWRAIRVRVIR; SEQ ID NO:43); and JK6 (VQWRRIRVWVIR; SEQ ID NO:44). Any of the above peptides, as well as fragments and analogs thereof, that display the appropriate biological activity, such as the ability to modulate an immune response, such as to enhance an immune response to a co-delivered antigen, will find use herein.

Exemplary, non-limiting examples of ISSs for use in the triple adjuvant composition, or individually include, CpG oligonucleotides or non-CpG molecules. By "CpG oligonucleotide" or "CpG ODN" is meant an immunostimulatory nucleic acid containing at least one cytosine-guanine dinucleotide sequence (i.e., a 5' cytidine followed by 3' guanosine and linked by a phosphate bond) and which activates the immune system. An "unmethylated CpG oligonucleotide" is a nucleic acid molecule which contains an unmethylated cytosine-guanine dinucleotide sequence (i.e., an unmethylated 5' cytidine followed by 3' guanosine and linked by a phosphate bond) and which activates the immune system. A "methylated CpG oligonucleotide" is a nucleic acid which contains a methylated cytosine-guanine dinucleotide sequence (i.e., a methylated 5' cytidine followed by a 3' guanosine and linked by a phosphate bond) and which activates the immune system. CpG oligonucleotides are well known in the art and described in, e.g., U.S. Pat. Nos. 6,194,388; 6,207,646; 6,214,806; 6,218,371; 6,239,116; and 6,339,068; PCT Publication No. WO 01/22990; PCT Publication No. WO 03/015711; US Publication No. 20030139364, which patents and publications are incorporated herein by reference in their entireties.

Examples of such CpG oligonucleotides include, without limitation, 5'TCCATGACGTTCCTGACGTT3' (SEQ ID NO:45), termed CpG ODN 1826, a Class B CpG; 5'TCGTCGTTGTCGTTTTGTCGTT3' (SEQ ID NO 29), termed CpG ODN 2007, a Class B CpG; 5'TCGTCGTTTTGTCGTTTTGTCGTT3' (SEQ ID NO:46), also termed CPG 20 7909 or 10103, a Class B CpG; 5' GGGGACGACGTCGTGGGGGGG 3' (SEQ ID NO:47), termed CpG 8954, a Class A CpG; and 5'TCGTCGTTTTCGGCGCGCGCCG 3' (SEQ ID NO:48), also termed CpG 2395 or CpG 10101, a Class C CpG. All of the foregoing class B and C molecules are fully phosphorothioated.

Non-CpG oligonucleotides for use in the present composition include the double stranded polyriboinosinic acid: polyribocytidylic acid, also termed poly(I:C); and a non-CpG oligonucleotide 5'AAAAAAGGTACCTAAATAGTATGTTTCTGAAA3' (SEQ ID NO:49).

Polyanionic polymers for use in the triple combination adjuvants or alone include polyphosphazines. Typically, polyphosphazenes for use with the present adjuvant compositions will either take the form of a polymer in aqueous solution or a polymer microparticle, with or without encapsulated or adsorbed substances such as antigens or other adjuvants. For example, the polyphosphazene can be a soluble polyphosphazene, such as a polyphosphazene polyelectrolyte with ionized or ionizable pendant groups that contain, for example, carboxylic acid, sulfonic acid or hydroxyl moieties, and pendant groups that are susceptible to hydrolysis under conditions of use to impart biodegradable properties to the polymer. Such polyphosphazene polyelectrolytes are well known and described in, for example, U.S. Pat. Nos. 5,494,673, 5,562,909, 5,855,895; 6,015,563; and 6,261,573, incorporated herein by reference in their entireties. Alternatively, polyphosphazene polymers in the form of cross-linked microparticles will also find use herein. Such cross-linked polyphosphazene polymer microparticles are well known in the art and described in, e.g., U.S. Pat. Nos. 5,053,451; 5,149,543; 5,308,701; 5,494,682; 5,529,777; 5,807,757; 5,985,354; and 6,207,171, incorporated herein by reference in their entireties.

Examples of particular polyphosphazene polymers for use herein include poly[di(sodium carboxylatophenoxy)phosphazene](PCPP) and poly(di-4-oxyphenylproprionate)phosphazene (PCEP), in various forms, such as the sodium salt, or acidic forms, as well as a polymer composed of varying percentages of PCPP or PCEP copolymer with hydroxyl groups, such as 90:10 PCPP/OH. Methods for synthesizing these compounds are known and described in the patents referenced above, as well as in Andrianov et al., *Biomacromolecules* (2004) 5:1999; Andrianov et al., *Macromolecules* (2004) 37:414; Mutwiri et al, *Vaccine* (2007) 25:1204

Additional adjuvants include chitosan-based adjuvants, and any of the various saponins, oils, and other substances known in the art, such as AMPHIGEN™ which comprises de-oiled lecithin dissolved in an oil, usually light liquid paraffin. In vaccine preparations AMPHIGEN™ is dispersed in an aqueous solution or suspension of the immunizing antigen as an oil-in-water emulsion. Other adjuvants are LPS, bacterial cell wall extracts, bacterial DNA, synthetic oligonucleotides and combinations thereof (Schijns et al., *Curr. Opi. Immunol.* (2000) 12:456), *Mycobacterial phlei* (*M. phlei*) cell wall extract (MCWE) (U.S. Pat. No. 4,744,984), *M. phlei* DNA (M-DNA), M-DNA-*M phlei* cell wall complex (MCC). For example, compounds which may serve as emulsifiers herein include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids (i.e., metallic soaps), and organic sulfonates such as sodium lauryl sulfate. Synthetic cationic agents include, for example, cetyltrimethylammonium bromide, while synthetic nonionic agents are exemplified by glyceryl esters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oil, or oil-in-water emulsions in which the oil component is mineral oil are preferred. Another oil component is the oil-in-water emulsion sold under the trade name of EMULSIGEN™, such as but not limited to EMULSIGEN PLUS™, comprising a light mineral oil as well as 0.05% formalin, and 30 μg/mL gentamicin as preservatives), available from MVP Laboratories, Ralston, NE. Also of use herein is an adjuvant known as "VSA3" which is a modified form of EMULSIGEN PLUS™ which includes DDA (see, U.S. Pat. No. 5,951,988, incorporated herein by reference in its entirety). Suitable animal oils include, for example, cod liver oil, halibut oil, menhaden oil, orange roughy oil and shark liver oil, all of which are available commercially. Suitable vegetable oils, include, without limitation, canola oil, almond oil, cottonseed oil, corn oil, olive oil, peanut oil, safflower oil, sesame oil, soybean oil, and the like.

Alternatively, a number of aliphatic nitrogenous bases can be used as adjuvants with the vaccine formulations. For example, known immunologic adjuvants include amines, quaternary ammonium compounds, guanidines, benzamidines and thiouroniums (Gall, D. (1966) *Immunology* 11:369 386). Specific compounds include dimethyldioctadecylammonium bromide (DDA) (available from Kodak) and N,N-dioctadecyl-N,N-bis(2-hydroxyethyl)propanediamine ("AVRIDINE"). The use of DDA as an immunologic adjuvant has been described; see, e.g., the *Kodak Laboratory Chemicals Bulletin* 56(1):1 5 (1986); *Adv. Drug Deliv. Rev.* 5(3):163 187 (1990); *J. Controlled Release* 7:123 132 (1988); *Clin. Exp. Immunol.* 78(2):256 262 (1989); *J. Immunol. Methods* 97(2):159 164 (1987); *Immunology* 58(2):245 250 (1986); and *Int. Arch. Allergy Appl. Immunol.* 68(3):201 208 (1982). AVRIDINE is also a well-known adjuvant. See, e.g., U.S. Pat. No. 4,310,550, incorporated herein by reference in its entirety, which describes the use of N,N-higher alkyl-N',N'-bis(2-hydroxyethyl)propane diamines in general, and AVRIDINE in particular, as vaccine adjuvants. U.S. Pat. No. 5,151,267 to Babiuk, incorporated herein by reference in its entirety, and Babiuk et al. (1986) *Virology* 159:57 66, also relate to the use of AVRIDINE as a vaccine adjuvant.

Moreover, the antigens may be conjugated to a carrier protein in order to enhance the immunogenicity thereof. The carrier molecule may be covalently conjugated to the antigen directly or via a linker. Such carriers and linkers are described in detail above. Any suitable conjugation reaction can be used, with any suitable linker where desired.

Once prepared, the formulations will contain a "pharmaceutically effective amount" of the active ingredient, that is, an amount capable of achieving the desired response in a subject to which the composition is administered. In the treatment and prevention of a *Mycoplasma* disease, a "pharmaceutically effective amount" would preferably be an amount which prevents, reduces or ameliorates the symptoms of the disease in question. The exact amount is readily determined by one skilled in the art using standard tests. The active ingredient will typically range from about 1% to about 95% (w/w) of the composition, or even higher or lower if appropriate. With the present formulations, 1 μg to 2 mg, such as 10 μg to 1 mg, e.g., 25 μg to 0.5 mg, 50 μg to 200 μg, or any values between these ranges of active ingredient per ml of injected solution should be adequate to treat or prevent infection when a dose of 1 to 5 ml per subject is administered. The quantity to be administered depends on the subject to be treated, the capacity of the subject's immune system to synthesize antibodies, and the degree of protection desired. Effective dosages can be readily established by one of ordinary skill in the art through routine trials establishing dose response curves.

The composition can be administered parenterally, e.g., by intratracheal, intramuscular, subcutaneous, intraperitoneal, intravenous injection, or by delivery directly to the lungs, such as through aerosol administration. The subject is administered at least one dose of the composition. Moreover, the subject may be administered as many doses as is required to bring about the desired biological effect.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject antigens by the nasal mucosa.

Controlled or sustained release formulations are made by incorporating the antigen into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The antigens described herein can also be delivered using implanted mini-pumps, well known in the art.

Prime-boost methods can be employed where one or more compositions are delivered in a "priming" step and, subsequently, one or more compositions are delivered in a "boosting" step. In certain embodiments, priming and boosting with one or more compositions described herein is followed by additional boosting. The compositions delivered can include the same antigens, or different antigens, given in any order and via any administration route.

E. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the *Mycoplasma* antigens in the compositions of the invention after administration of the composition. Another way of assessing the immunogenicity of the immunogenic compositions of the present invention is to screen the subject's sera by immunoblot. A positive reaction indicates that the subject has previously mounted an immune response to the *Mycoplasma* antigens, that is, the *Mycoplasma* protein is an immunogen. This method may also be used to identify epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum-specific antibody responses are determined post-immunization but pre-challenge whereas mucosal specific antibody body responses are determined post-immunization and post-challenge. The immunogenic compositions of the present invention can be evaluated in in vitro and in vivo animal models prior to host administration.

The efficacy of immunogenic compositions of the invention can also be determined in vivo by challenging animal models of infection with the immunogenic compositions. The immunogenic compositions may or may not be derived from the same strains as the challenge strains Preferably the immunogenic compositions are derivable from the same strains as the challenge strains.

The immune response may be one or both of a TH1 immune response and a TH2 response. The immune response may be an improved or an enhanced or an altered immune response. The immune response may be one or both of a systemic and a mucosal immune response. An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFN-γ, and TNFβ), an increase in activated macrophages, an increase in NK activity, or an increase in the production of IgG2a. Preferably, the enhanced TH1 immune response will include an increase in IgG2a production.

The immunogenic compositions of the invention will preferably induce long lasting immunity that can quickly respond upon exposure to one or more infectious antigens.

F. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-tilled with the immunogenic compositions of the invention.

Similarly, antibodies can be provided in kits, with suitable instructions and other necessary reagents. The kit can also contain, depending on if the antibodies are to be used in immunoassays, suitable labels and other packaged reagents and materials (i.e. wash buffers and the like). Standard immunoassays can be conducted using these kits.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Analysis of Immune Responses to Recombinant Proteins from *Mycoplasma mycoides*

1.1 Materials and Methods

Identification of *M. mycoides* Protein Antigens

The complete genome sequences of *M. mycoides* subsp. *mycoides* PG1 (Accession number BX293980, Westberg et al., *Genome Res.* (2004) 14:221-227); Gladysdale (Accession number CP002107, Wise et al., *J Bacteriol.* (2012) 194:4448-4449); and partial sequences of strains IS22, 138/5, 9809 (Accession numbers JQ307942 to JQ308103. Churchward et al., *Vet Microbiol.* (2012) 159:257-259; and 8676/93 (Accession number AJ515918.1, Botehlo et al. direct submission) were obtained from the NCBI Genome database for analysis.

A reverse-vaccinology pipeline was assembled and applied for *M. mycoides* antigen prediction. PSORTb 3.0 was used to identify non-cytoplasmic proteins, including extracellular, transmembrane and unknown-location ones (Yu et al., *Nucleic Acids Res.* (2011) 39:D241-244; Yu et al., *Bioinformatics* (2010) 26:1608-1615). The transmembrane and unknown-location proteins were further analyzed for their potential transmembrane topology with TMHMM 2.0 (cbs.dtu.dk/services/TMHMM, Krogh et al., *J. Molec. Biol.* (2001) 305:567-580) and in-house Perl scripts. The extracellular proteins predicted by PSORTb 3.0, and the extracellular proteins, 1-TM (transmembrane domain) proteins and the extracellular peptide fragments between TMs with lengths no shorter than 100 amino acids predicted by TMHMM 2.0, were further analyzed by SPAAN to estimate their adhesion probability (Krogh et al., *J Mol Biol.* (2001) 305:567-580). Those with an adhesin probability of more than or equal to 0.5 were selected for vaccine candidate prediction using Vaxign (He et al., *J Biomed Biotechnol.* (2010) 2010:297505). Those proteins with a Vaxign score of >0.4 were selected. Finally, the possible host self-antigens were removed by filtering the homologs of cattle proteins. The candidate antigenic proteins were compared among different *M. mycoides* strains to observe their conservation in *M. mycoides.*

Alternatively, after retrieving genome sequences from NCBI, potential lipoproteins were identified using LipoP 1.0 (Juncker et al., *Protein Sci.* (2003) 12:1652-1662 and homologies to other *Mycoplasma* species were investigated using BLASTP (Altschul et al., *J Mol. Biol.* (1990) 215: 403-410. Where applicable, the homologous protein sequences were provided from Minm strain Shawawa, a recent African outbreak strain. For expression of lipoproteins, the N-terminal signal sequences (SpII) were removed and not included in the synthetic gene sequences. Moreover, eight predicted surface proteins that have been described elsewhere were included (Hamsten et al., *Mol. Cel Proteomics* (2009) 8:2544-2554; Hamsten et al., *Microbiology* (2008) 154:539-549).

In total, 69 proteins were selected for initial use in vaccine trials. 38 of these proteins were Mmm proteins (those indicated as MSC_xxxx in Table 1) and 28 of these proteins were encoded by *M. mycoides* subsp. *capri* (Mmc, indicated as YP_0044xxxxxxxx.1 in Table 1).

Construction of Genes Encoding *M. mycoides* Proteins

The 69 gene sequences identified above were analyzed in silico for codon usage bias, GC content, CpG dinucleotide content, mRNA secondary structure, cryptic splicing sites, premature PolyA sites, internal chi sites and ribosomal binding sites, negative CpG islands, RNA instability motif (ARE), repeat sequences (direct repeat, reverse repeat, and Dyad repeat). Restriction sites that might interfere with cloning were excluded. The genes were codon-optimized for *Escherichia coli* expression, synthesized and subcloned into the expression plasmids pSG21a or pET-15b (Novagen) containing a histidine-tag for purification of the proteins by metal-chelate affinity chromatography.

Purification of Recombinant *M. mycoides* Proteins

The plasmids encoding the recombinant *M. mycoides* proteins were used to transform *E. coli* BL21 STAR (Life Technologies, Invitrogen™, Burlington ON, CA). The transformed strains were grown in LB medium containing 50 μg/ml carbenicillin to mid-exponential phase and induced with 0.2 mM IPTG for 2 hours. The bacterial cells (4.5 g/wet weight) were collected by centrifugation (4,000×g, 20 minutes) and suspended in lysis buffer (50 mM $Na_2HPO_4$, 300 mM NaCl, and 10 mM imidazole, pH 8.0) containing 1 mg/ml lysozyme. The cells were disrupted on ice by sonication (9 cycles of 10 seconds each with 10 second cooling intervals between each sonication). The cell debris was removed by centrifugation at 4° C. and the supernatant (cleared lysate) collected. The cleared lysates were incubated with the Ni-NTA resin (Qiagen) and the histidine-tagged proteins were allowed to bind to the matrix for 1 hour at 4° C. The mix was packed in columns, the unbound fraction collected, and the columns washed four times each with 4 ml of wash buffer (50 mM $Na_2HPO_4$, 300 mM NaCl, and 40 mM imidazole, pH 8.0). The bound proteins were eluted in elution buffer (50 mM $Na_2HPO_4$, 300 mM NaCl, and 250 mM imidazole, pH 8.0), buffer exchanged into 0.1 M PBS, pH 7.2, by repetitive washes using Ultrafree centrifugal filter devices (Millipore, Bedford, MA) with a cutoff size of 10 kDa. Contaminating LPS was removed by affinity chromatography using Detoxi-Gel™ (Pierce Biotechnology, Fisher Sci. ON, CA) and the purified proteins were stored at 4° C. for further use.

Development of Multiplex assays

Purified recombinant proteins were coupled to BioRad MaxPlex C™ microsphere beads (BioRad Laboratories Mississauga, ON) using the BioRad BioPlex™ amine coupling kit following manufacturer's instructions. For the coupling of cytokines MaxPlex C™ beads were primed in sulfo-NHS and EDC before coupling the antibodies against the cytokines. IL-1, IL-10 and IL-12 antibodies were purchased from AbD Serotec (Cedarlane Laboratories LTD. Burlington, ON); IL-6 and IL-17 antibodies from Kingfisher (Cedarlane Laboratories LTD. Burlington, ON), while antibodies against IFN-α, IFN-γ, and TNF-α were produced internally. Finally, antibodies against TGF-β were obtained from R&D (Cedarlane Laboratories LTD. Burlington, ON). Twenty micrograms of each antibody were coupled to the primed MaxPlex™ beads in 100 μl of 100 mM MES pH6 buffer for 2 hours at room temperature, shaking at 600 rpm. Tubes containing the beads were placed on the magnetic separator for 1 minute after which the supernatant was removed. Tubes were removed from the separator and suspended in 100 μl of PBS-BN (PBS, 1% BSA, 0.05% azide, pH 7.4) using vortex and a sonicator bath. The beads were incubated for 30 minutes at room temperature with shaking after which the tubes were placed in the magnetic separator for 1 minute. The supernatant was removed and beads were washed in 200 μl PBST three times. Beads were suspended in 75 μl of TE and stored at 4° C. until use.

Ranking of *M. mycoides* Antigens

The proteins were individually tested against 35 CBPP-positive and 15 CBPP-negative bovine sera by a multiplex ELISA assay as follows. Labeled beads (50 μl) suspended in PBS-T at a concentration of 10,000 beads/ml were applied to each well of a 96-well plate. Beads were washed in PBS and 50 μl of serial dilutions of test serum was applied to each well. The mix was incubated for 30 minutes at room temperature on a shaker at 750 rpm. After washing in PBS, the beads were incubated with 50 μl/well of anti-bovine IgG1, IgG2 or IgA coupled to biotin at a 1/5000 dilution and incubated for 30 minutes at room temperature on a shaker at 750 rpm. The beads were washed with PBS and 50 μl of a 1/2000 dilution of Strepavidin-Phycoerythrin (SA-PE) per well was added and incubated at room temperature for 10 minutes with shaking at 750 rpm The beads were washed in PBS after which, 125 μl of PBS was added to each well followed by shaking for 3 minutes at 750 rpm. The fluorescence on the beads was read on a BioRad BioPlex 200™ reader (BioRad Laboratories Mississauga, ON; 100 μl volume, 50 beads per region). The titres were calculated by the intersection of least-square regression of $A_{405}$ versus the logarithm of the serum dilution. The proteins were ranked according to the IgG1 titres of the 35-positive animals, i.e. the higher the titres, the higher the rank.

Vaccine Trials 170 male naïve Boran cattle (*Bos indicus*) aged 2-3 years were used. Prior to use, animals were screened for anti-Mmm antibodies using CFT. No positive animals were detected. Due to the large number of animals used, the trials were divided into three. In total, seventeen groups of 5 animals per group were used. The first trial consisted of 60 cattle placed into five test groups (designated Groups A-E) and a placebo group (Group F). The second trial consisted of 60 cattle also placed into five test groups (designated Groups G-K) and a placebo group (Group L). The third trial consisted of 50 cattle placed into four test groups (Groups M-P) and a placebo group (Group Q).

The proteins were assembled into pools for vaccine formulations according to their ranking order, i.e. the first five proteins were included in group A, the second five in group B and so on. See Table 1. In Table 1, Vaccines for the first and second trials were composed of five proteins while the vaccines for the third trial included four proteins, as shown in Table 1. The proteins were combined with CpG-ODN 2007 (5'TCGTCGTTGTCGTTTTGTCGTT3'; SEQ ID NO:29) and 30% Emulsigen™ (MVP Laboratories, Ralston, NE).

Animals were inoculated subcutaneously on the right neck with 2 ml of the vaccine formulation (50 μg of each antigen was present per inoculation) and a booster given 21 days later to the left neck. Rectal temperatures and other clinical signs were recorded daily. Blood was collected weekly for storage of serum and at three time points (pre-vaccination, post-vaccination and post-challenge) for preparation of peripheral blood mononuclear cell (PBMC) for use in proliferation assays. Samples collected on the day of primary vaccination represented day 0 of the trial.

ELISA and PBMC Proliferation Assays

ELISA tests were carried out on proteins coupled to magnetic beads as described above. The 66 recombinant proteins were tested for IgG1, IgG2, and IgA antibody responses on pre-vaccination (Day 0), pre-boost (Day 21) and post-boost (Day 35) serum samples as described above. Serum cytokine levels were measured on the same serum samples and on supernatants of PBMC cultures stimulated with the recall antigens by a multiplex ELISA assay. The cytokines tested were IL-1, IL-6, IL-10, IL-12, IL-17, IFN-α, IFN-γ, TNF-α, and TFG-β. After incubation of the beads with undiluted serum samples, beads were washed and biotinylated cytokine detection secondary antibodies were added and tubes incubated for 30 minutes at room temperature with shaking at 750 rpm. After washes, 50 μl of a 1/2000 dilution of Strepavidin-Phycoerythrin (SA-PE) per well was added and incubated at room temperature for 10 minutes with shaking at 750 rpm. The beads were washed in PBS after which 125 μl of PBS was added to each well followed by shaking for 3 minutes at 750 rpm. The fluorescence on the beads was read on a BioRad BioPlex 200™ reader (100 μl volume, 50 beads per region). The cytokine concentrations were calculated by comparing the fluorescence value to that of beads incubated with purified cytokines used as standards.

For the proliferation assays, blood samples (20 ml from each animal) were collected in Vacutainer™ tubes containing sodium EDTA. The PBMC were separated by centrifugation (2500×g for 20 minutes) and the PBMCs (buffy coat) removed and transferred to Ficoll™ gradients (GE Healthcare, Mississauga, ON). The PBMCs were collected from the gradient, washed three times with PBSA (137 mM NaCl, 2.7 mM KCl, 7 mM $Na_3PO_4$ and 1.5 mM $KH_2PO_4$) containing EDTA and suspended in tissue culture media (MEM) to $1\times10^7$ cells/ml. The proliferation of PBMCs after stimulation with Concanavalin A (ConA) (Sigma-Aldrich, Oakville, ON) and/or recombinant proteins was determined by seeding 96-well Nunclon Delta Surface plates (Fisher Thermo Sci., NY, USA) at a concentration of $3\times10^5$ PBMCs/well. Cells were incubated at 37° C. in 5% $CO_2$ in the presence of 1 μg/ml of ConA and/or recombinant proteins for 72 h in triplicate. A solution containing 0.4 μCi/well of $^3$H-thymidine (GE Healthcare, Mississauga, ON) was added and the cells incubated for 18 hours. Cells were harvested (Packard, Filtermate Harvester) and the amount of incorporated $^3$H-thymidine was determined in a scintillation counter (Packard, Top Count NXT™) and the stimulation index determined by dividing the treated cell counts by media counts.

Statistical Analyses

The immune responses to the antigens between day 0, 21, and 35 titers for each antigen and between day 35 titres in the same group were analyzed using non-parametric Kruskal-Wallis with Dunn's multiple comparison tests. The day 35 responses between vaccinated and placebo group for each antigen were analyzed by Mann-Whitney test. For the statistical analyses Prism version 6 for Mac OS X was used. GraphPad Software, San Diego California USA. Data was considered statistically different if the P value was 0.05 or less.

1.2 Humoral Immune Responses to the Recombinant Proteins

Candidate antigens were identified by reverse vaccinology as described above and are listed in Table 1. The genes coding for these putative antigens were cloned and expressed in *E. coli* and 66 recombinant proteins were tested against CBPP-positive and CBPP-negative sera from infected Kenyan animals. The proteins were ranked based on their respective antibody titres in sera from immune, but not naïve animals. Before using these proteins to vaccinate African cattle breeds, Canadian crossbreed cattle were vaccinated to evaluate the magnitude and quality of immune responses. Due to the large number of animals and vaccine groups, Three animal trials were conducted as described above, with each trial composed of a placebo group and either five (trials 1 and 2) or four test groups (trial 3). The vaccine groups and treatments are shown in Table 1. For each group (including the respective placebo group) pre- and post-vaccination serum IgG1 and IgG2 responses were tested to the cognate recombinant proteins.

In the first trial, recombinant proteins ranked 1$^{st}$ to 25$^{th}$ were tested and the results are shown in FIGS. 1A-1E. Compared to the day 0 levels, at day 35 the IgG1 titres against the proteins from each group were significantly higher in groups A to E with P values ranging from <0.05 to <0.01, FIGS. 1A-1E). The day 35 IgG1 titres in the vaccinated groups were also compared to the placebo titres and the results are also shown in FIGS. 1A-1E. For all the proteins in this trial, the IgG1 titres in the vaccinated groups were significantly different than the placebo groups with P values ranging from <0.05 to <0.01, FIGS. 1A-1E). Finally, the day 35 titres for each protein in the each of the vaccinated groups were compared to each other and with the exception of YP_004400559.1 (SEQ ID NO:12) to YP_004399807.1 (SEQ ID NO:14) and MSC_0816 (SEQ ID NO:16), there were no significant differences between the IgG1 levels (FIG. 1C, group C).

The IgG2 titres were also determined in this trial and the results are shown in FIGS. 2A-2E. Like IgG1, in all the groups there were significant differences between the day 0 and 35 IgG2 titres, between the vaccinated and placebo groups at day 35 and also the IgG2 titres to YP_004400559.1 (SEQ ID NO:12) were significantly lower than MSC_0816 (SEQ TD NO:16) and MSC_0160 (SEQ ID NO:18) (FIG. 2C, group C).

In the second trial, humoral responses to the recombinant proteins ranked 26$^{th}$ to 50$^{th}$ were tested and the results are shown in FIGS. 3A-3E. Compared to the day 0 levels, at day 35 the IgG1 titres against the proteins from each group were significantly higher in groups G to K with P values ranging from <0.05 to <0.01 (FIGS. 3A-3E, groups G to K). As in trial 1, the day 35 IgG1 titres in the vaccinated groups were significantly different to the placebo groups with P values ranging from <0.05 to <0.01 (FIG. 2). With the exception of MSC_0453 (FIG. 3B, group H), and YP_004400226.1 (FIG. 3E, group K), the day 35 IgG1 titres to the proteins in each group were not significantly different between each other (FIGS. 3A-3E).

The IgG2 titres were measured and the results are shown in FIG. 4A-4E. Like the IgG I titres, all the IgG2 levels were significantly different between days 0 and 35 in all the groups with the exception of YP_004400226.1 (FIG. 4E, group K). When the day 35 titres for each protein in the same group were compared, some of these were significantly lower MSC_0782 (FIG. 4A, group G); MSC_0453 (FIG. 4B, group H); YP_004400602.1 and YP_004400291.1 (FIG. 4C, group I); YP_004400622.1 and YP_004400371.1 (FIG. 4E, group K).

In the third trial, humoral responses to the recombinant proteins ranked 51$^{st}$ to 66$^{th}$ were tested and the results are shown in FIGS. 5A-5D. Compared to the day 0 levels, at day 35 the IgG1 titres against the proteins from each group were significantly higher in groups M to P with P values ranging from <0.05 to <0.01 (FIGS. 5A-5D, groups M to P). Serum IgG1 titres at day 35 in the vaccinated groups were significantly different than the placebo groups with P values ranging from <0.05 to <0.01 (FIGS. 5A-5D). With the exception of YP_004400171.1 (FIG. 5C, group O), there were no significant differences between the day 35 titres in the proteins from the same group.

The IgG2 titres were measured and like the IgG1 levels, most titres were significantly different between day 0 and 35 (FIGS. 6A-6D) with the exception of YP_004400399927.1 (FIG. 6D, group P). Most proteins showed significant differences in the day 35 titres between vaccinated and placebo groups with the exception of YP_0044004399927.1.1 (FIG. 6D, group P). When the day 35 titres for each protein in the same group were compared, some of these were significantly lower YP_004400581.1 (FIG. 6A, group M); MSC_0453 (FIG. 6B, group N); YP_004400446.1 and YP_004399927.1 (FIG. 6D, group P).

1.3 Cell-Mediated Immune Responses

Cell-mediated immune responses in each group were determined by measuring proliferation of bovine PBMC collected at days 0 and 35 in response to the cognate recall antigens. At day 0, there were no significant differences between the stimulation indexes (Si) of the placebo and vaccinated groups for all the antigens in all the trials. In the first trial, there were no significant differences between the stimulation indexes of PBMC collected at day 35 and incubated with the recall antigens in groups A, B, C, D, and E (FIGS. 7A-7E).

Similar results were observed for the second and third trials. In the second trial, there were no significant differences between the stimulation indexes of PBMC collected at day 35 and incubated with the recall antigens used on groups G, H, I, J, and K (FIGS. 8A-8E). Finally, there were no significant differences between the stimulation indexes of PBMC collected at day 35 and incubated with the recall antigens used on groups M, N, O and P (FIGS. 9A-9D).

1.4 Cytokine Levels

Figure 10A:
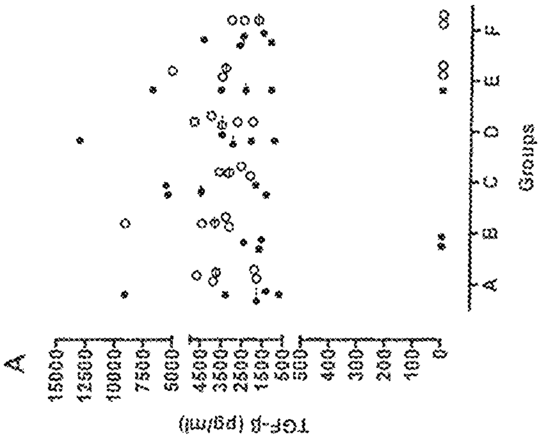
FIGS. 10A-10C show serum TGF-β levels in the three trials as described in the examples. The day 0 and day 35 serum TGF-β levels for trials 1, 2 and 3 are shown in A, B, and C respectively. The black circles indicate the levels at day 0 while white circles show the levels at day 35. The groups including the placebo groups F, L, and Q are indicated on the X-axis. In trials 1 and 2, there were no significant differences between day 0 and day 35 TGF-β levels. The TGF-β levels at day 35 were significantly lower (P<0.05) than the day 0 values in the groups M and P of the third trial.
Figure 10B:
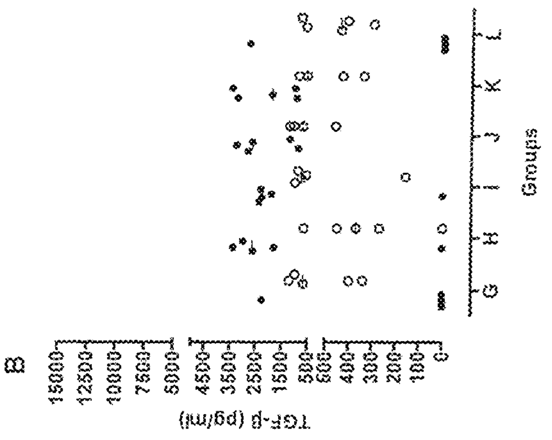
Figure 10C:
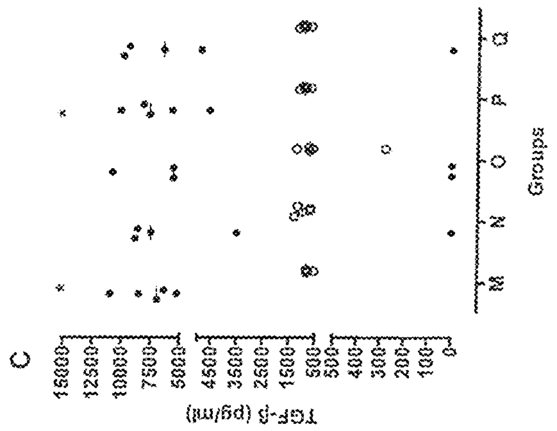

The presence of cytokines on the supernatants of PBMC stimulated with the recall antigens was determined. Cytokines (mostly TGF-β) were detected in only a few of the supernatant tests. The assays were repeated on serum samples and out of all the cytokines tested, TGF-β was consistently detected, however pre- and post-vaccination levels did not significantly differ in animals of the first and second trial (FIGS. 10A and 10B, respectively). In the third trial, the TGF-β pre-vaccination levels were higher than the post vaccination levels with significant differences in groups M and P (FIG. 10C).

In sum, the serum IgG1 responses to all 66 proteins were significantly different at day 35 compared to day zero (FIGS. 1, 3 and 5). Similar results for most of the proteins were observed for the IgG2 titres with the exception of YP_004400226.1 that failed to elicit significant IgG2 responses (FIG. 4C, group 1), YP_004400581.1, YP_0043999851.1, YP_004399914.1 (FIG. 6A, group M); YP_004399927.1 and YP_004400204.1 (FIG. 6D, group P). These results indicate that most of the proteins tested were able to elicit IgG1 and IgG2 responses and thus could be part of a panel of vaccine molecules to be tested in immunization and challenge experiments as detailed below. The proteins identified in this study included 15 lipoproteins, 15 hypothetical proteins, 6 transmembrane proteins and 4 transport proteins (Table 1). These proteins represent new vaccine targets.

The approach of first selecting antigens by reverse vaccinology, followed by ranking them in order of strong antibody responses, therefore proved to be successful in identifying several targets for a protective vaccine against CBPP.

TABLE 1

Proteins and Vaccine Groups

| Name (NCBI Accession #) | Description | Size | Vaccine group[a] |
|---|---|---|---|
| MSC_0136 | Hypothetical lipoprotein | 66 kDa | A |
| MSC_0957 | Prolipoprotein | 79 kDa | |
| MSC_0499 | Prolipoprotein | 111 kDa | |
| MSC_0431 | Prolipoprotein | 70 kDa | |
| MSC_0776 | Prolipoprotein | 120 kDa | |
| MSC_0519 | Prolipoprotein | 99 kDa | B |
| MSC_0500 | Hypothetical lipoprotein | 138 kDa | |
| MSC_0575 | Hypothetical lipoprotein | 69 kDa | |
| MSC_0653 | Prolipoprotein | 75 kDa | |
| MSC_0397 | Prolipoprotein | 45 kDa | |
| YP_004400559.1 | Hypothetical protein | 18 kDa | C |
| YP_004399807.1 | Hypothetical protein | 41 kDa | |
| MSC_0816 | Variable surface lipoprotein | 76 kDa | |
| MSC_0160 | Translation elongation factor Tu | 75 kDa | |
| MSC_0775 | Prolipoprotein | 81 kDa | |
| MSC_0013 | Prolipoprotein | 92 kDa | D |
| MSC_0610 | DnaK | 64 kDa | |
| MSC_0265 | Pyruvate dehydrogenase α-chain | 74 kDa | |
| MSC_0052 | Hypothetical lipoprotein | 111 kDa | |
| MSC_0240 | Immunodomiant protein P72 | 94 kDa | |
| MSC_0014 | Prolipoprotein A/P72 | 91 kDa | E |
| MSC_0011 | Ribose-galactose ABC transporter | | |
| YP_004400534.1 | Transmembrane protein | 229 kDa | |
| MSC_0813 | Variable surface protein | 88 kDa | |
| MSC_0184 | Oligopeptide ABC transporter substrate-binding component | 149 kDa | |
| MSC_0782 | Prolipoprotein | 101 kDa | G |
| MSC_0401 | Prolipoprotein | 34 kDa | |
| MMS_A0381 | Conserved hypothetical lipoprotein | 100 kDa | |
| MSC_1058 | Variable prolipoprotein | 45 kDa | |
| MSC_0790 | Alkyl-phosphonate ABC transporter substrate-binding protein | 85 kDa | |
| MSC_0453 | FKBP-type peptidyl-prolyl isomerase | 81 kDa | H |
| MMS_A0108 | Putative lipoprotein | 71 kDa | |
| MSC_0798 | Prolipoprotein | 107 kDa | |
| MSC_0266 | Pyruvate dehydrogenase β-chain | 68 kDa | |
| MSC_0456 | Prolipoprotein | 125 kDa | |
| YP_004400602.1 | Transmembrane protein | 15 kDa | I |
| YP_004400291.1 | Transmembrane protein | 82 kDa | |
| YP_004400300.1 | Lipoprotein | 98 kDa | |
| YP_004400620.1 | Hypothetical protein | 24 kDa | |
| MSC_1005 | Variable surface prolipoprotein | 77 kDa | |
| YP_004400616.1 | Hypothetical protein | 18 kDa | J |
| YP_004400615.1 | Hypothetical protein | 23 kDa | |
| MMS_A0415 | Putative lipoprotein | 45 kDa | |
| MSC_0927 | Hypothetical lipoprotein | 45 kDa | |
| MSC_0804 | ABC transporter substrate-binding component | 83 kDa | |
| YP_004400622.1 | Hypothetical protein | 24 kDa | K |
| YP_004400371.1 | Permease | 84 kDa | |
| YP_004400226.1 | Hypothetical protein | 15 kDa | |
| YP_004400021.1 | PTS transporter | 36 kDa | |
| MSC_0163 | Lencyl aminopeptidase | 82 kDa | |
| YP_004400581.1 | Transmembrane proteins | 52 kDa | M |
| YP_004400296.1 | Lipoprotein | 101 kDa | |
| YP_004399851.1 | PTS transporter | 19 kDa | |
| YP_004399914.1 | Hypothetical protein | 16 kDa | |

TABLE 1-continued

| Proteins and Vaccine Groups | | | |
|---|---|---|---|
| Name (NCBI Accession #) | Description | Size | Vaccine group[a] |
| YP_004400127.1 | Hypothetical protein | 27 kDa | N |
| YP_004399790.1 | Hypothetical protein | 38 kDa | |
| YP_004400580.1 | Lipoprotein | 49 kDa | |
| YP_004400610.1 | Hypothetical protein | 23 kDa | |
| YP_004400171.1 | ABC transporter | 41 kDa | O |
| MSC_0139 | Fructose-bisphosphate aldolase class II | 65 kDa | |
| YP_004399939.1 | Transmembrane protein | 55 kDa | |
| YP_004400004.1 | Transmembrane protein | 41 kDa | |
| YP_004400446.1 | Hypothetical protein | 20 kDa | P |
| YP_004399927.1 | Hypothetical protein | 41 kDa | |
| YP_004400204.1 | Hypothetical protein | 149 kDa | |
| YP_004400368.1 | Hypothetical protein | 105 kDa | |

References for all proteins in Table 1 are provided in Perez-Cascal et al., Vet. Immunol. Immunopathol. (2015) 168:103-110.

[a]In addition to these vaccine groups, three placebo groups were included (groups F, L, and Q).

Vaccines were formulated with 50 μg of each antigen per dose. In all the groups, the vaccines were adjuvanted with 30% Emulsigen and 250 μg CpG 2007 per dose.

Example 2

Protective Immune Responses to Recombinant Proteins from *M. mycoides* against CBPP

2.1 Materials and Methods

*M. mycoides* Protein Antigens, Vaccines and Administration

*M. mycoides* protein antigens were identified, ranked and produced as described in Example 1. Cattle were grouped and vaccines were prepared and administered to cattle as described above. As explained, three challenge trials (comprising 60 cattle each for trials 1 and 2 and 50 for trial 3) were conducted, with each trial having vaccinated groups of 10 cattle each and a placebo group as indicated in Table 1. Each group of animals was immunized with a pool of five proteins as described above.

Mmm Strain and Growth Conditions

The Mmm Afadé strain was grown in Gourlay's medium (Gourlay, R. N, *Research in Veterinary Science* (1964) 5:473-482) containing 20% heat-inactivated pig serum, 0.25 mg penicillin/ml, 0.025% thallous acetate. The medium was stored at 4° C. and used within 14 days.

For the culture of Mmm, 1 ml aliquot of the master seed culture was thawed for 30 minutes at room temperature and inoculated into bijou bottles containing fresh Gourlay broth pre-warmed at 37° C. Ten-fold dilutions were made into bijou bottles containing the broth and a portion of these dilutions was streaked on Gourlay agar plates. These were then incubated at 37° C. in humidified incubator containing 5% $CO_2$ for 48 hours. Colonies were screened for the typical fried egg appearance of Mmm. Cultures were upscaled every 24 hours, ensuring that *Mycoplasma* were always kept in log phase. The cultures were pooled and aliquoted in samples of 50 ml (around $10^{10}$ CFU/ml) and stored at −80° C. to provide a standardized source of inocula.

Animal Challenge

Two weeks post-boost administration, cattle were challenged by introducing the Mmm Afade strain into the lungs, as previously described (Nkando et al., *Tropical Animal Health and Production* (2010) 42:1743-1747). Briefly, all cattle were sedated with 0.05 mg/kg body weight of xylazine hydrochloride (Rompun™) intramuscularly. In a standing position, a lubricated endotracheal rubber tube was introduced through the nostrils to the larynx and down to the distal trachea. Using a syringe, 100 ml of the Mmm culture containing approximately $10^{10}$ CFU/ml was deposited, followed by 15 ml of pre-warmed 1.5% low temperature melting agar (Sigma, UK), suspended in sterile distilled water. This was followed by 30 ml of PBS to flush down the suspension to the target site.

Preparation of Cell Samples for Proliferative Assay

Blood was collected by venipuncture into a syringe containing an equal volume of Alsever's solution and mixed gently. PBMC were separated from whole blood by density gradient centrifugation over Ficoll-Paque™ PLUS solution (GE Healthcare Bio-Sciences AB, Sweden). In brief, 10 ml of Ficoll-paque solution was placed in a centrifuge tube and blood was layered on top. This was centrifuged at 400×g for 30 minutes at room temperature. The layer containing PBMCs was aspirated from the interface and transferred into another sterile centrifuge tube and washed with Alsever's solution by centrifuging at 200× g for 15 minutes at room temperature. The pellet was suspended in 2 ml of pre-warmed lysis buffer (Tris-buffered ammonium chloride solution: 0.16M $NH_4Cl$ and 0.17M Tris HCL, pH 7.2) and incubated at room temperature for 10 minutes with gentle shaking. A second wash was performed with Alsever's solution by centrifuging at 200× g for 10 minutes at room temperature. The resulting pellet was suspended in RPMI 1640 medium containing 10% fetal bovine serum (FBS) (Sigma-Aldrich), 20 mM HEPES, 2-mercaptoethanol at $1\times10^{-5}$, 2 mM L-Glutamine and Gentamicin 50 μg/ml. An aliquot of the cell suspension was taken and cells counted on an automated hematology analyzer (Nihon Kohden Corporation, Japan).

Cell Stimulation Assays

The PBMC at a cell density of $3.5\times10^6$ cells/ml were distributed into each well (100 ml/well) of a 96-well round-bottomed microtitre plate in triplicates. Cells were left untreated (negative control; RPMI 1640 with 10% FBS) or were stimulated with either mitogen Concanavalin A (ConA at 2 μg/ml; Sigma-Aldrich) or Mmm antigen (at a concentration of 10 μg/ml). These were incubated for 72 hours at 37° C. in a humidified 5% $CO_2$ incubator. Tritiated [$^3$H] thymidine (25 μl, 0.5 μCi per well) was added and the plates were returned to the $CO_2$ incubator to pulse for 18 to 24 hours. Cells were harvested onto glass fiber filter mats using a semi-automated cell harvester (Perkin Elmer, Inc.). The samples were analyzed in a scintillation counter (Perkin Elmer, Inc.) and data was expressed as the mean of the triplicate cultures. Results were presented as stimulation indices (calculated as counts obtained with cells cultured in presence of antigen divided by counts obtained with cells cultured in medium alone).

Clinical Examination

Animals were observed daily and clinical findings suggestive of CBPP were recorded over the whole period of the trial (Nkando et al., *Research in Veterinary Science* (2012) 93:568-573). These included rectal temperatures, cough, nasal discharge, dyspnea, anorexia, weight-loss and eye discharges.

Serological Examination

Animals were bled weekly during the whole period of the trial. Blood samples were collected via jugular venepuncture into Vacutainer® tubes and allowed to clot at room temperature. Serum was thereafter separated and aliquoted into sterile vials, labeled, packed and stored at −20° C. until the end of the trial. Samples from each animal were tested serially for the presence of Mmm antibodies using CFT and indirect ELISA (iELISA). The CFT was carried out according to the method of Campbell and Turner (Campbell et al., *Australian Vetermnary Journal*(1953) 29:154-163), with some modifications. The ELISA tests were carried out on proteins coupled to magnetic beads as described in Example 1. Briefly, purified recombinant proteins were coupled to BioRad MaxPlex-C microsphere beads using the BioRad BioPlex amine coupling kit following manufacturer's instructions. Labeled beads (50 μl) suspended in PBS-T at a concentration of 10,000 beads/ml were applied on each well of a 96-well plate. Beads were washed in PBS and 50 μl of serial dilutions of test serum were applied to each well. The mix was incubated for 30 minutes at room temperature on a shaker at 750 rpm. After washing in PBS, the beads were incubated with 50 μl/well of anti-bovine IgG1, IgG2 or IgA coupled to biotin at a 1/5000 dilution and incubated for 30 minutes at room temperature on a shaker at 750 rpm. The beads were washed with PBS and 50 μl of a 1/2000 dilution of Strepavidin-Phycoerythrin (SA-PE) per well were added and incubated at room temperature for 10 minutes with shaking at 750 rpm. The beads were washed in PBS after which, 125 μl of PBS was added to each well followed by shaking for 3 minutes at 750 rpm. The fluorescence on the beads was read on a BioRad BioPlex 200 reader (100 μl volume, 50 beads per region). The titres were calculated by the intersection of least-square regression of $A_{405}$ versus the logarithm of the serum dilution.

Postmortem Examination

At six weeks post-challenge, cattle were euthanized. Blood for serum was collected in Vacutainer® tubes. Upon opening the carcass, pleural fluid, where present, was aspirated into a 10 ml syringe and immediately stored in a cool box. The lungs were then examined for CBPP lesions. Lesions type and size (diameter in cm) were recorded. Pieces of lung from an area between the lesion and the grossly normal tissue were cut and placed in sterile polyethylene bags, transferred to a cool box and transported to the laboratory where they were processed and cultured for isolation of *Mycoplasma* organisms.

Lesion scoring and protection rates

To determine severity of the disease in individual animals, the size of lung lesions was recorded and lung pathology scored according to the system described by Hudson and Turner (Hudson et al., *Australian Veterinary Journal* (1963) 39:373-385), in which the score is a combination of the type, the size of lesions, and the isolation of Mmm from tissues. Briefly, the presence of only encapsulated, resolving or fibrous lesions or pleural adhesions only, was rated one (1). The presence of other types of lesions such as consolidation, necrosis or sequestration was rated two (2). If in addition Mmm was isolated, a two (2) was added to the above rating. The resulting score was then multiplied by a factor depending on the lesion size i.e., multiplied by factor 1 if the lesion size was under 5 cm in diameter, by factor 2 if the size was over 5 cm and under 20 cm, and by factor 3 if the size was over 20 cm in diameter. Hence, the maximum pathology score was (2+2)3=12. Protection rate (defined as the percentage reduction in lung pathology brought about by vaccination) was calculated from the lesion scores of control and vaccinated animals, according to Hudson and Turner (Hudson et al., *Australian Veterinary Journal* (1963) 39:373-385), using the formula (NV−V)×100/NV, where NV is the score of the non-vaccinated group and V is the score of the vaccinated group.

Bacteriological Examination

Lung tissue samples were sliced into small pieces using sterile scalpels and immersed in bijou bottles containing pre-warmed Gourlay's medium containing 20% heat-inactivated pig serum, 0.25 mg penicillin/ml, 0.025% thallous acetate and phenol red indicator. Pleural fluid was inoculated directly into the broth medium. The bijou bottles were incubated at 37° C. in a humidified 5% $CO_2$ incubator. The following day, 1 ml of the supernatant was diluted using a 10-fold dilution series and returned in the same incubator under the same conditions for 3 days. From these dilutions, 0.2 ml was streaked onto agar plates containing Gourlay's solid medium. The remaining (0.8 ml) broth cultures and the agar plates were incubated at 37° C. in a humidified 5% $CO_2$ incubator. These were examined daily for ten days for evidence of growth, indicated by color change from pink to yellow, and in some cases by filamentous growth or turbidity with a whitish deposit at the bottom of the bottles. The plates were examined under inverted microscope for *Mycoplasma* microcolonies at day 1, 5 and 10, respectively. Growth on solid medium was characterized by the presence of micro-colonies with the classical fried egg appearance.

2.2 Post-Inoculation Clinical Response (Safety) and Serological Response to Proteins Following vaccination (and before challenge) seroconversion by CFT was not observed in any cattle in trial 1. However, seroconversion was detected seven days post-vaccination in trial 2 (15 out of 50 immunized animals) and 3 (7 out of 40 immunized animals), but none of the cattle exceeded titres of 1/10, and as expected, no serocoversion was observed in the control group. By the time of challenge however, no titres were detected in any of these cattle.

2.3 Clinical and Serological Findings Post-Challenge

Table 2 shows highest temperature recorded (clinical) and serological (CFT and iELISA) findings. In all three trials, almost every animal that contracted CBPP, as assessed post-mortem, from either the vaccinated or the control group presented clinical signs typical of the disease that included fever, cough, nasal discharge, dyspnoea and disinclination to move and adopt postures, suggestive of oxygen deficiency. Clinical signs commenced six days post-infection (dpi) for trials 1 and 2 but the first case in trial 3 was observed on day 9 post-infection (p.i.). In all trials, the signs peaked between days 16 and 21 p.i. Fever (in this study considered to be >39.5° C.) was intermittent and ranged between 39.5 and 40.5° C. in the three trials. The first febrile reaction was observed on day 20 p.i. in trial 1, on day 9 and 21 p.i in trial 2 and 3, respectively. Out of the eleven cattle in trial 1 that exhibited fever, two 1 5 were from the control group whereas the rest were from the vaccinated groups.

In trial 2, fever was observed in seven animals in the vaccinated groups and none in the control group. The number of cattle showing fever was highest in trial 3 where 37 cases were observed. Out of these, four were from the control group Some animals manifested severe clinical symptoms and had to be euthanized before the planned end of the experiment. These included five from trial 1 (two from group E and one from group A and B, and control, respectively). Three animals, all from the vaccinated groups in trial 2, were euthanized. None of the animals in trial 3 was euthanized before the planned end of trial.

In all trials, CFT titres were detected 2 weeks post challenge and ranged between 1/10 and 1/640. Trial 1 had 17/60 cattle seroconverting including 4/10 from the control group, 2/10 from group A and C, respectively, and 4/10 from group B and E, respectively. Group D had one cattle seroconverting. More than half of the cattle (35/60) in trial 2 had serum CFT titres. Out of these, three were from the control group while group G, J and K had each 8 cattle seroconverting, and group H and I had 4 cases each. In trial 3, 10/50 cattle comprising 4/10 and 1/10, in group M and N, respectively, developed CFT titres. Groups O and P each had 2/10 while the control group had only one animal seroconverting.

2.4 Cell Stimulation Indices

Mmm-specific recall proliferation was detected in cattle following vaccination at varying magnitudes. Some animals demonstrated marginal responses in the assays performed before vaccination. However, following vaccination, responses were detected in all vaccinates indicating this was as a result of vaccination. The results of lymphocyte stimulation to the immunized antigens are shown in Table 3. The stimulation indices shown are compared to a medium-only value of 1.

In trial 1, SI values for the vaccinated groups were all above the pre-immunization value except one antigen in group E (MSC_0813). The values in the control group were all within the pre-immunization values except for two proteins (MSC_0775 and MSC_0500) which showed a relatively higher value post vaccination. In general, the responses detected in group A (group average of 4.2) post-vaccination were higher than in other vaccinated groups and lowest in group E. The strongest responses post vaccination were observed in presence of proteins MSC_0957, MSC_0500 and MSC_0775 which were in groups A, B and C, respectively.

In trial 2, the reactivity detected in group H was higher than in other groups following vaccination and lowest in group K.

In trial 3, there was no reactivity detected in any of the groups following vaccination.

Following challenge, the responses detected in all groups in trial 1 were weak and almost comparable to those of day 0 (pre-vaccination). This was in contrast to the control group where the values were slightly higher than those observed pre-vaccination.

In trial 2, the reactivity detected following challenge increased in all vaccinated groups with groups J and G triggering the strongest and weakest responses, respectively. Proteins MSC 0456 and MMS A0415 triggered the strongest responses as compared to the other proteins. There were no responses observed in the control group.

In trial 3, following challenge, the responses in the vaccinated groups increased marginally.

2.5 Necropsy and Bacteriological Findings

Table 2 shows the number of animals with lesions and those from which Mmm was isolated in each group. Postmortem examination revealed gross pathological lesions characteristic of CBPP including: consolidation of the lung parenchyma and pleuritis, hepatization and marbling appearance, well-developed sequestra that were either unilateral or bilateral. In all trials, extension and lesion severity were variable among the cattle within the groups. Some cattle displayed large sequestra encompassing the whole lung lobe while others had multiple sequestra ranging between 2 and 46 cm in diameter. In some cases, the pleural cavity contained copious amounts of clear amber-colored fluid (up to 6 liters) with fibrinous flecks. Fibrous adhesions of the parietal and visceral pleurae were observed in those with sequestra.

In trial 1, lung lesions were observed in 28/60 cattle. Out of these, nine were from the control group whereas 19 were from the vaccinated groups. With the exception of group E, the occurrence of lung lesions in other vaccinated groups was 2-4 times less frequent as compared to the control group. The mean pathology scores in the vaccinated groups was also about 2-6 times lower than that of the control group, except for groups B and E. Apart from group C, Mmm was isolated from the lung samples of the other groups.

In trial 2, lung lesions were observed in 29/60 cattle. Out of these, four were from the control group whereas 25 were from the vaccinated groups. The occurrence of lung lesions in the vaccinated groups was comparable to the control group, although mean pathology indices were higher in the vaccinated groups as compared to the control group. Isolation of Mmm was also higher in the vaccinated groups as compared to the control group.

In trial 3, lung lesions were observed in 27/50 cattle. Out of these, 19 were vaccinates (4/10, 4/10, 5/10, and 6/10, in groups M, N, O and P, respectively) and 8 were controls. With the exception of group N, all other groups had at least one animal harboring sequestra. The occurrence of lung lesions in vaccinated groups (Group M and N) was 2 times less frequent as compared to the control group. However, the lung lesions exhibited by the 4 animals in Group N were very mild and of a resolved nature as compared to those that were exhibited by the 4 animals in group M which were severe. Average scores for lesion size were extremely low in Group N as compared to the other groups. The average score in Group N was about 4 times lower than that of the control group. A score of 0.4 and 1.5 was recorded in Group N and the control, respectively. At the time of necropsy, Mmm was not recovered from any cattle in group N.

2.6 Protection Rates

The protection rates in the different groups of cattle, defined as the percentage reduction in lung pathology brought about by vaccination, are illustrated in Table 2. In trial 1, protection was observed in Groups A, C and D, with the rates of 79.2%, 83.0%, 84.9%, respectively. Protection was not observed in any group in trial 2, and pathology was significantly higher than in the non-immunized animals. In trial 3, however, protection of 73.3% was observed in group N, the other had a higher pathology.

TABLE 2

Pathology and protection rates for the various pools of the prototype vaccines

| | Group | No. of cattle | No. with lung lesions | No. with Mmm isolation | Protection rate |
|---|---|---|---|---|---|
| Trial 1 | A | 10 | 2 | 2 | 79.2% |
| | B | 10 | 4 | 5 | 37.7% |
| | C | 10 | 3 | 0 | 83.0% |
| | D | 10 | 2 | 3 | 84.9% |
| | E | 10 | 8 | 4 | 20.8% |
| | F, placebo | 10 | 9 | 4 | 0% |
| Trial 2 | G | 10 | 5 | 5 | −47.6% |
| | H | 10 | 6 | 7 | −38.1% |
| | I | 10 | 6 | 7 | −52.4% |
| | J | 10 | 5 | 4 | −57.1% |
| | K | 10 | 4 | 6 | −61.9% |
| | L, placebo | 10 | 5 | 4 | 0% |
| Trial 3 | M | 10 | 4 | 6 | −153.3% |
| | N | 10 | 4 | 0 | 73.3% |
| | O | 10 | 5 | 4 | −66.7% |
| | P | 10 | 6 | 2 | −73.3% |
| | Q, placebo | 10 | 8 | 1 | 0% |

TABLE 3

Stimulation index (average and standard deviation for each group of 10 animals) for each protein pro-vaccination and at two weeks post vaccination and two weeks after challenge

| | AVERAGE STIMULATION INDICES | | | | | |
|---|---|---|---|---|---|---|
| | Vaccinated groups | | | Placebo groups | | |
| | Pre-vaccination | Post vaccination | Post challenge | Pre-vaccination | Post vaccination | Post challenge |
| Trial 1 | | | | | Group F | |
| Group A | | | | | | |
| MSC_0136 | 1.0 ± 0.5 | 3.9 ± 5.8 | 0.9 ± 0.2 | 0.8 ± 0.1 | 1.0 ± 0.3 | 1.3 ± 0.8 |
| MSC_0957 | 1.4 ± 0.7 | 6.1 ± 4.2 | 0.9 ± 0.3 | 0.7 ± 0.2 | 1.3 ± 0.4 | 1.5 ± 0.8 |
| MSC_0499 | 1.5 ± 1.1 | 3.6 ± 3.3 | 0.9 ± 0.3 | 0.7 ± 0.2 | 1.5 ± 0.4 | 1.6 ± 0.8 |
| MSC_0431 | 1.7 ± 1.1 | 2.7 ± 2.0 | 0.9 ± 0.3 | 0.6 ± 0.1 | 1.3 ± 0.3 | 1.7 ± 1.1 |
| MSC_0776 | 1.5 ± 1.1 | 4.6 ± 4.7 | 1.1 ± 0.4 | 0.6 ± 0.1 | 1.4 ± 0.3 | 2.0 ± 1.4 |
| Group B | | | | | | |
| MSC_0519 | 1.0 ± 0.3 | 1.2 ± 1.1 | 0.9 ± 0.3 | 0.7 ± 0.1 | 1.8 ± 0.9 | 1.7 ± 1.3 |
| MSC_0500 | 0.9 ± 0.3 | 6.1 ± 5.7 | 1.1 ± 0.4 | 0.7 ± 0.2 | 4.1 ± 2.3 | 1.9 ± 1.5 |
| MSC_0575 | 1.0 ± 0.3 | 2.3 ± 2.0 | 1.0 ± 0.4 | 0.7 ± 0.2 | 1.3 ± 0.3 | 1.4 ± 0.4 |
| MSC_0653 | 1.1 ± 0.5 | 2.3 ± 1.8 | 1.2 ± 0.5 | 0.7 ± 0.2 | 1.0 ± 0.3 | 1.5 ± 0.6 |
| MSC_0397 | 1.1 ± 0.2 | 1.8 ± 1.3 | 1.4 ± 0.8 | 0.7 ± 0.1 | 1.2 ± 0.3 | 1.6 ± 0.9 |
| Group C | | | | | | |
| YP_004400559 | 1.0 ± 0.3 | 2.5 ± 3.3 | 1.0 ± 0.3 | 0.8 ± 0.3 | 1.4 ± 0.4 | 2.1 ± 1.5 |
| YP_004399807 | 1.1 ± 0.3 | 1.8 ± 1.0 | 1.4 ± 0.5 | 0.7 ± 0.2 | 1.4 ± 0.5 | 2.1 ± 1.5 |
| MSC_0816 | 1.2 ± 0.3 | 2.7 ± 1.0 | 1.7 ± 1.4 | 0.8 ± 0.2 | 1.6 ± 0.6 | 2.1 ± 1.7 |
| MSC_0160 | 1.1 ± 0.3 | 1.8 ± 1.0 | 2.0 ± 1.8 | 0.8 ± 0.4 | 1.7 ± 0.8 | 1.9 ± 1.7 |
| MSC_0775 | 1.1 ± 0.5 | 6.2 ± 4.7 | 2.2 ± 2.1 | 0.7 ± 0.2 | 2.4 ± 1.7 | 1.8 ± 1.7 |
| Group D | | | | | | |
| MSC_0013 | 0.9 ± 0.2 | 1.4 ± 1.0 | 1.0 ± 0.4 | 0.7 ± 0.1 | 1.5 ± 0.4 | 2.0 ± 1.3 |
| MSC_0610 | 0.9 ± 0.2 | 1.7 ± 1.4 | 1.3 ± 0.4 | 0.7 ± 0.1 | 1.4 ± 0.3 | 1.6 ± 0.8 |
| MSC_0265 | 1.0 ± 0.3 | 1.6 ± 1.1 | 1.2 ± 0.6 | 0.6 ± 0.2 | 1.1 ± 0.5 | 1.8 ± 1.1 |
| MSC_0052 | 1.3 ± 0.4 | 2.4 ± 1.5 | 1.6 ± 0.9 | 0.8 ± 0.1 | 1.9 ± 0.9 | 2.2 ± 2.0 |
| MSC_0240 | 1.4 ± 0.4 | 3.2 ± 3.6 | 1.7 ± 1.0 | 0.9 ± 0.5 | 1.7 ± 0.8 | 2.0 ± 1.2 |
| Group E | | | | | | |
| MSC_0014 | 1.0 ± 0.5 | 1.2 ± 0.8 | 0.9 ± 0.4 | 1.0 ± 0.9 | 2.0 ± 0.6 | 2.0 ± 1.6 |
| MSC_0011 | 1.0 ± 0.3 | 1.2 ± 1.0 | 0.9 ± 0.3 | 0.7 ± 0.2 | 1.7 ± 0.6 | 2.1 ± 1.7 |
| YP_004400534 | 1.1 ± 0.4 | 1.9 ± 1.6 | 0.9 ± 0.2 | 0.7 ± 0.2 | 1.5 ± 0.5 | 1.9 ± 1.5 |
| MSC_0813 | 1.0 ± 0.2 | 0.8 ± 0.2 | 0.8 ± 0.2 | 0.8 ± 0.3 | 1.4 ± 0.7 | 1.8 ± 1.5 |
| MSC_0184 | 0.9 ± 0.3 | 1.2 ± 0.7 | 0.8 ± 0.2 | 0.7 ± 0.1 | 1.1 ± 0.3 | 1.7 ± 1.4 |
| Trial 2 | | | | | Group L | |
| Group G | | | | | | |
| MSC_0782 | 0.7 ± 0.4 | 0.7 ± 0.2 | 0.9 ± 0.3 | 0.5 ± 0.4 | 0.9 ± 0.3 | 0.8 ± 0.4 |
| MSC_0401 | 0.9 ± 0.2 | 1.4 ± 0.8 | 1.4 ± 0.7 | 0.6 ± 0.3 | 1.3 ± 0.5 | 1.2 ± 0.8 |
| MMS_A0381 | 0.9 ± 0.2 | 1.4 ± 0.9 | 1.7 ± 0.9 | 0.7 ± 0.5 | 1.3 ± 0.5 | 1.1 ± 0.2 |
| MSC_1058 | 0.9 ± 0.3 | 1.4 ± 0.7 | 1.8 ± 1.4 | 1.1 ± 1.4 | 1.5 ± 0.7 | 1.1 ± 0.4 |
| MSC_0790 | 1.0 ± 0.4 | 2.9 ± 2.3 | 2.6 ± 1.9 | 1.0 ± 0.8 | 1.9 ± 0.7 | 1.4 ± 0.4 |
| Group H | | | | | | |
| MSC_0453 | 1.3 ± 0.5 | 1.7 ± 0.9 | 4.3 ± 4.8 | 1.0 ± 0.6 | 2.1 ± 0.6 | 1.2 ± 0.5 |
| MMS_A0108 | 1.2 ± 0.7 | 1.7 ± 1.0 | 3.5 ± 4.3 | 1.2 ± 0.8 | 2.1 ± 0.5 | 1.5 ± 0.9 |
| MSC_0798 | 1.2 ± 0.9 | 1.3 ± 0.4 | 1.6 ± 0.6 | 0.6 ± 0.3 | 1.4 ± 0.2 | 0.9 ± 0.2 |
| MSC_0266 | 0.9 ± 0.2 | 1.2 ± 0.3 | 1.3 ± 0.3 | 0.3 ± 0.3 | 1.2 ± 0.4 | 1.0 ± 0.4 |
| MSC_0456 | 1.2 ± 0.4 | 3.2 ± 0.7 | 11.6 ± 11.4 | 0.8 ± 0.7 | 1.7 ± 0.5 | 1.8 ± 1.9 |
| Group I | | | | | | |
| YP_004400602 | 1.0 ± 0.3 | 1.0 ± 0.3 | 2.0 ± 0.8 | 0.5 ± 0.3 | 1.8 ± 0.8 | 1.0 ± 0.2 |
| YP_004400291 | 1.1 ± 0.3 | 1.6 ± 0.9 | 4.4 ± 3.2 | 0.9 ± 1.1 | 1.9 ± 0.7 | 1.7 ± 0.6 |
| YP_004400300 | 1.0 ± 0.2 | 1.0 ± 0.4 | 3.0 ± 3.0 | 0.8 ± 0.7 | 1.5 ± 0.6 | 0.9 ± 0.2 |
| YP_004400620 | 1.0 ± 0.2 | 1.3 ± 0.5 | 8.7 ± 17.9 | 0.8 ± 0.8 | 1.8 ± 0.7 | 1.5 ± 1.1 |
| MSC_1005 | 1.0 ± 0.2 | 1.2 ± 0.4 | 5.7 ± 10.1 | 1.0 ± 0.8 | 2.0 ± 0.5 | 1.2 ± 0.4 |
| Group J | | | | | | |
| YP_004400616 | 1.0 ± 0.4 | 0.9 ± 0.2 | 5.6 ± 7.9 | 0.6 ± 0.3 | 1.3 ± 0.4 | 0.8 ± 0.2 |
| YP_004400615 | 0.9 ± 0.2 | 0.9 ± 0.3 | 6.4 ± 8.3 | 0.6 ± 0.3 | 1.4 ± 0.3 | 1.1 ± 0.3 |
| MMS_A0415 | 1.3 ± 0.5 | 1.2 ± 0.4 | 16.6 ± 15.3 | 0.6 ± 0.3 | 1.6 ± 0.5 | 1.1 ± 0.3 |
| MSC_0927 | 1.2 ± 0.5 | 1.1 ± 0.5 | 6.3 ± 4.6 | 0.7 ± 0.5 | 1.7 ± 0.6 | 1.0 ± 0.3 |
| MSC_0804 | 1.1 ± 0.4 | 1.2 ± 0.5 | 7.6 ± 5.0 | 0.8 ± 0.7 | 1.5 ± 0.6 | 1.1 ± 0.3 |

TABLE 3-continued

| | | | | | | |
|---|---|---|---|---|---|---|
| Group K | | | | | | |
| YP_004400622 | 0.8 ± 0.2 | 0.9 ± 0.3 | 3.8 ± 4.1 | 0.9 ± 0.7 | 1.6 ± 0.6 | 1.4 ± 0.7 |
| YP_004400371 | 0.9 ± 0.3 | 1.1 ± 0.5 | 3.6 ± 3.2 | 0.7 ± 0.5 | 1.8 ± 0.6 | 1.4 ± 0.5 |
| YP_004400226 | 1.0 ± 0.3 | 0.8 ± 0.2 | 3.3 ± 3.2 | 1.3 ± 0.6 | 2.0 ± 0.5 | 1.3 ± 0.3 |
| YP_004400021 | 0.8 ± 0.2 | 1.0 ± 0.4 | 5.3 ± 4.1 | 0.7 ± 0.3 | 1.7 ± 0.7 | 1.1 ± 0.4 |
| MSC_0163 | 0.8 ± 0.2 | 1.0 ± 0.3 | 3.9 ± 3.0 | 0.5 ± 0.3 | 1.4 ± 0.5 | 1.2 ± 0.4 |
| Trial 3 | | | | | Group Q | |
| Group M | | | | | | |
| YP_004400581 | 1.1 ± 0.6 | 0.8 ± 0.2 | 1.1 ± 0.4 | 1.1 ± 0.2 | 0.5 ± 0.3 | 0.6 ± 0.4 |
| YP_004400296 | 1.3 ± 0.7 | 0.9 ± 0.2 | 1.0 ± 0.1 | 0.8 ± 0.5 | 0.6 ± 0.4 | 0.6 ± 0.3 |
| YP_004399851 | 1.5 ± 1.1 | 1.0 ± 0.3 | 1.2 ± 0.3 | 1.3 ± 1.2 | 0.8 ± 1.1 | 0.6 ± 0.3 |
| YP_004399914 | 1.2 ± 0.5 | 0.8 ± 0.2 | 1.1 ± 0.3 | 1.0 ± 0.8 | 0.6 ± 0.5 | 0.6 ± 0.2 |
| Group N | | | | | | |
| YP_004400127 | 1.5 ± 0.9 | 0.6 ± 0.2 | 1.0 ± 0.4 | 0.9 ± 0.6 | 0.9 ± 0.9 | 0.6 ± 0.2 |
| YP_004399790 | 2.3 ± 2.8 | 1.2 ± 0.8 | 1.4 ± 0.5 | 1.4 ± 1.1 | 1.3 ± 1.2 | 0.7 ± 0.5 |
| YP_004400580 | 1.4 ± 0.7 | 0.6 ± 0.2 | 1.2 ± 0.4 | 1.2 ± 0.5 | 1.3 ± 1.2 | 0.9 ± 0.5 |
| YP_004400610 | 1.7 ± 1.9 | 0.7 ± 0.2 | 1.4 ± 0.6 | 0.8 ± 0.5 | 0.8 ± 0.3 | 0.6 ± 0.2 |
| Group O | | | | | | |
| YP_004400171 | 0.8 ± 0.5 | 0.8 ± 0.3 | 1.0 ± 0.3 | 1.0 ± 0.8 | 0.6 ± 0.3 | 0.6 ± 0.2 |
| MSC_0139 | 0.9 ± 0.6 | 0.9 ± 0.3 | 0.9 ± 0.4 | 0.9 ± 0.5 | 0.7 ± 0.4 | 0.6 ± 0.3 |
| YP_004399939 | 0.9 ± 0.4 | 0.8 ± 0.3 | 1.1 ± 0.5 | 1.3 ± 1.4 | 0.9 ± 0.5 | 0.8 ± 0.4 |
| YP_004400004 | 1.0 ± 0.6 | 0.8 ± 0.3 | 1.2 ± 0.6 | 1.4 ± 1.6 | 0.6 ± 0.2 | 0.9 ± 0.6 |
| Group P | | | | | | |
| YP_004400446 | 0.7 ± 0.3 | 0.8 ± 0.3 | 2.3 ± 2.7 | 0.8 ± 0.6 | 1.0 ± 1.2 | 0.6 ± 0.3 |
| YP_004399927 | 0.7 ± 0.3 | 1.0 ± 0.4 | 1.7 ± 1.9 | 1.4 ± 1.7 | 0.9 ± 0.6 | 0.9 ± 0.5 |
| YP_004400204 | 0.6 ± 0.3 | 0.6 ± 0.1 | 1.3 ± 1.1 | 1.3 ± 1.1 | 1.2 ± 0.8 | 0.9 ± 0.7 |
| YO-004400368 | 0.7 ± 0.4 | 0.7 ± 0.3 | 1.8 ± 2.6 | 1.1 ± 1.3 | 0.9 ± 0.5 | 1.0 ± 0.9 |

To summarize, pools of five recombinant *M. mycoides* proteins were administered per animal to test for their capacity to protect cattle from CBPP. Proteins had previously been ranked according to their likelihood of being protective after analyzing their surface expression and possible exposure to antibodies and their reactivity with sera from CBPP-positive cattle that are accepted to be immune (see, Example 1). Three trials were carried out, with three groups of cattle receiving a placebo while 14 groups were immunized with pools of recombinant proteins in order of their rank. The cattle were challenged by intubation with Mmm of the virulent strain Afadé.

The results showed protection against CBPP in several groups of immunized cattle. In the first trial, at least three groups (A, C and D) showed a reduction of approximately 80% in the pathology score compared to the control group with non-immunized cattle. This level of reduction is similar to what has been reported in experiments with a live vaccine and can be considered very significant. Group B also showed protection, albeit weaker than those above (just under 40%). Reduction in pathology in group E was not significant.

From the data, it is clear that proteins that were highly ranked in the priority list also contain the most antigens that had a protective effect, suggesting that the criteria used in the priority ranking were appropriate for selecting protective antigens. Although classified with lower priority, group N, immunized with four heretofore unknown proteins, also conferred a significant protection of over 70%.

Example 3

Production of *M. mycoides* Antigen Fusions and Conjugates with Leukotoxin Carrier Protein The *M. mycoides* genes used in the fusions and LtxA conjugates were codon-optimized for *E. coli* expression, synthesized and cloned, as described above. For fusions, the genes were designed such that the resulting fusion protein included amino acid linkers between the two proteins. Fusions constructed included YP_004400127.1-YP_004399790.1; YP_004400610.1-YP_004400580.1; MSC_0446-MSC_0117; and MSC_0922-MSC_1058. As shown in the Figures, the YP_004400127.1-YP_004399790.1 fusion includes a $Gly_6$ amino acid linker between the YP_004400127.1 and YP_004399790.1 proteins (see, FIGS. 25B and 27B); the YP_004400610.1-YP_004400580.1 fusion includes a $Gly_5$ linker between the two proteins (see, FIGS. 26B and 28B); the MSC_0446-MSC_0117 fusion includes a $Gly_3$ linker between the proteins (See FIG. 37B); and the MSC_0922-MSC_1058 fusion includes a $Gly_3$ linker between the proteins (See FIG. 38B).

To produce conjugates with leukotoxin, sequences encoding the desired fusions or individual antigens described in Table 4 were subcloned into plasmid pAA352, to be expressed as C-terminal fusions to the LKT protein, as described in U.S. Pat. Nos. 5,476,657; 5,422,110; 5,723,129 and 5,837,268, incorporated herein by reference in their entireties. Plasmid pAA352 expresses LKT 352, the sequence of which is depicted in FIG. 41. As explained above, LKT 352 is derived from the IktA gene of *Pasteurella haemolytica* leukotoxin and is a truncated leukotoxin molecule which lacks the cytotoxic portion of the molecule. The highly immunogenic leukotoxin carrier has been shown to be effective for inducing antibody responses against numerous proteins. See, e.g., U.S. Pat. Nos. 6,521,746, 6,022,960, 5,969,126, 5,837,268 and 5,723,129 incorporated herein in their entireties) and (Hedlin et al., *Vaccine* (2010) 28:981-988).

The expression vectors were transformed into BL21 (DE3) followed by growth and IPTG induction by standard protocols. The recombinant proteins were produced as inclusion bodies and resolubilized in 4M Guanidine-HCl as described previously (Hedlin et al., Vaccine (2010):28:981-988; Gupta et al., *Vet. Microbiol.* (2005) 108:207-214; and U.S. Pat. No. 6,100,066, incorporated herein by reference in its entirety).

The nucleotide sequences and amino acid sequences of the *M. mycoides* antigens, fusions and conjugates are indicated in Table 4 and shown in the figures.

TABLE 4

| Antigen Fusions and Carrier Conjugates | | | |
|---|---|---|---|
| DNA sequences of antigen fusions and conjugates with leukotoxin | SEQ ID NO: | Protein sequences of antigen fusions and conjugates with leukotoxin | SEQ ID NO: |
| YP_004400127.1-YP_004399790.1 | 50 | YP_004400127.1-YP_004399790.1 | 51 |
| YP_004400610.1-YP_004400580.1 | 52 | YP_004400580.1-YP_004400610.1 | 53 |
| pAA352-YP_004400127.1-YP_004399790.1 | 54 | LtxA-YP_004400127.1-YP_004399790.1 | 55 |
| pAA352-YP_004400610.1-YP_004400580.1 | 56 | LtxA-YP_004400610.1-YP_004400580.1 | 57 |
| pAA352-YP_004400559.1 | 80 | LtxA-YP_004400559.1 | 81 |
| pAA352-MSC_0776 | 68 | LtxA-MSC_0776 | 69 |
| pAA352-MSC_0499 | 64 | LtxA-MSC_0499 | 65 |
| pAA352-MSC_0160 | 58 | LtxA-MSC_0160 | 59 |
| pAA352-MSC_0816 | 70 | LtxA-MSC_0816 | 71 |
| pAA352-MSC_0431 | 62 | LtxA-MSC_0431 | 63 |
| pAA352-YP_004399807.1 | 78 | LtxA-YP_004399807.1 | 79 |
| pAA352-MSC_0957 | 72 | LtxA-MSC_0957 | 73 |
| pAA352-MSC_0775 | 66 | LtxA-MSC_0775 | 67 |
| pAA352-MSC_0136 | 60 | LtxA-MSC_0136 | 61 |
| pAA352-MSC_0446-MSC_0117 | 74 | LtxA-MSC_0446-MSC_0117 | 75 |
| pAA352-MSC_0922-MSC_1058 | 76 | LtxA-MSC_0922-MSC_1058 | 77 |

Example 4

Immune Responses to Recombinant *M. mycoides* Proteins, and LKT 352 *M. mycoides* Protein Conjugates Immune responses to individual *M. mycoides* antigens, *M. mycoides* fusions conjugated to an LKT 352 (LtxA) carrier and a representative individual Mmm antigen (MSC-0160) fused to the LtxA carrier were studied. The individual antigens and conjugates used in this study are shown in the Table 5. The individual antigens were recombinantly produced as described in Example 1. As explained in Example 1, the individual antigens contained a histidine-tag for purification of the proteins by metal-chelate affinity chromatography. The fusions and conjugates with LKT 352 were produced as described in Example 3.

TABLE 5

| GROUP | ANTIGENS (50 μg/dose) |
|---|---|
| A | YP_004400127.1<br>YP_004399790.1<br>YP_004400580.1<br>YP_004400610.1<br>MSC_0160<br>LtxA |
| B | LtxA-YP_004400127.1-YP_004399790.1<br>LtxA-YP_004400610.1-YP_004400580.1<br>LtxA-MSC_0160 |

16 animals were divided into two groups (Groups A and B) of eight animals and vaccinated using vaccines including the proteins described in Table 5. The proteins were combined with 250 μg CpG-ODN 2007 (5'TCGTCGTTGTCGTTTTGTCGTT3'; SEQ ID NO:29) and 30% Emulsigen™ (MVP Laboratories, Ralston, NE). Animals were inoculated subcutaneously with 2 ml of the vaccine formulation (50 μg of each antigen was present per inoculation) and a booster given 28 days later. Serum and nasal IgG1, IgG2 and IgA levels were determined against each antigen at days 0, 28 and 56. Cell-mediated immune responses were determined by PBMC proliferation assays (described above) at days 0 and 56 using the proteins as recall antigens.

Compared to day 0, serum IgG1 and IgG2 responses at day 56 were significant for all proteins. Compared to day 0, serum IgA titers significantly increased at day 56 for LtxA-YP_004400127.1-YP_004399790.1 (Group A); His-YP_004400610.1 (Group A); His-YP_004400580.1 (group A); and LtxA-MSC_0160 (Group A).

Compared to day 0, nasal IgG1 titers significantly increased at day 56 for his-YP 004400127.1 (Group A); LtxA (Group A); LtxA-YP 004400127-1-YP 004399790.1 (Group B); his-YP_004400580 1 (Group A); his-YP_004400610.1 (Group A); LtxA-YP_004400610.1-YP_004400580.1 (Groups A and B); his-MSC_0160 (Groups A and B); and LtxA-MSC_0160 (Group B).

Compared to day 0, nasal IgG2 titers significantly increased at day 56 for his-YP_004400127.1 (Groups A and B), LtxA-YP_004400127.1-YP_004399790.1 (Groups A and B); LtxA (Groups A and B); his-YP_004400610.1 (Group A); LtxA-YP_004400610.1-YP_004400580.1 (Groups A and B); and LtxA-MSC_0160 (Groups A and B).

Compared to day 0, nasal IgA responses at day 56 were significant for all proteins. The median of the proliferative responses were slightly higher at day 56 but the differences were not statistically significant.

Overall, the antibody titers of animals vaccinated with the individual proteins and animals that received the chimeric proteins were similar.

A more balanced immune response (serum IgG1/IgG2 ratios near 1) was observed for the proteins that contained the LtxA carrier.

Thus, immunogenic compositions and methods of making and using the same for treating and preventing *Mycoplasma* infection using pools of *Mycoplasma* recombinant antigens are described. Although preferred embodiments of the subject invention have been described in some detail, it is understood that obvious variations can be made without departing from the spirit and the scope of the invention as defined by the appended claims.

The invention claimed is:

1. A method of treating, inducing an immune response, or reducing lung Pathology in a bovine subject having a *Mycoplasma mycoides* infection, comprising administering a composition comprising at least one protein selected from the group consisting of:

a) the protein comprising the amino acid sequence of SEQ ID NO:2;
b) the protein comprising the amino acid sequence of SEQ ID NO:4;
c) the protein comprising the amino acid sequence of SEQ ID NO:6;
d) the protein comprising the amino acid sequence of SEQ ID NO:8;
e) the protein comprising the amino acid sequence of SEQ ID NO:10;
f) the protein comprising the amino acid sequence of SEQ ID NO:12;
g) the protein comprising the amino acid sequence of SEQ ID NO:14;
h) the protein comprising the amino acid sequence of SEQ ID NO:16;
i) the protein comprising the amino acid sequence of SEQ ID NO:18; and
j) the protein comprising the amino acid sequence of SEQ ID NO:20.

2. The method of claim 1, wherein the composition further comprises at least two proteins each with at least 95% sequence identity to a protein selected from the group consisting of a)-j).

3. The method of claim 1, wherein the composition further comprises at least three proteins each with at least 95% sequence identity to a protein selected from the group consisting of a)-j).

4. The method of claim 1, wherein the composition comprises:

the protein comprising the amino acid sequence of SEQ ID NO:2;
the protein comprising the amino acid sequence of SEQ ID NO:6;
the protein comprising the amino acid sequence of SEQ ID NO:8; and
the protein comprising the amino acid sequence of SEQ ID NO:20.

5. The method of claim 1, wherein the composition further comprises at least four proteins each with at least 95% sequence identity to a protein selected from the group consisting of a)-j).

6. The method of claim 1, wherein at least one of the at least one proteins is conjugated with a carrier.

7. The method of claim 6, wherein the carrier is an RTX toxin.

8. The method of claim 6, wherein the carrier is a detoxified leukotoxin molecule.

9. The method of claim 1, wherein the composition further comprises a pharmaceutically acceptable excipient.

10. The method of claim 1, wherein the composition further comprises an immunological adjuvant.

11. The method of claim 10, wherein the adjuvant is a water-in-oil emulsion, or wherein the adjuvant comprises: (a) a polyphosphazene; (b) a CpG oligonucleotide or a poly (I:C); and (c) a host defense peptide.

12. The method of claim 1, wherein the *Mycoplasma mycoides* infection is contagious bovine pleuropneumonia.

13. The method of claim 1, wherein the composition is administered parenterally, intramuscularly, intravenously, intraperitoneally, subcutaneously, orally, intranasally, or as an aerosol.

14. The method of claim 1, wherein the at least one protein comprises one or more fusion proteins.

15. The method of claim 14, wherein the one or more fusion proteins comprises a protein selected from the group consisting of:

the protein comprising the amino acid sequence of SEQ ID NO:2;

the protein comprising the amino acid sequence of SEQ ID NO:6:

the protein comprising the amino acid sequence of SEQ ID NO:8; and the protein comprising the amino acid sequence of SEQ ID NO:20.

16. The method of claim 14, wherein the one or more fusion proteins comprises two fusion proteins.

17. The method of claim 15, wherein the one or more fusion proteins comprises two fusion proteins.

18. The method of claim 1, wherein the composition further comprises at least one protein with at least 95% sequence identity to a protein selected from the group consisting of a)-j).

* * * * *

SEQUENCE LISTING

```
<160> NUMBER OF SEQ ID NOS: 84

<210> SEQ ID NO 1
<211> LENGTH: 894
```

-continued

<212> TYPE: DNA
<213> ORGANISM: Artificial Sequence
<220> FEATURE:
<223> OTHER INFORMATION: Nucleotide sequence encoding MSC_0136 shown in SEQ ID NO:2, modified for expression in E. coli

<400> SEQUENCE: 1

```
aaaaacgaaa accatttcaa catcaactac aaaatgaaaa tggaaatgaa aacccagaaa      60

acggaacaac cgcacaaata taaagaaggc gatcgtaccg aaattgtgca gatcggcttt     120

tacaaacgcg gtaacgaaat cacgatcaaa caaatcccgt actacgttaa aaaagtcccg     180

gataaactgc cggacgaaat ccagtccctg tatcgtgcat ttgctcatcg ctacaaagat     240

caaaaccacc cgaccgtcac gggcttcgaa aaatgggaca ccagcaaaat caaaaacatg     300

tcttatgtgt tttacgataa ccagctgatc gatgcggacc tgtcagaatg gaaaacctcg     360

aatgttacga acatggacgg catgttcaaa aacgccatca aattcaacaa caaagaaaaa     420

ccgctgaaat ggaacaccga aaaagtcgaa agtatggaat ccatgtttga tggcgcagaa     480

tcttttaaac agaacctgaa agattggaaa gtggacaaag ttaccaaaaa caaaaacttc     540

tcacgtgctt cgggtatttt cgaacatatc gataaaaaac cgtcatggaa aatcaccgaa     600

cacaacgacc cgattatcaa aaaaccggaa tcgacggaac cgaaagtgat tatccatccg     660

agcccgtctc gcccgaaaca gaccattccg ctgacgaaac tgatcaatcc gattatcaaa     720

agcaccccga actctaatca aaacctgggc atcccgaaaa cgaacctgag caccacgccg     780

cagcaaagta aaaaactgtc caccccggca attgttggca tcgtggttgg tagtcaggtc     840

gtgctgacgt ccctggcagc aggtattccg tacctgatca aacgtttcaa aaaa           894
```

<210> SEQ ID NO 2
<211> LENGTH: 298
<212> TYPE: PRT
<213> ORGANISM: Artificial Sequence
<220> FEATURE:
<223> OTHER INFORMATION: Amino acid sequence of MSC_0136 from M. mycoides subsp. mycoides (Mmm), lacking the signal sequence

<400> SEQUENCE: 2

```
Lys Asn Glu Asn His Phe Asn Ile Asn Tyr Lys Met Lys Met Glu Met
1               5                   10                  15

Lys Thr Gln Lys Thr Glu Gln Pro His Lys Tyr Lys Glu Gly Asp Arg
            20                  25                  30

Thr Glu Ile Val Gln Ile Gly Phe Tyr Lys Arg Gly Asn Glu Ile Thr
        35                  40                  45

Ile Lys Gln Ile Pro Tyr Tyr Val Lys Lys Val Pro Asp Lys Leu Pro
    50                  55                  60

Asp Glu Ile Gln Ser Leu Tyr Arg Ala Phe Ala His Arg Tyr Lys Asp
65                  70                  75                  80

Gln Asn His Pro Thr Val Thr Gly Phe Glu Lys Trp Asp Thr Ser Lys
                85                  90                  95

Ile Lys Asn Met Ser Tyr Val Phe Tyr Asp Asn Gln Leu Ile Asp Ala
            100                 105                 110

Asp Leu Ser Glu Trp Lys Thr Ser Asn Val Thr Asn Met Asp Gly Met
        115                 120                 125

Phe Lys Asn Ala Ile Lys Phe Asn Asn Lys Glu Lys Pro Leu Lys Trp
    130                 135                 140

Asn Thr Glu Lys Val Glu Ser Met Glu Ser Met Phe Asp Gly Ala Glu
145                 150                 155                 160
```

-continued

```
Ser Phe Lys Gln Asn Leu Lys Asp Trp Lys Val Asp Lys Val Thr Lys
                165                 170                 175

Asn Lys Asn Phe Ser Arg Ala Ser Gly Ile Phe Glu His Ile Asp Lys
            180                 185                 190

Lys Pro Ser Trp Lys Ile Thr Glu His Asn Asp Pro Ile Ile Lys Lys
        195                 200                 205

Pro Glu Ser Thr Glu Pro Lys Val Ile Ile His Pro Ser Pro Ser Arg
    210                 215                 220

Pro Lys Gln Thr Ile Pro Leu Thr Lys Leu Ile Asn Pro Ile Ile Lys
225                 230                 235                 240

Ser Thr Pro Asn Ser Asn Gln Asn Leu Gly Ile Pro Lys Thr Asn Leu
                245                 250                 255

Ser Thr Thr Pro Gln Gln Ser Lys Lys Leu Ser Thr Pro Ala Ile Val
            260                 265                 270

Gly Ile Val Val Gly Ser Gln Val Val Leu Thr Ser Leu Ala Ala Gly
        275                 280                 285

Ile Pro Tyr Leu Ile Lys Arg Phe Lys Lys
    290                 295
```

<210> SEQ ID NO 3
<211> LENGTH: 1230
<212> TYPE: DNA
<213> ORGANISM: Artificial Sequence
<220> FEATURE:
<223> OTHER INFORMATION: Nucleotide sequence encoding MSC_0957 shown in
      SEQ ID NO:4, modified for expression in E. coli

<400> SEQUENCE: 3

```
tgcagtacca cgattaccca tacgatcaaa acgtccttta acgataacgt taaagtcgaa     60

aaattcacct gggacggcaa taaatatacc tccaaagaac agtcaacgaa cattcaagat    120

atcaccaata gcctgaacgg taccacgaat gcatactcta aaaccattac ggacgtgctg    180

aacctgttta cccgtaatat ccaggaagtt cgcaacctga aagaaagcta tgacctgttt    240

cgtggcaaag cagaaaatac gtcggtggtt ggctattaca ccggtgctaa cagtcagcgc    300

caaaaaatct cccagcaaga tttctacaaa aaactggatg acagtgacac ccacatcagc    360

tctctgaaag gtctgctgca gctgcgtgaa ttcgttaacg ataacaaaaa caaaaccacg    420

gtcgaaccgt ggaaaaatag cctgaaaacg gatgcggacg aagttaaaaa atggtctgat    480

gaattcacca aaaatctgga caacattgtc aacagttcca tcgataacaa aatcaaaaac    540

atcaaactgg tgtctaaagt tagtaaaacg tcatcgagct ttgccacctt cgaacaggac    600

gtgaaaacca gcccgacggg ctctagtatt aacctgacgg aacgcaacaa tgaaaccgtc    660

gtgggcgata tcaaaaacct gaaagaccat aatccgtatg tctttggtac cagtccggtg    720

aatgatccgt tcggcatgaa cgtgattggt gaaaataaag atccggacat taaaaacctg    780

aaaccgacca tcaaatattc caccgaaaaa ctgacgaaaa aagatgactc atacattaat    840

ctgtcgaaca atggtaacaa caacaaccag ttcgtttaca acatcaacca aaaatgggaa    900

ctgtcctcag cacataattt ctattacatg agcaaagatc cggaaacgct ggaactgcag    960

attacccaca gcatcgaaaa caaatctttt accttctacg tccaatttgg cggtctgcgt   1020

aaaatttata ccccgatcgt ggaatcttac accccgaaaa atacgaactc agcggataaa   1080

cgttattcgt ttgtgggctg ggccttcaat tcgtaccgct ttagcgatga cttctctaag   1140

ggtaactcga gcccgtacaa attcaaagat attagtctga aatctccca gaacgctttc   1200

accacgaata ccggcagcgt taacggtaaa                                    1230
```

```
<210> SEQ ID NO 4
<211> LENGTH: 410
<212> TYPE: PRT
<213> ORGANISM: Artificial Sequence
<220> FEATURE:
<223> OTHER INFORMATION: Amino acid sequence of MSC_0957 from M.
      mycoides subsp. mycoides (Mmm), lacking the signal sequence

<400> SEQUENCE: 4

Cys Ser Thr Thr Ile Thr His Thr Ile Lys Thr Ser Phe Asn Asp Asn
1               5                   10                  15

Val Lys Val Glu Lys Phe Thr Trp Asp Gly Asn Lys Tyr Thr Ser Lys
            20                  25                  30

Glu Gln Ser Thr Asn Ile Gln Asp Ile Thr Asn Ser Leu Asn Gly Thr
        35                  40                  45

Thr Asn Ala Tyr Ser Lys Thr Ile Thr Asp Val Leu Asn Leu Phe Thr
    50                  55                  60

Arg Asn Ile Gln Glu Val Arg Asn Leu Lys Glu Ser Tyr Asp Leu Phe
65                  70                  75                  80

Arg Gly Lys Ala Glu Asn Thr Ser Val Val Gly Tyr Tyr Thr Gly Ala
                85                  90                  95

Asn Ser Gln Arg Gln Lys Ile Ser Gln Gln Asp Phe Tyr Lys Lys Leu
            100                 105                 110

Asp Asp Ser Asp Thr His Ile Ser Ser Leu Lys Gly Leu Leu Gln Leu
        115                 120                 125

Arg Glu Phe Val Asn Asp Asn Lys Asn Lys Thr Thr Val Glu Pro Trp
    130                 135                 140

Lys Asn Ser Leu Lys Thr Asp Ala Asp Glu Val Lys Lys Trp Ser Asp
145                 150                 155                 160

Glu Phe Thr Lys Asn Leu Asp Asn Ile Val Asn Ser Ser Ile Asp Asn
                165                 170                 175

Lys Ile Lys Asn Ile Lys Leu Val Ser Lys Val Ser Lys Thr Ser Ser
            180                 185                 190

Ser Phe Ala Thr Phe Glu Gln Asp Val Lys Thr Ser Pro Thr Gly Ser
        195                 200                 205

Ser Ile Asn Leu Thr Glu Arg Asn Asn Glu Thr Val Val Gly Asp Ile
    210                 215                 220

Lys Asn Leu Lys Asp His Asn Pro Tyr Val Phe Gly Thr Ser Pro Val
225                 230                 235                 240

Asn Asp Pro Phe Gly Met Asn Val Ile Gly Glu Asn Lys Asp Pro Asp
                245                 250                 255

Ile Lys Asn Leu Lys Pro Thr Ile Lys Tyr Ser Thr Glu Lys Leu Thr
            260                 265                 270

Lys Lys Asp Asp Ser Tyr Ile Asn Leu Ser Asn Asn Gly Asn Asn Asn
        275                 280                 285

Asn Gln Phe Val Tyr Asn Ile Asn Gln Lys Trp Glu Leu Ser Ser Ala
    290                 295                 300

His Asn Phe Tyr Tyr Met Ser Lys Asp Pro Glu Thr Leu Glu Leu Gln
305                 310                 315                 320

Ile Thr His Ser Ile Glu Asn Lys Ser Phe Thr Phe Tyr Val Gln Phe
                325                 330                 335

Gly Gly Leu Arg Lys Ile Tyr Thr Pro Ile Val Glu Ser Tyr Thr Pro
            340                 345                 350
```

```
Lys Asn Thr Asn Ser Ala Asp Lys Arg Tyr Ser Phe Val Gly Trp Ala
        355                 360                 365

Phe Asn Ser Tyr Arg Phe Ser Asp Asp Phe Ser Lys Gly Asn Ser Ser
    370                 375                 380

Pro Tyr Lys Phe Lys Asp Ile Ser Leu Lys Ile Ser Gln Asn Ala Phe
385                 390                 395                 400

Thr Thr Asn Thr Gly Ser Val Asn Gly Lys
                405                 410


<210> SEQ ID NO 5
<211> LENGTH: 2082
<212> TYPE: DNA
<213> ORGANISM: Artificial Sequence
<220> FEATURE:
<223> OTHER INFORMATION: Nucleotide sequence encoding MSC_0499 shown in
      SEQ ID NO:6, modified for expression in E. coli

<400> SEQUENCE: 5

tgcaccacga aaaacgataa attcaacaaa ccgttcatca ccgacgaact ggcgcagaaa     60

attatctcag gtctgaaact gtcggatgac tttaatttca ccacgggcga acgtttcagt    120

aaactggatt acaaatccct gattctggac atgatcaacg aaatcatctc caaaaacaaa    180

tacaccgata actggaacaa cctgagcaaa aaatttggtc tggaaattga acaggcgaaa    240

gaattcggca acaaaaaagc cgaaaacgtt ctgaaaaacc tgagcaccat caaactgttc    300

gcagattata cgtctaaacg cgcttttgaa gaagatttcg acagtgtgga tctgagttat    360

tccgaaaatt acccgctgaa tccgtataac ctggaaagca aaaacggtca gaaagataaa    420

accgtttacg cgatctacta caaaaacaac aacggcggta gctctagtgg ttcctcatcg    480

aatggcggtg gcaccaacgg tgaagcaacg tggctgcgtt ggcagaccac gggtgaattt    540

gataatattg acaacccgat cccgtcaacc ccgcaactgc cgaatatctc gctgctgacc    600

gatacgagct ctaaaaactt ccgcattgcc aaactgtcca aaccgaaaga tcaggaatat    660

atcaccaata cggcaagtgt taaagaagac ggtaaagcta ccaataacgg caataacgaa    720

tttgtcgaat ggtacaaaaa cagttccgac aaattcgaaa ccgatggtca gggcatcatg    780

caataccgtt tcatgtacca tttcaaaacg aaaatcgaag cgaaactgtt taatgatctg    840

ctgggtcacg cctatattga cagcaacctg ttcgtggata aaaacgacaa caaatcagca    900

tcgaacaaga aaattatcct gaacaacgtc agtaaactga tttccgatat ccagagcaat    960

tattctcaag tggacaaaac cattagtaac gtgaaaatgg tttgggcatt tagcctggat   1020

aaacagaaag tctctgaagt gaacggtgct atcaatcaat atgtcaaccc ggatggcagc   1080

ctgaccaatg aagacaacaa gaaaaccctg aaaaacgtgt tcgataaaat caaatacaaa   1140

gcgaccaacg aatcaaaaca gggtacggat tcgctgctga gcatttctgg tttcaacggc   1200

ttcgttaaaa acaaagataa caacatcgaa agtctgtccg gcgacctgaa actgaccgaa   1260

gaagcgaaaa aagcggtcgc ccgcgtgaat gttccgtctc tgctgacgaa taacaataac   1320

ggctttgcca gtgaaaactc caataacgtg gattatgtct ttgtgctgcc gatttacctg   1380

aatgacctgt ttagctcgaa cgacatgcag atcaaacgtg aaaccgaaag ctctggtggc   1440

gccggttcaa atggctcgaa ctatgaactg aatgttctgg aaaacacctg ggtcaacctg   1500

aatgacaaat ttagcctgga taatcgctac ttcgacaacc tgacgatcaa aaaagtggaa   1560

tctcaaaata acggtgaagc actggtggct aacaacaacg ataaatggta cgttagcctg   1620

aaaaacggca atgacaacaa aaaagttgaa gtcacctaca gcgatgacag caagaaaatt   1680
```

atcacgctga aaaaagttga taaaaacaac atcaaaaccc tggacttcac gtacaaactg 1740
tcacagtcgg atttcaacaa acagctgttc aaacaaaacc cgaccgcaaa catcacgtat 1800
gatatcaacc tgaaaaacta cgataacatc aaagacaaac agaacgatgc ttatatctgg 1860
aaaaacgatc cgaaaaaatc taacgatatc caagacctgt ccgcggccaa aaaacaggtg 1920
ctgctggatc aactggaagc gatcaccgcc aaaaatccgg acgttcagaa cgcagctaaa 1980
accgaactgt attcggcata tctgtacacg gatggtatct actacaaatc actgttcgac 2040
gaaatcagca aatacatcga atctgaaaaa ccgaccctgg at 2082

<210> SEQ ID NO 6
<211> LENGTH: 694
<212> TYPE: PRT
<213> ORGANISM: Artificial Sequence
<220> FEATURE:
<223> OTHER INFORMATION: Amino acid sequence of MSC_0499 from M. mycoides subsp. mycoides (Mmm), lacking the signal sequence

<400> SEQUENCE: 6

Cys Thr Thr Lys Asn Asp Lys Phe Asn Lys Pro Phe Ile Thr Asp Glu
1 5 10 15

Leu Ala Gln Lys Ile Ile Ser Gly Leu Lys Leu Ser Asp Asp Phe Asn
20 25 30

Phe Thr Thr Gly Glu Arg Phe Ser Lys Leu Asp Tyr Lys Ser Leu Ile
35 40 45

Leu Asp Met Ile Asn Glu Ile Ile Ser Lys Asn Lys Tyr Thr Asp Asn
50 55 60

Trp Asn Asn Leu Ser Lys Lys Phe Gly Leu Glu Ile Glu Gln Ala Lys
65 70 75 80

Glu Phe Gly Asn Lys Lys Ala Glu Asn Val Leu Lys Asn Leu Ser Thr
85 90 95

Ile Lys Leu Phe Ala Asp Tyr Thr Ser Lys Arg Ala Phe Glu Glu Asp
100 105 110

Phe Asp Ser Val Asp Leu Ser Tyr Ser Glu Asn Tyr Pro Leu Asn Pro
115 120 125

Tyr Asn Leu Glu Ser Lys Asn Gly Gln Lys Asp Lys Thr Val Tyr Ala
130 135 140

Ile Tyr Tyr Lys Asn Asn Asn Gly Gly Ser Ser Ser Gly Ser Ser Ser
145 150 155 160

Asn Gly Gly Gly Thr Asn Gly Glu Ala Thr Trp Leu Arg Trp Gln Thr
165 170 175

Thr Gly Glu Phe Asp Asn Ile Asp Asn Pro Ile Pro Ser Thr Pro Gln
180 185 190

Leu Pro Asn Ile Ser Leu Leu Thr Asp Thr Ser Ser Lys Asn Phe Arg
195 200 205

Ile Ala Lys Leu Ser Lys Pro Lys Asp Gln Glu Tyr Ile Thr Asn Thr
210 215 220

Ala Ser Val Lys Glu Asp Gly Lys Ala Thr Asn Asn Gly Asn Asn Glu
225 230 235 240

Phe Val Glu Trp Tyr Lys Asn Ser Ser Asp Lys Phe Glu Thr Asp Gly
245 250 255

Gln Gly Ile Met Gln Tyr Arg Phe Met Tyr His Phe Lys Thr Lys Ile
260 265 270

Glu Ala Lys Leu Phe Asn Asp Leu Leu Gly His Ala Tyr Ile Asp Ser
275 280 285

-continued

```
Asn Leu Phe Val Asp Lys Asn Asp Asn Lys Ser Ala Ser Asn Lys Lys
    290                 295                 300

Ile Ile Leu Asn Asn Val Ser Lys Leu Ile Ser Asp Ile Gln Ser Asn
305                 310                 315                 320

Tyr Ser Gln Val Asp Lys Thr Ile Ser Asn Val Lys Met Val Trp Ala
                325                 330                 335

Phe Ser Leu Asp Lys Gln Lys Val Ser Glu Val Asn Gly Ala Ile Asn
            340                 345                 350

Gln Tyr Val Asn Pro Asp Gly Ser Leu Thr Asn Glu Asp Asn Lys Lys
        355                 360                 365

Thr Leu Lys Asn Val Phe Asp Lys Ile Lys Tyr Lys Ala Thr Asn Glu
    370                 375                 380

Ser Lys Gln Gly Thr Asp Ser Leu Leu Ser Ile Ser Gly Phe Asn Gly
385                 390                 395                 400

Phe Val Lys Asn Lys Asp Asn Asn Ile Glu Ser Leu Ser Gly Asp Leu
                405                 410                 415

Lys Leu Thr Glu Glu Ala Lys Lys Ala Val Ala Arg Val Asn Val Pro
            420                 425                 430

Ser Leu Leu Thr Asn Asn Asn Asn Gly Phe Ala Ser Glu Asn Ser Asn
        435                 440                 445

Asn Val Asp Tyr Val Phe Val Leu Pro Ile Tyr Leu Asn Asp Leu Phe
    450                 455                 460

Ser Ser Asn Asp Met Gln Ile Lys Arg Glu Thr Glu Ser Ser Gly Gly
465                 470                 475                 480

Ala Gly Ser Asn Gly Ser Asn Tyr Glu Leu Asn Val Leu Glu Asn Thr
                485                 490                 495

Trp Val Asn Leu Asn Asp Lys Phe Ser Leu Asp Asn Arg Tyr Phe Asp
            500                 505                 510

Asn Leu Thr Ile Lys Lys Val Glu Ser Gln Asn Asn Gly Glu Ala Leu
        515                 520                 525

Val Ala Asn Asn Asn Asp Lys Trp Tyr Val Ser Leu Lys Asn Gly Asn
    530                 535                 540

Asp Asn Lys Lys Val Glu Val Thr Tyr Ser Asp Asp Ser Lys Lys Ile
545                 550                 555                 560

Ile Thr Leu Lys Lys Val Asp Lys Asn Asn Ile Lys Thr Leu Asp Phe
                565                 570                 575

Thr Tyr Lys Leu Ser Gln Ser Asp Phe Asn Lys Gln Leu Phe Lys Gln
            580                 585                 590

Asn Pro Thr Ala Asn Ile Thr Tyr Asp Ile Asn Leu Lys Asn Tyr Asp
        595                 600                 605

Asn Ile Lys Asp Lys Gln Asn Asp Ala Tyr Ile Trp Lys Asn Asp Pro
    610                 615                 620

Lys Lys Ser Asn Asp Ile Gln Asp Leu Ser Ala Ala Lys Lys Gln Val
625                 630                 635                 640

Leu Leu Asp Gln Leu Glu Ala Ile Thr Ala Lys Asn Pro Asp Val Gln
                645                 650                 655

Asn Ala Ala Lys Thr Glu Leu Tyr Ser Ala Tyr Leu Tyr Thr Asp Gly
            660                 665                 670

Ile Tyr Tyr Lys Ser Leu Phe Asp Glu Ile Ser Lys Tyr Ile Glu Ser
        675                 680                 685

Glu Lys Pro Thr Leu Asp
    690
```

<210> SEQ ID NO 7
<211> LENGTH: 990
<212> TYPE: DNA
<213> ORGANISM: Artificial Sequence
<220> FEATURE:
<223> OTHER INFORMATION: Nucleotide sequence encoding MSC_0431 shown in SEQ ID NO:8, modified for expression in E. coli

<400> SEQUENCE: 7

```
tgcgcaaaca tcgaaatgtc aaaaaacaaa aaagataaag acaaagatct gaaatcggac     60

aaaaacaaag atcagaacaa caaattcgac aaaagcaaag ataaaaacca aaactctaaa    120

ccgaacaaca acgatcagaa tagtaaatcc aaccaagaca aaacctcacc gaaagataat    180

ccgtcgacgc agtcagaatc ggaaaaacag gaaaactcca aacaatatga cctggataaa    240

ctgatcacga acaaattcat cagcatcgac ggctctggta ccggcgatgg taaactggct    300

aaactgccgc agaacctgca agaatatctg gatctgatca aaaaacagaa cccgaaattc    360

accctgacgc tgaataacgt cagtttcaat gtggaagaaa atgataactc cggctacaaa    420

aaagtcagcg tgtctacgaa gggtaactct aaaaacccgg ttatcgtcta cttctacaaa    480

gaccgtcatg ataccgttta tgaaggcgag aaaaaagaag tggttaaaga aatcggttgg    540

agtaaatcca cctacagtac ggacatcctg cacttcgatg aacagacgaa agaagtcccg    600

gaaaacctgc cgccgtttat caccagcctg gaaggcgcgt tccgcaacaa catccaagaa    660

accatcaaaa acctggacaa atgggatacg agcaacatcg aattcatgaa cgaaaccttc    720

tacgaagcga aaaattttaa ccaggatatc tctggttgga aaaccaataa cgttagtaac    780

atggattcca tgttttatgg cgccagctct ttcgaccgta atctgagcgg ttggaacgtg    840

gataaagtta ttacctacat cgaattcaac aaagattcaa aaatctcgga acgtaacaaa    900

ccgaaattca aagaactgaa acgcattcat cagggccaag gtgcaaccaa aatcctgcac    960

aatcgcggct ttctgaataa aatgaacctg                                     990
```

<210> SEQ ID NO 8
<211> LENGTH: 330
<212> TYPE: PRT
<213> ORGANISM: Artificial Sequence
<220> FEATURE:
<223> OTHER INFORMATION: Amino acid sequence of MSC_0431 from M. mycoides subsp. mycoides (Mmm), lacking the signal sequence

<400> SEQUENCE: 8

```
Cys Ala Asn Ile Glu Met Ser Lys Asn Lys Lys Asp Lys Asp Lys Asp
1               5                   10                  15

Leu Lys Ser Asp Lys Asn Lys Asp Gln Asn Asn Lys Phe Asp Lys Ser
            20                  25                  30

Lys Asp Lys Asn Gln Asn Ser Lys Pro Asn Asn Asn Asp Gln Asn Ser
        35                  40                  45

Lys Ser Asn Gln Asp Lys Thr Ser Pro Lys Asp Asn Pro Ser Thr Gln
    50                  55                  60

Ser Glu Ser Glu Lys Gln Glu Asn Ser Lys Gln Tyr Asp Leu Asp Lys
65                  70                  75                  80

Leu Ile Thr Asn Lys Phe Ile Ser Ile Asp Gly Ser Gly Thr Gly Asp
                85                  90                  95

Gly Lys Leu Ala Lys Leu Pro Gln Asn Leu Gln Glu Tyr Leu Asp Leu
            100                 105                 110

Ile Lys Lys Gln Asn Pro Lys Phe Thr Leu Thr Leu Asn Asn Val Ser
        115                 120                 125
```

-continued

```
Phe Asn Val Glu Glu Asn Asp Asn Ser Gly Tyr Lys Lys Val Ser Val
    130                 135                 140

Ser Thr Lys Gly Asn Ser Lys Asn Pro Val Ile Val Tyr Phe Tyr Lys
145                 150                 155                 160

Asp Arg His Asp Thr Val Tyr Glu Gly Glu Lys Lys Glu Val Val Lys
                165                 170                 175

Glu Ile Gly Trp Ser Lys Ser Thr Tyr Ser Thr Asp Ile Leu His Phe
            180                 185                 190

Asp Glu Gln Thr Lys Glu Val Pro Glu Asn Leu Pro Pro Phe Ile Thr
        195                 200                 205

Ser Leu Glu Gly Ala Phe Arg Asn Asn Ile Gln Glu Thr Ile Lys Asn
    210                 215                 220

Leu Asp Lys Trp Asp Thr Ser Asn Ile Glu Phe Met Asn Glu Thr Phe
225                 230                 235                 240

Tyr Glu Ala Lys Asn Phe Asn Gln Asp Ile Ser Gly Trp Lys Thr Asn
                245                 250                 255

Asn Val Ser Asn Met Asp Ser Met Phe Tyr Gly Ala Ser Ser Phe Asp
            260                 265                 270

Arg Asn Leu Ser Gly Trp Asn Val Asp Lys Val Ile Thr Tyr Ile Glu
        275                 280                 285

Phe Asn Lys Asp Ser Lys Ile Ser Glu Arg Asn Lys Pro Lys Phe Lys
    290                 295                 300

Glu Leu Lys Arg Ile His Gln Gly Gln Gly Ala Thr Lys Ile Leu His
305                 310                 315                 320

Asn Arg Gly Phe Leu Asn Lys Met Asn Leu
                325                 330


<210> SEQ ID NO 9
<211> LENGTH: 2265
<212> TYPE: DNA
<213> ORGANISM: Artificial Sequence
<220> FEATURE:
<223> OTHER INFORMATION: Nucleotide sequence encoding MSC_0776 shown in
      SEQ ID NO:10, modified for expression in E. coli

<400> SEQUENCE: 9

tgtaaaacga cgcaaaatca acagggcatc tataaaattg tggacttcga aaaagaaaat      60

caaatcaaca ttctgagcga aatcaaccag tttttcgaaa aacatgattt caacgaacag     120

ctggttcaat tcgtcaacaa agatagccac aattatatta ccctggactc tctgatgaaa     180

aacaattatg cggccaaata cgtgaaattt gataaagaca aattcaaaca gatcatcaaa     240

aaagaattca acctgagtga tgcatacctg aataaactgg aaatcgaagt tgactatacc     300

aacattgatc gcgactactc caacaatttt gatattgtct tcccgattcg tatcaaacgc     360

cagctggaaa atcataaaaa agcgagctat caaccgggcc tgtttacgga acagattatc     420

aaattccgcc tgaaaaacgt gaaaagctct ccgtcggaag catttttcgc tgaagaactg     480

aaagatgttt tcaacaaact gaaagaactg aaatacgata acttcaccgc gcgtctgaaa     540

acgaacatca gtaacgaact gaaaaaacag atcgatcaat ggaacatcaa cgaactggac     600

agtacccaac tgtccaacat cttcgaaatc aacatctccg aattcgatca gctgaaaacc     660

aacaatccga attttgtgtt caaaagtacg atctttggtg ttgatttctc cgacaaaaac     720

ctggcgctga atgaaggcta tctgaaagtg cgttttgccg ttaaagaagg tttcgatagt     780

aaagacaaaa ccaaacagat caacctgatc aacaaagaaa tcaacgaact gatcgtgaaa     840
```

-continued

```
aaagaaaacc tggaaaaaac caacaactca gattcgaaca aaacggaaat cgacaaactg    900

atccagatca tcaaacaaaa aagcgcgcag ctgaccaaaa ttaaacaaaa agccctgccg    960

gcggaagccg gcatcacgaa actgatcaaa ttcaaattcg attggaacga ccagttttgg   1020

aaaaacatca aactgaacga agtgatcaaa atcgatacca tcaaatatgg tatcagcaat   1080

accgatttcc tgtctctgac gaaagacaac ctgattgtta aatcctgaa caaagatgtg   1140

cgtaacgttg acattaagaa aattgaaaaa accaacgatt tccgcaacgc gaaactggtc   1200

ctggatgtgc tgctgaaaga caacaaaaaa ctggaactga acaagaaaat tggcgtgggt   1260

aaatatagcc tgctgtacga aaatgatttc atcaaaaaca acatccaggc cccgtatttc   1320

accacggaac gtctgaccca agaaaacctg cagtctgtta ataaagattt ctttcgccag   1380

tttgactcag aactgttctc gggcggttat gcaagttccc gtggctttta cgctccgaaa   1440

attaccacgc cgatcttcat gcacattggt gaagattata ttgcgaatga ctttcaggcc   1500

gtgctgatgc cgtatgatgg cgaaattatc gcagcttacg aactgagcac caacgtcccg   1560

ttcgcaggcg tgggtacggt ggttgtcgtg aaaattaaag tttctgatct ggactggacc   1620

ccgaaagaaa aagaaatcta tctgaacaac aacaaagatc atatctacat gtcatttctg   1680

cacctggacg catcgcgcac gctgaataac cagaaactgg gttggtcagc tgaaaaagtt   1740

gtcctgaata acaatcgtac cattcaagtg gttaaatcgc tgacgccgga aaaaccgcag   1800

aaagtcgcca aaaataccat tatcggctat ctgggtaaca atgcaagtaa cggcggttgg   1860

atgtcccatg ctcacgttaa cctgtacacc aatcgcccgt catatctgtc ggaaaactac   1920

tttagcacga aatctaatca aggcctgagc gaagatcgta tcaaacagta ccatcaaaac   1980

atcaacggta aagaaacctg gcgtcagttt ggcaatattg gtctgcacca gtctccgcaa   2040

cgtccgccgt acaccatcaa cgaagttgat caaattacgg gcgtcgaaaa actggacgaa   2100

aacaaaaaga aaattgtcgt gaaaaacgaa caggcgctgt ttctgccgaa cctgagcatg   2160

tctctgttcg aaaaacgcct gggttatgcc aacccgaatc tggtctaccg tctgcgcgat   2220

aataaaaccg tgagtttttc cgttaaagaa gtcaacaaac tgacg                   2265
```

```
<210> SEQ ID NO 10
<211> LENGTH: 755
<212> TYPE: PRT
<213> ORGANISM: Artificial Sequence
<220> FEATURE:
<223> OTHER INFORMATION: Amino acid sequence of MSC_0776 from M.
      mycoides subsp. mycoides (Mmm), lacking the signal sequence

<400> SEQUENCE: 10

Cys Lys Thr Thr Gln Asn Gln Gln Gly Ile Tyr Lys Ile Val Asp Phe
1               5                   10                  15

Glu Lys Glu Asn Gln Ile Asn Ile Leu Ser Glu Ile Asn Gln Phe Phe
            20                  25                  30

Glu Lys His Asp Phe Asn Glu Gln Leu Val Gln Phe Val Asn Lys Asp
        35                  40                  45

Ser His Asn Tyr Ile Thr Leu Asp Ser Leu Met Lys Asn Asn Tyr Ala
    50                  55                  60

Ala Lys Tyr Val Lys Phe Asp Lys Asp Lys Phe Lys Gln Ile Ile Lys
65                  70                  75                  80

Lys Glu Phe Asn Leu Ser Asp Ala Tyr Leu Asn Lys Leu Glu Ile Glu
                85                  90                  95

Val Asp Tyr Thr Asn Ile Asp Arg Asp Tyr Ser Asn Asn Phe Asp Ile
            100                 105                 110
```

-continued

```
Val Phe Pro Ile Arg Ile Lys Arg Gln Leu Glu Asn His Lys Lys Ala
        115                 120                 125

Ser Tyr Gln Pro Gly Leu Phe Thr Glu Gln Ile Ile Lys Phe Arg Leu
    130                 135                 140

Lys Asn Val Lys Ser Ser Pro Ser Glu Ala Phe Phe Ala Glu Glu Leu
145                 150                 155                 160

Lys Asp Val Phe Asn Lys Leu Lys Glu Leu Lys Tyr Asp Asn Phe Thr
                165                 170                 175

Ala Arg Leu Lys Thr Asn Ile Ser Asn Glu Leu Lys Lys Gln Ile Asp
            180                 185                 190

Gln Trp Asn Ile Asn Glu Leu Asp Ser Thr Gln Leu Ser Asn Ile Phe
        195                 200                 205

Glu Ile Asn Ile Ser Glu Phe Asp Gln Leu Lys Thr Asn Asn Pro Asn
    210                 215                 220

Phe Val Phe Lys Ser Thr Ile Phe Gly Val Asp Phe Ser Asp Lys Asn
225                 230                 235                 240

Leu Ala Leu Asn Glu Gly Tyr Leu Lys Val Arg Phe Ala Val Lys Glu
                245                 250                 255

Gly Phe Asp Ser Lys Asp Lys Thr Lys Gln Ile Asn Leu Ile Asn Lys
            260                 265                 270

Glu Ile Asn Glu Leu Ile Val Lys Lys Glu Asn Leu Glu Lys Thr Asn
        275                 280                 285

Asn Ser Asp Ser Asn Lys Thr Glu Ile Asp Lys Leu Ile Gln Ile Ile
    290                 295                 300

Lys Gln Lys Ser Ala Gln Leu Thr Lys Ile Lys Gln Lys Ala Leu Pro
305                 310                 315                 320

Ala Glu Ala Gly Ile Thr Lys Leu Ile Lys Phe Lys Phe Asp Trp Asn
                325                 330                 335

Asp Gln Phe Trp Lys Asn Ile Lys Leu Asn Glu Val Ile Lys Ile Asp
            340                 345                 350

Thr Ile Lys Tyr Gly Ile Ser Asn Thr Asp Phe Leu Ser Leu Thr Lys
        355                 360                 365

Asp Asn Leu Ile Val Lys Ile Leu Asn Lys Asp Val Arg Asn Val Asp
    370                 375                 380

Ile Lys Lys Ile Glu Lys Thr Asn Asp Phe Arg Asn Ala Lys Leu Val
385                 390                 395                 400

Leu Asp Val Leu Leu Lys Asp Asn Lys Lys Leu Glu Leu Asn Lys Lys
                405                 410                 415

Ile Gly Val Gly Lys Tyr Ser Leu Leu Tyr Glu Asn Asp Phe Ile Lys
            420                 425                 430

Asn Asn Ile Gln Ala Pro Tyr Phe Thr Thr Glu Arg Leu Thr Gln Glu
        435                 440                 445

Asn Leu Gln Ser Val Asn Lys Asp Phe Phe Arg Gln Phe Asp Ser Glu
    450                 455                 460

Leu Phe Ser Gly Gly Tyr Ala Ser Ser Arg Gly Phe Tyr Ala Pro Lys
465                 470                 475                 480

Ile Thr Thr Pro Ile Phe Met His Ile Gly Glu Asp Tyr Ile Ala Asn
                485                 490                 495

Asp Phe Gln Ala Val Leu Met Pro Tyr Asp Gly Glu Ile Ile Ala Ala
            500                 505                 510

Tyr Glu Leu Ser Thr Asn Val Pro Phe Ala Gly Val Gly Thr Val Val
        515                 520                 525
```

-continued

```
Val Val Lys Ile Lys Val Ser Asp Leu Asp Trp Thr Pro Lys Glu Lys
    530                 535                 540

Glu Ile Tyr Leu Asn Asn Asn Lys Asp His Ile Tyr Met Ser Phe Leu
545                 550                 555                 560

His Leu Asp Ala Ser Arg Thr Leu Asn Asn Gln Lys Leu Gly Trp Ser
                565                 570                 575

Ala Glu Lys Val Val Leu Asn Asn Asn Arg Thr Ile Gln Val Val Lys
            580                 585                 590

Ser Leu Thr Pro Glu Lys Pro Gln Lys Val Ala Lys Asn Thr Ile Ile
        595                 600                 605

Gly Tyr Leu Gly Asn Asn Ala Ser Asn Gly Gly Trp Met Ser His Ala
    610                 615                 620

His Val Asn Leu Tyr Thr Asn Arg Pro Ser Tyr Leu Ser Glu Asn Tyr
625                 630                 635                 640

Phe Ser Thr Lys Ser Asn Gln Gly Leu Ser Glu Asp Arg Ile Lys Gln
                645                 650                 655

Tyr His Gln Asn Ile Asn Gly Lys Glu Thr Trp Arg Gln Phe Gly Asn
            660                 665                 670

Ile Gly Leu His Gln Ser Pro Gln Arg Pro Pro Tyr Thr Ile Asn Glu
        675                 680                 685

Val Asp Gln Ile Thr Gly Val Glu Lys Leu Asp Glu Asn Lys Lys Lys
    690                 695                 700

Ile Val Val Lys Asn Glu Gln Ala Leu Phe Leu Pro Asn Leu Ser Met
705                 710                 715                 720

Ser Leu Phe Glu Lys Arg Leu Gly Tyr Ala Asn Pro Asn Leu Val Tyr
                725                 730                 735

Arg Leu Arg Asp Asn Lys Thr Val Ser Phe Ser Val Lys Glu Val Asn
            740                 745                 750

Lys Leu Thr
        755
```

<210> SEQ ID NO 11
<211> LENGTH: 408
<212> TYPE: DNA
<213> ORGANISM: Artificial Sequence
<220> FEATURE:
<223> OTHER INFORMATION: Nucleotide sequence encoding YP_004400559.1
shown in SEQ ID NO:12, modified for expression in E. coli

<400> SEQUENCE: 11

```
atgagcaaca acaacaaaaa agaagaaaag caatcaaagg aaatgaataa aaatcaaacc     60

tctaactcca cgagcaccaa tatgaacaac acgcagggca gcaatagctc taccacgacc    120

aacattacct ctaacccgat caatagtgtc acgtccatgg cgacccaacc gaaaaacgaa    180

acctttttca ataaggaacc gctgatcttt tcagaactgg attatgtgtc ggaatacttc    240

aagcgtaagg aacatattgc gcgcaccagc gaactgatcc tggaaaactc tgaaggcatt    300

aaacgtcgta tgcagaatag tacggttgaa acgacccacc gtgattccct ggccgaaacc    360

caagacctga ttctggaaaa cagcaacggt gtggttaact tcaagaag                 408
```

<210> SEQ ID NO 12
<211> LENGTH: 136
<212> TYPE: PRT
<213> ORGANISM: Artificial Sequence
<220> FEATURE:
<223> OTHER INFORMATION: Amino acid sequence of YP_004400559.1 from M.
mycoides subsp. capri (Mmc), lacking the signal sequence and
including an N-terminal methionine

<400> SEQUENCE: 12

Met Ser Asn Asn Asn Lys Lys Glu Glu Lys Gln Ser Lys Glu Met Asn
1 5 10 15

Lys Asn Gln Thr Ser Asn Ser Thr Ser Thr Asn Met Asn Asn Thr Gln
20 25 30

Gly Ser Asn Ser Ser Thr Thr Thr Asn Ile Thr Ser Asn Pro Ile Asn
35 40 45

Ser Val Thr Ser Met Ala Thr Gln Pro Lys Asn Glu Thr Phe Phe Asn
50 55 60

Lys Glu Pro Leu Ile Phe Ser Glu Leu Asp Tyr Val Ser Glu Tyr Phe
65 70 75 80

Lys Arg Lys Glu His Ile Ala Arg Thr Ser Glu Leu Ile Leu Glu Asn
85 90 95

Ser Glu Gly Ile Lys Arg Arg Met Gln Asn Ser Thr Val Glu Thr Thr
100 105 110

His Arg Asp Ser Leu Ala Glu Thr Gln Asp Leu Ile Leu Glu Asn Ser
115 120 125

Asn Gly Val Val Asn Phe Lys Lys
130 135

<210> SEQ ID NO 13
<211> LENGTH: 1044
<212> TYPE: DNA
<213> ORGANISM: Artificial Sequence
<220> FEATURE:
<223> OTHER INFORMATION: Nucleotide sequence encoding YP_004399807.1
shown in SEQ ID NO:14, modified for expression in E. coli

<400> SEQUENCE: 13
atgagcagca aagttcaggt tatcaacaag ttcgatgaca ttacgtccat taaaaacacg 60
ggtgcgttca aaaacaatca ggcattcatt tcccgttcag aactgaaaga aatcgtcagc 120
tctaacaata ccacgatttc taataccacg agttccaccg cagtgatgac ctcgacgagc 180
accacgtcta tcggcaccca gacgaacaat aacaatgacc tgaagaacgc gagtgaacgc 240
ctgaaagccc tggcggccaa caacttcacc aagaacaaga agcaggcatg ggattccctg 300
caaaacgctt caatgacctt ctataaaaag gtgcagccga ccgcggtcaa tgtgctgggt 360
tacgaacaaa ttaccaaaga caacgttgaa aaactggata aggaactgaa aaccgttttt 420
ctggtcttca aggacaatac caaagaaacg gaaaagctgg aagtggaact gctgccggaa 480
attaacaatg gcaacaaagt tatcgacaat ggtaacctgt atctggatct gctggaaaaa 540
ccggaaaatc tgaagctggc gaaccagaaa agcattatcg aagtgctgcg tccggaaatt 600
accaaaatca aggtggttct gcaaaatacc aaaaacaata actccacgaa caaagaagat 660
atcaagaaca ccgaagtttt caacctgctg attaaacagc tgagcatcta tctggcaaat 720
gctgtcaaat actttaactc tgaaagtggc attatcacca cgaatccgac cttctcgtat 780
aaaacgcgca gcaatcaaat ctacgactac atcgttaaga acaagaagga tgaactgtac 840
aagaagctgg aaaccgcgtt tacgtcagaa ttcaacaaga tcaacttcat cgatatcttc 900
aaagacttcc agttcgatga aaacaacagt aacgataaca aaaagattat caccaagatt 960
atcaaatcat cgacgaatag ctctgccagt tcctcaaact cgagcaccac gaccacgacc 1020
gaactgtcta gtacgaccac gcgt 1044

<210> SEQ ID NO 14

-continued

```
<211> LENGTH: 348
<212> TYPE: PRT
<213> ORGANISM: Artificial Sequence
<220> FEATURE:
<223> OTHER INFORMATION: Amino acid sequence of YP_004399807.1 from M.
      mycoides subsp. capri (Mmc), lacking the signal sequence and
      including an N-terminal methionine

<400> SEQUENCE: 14

Met Ser Ser Lys Val Gln Val Ile Asn Lys Phe Asp Asp Ile Thr Ser
1               5                   10                  15

Ile Lys Asn Thr Gly Ala Phe Lys Asn Asn Gln Ala Phe Ile Ser Arg
            20                  25                  30

Ser Glu Leu Lys Glu Ile Val Ser Ser Asn Asn Thr Thr Ile Ser Asn
        35                  40                  45

Thr Thr Ser Ser Thr Ala Val Met Thr Ser Thr Ser Thr Thr Ser Ile
    50                  55                  60

Gly Thr Gln Thr Asn Asn Asn Asn Asp Leu Lys Asn Ala Ser Glu Arg
65                  70                  75                  80

Leu Lys Ala Leu Ala Ala Asn Asn Phe Thr Lys Asn Lys Lys Gln Ala
                85                  90                  95

Trp Asp Ser Leu Gln Asn Ala Ser Met Thr Phe Tyr Lys Lys Val Gln
            100                 105                 110

Pro Thr Ala Val Asn Val Leu Gly Tyr Glu Gln Ile Thr Lys Asp Asn
        115                 120                 125

Val Glu Lys Leu Asp Lys Glu Leu Lys Thr Val Phe Leu Val Phe Lys
    130                 135                 140

Asp Asn Thr Lys Glu Thr Glu Lys Leu Glu Val Glu Leu Leu Pro Glu
145                 150                 155                 160

Ile Asn Asn Gly Asn Lys Val Ile Asp Asn Gly Asn Leu Tyr Leu Asp
                165                 170                 175

Leu Leu Glu Lys Pro Glu Asn Leu Lys Leu Ala Asn Gln Lys Ser Ile
            180                 185                 190

Ile Glu Val Leu Arg Pro Glu Ile Thr Lys Ile Lys Val Val Leu Gln
        195                 200                 205

Asn Thr Lys Asn Asn Asn Ser Thr Asn Lys Glu Asp Ile Lys Asn Thr
    210                 215                 220

Glu Val Phe Asn Leu Leu Ile Lys Gln Leu Ser Ile Tyr Leu Ala Asn
225                 230                 235                 240

Ala Val Lys Tyr Phe Asn Ser Glu Ser Gly Ile Ile Thr Thr Asn Pro
                245                 250                 255

Thr Phe Ser Tyr Lys Thr Arg Ser Asn Gln Ile Tyr Asp Tyr Ile Val
            260                 265                 270

Lys Asn Lys Lys Asp Glu Leu Tyr Lys Lys Leu Glu Thr Ala Phe Thr
        275                 280                 285

Ser Glu Phe Asn Lys Ile Asn Phe Ile Asp Ile Phe Lys Asp Phe Gln
    290                 295                 300

Phe Asp Glu Asn Asn Ser Asn Asp Asn Lys Lys Ile Ile Thr Lys Ile
305                 310                 315                 320

Ile Lys Ser Ser Thr Asn Ser Ser Ala Ser Ser Ser Asn Ser Ser Thr
                325                 330                 335

Thr Thr Thr Thr Glu Leu Ser Ser Thr Thr Thr Arg
            340                 345


<210> SEQ ID NO 15
<211> LENGTH: 1146
```

<212> TYPE: DNA
<213> ORGANISM: Artificial Sequence
<220> FEATURE:
<223> OTHER INFORMATION: Nucleotide sequence encoding MSC_0816 shown in SEQ ID NO:16, modified for expression in E. coli

<400> SEQUENCE: 15

```
gcaaacaaaa actctgtcga aaacaacatc tatatcagta aacagattca acgcaaaccg     60

cataaaatcg aaggcgataa actgattgaa atcggttatt actgggattc tcacgaccgt    120

caggtgcgca ttatgcgtat cccgccgacc gtgaaagtta tcgcggccca gctgccgccg    180

attatcacga gtctgaaagg cgcatttcaa gctcgcatta acgacgttat ctggcatgtc    240

ccgtgggata ccaaaaacat cacgaacatg aacagcatgt tctacaacaa tatttggttc    300

aacagctcta gtatcctgga atgggatacc tccaatgtta cggacatggg tgaaatgttt    360

ggccgtaccg gtagcttcaa ccaggatctg tccaaatggg acgtctcaaa agtgaaaaac    420

ttcaagaaaa tgttctacaa cgcgaaaaaa tacaacaaca acgataaacc gctgaaatgg    480

aacgacaaac tgaaatctgc agtcaatatg gaagatatgt ttcaaggcgc tagtgacttc    540

aaacatagtc tgtccgattg gaaactggaa accgaaatca acaacaaaaa cttcggtctg    600

ctggaagatc gccacccgaa atggaaagaa aaactgatta aaccgtcctc accgatctcg    660

agctctaatt ccctgagttc caataacatc aatgatcgct cagatgacaa ccagattaat    720

cgtaactcat cgaccccgac gaatagcaac accatctcta cgaatccgag taacgatctg    780

agctctaata ccacgaataa cgaaaacatt tcggaaagtt ccatgagcaa taacatgctg    840

gaaattccga tcaatagcga aaacaaaccg gaaaacccga aaaacaacga aaacatcaac    900

tacaaaatcc tgccgaaagt ggacaaaacc aaaaaaacaga gcgaagcgaa aaacaaaatc    960

ccggttgaaa aaggcgaact gtcgaaagat gaaaatcaaa ccacgaaaac cagcaacgcc   1020

atcaaagaca aagaaaactc atcgatcaaa tcagattcgc tgtacaaaat tccgccgaaa   1080

ccgaacacca ttatcagcaa actgagctct ccgaatgcgg gcattatcac gggtgccgtg   1140

tttcgt                                                              1146
```

<210> SEQ ID NO 16
<211> LENGTH: 382
<212> TYPE: PRT
<213> ORGANISM: Artificial Sequence
<220> FEATURE:
<223> OTHER INFORMATION: Amino acid sequence of MSC_0816 from M. mycoides subsp. mycoides (Mmm), lacking the signal sequence

<400> SEQUENCE: 16

```
Ala Asn Lys Asn Ser Val Glu Asn Asn Ile Tyr Ile Ser Lys Gln Ile
1               5                   10                  15

Gln Arg Lys Pro His Lys Ile Glu Gly Asp Lys Leu Ile Glu Ile Gly
            20                  25                  30

Tyr Tyr Trp Asp Ser His Asp Arg Gln Val Arg Ile Met Arg Ile Pro
        35                  40                  45

Pro Thr Val Lys Val Ile Ala Ala Gln Leu Pro Pro Ile Ile Thr Ser
    50                  55                  60

Leu Lys Gly Ala Phe Gln Ala Arg Ile Asn Asp Val Ile Trp His Val
65                  70                  75                  80

Pro Trp Asp Thr Lys Asn Ile Thr Asn Met Asn Ser Met Phe Tyr Asn
                85                  90                  95

Asn Ile Trp Phe Asn Ser Ser Ser Ile Leu Glu Trp Asp Thr Ser Asn
            100                 105                 110
```

-continued

```
Val Thr Asp Met Gly Glu Met Phe Gly Arg Thr Gly Ser Phe Asn Gln
        115                 120                 125

Asp Leu Ser Lys Trp Asp Val Ser Lys Val Lys Asn Phe Lys Lys Met
    130                 135                 140

Phe Tyr Asn Ala Lys Lys Tyr Asn Asn Asn Asp Lys Pro Leu Lys Trp
145                 150                 155                 160

Asn Asp Lys Leu Lys Ser Ala Val Asn Met Glu Asp Met Phe Gln Gly
                165                 170                 175

Ala Ser Asp Phe Lys His Ser Leu Ser Asp Trp Lys Leu Glu Thr Glu
            180                 185                 190

Ile Asn Asn Lys Asn Phe Gly Leu Leu Glu Asp Arg His Pro Lys Trp
        195                 200                 205

Lys Glu Lys Leu Ile Lys Pro Ser Ser Pro Ile Ser Ser Ser Asn Ser
    210                 215                 220

Leu Ser Ser Asn Asn Ile Asn Asp Arg Ser Asp Asp Asn Gln Ile Asn
225                 230                 235                 240

Arg Asn Ser Ser Thr Pro Thr Asn Ser Asn Thr Ile Ser Thr Asn Pro
                245                 250                 255

Ser Asn Asp Leu Ser Ser Asn Thr Thr Asn Asn Glu Asn Ile Ser Glu
            260                 265                 270

Ser Ser Met Ser Asn Asn Met Leu Glu Ile Pro Ile Asn Ser Glu Asn
        275                 280                 285

Lys Pro Glu Asn Pro Lys Asn Asn Glu Asn Ile Asn Tyr Lys Ile Leu
    290                 295                 300

Pro Lys Val Asp Lys Thr Lys Lys Gln Ser Glu Ala Lys Asn Lys Ile
305                 310                 315                 320

Pro Val Glu Lys Gly Glu Leu Ser Lys Asp Glu Asn Gln Thr Thr Lys
                325                 330                 335

Thr Ser Asn Ala Ile Lys Asp Lys Glu Asn Ser Ser Ile Lys Ser Asp
            340                 345                 350

Ser Leu Tyr Lys Ile Pro Pro Lys Pro Asn Thr Ile Ile Ser Lys Leu
        355                 360                 365

Ser Ser Pro Asn Ala Gly Ile Ile Thr Gly Ala Val Phe Arg
    370                 375                 380
```

<210> SEQ ID NO 17
<211> LENGTH: 1185
<212> TYPE: DNA
<213> ORGANISM: Artificial Sequence
<220> FEATURE:
<223> OTHER INFORMATION: Nucleotide sequence encoding MSC_0160 shown in SEQ ID NO:18, modified for expression in E. coli

<400> SEQUENCE: 17

```
atggcgaaag aacagtttga tcgtagcctg ccgcatgtga acattggcac catcggtcat     60

gttgaccacg gcaaaaccac gctgaccgcg gccattacga aagttctgtc tgaacagggt    120

aacgcagaat tcaaagatta cgcaaacatc gacaatgctc cggaagaacg tgaacgcggc    180

attaccatca acacggcgca tgtggaatat aaaaccgcga atcgccatta cgcccacgtc    240

gattgcccgg gtcacgcaga ctacgtgaaa aacatgatta cgggtgcagc tcagatggat    300

ggcgctatcc tggtggttgc agcaaccgac ggtccgatgc cgcagacgcg tgaacacatt    360

ctgctgtccc gccaagtggg tgttccgaaa atcgtcgtgt ttctgaacaa atgtgatatg    420

gttgaagatg acgaaatgat tgatctggtg gaaatggaaa tccgtgacct gctgaccgaa    480
```

```
tatgatttcg acggcgaagg tgccccggtt attcgtggca gcgcactggg tgctctgaac    540

ggtgattcta aatggaccgg cgcgattaat gaactgatgg cagctgtgga tgaatacatc    600

ccgaccccgc agcgtgatgc cgacaaaacg tttctgatgc cggtggaaga tgttttcacc    660

atcacgggtc gtggtaccgt tgcaacgggt cgtgtcgaac gcggcaccgt caaagtgaac    720

gaagaagttg aaattatcgg cctgaaagaa gaaccgacca aaacggttgt cacgggtctg    780

gaaatgtttc gtaaactgct ggatttcgcg gtggccggtg acaatgttgg tgcactgctg    840

cgtggtgtcg atcgtcattc agtggaacgc ggtcaggttc tggccaaacc gggcaccatt    900

aaaccgcaca cggtcctgaa agcgtcggtg tatgccctga cccaggaaga aggcggtcgt    960

cataaaccgt tttcaacaa atatcgtccg caattttact tccgcaccac ggatgtcacc    1020

ggtgaagtga cgctgccgga aggcaccgat atggttatgc cgggtgacaa tgtcgaaatg    1080

gaaattcaac tgatcaaacc ggttgcagtc gaagaaggta ccaaatttag tattcgtgaa    1140

ggcggtcgta ccatcggtgc tggtacggtg atttccatcg aaaaa                    1185


<210> SEQ ID NO 18
<211> LENGTH: 395
<212> TYPE: PRT
<213> ORGANISM: Mycoplasma mycoides

<400> SEQUENCE: 18

Met Ala Lys Glu Gln Phe Asp Arg Ser Leu Pro His Val Asn Ile Gly
1               5                   10                  15

Thr Ile Gly His Val Asp His Gly Lys Thr Thr Leu Thr Ala Ala Ile
            20                  25                  30

Thr Lys Val Leu Ser Glu Gln Gly Asn Ala Glu Phe Lys Asp Tyr Ala
        35                  40                  45

Asn Ile Asp Asn Ala Pro Glu Glu Arg Glu Arg Gly Ile Thr Ile Asn
    50                  55                  60

Thr Ala His Val Glu Tyr Lys Thr Ala Asn Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Ser Arg Gln Val Gly Val
        115                 120                 125

Pro Lys Ile Val Val Phe Leu Asn Lys Cys Asp Met Val Glu Asp Asp
    130                 135                 140

Glu Met Ile Asp Leu Val Glu Met Glu Ile Arg Asp Leu Leu Thr Glu
145                 150                 155                 160

Tyr Asp Phe Asp Gly Glu Gly Ala Pro Val Ile Arg Gly Ser Ala Leu
                165                 170                 175

Gly Ala Leu Asn Gly Asp Ser Lys Trp Thr Gly Ala Ile Asn Glu Leu
            180                 185                 190

Met Ala Ala Val Asp Glu Tyr Ile Pro Thr Pro Gln Arg Asp Ala Asp
        195                 200                 205

Lys Thr Phe Leu Met Pro Val Glu Asp Val Phe Thr Ile Thr Gly Arg
    210                 215                 220

Gly Thr Val Ala Thr Gly Arg Val Glu Arg Gly Thr Val Lys Val Asn
225                 230                 235                 240

Glu Glu Val Glu Ile Ile Gly Leu Lys Glu Glu Pro Thr Lys Thr Val
                245                 250                 255
```

```
Val Thr Gly Leu Glu Met Phe Arg Lys Leu Leu Asp Phe Ala Val Ala
            260                 265                 270

Gly Asp Asn Val Gly Ala Leu Leu Arg Gly Val Asp Arg His Ser Val
        275                 280                 285

Glu Arg Gly Gln Val Leu Ala Lys Pro Gly Thr Ile Lys Pro His Thr
    290                 295                 300

Val Leu Lys Ala Ser Val Tyr Ala Leu Thr Gln Glu Glu Gly Gly Arg
305                 310                 315                 320

His Lys Pro Phe Phe Asn Lys Tyr Arg Pro Gln Phe Tyr Phe Arg Thr
                325                 330                 335

Thr Asp Val Thr Gly Glu Val Thr Leu Pro Glu Gly Thr Asp Met Val
            340                 345                 350

Met Pro Gly Asp Asn Val Glu Met Glu Ile Gln Leu Ile Lys Pro Val
        355                 360                 365

Ala Val Glu Glu Gly Thr Lys Phe Ser Ile Arg Glu Gly Gly Arg Thr
    370                 375                 380

Ile Gly Ala Gly Thr Val Ile Ser Ile Glu Lys
385                 390                 395
```

<210> SEQ ID NO 19
<211> LENGTH: 2106
<212> TYPE: DNA
<213> ORGANISM: Artificial Sequence
<220> FEATURE:
<223> OTHER INFORMATION: Nucleotide sequence encoding MSC_0775 shown in SEQ ID NO:20, modified for expression in E. coli

<400> SEQUENCE: 19

```
tgtaaaaacc cgctgttcaa tcaatcactg agcgaaaaaa tctacctgaa ctacaatctg     60

caaacggaaa aagacaaaca agaatttgaa aactataatc agattaacat gctgagcgaa    120

atcaatcaat acttcaccaa acatgatcac aacaaagacc tggtgaaatt taccacggat    180

ggcgcgtccg gtgacaccgt tgaattcaac aacatcatga aaaacaacta tgcctcaaaa    240

tacatcaaat tcgatcagga caaattcaaa gaaatcatca aaaaagaatt caatctgtca    300

gattcgttcc tgaaacgtct ggaattcgaa gtcgactaca acaacatctc gcgcgattac    360

ggcaacaatt ttgacgttat tttcccgatc cgtgttaaac tgccgctggt cagccataac    420

aatttcaaat atcagcaagg cctgtttatt gaacagacct ttaaattccg catcaaaaac    480

gtcaaagcga gcggttctga aaaaatcgat gtgtctaaaa tcaaagacat ctacaacgaa    540

ctggtgaaac tgaaagataa aaacaacttc acggccagtg tgaaaaccgt tacggaagaa    600

accaaaaaac tggttgatga atggggtatt catgaactga acagcacgca actgagctct    660

atcttcgata tcaaaaccga agaattcgat aacctgatca aagacaaaaa agaagtggaa    720

cacaaagtta ccatcacgga tgtggacctg agtgatccgt ccctggcgat taacgaaggc    780

ctgctgaaac tgcgtctggg cgttaaaatc aagggtaaag aaaccgaaac gggtgtcaac    840

gtgtggatca aattcaactt cgatcagaaa gacacctttt ggaaagaact gaaaatcagt    900

gaatccatca aagtcaacac ggtgaaattc agtgaaacca atacggattt taccaaactg    960

atgaacgaca acctgatcat caaatcaaaa tcgaaattca tcaaaaacat caaactgagt   1020

tccatcgata aaaccacgga ctatcgtaat tccggcgtcc tgctggaagt gctgaccaac   1080

gaatcaaaag ataacgtgat caaactgcat aaaaaaccgg gcgttggtaa atataccgat   1140

ctgtactccg cagacttcac gaaaaacaat atccacgcgc cgaattttgc caccgaaaaa   1200
```

-continued

```
ctgacgcagg aaaacctgaa atctatcaac aaagatttct ttcgccaatt tgactcagaa   1260

ctgttctcgg gcggttatgc tcgttcacgc ggcttctact cggaaaaagt gaaaagcccg   1320

aaattcatgc atatcggtga agattacatc gcaaacgact ttcaggctgt tctgatgccg   1380

tatgatggtg aaattatcgc ggcctacgaa ctgagcacca atgtgccgtt cgcaggcgtt   1440

ggtacggttc tggtcgctaa agtgccgatc accagcctgc cgtggtctcc gaaacagaaa   1500

gaaatcgaac tgaacgataa caaaacgcat atctacatca gctttctgca cctggatgcc   1560

caacgcaccc tgaacaatga caaactgggc tgggtggcag aaaccgctaa actgaaaaaa   1620

gataaaacgg ttaaagtggt taaaagtgtc accccgtcca cgccgaaaaa agtcagcaaa   1680

ggtaccgtga tcggctatct gggtgatcac tcatcgaacg gcggttggat gtctcatgca   1740

cacattaatc tgtacacgaa ccgtccgaat tatctgagtg aaaactactt tagctctaaa   1800

accattcgtg cgcagctgga tgacaaacgc gccaaaggct ataaaagttc cgtgtctaac   1860

aatgatttca gtgccattgg caatatcggt gttgaacgca aaattgatac gaaaatctat   1920

caggtcgacc cgaaaaccgg cattgaagat aaacaaaaag caatttcgga cgaaatcccg   1980

ctgtacttca acggcctgag catgctgggt tttgaaaaaa ccaaaggtta tgctaacccg   2040

aatctgatgt acaaactgcg tgatgaacgc accgtgagct tttctgttaa agaagtcaat   2100

aaactg                                                              2106
```

<210> SEQ ID NO 20
<211> LENGTH: 702
<212> TYPE: PRT
<213> ORGANISM: Artificial Sequence
<220> FEATURE:
<223> OTHER INFORMATION: Amino acid sequence of MSC_0775 from M. mycoides subsp. mycoides (Mmm), lacking the signal sequence

<400> SEQUENCE: 20

```
Cys Lys Asn Pro Leu Phe Asn Gln Ser Leu Ser Glu Lys Ile Tyr Leu
1               5                   10                  15

Asn Tyr Asn Leu Gln Thr Glu Lys Asp Lys Gln Glu Phe Glu Asn Tyr
            20                  25                  30

Asn Gln Ile Asn Met Leu Ser Glu Ile Asn Gln Tyr Phe Thr Lys His
        35                  40                  45

Asp His Asn Lys Asp Leu Val Lys Phe Thr Thr Asp Gly Ala Ser Gly
    50                  55                  60

Asp Thr Val Glu Phe Asn Asn Ile Met Lys Asn Asn Tyr Ala Ser Lys
65                  70                  75                  80

Tyr Ile Lys Phe Asp Gln Asp Lys Phe Lys Glu Ile Ile Lys Lys Glu
                85                  90                  95

Phe Asn Leu Ser Asp Ser Phe Leu Lys Arg Leu Glu Phe Glu Val Asp
            100                 105                 110

Tyr Asn Asn Ile Ser Arg Asp Tyr Gly Asn Asn Phe Asp Val Ile Phe
        115                 120                 125

Pro Ile Arg Val Lys Leu Pro Leu Val Ser His Asn Asn Phe Lys Tyr
    130                 135                 140

Gln Gln Gly Leu Phe Ile Glu Gln Thr Phe Lys Phe Arg Ile Lys Asn
145                 150                 155                 160

Val Lys Ala Ser Gly Ser Glu Lys Ile Asp Val Ser Lys Ile Lys Asp
                165                 170                 175

Ile Tyr Asn Glu Leu Val Lys Leu Lys Asp Lys Asn Asn Phe Thr Ala
            180                 185                 190
```

-continued

```
Ser Val Lys Thr Val Thr Glu Glu Thr Lys Lys Leu Val Asp Glu Trp
        195                 200                 205

Gly Ile His Glu Leu Asn Ser Thr Gln Leu Ser Ser Ile Phe Asp Ile
    210                 215                 220

Lys Thr Glu Glu Phe Asp Asn Leu Ile Lys Asp Lys Lys Glu Val Glu
225                 230                 235                 240

His Lys Val Thr Ile Thr Asp Val Asp Leu Ser Asp Pro Ser Leu Ala
                245                 250                 255

Ile Asn Glu Gly Leu Leu Lys Leu Arg Leu Gly Val Lys Ile Lys Gly
            260                 265                 270

Lys Glu Thr Glu Thr Gly Val Asn Val Trp Ile Lys Phe Asn Phe Asp
        275                 280                 285

Gln Lys Asp Thr Phe Trp Lys Glu Leu Lys Ile Ser Glu Ser Ile Lys
    290                 295                 300

Val Asn Thr Val Lys Phe Ser Glu Thr Asn Thr Asp Phe Thr Lys Leu
305                 310                 315                 320

Met Asn Asp Asn Leu Ile Ile Lys Ser Lys Ser Lys Phe Ile Lys Asn
                325                 330                 335

Ile Lys Leu Ser Ser Ile Asp Lys Thr Thr Asp Tyr Arg Asn Ser Gly
            340                 345                 350

Val Leu Leu Glu Val Leu Thr Asn Glu Ser Lys Asp Asn Val Ile Lys
        355                 360                 365

Leu His Lys Lys Pro Gly Val Gly Lys Tyr Thr Asp Leu Tyr Ser Ala
    370                 375                 380

Asp Phe Thr Lys Asn Asn Ile His Ala Pro Asn Phe Ala Thr Glu Lys
385                 390                 395                 400

Leu Thr Gln Glu Asn Leu Lys Ser Ile Asn Lys Asp Phe Phe Arg Gln
                405                 410                 415

Phe Asp Ser Glu Leu Phe Ser Gly Gly Tyr Ala Arg Ser Arg Gly Phe
            420                 425                 430

Tyr Ser Glu Lys Val Lys Ser Pro Lys Phe Met His Ile Gly Glu Asp
        435                 440                 445

Tyr Ile Ala Asn Asp Phe Gln Ala Val Leu Met Pro Tyr Asp Gly Glu
    450                 455                 460

Ile Ile Ala Ala Tyr Glu Leu Ser Thr Asn Val Pro Phe Ala Gly Val
465                 470                 475                 480

Gly Thr Val Leu Val Ala Lys Val Pro Ile Thr Ser Leu Pro Trp Ser
                485                 490                 495

Pro Lys Gln Lys Glu Ile Glu Leu Asn Asp Asn Lys Thr His Ile Tyr
            500                 505                 510

Ile Ser Phe Leu His Leu Asp Ala Gln Arg Thr Leu Asn Asn Asp Lys
        515                 520                 525

Leu Gly Trp Val Ala Glu Thr Ala Lys Leu Lys Lys Asp Lys Thr Val
    530                 535                 540

Lys Val Val Lys Ser Val Thr Pro Ser Thr Pro Lys Lys Val Ser Lys
545                 550                 555                 560

Gly Thr Val Ile Gly Tyr Leu Gly Asp His Ser Ser Asn Gly Gly Trp
                565                 570                 575

Met Ser His Ala His Ile Asn Leu Tyr Thr Asn Arg Pro Asn Tyr Leu
            580                 585                 590

Ser Glu Asn Tyr Phe Ser Ser Lys Thr Ile Arg Ala Gln Leu Asp Asp
        595                 600                 605
```

Lys Arg Ala Lys Gly Tyr Lys Ser Ser Val Ser Asn Asn Asp Phe Ser
    610                 615                 620

Ala Ile Gly Asn Ile Gly Val Glu Arg Lys Ile Asp Thr Lys Ile Tyr
625                 630                 635                 640

Gln Val Asp Pro Lys Thr Gly Ile Glu Asp Lys Gln Lys Ala Ile Ser
                645                 650                 655

Asp Glu Ile Pro Leu Tyr Phe Asn Gly Leu Ser Met Leu Gly Phe Glu
            660                 665                 670

Lys Thr Lys Gly Tyr Ala Asn Pro Asn Leu Met Tyr Lys Leu Arg Asp
        675                 680                 685

Glu Arg Thr Val Ser Phe Ser Val Lys Glu Val Asn Lys Leu
    690                 695                 700

<210> SEQ ID NO 21
<211> LENGTH: 642
<212> TYPE: DNA
<213> ORGANISM: Artificial Sequence
<220> FEATURE:
<223> OTHER INFORMATION: Nucleotide sequence encoding YP_004400127.1
      shown in SEQ ID NO:22, modified for expression in E. coli

<400> SEQUENCE: 21
atgaagacgg acaacacgaa ccaaaaaatc aaggaaaagg acaacgaaac gggtagtaaa     60
gacaaggaca aaccgaataa taacctgaac agctctgaac aggatctgcc gaaagaccaa    120
ccgattacca aaaaggaaaa agatgaaaag acggacagct ttgcggataa actgaaaaag    180
gatctgaaaa agatcctgga caagaaggaa gatctgaaga tccgtgaata cagcaccaaa    240
ctgatctcta aatacttcca gaaaagttcc gaaaaacaac tgctgaaaga ttggttcgac    300
ctggaaaaga aaattaaaaa atggttcgac gaatctgaac tgaacgaaat caaaaaggaa    360
atcaccatcc tgttttcaga atcgctggat aacaatagta acaatcagga atcccgcaaa    420
ctgaaggatc tgctggacaa agtgacgaag gataacaaag aaggcattct ggaagaagtt    480
aaaaacctgt ttggtcagaa gatctcaaaa gaactggaag aaaaactgaa gtcggaaacc    540
gatggcatca acaatctgct gtcaaaaaag caatacgaaa ccatcaagac gaagctgttc    600
gatatcgtgg ataaaacggc cgaactggaa aagaacatca aa                       642

<210> SEQ ID NO 22
<211> LENGTH: 214
<212> TYPE: PRT
<213> ORGANISM: Artificial Sequence
<220> FEATURE:
<223> OTHER INFORMATION: Amino acid sequence of YP_004400127.1 from M.
      mycoides subsp. capri (Mmc), lacking the signal sequence and
      including an N-terminal methionine

<400> SEQUENCE: 22

Met Lys Thr Asp Asn Thr Asn Gln Lys Ile Lys Glu Lys Asp Asn Glu
1               5                   10                  15

Thr Gly Ser Lys Asp Lys Asp Lys Pro Asn Asn Asn Leu Asn Ser Ser
            20                  25                  30

Glu Gln Asp Leu Pro Lys Asp Gln Pro Ile Thr Lys Lys Glu Lys Asp
        35                  40                  45

Glu Lys Thr Asp Ser Phe Ala Asp Lys Leu Lys Lys Asp Leu Lys Lys
    50                  55                  60

Ile Leu Asp Lys Lys Glu Asp Leu Lys Ile Arg Glu Tyr Ser Thr Lys
65                  70                  75                  80

```
Leu Ile Ser Lys Tyr Phe Gln Lys Ser Ser Glu Lys Gln Leu Leu Lys
                85                  90                  95

Asp Trp Phe Asp Leu Glu Lys Lys Ile Lys Lys Trp Phe Asp Glu Ser
            100                 105                 110

Glu Leu Asn Glu Ile Lys Lys Glu Ile Thr Ile Leu Phe Ser Glu Ser
        115                 120                 125

Leu Asp Asn Asn Ser Asn Asn Gln Glu Ser Arg Lys Leu Lys Asp Leu
    130                 135                 140

Leu Asp Lys Val Thr Lys Asp Asn Lys Glu Gly Ile Leu Glu Glu Val
145                 150                 155                 160

Lys Asn Leu Phe Gly Gln Lys Ile Ser Lys Glu Leu Glu Glu Lys Leu
                165                 170                 175

Lys Ser Glu Thr Asp Gly Ile Asn Asn Leu Leu Ser Lys Lys Gln Tyr
            180                 185                 190

Glu Thr Ile Lys Thr Lys Leu Phe Asp Ile Val Asp Lys Thr Ala Glu
        195                 200                 205

Leu Glu Lys Asn Ile Lys
    210
```

<210> SEQ ID NO 23
<211> LENGTH: 936
<212> TYPE: DNA
<213> ORGANISM: Artificial Sequence
<220> FEATURE:
<223> OTHER INFORMATION: Nucleotide sequence encoding YP_004399790.1
      shown in SEQ ID NO:24, modified for expression in E. coli

<400> SEQUENCE: 23

```
atgaaaaaac tgctggcgat tctgggcacg atggctatct cctccaccgg cgcttccctg      60

gttattgctt gcgacaaccc gacgaaaaac gatagcaaaa agccggaaac caaaccggaa     120

accccgacga attccggctc aaacgaaacg tccaatcagg gctcaaacga aggttcgaat     180

aaagaaaagg ataattcgga accgagcaag ccgaccaaac cggtgaagcc ggcatcaggc     240

accgcttctc tggttagcaa aacggatatc tcagcatgga gcagcatttt tatggactcg     300

atcaccggtg aagatattca agaccattct gtggaagaaa aagaaaaggc ggataaagcc     360

aagaacaaag aattcgtgga agttctggac gaaatcaaca aactgacccc gacgctggaa     420

aatgaactga aacagctggc acaaaagttc aaggaaatca aggaaaaact ggctaaggaa     480

aaggaactga aggatcagaa gaacaacaag gaattcgtcg aagtgctgga tgaaattaac     540

aaactgagtg tgacctttga aaaggaactg aaagccctgt tcaaaaagat tggtgaaaac     600

gaactggaaa aggaacgtct gtacaaggaa ttcaccacga gttcctcaaa tgcgaccaaa     660

tattacttcg aagccctgga tacgaaaaag gaagttagcg aatggaattt tgaacgtggc     720

cgcctggtcg aactgatttc gagcatcgac cgccaggtga aggaactgaa atctagtggc     780

aaggatatca aaagcgttat cgacaccgtc aaatctaacc tggaaaacta caagaacagt     840

atcaaggaac ataagaactc caaggttttc tggaagtacg aaatgtggac ccactggctg     900

gaagatgtcc tgacgaatct gaaaaaccag aatcaa                              936
```

<210> SEQ ID NO 24
<211> LENGTH: 312
<212> TYPE: PRT
<213> ORGANISM: Mycoplasma mycoides

<400> SEQUENCE: 24

Met Lys Lys Leu Leu Ala Ile Leu Gly Thr Met Ala Ile Ser Ser Thr
1 5 10 15

Gly Ala Ser Leu Val Ile Ala Cys Asp Asn Pro Thr Lys Asn Asp Ser
20 25 30

Lys Lys Pro Glu Thr Lys Pro Glu Thr Pro Thr Asn Ser Gly Ser Asn
35 40 45

Glu Thr Ser Asn Gln Gly Ser Asn Glu Gly Ser Asn Lys Glu Lys Asp
50 55 60

Asn Ser Glu Pro Ser Lys Pro Thr Lys Pro Val Lys Pro Ala Ser Gly
65 70 75 80

Thr Ala Ser Leu Val Ser Lys Thr Asp Ile Ser Ala Trp Ser Ser Ile
85 90 95

Phe Met Asp Ser Ile Thr Gly Glu Asp Ile Gln Asp His Ser Val Glu
100 105 110

Glu Lys Glu Lys Ala Asp Lys Ala Lys Asn Lys Glu Phe Val Glu Val
115 120 125

Leu Asp Glu Ile Asn Lys Leu Thr Pro Thr Leu Glu Asn Glu Leu Lys
130 135 140

Gln Leu Ala Gln Lys Phe Lys Glu Ile Lys Glu Lys Leu Ala Lys Glu
145 150 155 160

Lys Glu Leu Lys Asp Gln Lys Asn Asn Lys Glu Phe Val Glu Val Leu
165 170 175

Asp Glu Ile Asn Lys Leu Ser Val Thr Phe Glu Lys Glu Leu Lys Ala
180 185 190

Leu Phe Lys Lys Ile Gly Glu Asn Glu Leu Glu Lys Glu Arg Leu Tyr
195 200 205

Lys Glu Phe Thr Thr Ser Ser Ser Asn Ala Thr Lys Tyr Tyr Phe Glu
210 215 220

Ala Leu Asp Thr Lys Lys Glu Val Ser Glu Trp Asn Phe Glu Arg Gly
225 230 235 240

Arg Leu Val Glu Leu Ile Ser Ser Ile Asp Arg Gln Val Lys Glu Leu
245 250 255

Lys Ser Ser Gly Lys Asp Ile Lys Ser Val Ile Asp Thr Val Lys Ser
260 265 270

Asn Leu Glu Asn Tyr Lys Asn Ser Ile Lys Glu His Lys Asn Ser Lys
275 280 285

Val Phe Trp Lys Tyr Glu Met Trp Thr His Trp Leu Glu Asp Val Leu
290 295 300

Thr Asn Leu Lys Asn Gln Asn Gln
305 310

<210> SEQ ID NO 25
<211> LENGTH: 1146
<212> TYPE: DNA
<213> ORGANISM: Artificial Sequence
<220> FEATURE:
<223> OTHER INFORMATION: Nucleotide sequence encoding YP_004400580.1
shown in SEQ ID NO:26, modified for expression in E. coli

<400> SEQUENCE: 25
atgaagaagc tgctgattgg ttttagtagt atttttgcgt tcctgaccgt ctcgtgttcc 60
attagtaccc cgaagattaa cccgacgatc aacaagaacg aaaacaagct gtacaagaat 120
aaatacgtga gcgaactgct gaacctgtat ctgtcagact cgaaactgcg tgatagttac 180

-continued

```
atcaatgacc aggaaaacgt tagcgattct aaattttccg aactgaagta tggcctgacc    240

ttttacccga ttttcatcca tcgttcactg gattatcata ttggtcagca ctaccgcgtt    300

attatccaaa agtcgaaaaa tgctctggaa cagacgctga aaaacgattg gtattgggtc    360

ctggacaaca tcaccaactt caagtacaac ttcaacccgt atggcgatct gtacaacgat    420

ttcgacaagg atgaaaacct gtttaaccag ctggaaaaag acctgggttc tctgattagc    480

tctgtcaaga acaagaacgt gcaaaagatc atcaagatca acctggatga agtggttaac    540

gaaaagatca aagatgacta tctgaaaaag gaagccctgt acctgatctt cgataacaac    600

aaggcaatca agatctggaa gtacgaaaac cagaataaaa ccgaattcct gatgaccacg    660

gacctgttta tcttcaaaga cacgaacaac ctggaaaacc aaatcaagga actggaaaac    720

accatcttcg aaaagcgtaa ggtcgaatac aacaacaacc tggaaaacat caacaagaac    780

atcgaagcta ccaaaaagcg caaggaaaaa gcgcagcaag aaatccagga tctgaaggaa    840

aagatcaaaa agctggaaaa gacgaacacc acgaccacga ccccgctggc actgaccagt    900

tccgccattc tgctgagcgc accgaaaaac gataaaaaga aagaaccgac gctggaagaa    960

ctgaagaaag atctggaaaa gaaagaaaaa cagagccagc aattcgacga aaacgttaag   1020

aaatacgaaa agaacatcga agatctgccg cagaagtcta acgacaagaa gttcctggaa   1080

ttccacgcaa ccgatcaata caacgaacgc ctgaaagaaa gtctgaatga aatcaacaaa   1140

gacggc                                                              1146


<210> SEQ ID NO 26
<211> LENGTH: 382
<212> TYPE: PRT
<213> ORGANISM: Artificial Sequence
<220> FEATURE:
<223> OTHER INFORMATION: Amino acid sequence of YP_004400580.1 from M.
      mycoides subsp. capri (Mmc), lacking 15 amino acids from the
      C-terminus

<400> SEQUENCE: 26

Met Lys Lys Leu Leu Ile Gly Phe Ser Ser Ile Phe Ala Phe Leu Thr
1               5                   10                  15

Val Ser Cys Ser Ile Ser Thr Pro Lys Ile Asn Pro Thr Ile Asn Lys
            20                  25                  30

Asn Glu Asn Lys Leu Tyr Lys Asn Lys Tyr Val Ser Glu Leu Leu Asn
        35                  40                  45

Leu Tyr Leu Ser Asp Ser Lys Leu Arg Asp Ser Tyr Ile Asn Asp Gln
    50                  55                  60

Glu Asn Val Ser Asp Ser Lys Phe Ser Glu Leu Lys Tyr Gly Leu Thr
65                  70                  75                  80

Phe Tyr Pro Ile Phe Ile His Arg Ser Leu Asp Tyr His Ile Gly Gln
                85                  90                  95

His Tyr Arg Val Ile Ile Gln Lys Ser Lys Asn Ala Leu Glu Gln Thr
            100                 105                 110

Leu Lys Asn Asp Trp Tyr Trp Val Leu Asp Asn Ile Thr Asn Phe Lys
        115                 120                 125

Tyr Asn Phe Asn Pro Tyr Gly Asp Leu Tyr Asn Asp Phe Asp Lys Asp
    130                 135                 140

Glu Asn Leu Phe Asn Gln Leu Glu Lys Asp Leu Gly Ser Leu Ile Ser
145                 150                 155                 160

Ser Val Lys Asn Lys Asn Val Gln Lys Ile Ile Lys Ile Asn Leu Asp
                165                 170                 175
```

```
Glu Val Val Asn Glu Lys Ile Lys Asp Asp Tyr Leu Lys Lys Glu Ala
            180                 185                 190

Leu Tyr Leu Ile Phe Asp Asn Asn Lys Ala Ile Lys Ile Trp Lys Tyr
        195                 200                 205

Glu Asn Gln Asn Lys Thr Glu Phe Leu Met Thr Thr Asp Leu Phe Ile
    210                 215                 220

Phe Lys Asp Thr Asn Asn Leu Glu Asn Gln Ile Lys Glu Leu Glu Asn
225                 230                 235                 240

Thr Ile Phe Glu Lys Arg Lys Val Glu Tyr Asn Asn Asn Leu Glu Asn
                245                 250                 255

Ile Asn Lys Asn Ile Glu Ala Thr Lys Lys Arg Lys Glu Lys Ala Gln
            260                 265                 270

Gln Glu Ile Gln Asp Leu Lys Glu Lys Ile Lys Lys Leu Glu Lys Thr
        275                 280                 285

Asn Thr Thr Thr Thr Thr Pro Leu Ala Leu Thr Ser Ser Ala Ile Leu
    290                 295                 300

Leu Ser Ala Pro Lys Asn Asp Lys Lys Lys Glu Pro Thr Leu Glu Glu
305                 310                 315                 320

Leu Lys Lys Asp Leu Glu Lys Lys Glu Lys Gln Ser Gln Gln Phe Asp
                325                 330                 335

Glu Asn Val Lys Lys Tyr Glu Lys Asn Ile Glu Asp Leu Pro Gln Lys
            340                 345                 350

Ser Asn Asp Lys Lys Phe Leu Glu Phe His Ala Thr Asp Gln Tyr Asn
        355                 360                 365

Glu Arg Leu Lys Glu Ser Leu Asn Glu Ile Asn Lys Asp Gly
    370                 375                 380
```

<210> SEQ ID NO 27
<211> LENGTH: 567
<212> TYPE: DNA
<213> ORGANISM: Artificial Sequence
<220> FEATURE:
<223> OTHER INFORMATION: Nucleotide sequence encoding YP_004400610.1
      shown in SEQ ID NO:28, modified for expression in E. coli

<400> SEQUENCE: 27

```
atgggtgacc gtgccccgag tgcgaaatct gcggaaaagg tggaaaacaa ggaaaaaacg      60

aagccgagcg aagcgccgaa gaaaggtgaa aagagtgaag aaaaggaaaa cgaaaaggat     120

aaggaactga aggcagtgtt ttcaaaagtt gagggtcaga acattggcaa cttccaaccg     180

aacaacaaga acatcgttag ccagggtgat atcaaaaagg aactggcgaa taaactgggt     240

gtcagcgaat ctgacctgca aggcctgaag ctgaactatg atgacaaatc cggtgaagtc     300

accctgccga agttcaacaa caagaacctg aagttcaagt tcaccacgtt ctaccagctg     360

ggcaaaatta agacgtcaaa aatcgataac gtgctgtttc tgtcgcaact ggacattaaa     420

aaggaactgg ccaacaaact gaaggttaaa gaaagcgatc tgcaagaact gaaaaccgac     480

tctacgaacg gcatcggtgc cggcagtgtc cgttccaaaa ccttcgtggg cattctggaa     540

tttaaattcg aaatcgatga aaataaa                                         567
```

<210> SEQ ID NO 28
<211> LENGTH: 189
<212> TYPE: PRT
<213> ORGANISM: Artificial Sequence
<220> FEATURE:
<223> OTHER INFORMATION: Amino acid sequence of YP_004400610.1 from M. mycoides subsp. capri (Mmc), lacking the signal sequence and including an N-terminal methionine

<400> SEQUENCE: 28

```
Met Gly Asp Arg Ala Pro Ser Ala Lys Ser Ala Glu Lys Val Glu Asn
1               5                   10                  15

Lys Glu Lys Thr Lys Pro Ser Glu Ala Pro Lys Lys Gly Glu Lys Ser
            20                  25                  30

Glu Glu Lys Glu Asn Glu Lys Asp Lys Glu Leu Lys Ala Val Phe Ser
        35                  40                  45

Lys Val Glu Gly Gln Asn Ile Gly Asn Phe Gln Pro Asn Asn Lys Asn
    50                  55                  60

Ile Val Ser Gln Gly Asp Ile Lys Lys Glu Leu Ala Asn Lys Leu Gly
65                  70                  75                  80

Val Ser Glu Ser Asp Leu Gln Gly Leu Lys Leu Asn Tyr Asp Asp Lys
                85                  90                  95

Ser Gly Glu Val Thr Leu Pro Lys Phe Asn Asn Lys Asn Leu Lys Phe
            100                 105                 110

Lys Phe Thr Thr Phe Tyr Gln Leu Gly Lys Ile Lys Thr Ser Lys Ile
        115                 120                 125

Asp Asn Val Leu Phe Leu Ser Gln Leu Asp Ile Lys Lys Glu Leu Ala
    130                 135                 140

Asn Lys Leu Lys Val Lys Glu Ser Asp Leu Gln Glu Leu Lys Thr Asp
145                 150                 155                 160

Ser Thr Asn Gly Ile Gly Ala Gly Ser Val Arg Ser Lys Thr Phe Val
                165                 170                 175

Gly Ile Leu Glu Phe Lys Phe Glu Ile Asp Glu Asn Lys
            180                 185
```

<210> SEQ ID NO 29
<211> LENGTH: 22
<212> TYPE: DNA
<213> ORGANISM: Artificial Sequence
<220> FEATURE:
<223> OTHER INFORMATION: CpG ODN 2007, a Class B CpG, phosphorothioated

<400> SEQUENCE: 29

```
tcgtcgttgt cgttttgtcg tt                                                22
```

<210> SEQ ID NO 30
<211> LENGTH: 12
<212> TYPE: PRT
<213> ORGANISM: Artificial Sequence
<220> FEATURE:
<223> OTHER INFORMATION: host defense peptide HH2

<400> SEQUENCE: 30

```
Val Gln Leu Arg Ile Arg Val Ala Val Ile Arg Ala
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: host defense peptide 1002

<400> SEQUENCE: 31

Val Gln Arg Trp Leu Ile Val Trp Arg Ile Arg Lys
1               5                   10

<210> SEQ ID NO 32
<211> LENGTH: 12
<212> TYPE: PRT
<213> ORGANISM: Artificial Sequence
<220> FEATURE:
<223> OTHER INFORMATION: host defense peptide 1018

<400> SEQUENCE: 32

Val Arg Leu Ile Val Ala Val Arg Ile Trp Arg Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: host defense peptide Indolicidin

<400> SEQUENCE: 33

Ile Leu Pro Trp Lys Trp Pro Trp Trp Pro Trp Arg Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: host defense peptide HH111

<400> SEQUENCE: 34

Ile Leu Lys Trp Lys Trp Pro Trp Trp Pro Trp Arg Arg
1               5                   10

<210> SEQ ID NO 35
<211> LENGTH: 13
<212> TYPE: PRT
<213> ORGANISM: Artificial Sequence
<220> FEATURE:
<223> OTHER INFORMATION: host defense peptide HH113

<400> SEQUENCE: 35

Ile Leu Pro Trp Lys Lys Pro Trp Trp Pro Trp Arg Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: host defense peptide HH970

<400> SEQUENCE: 36

Ile Leu Lys Trp Lys Trp Pro Trp Trp Lys Trp Arg Arg
1               5                   10

<210> SEQ ID NO 37
<211> LENGTH: 13
<212> TYPE: PRT
<213> ORGANISM: Artificial Sequence
<220> FEATURE:
<223> OTHER INFORMATION: host defense peptide HH1010

```
<400> SEQUENCE: 37

Ile Leu Arg Trp Lys Trp Arg Trp Trp Arg Trp Arg Arg
1               5                   10


<210> SEQ ID NO 38
<211> LENGTH: 34
<212> TYPE: PRT
<213> ORGANISM: Artificial Sequence
<220> FEATURE:
<223> OTHER INFORMATION: Host defence peptide Nisin Z
<220> FEATURE:
<221> NAME/KEY: Variant
<222> LOCATION: (2)..(2)
<223> OTHER INFORMATION: Xaa is didehydroaminobutyric acid
<220> FEATURE:
<221> NAME/KEY: Variant
<222> LOCATION: (5)..(5)
<223> OTHER INFORMATION: Xaa is didehydroalanine
<220> FEATURE:
<221> NAME/KEY: Variant
<222> LOCATION: (8)..(8)
<223> OTHER INFORMATION: Xaa is Abu
<220> FEATURE:
<221> NAME/KEY: Variant
<222> LOCATION: (13)..(13)
<223> OTHER INFORMATION: Xaa is Abu
<220> FEATURE:
<221> NAME/KEY: Variant
<222> LOCATION: (23)..(23)
<223> OTHER INFORMATION: Xaa is Abu
<220> FEATURE:
<221> NAME/KEY: Variant
<222> LOCATION: (25)..(25)
<223> OTHER INFORMATION: Xaa is Abu
<220> FEATURE:
<221> NAME/KEY: Variant
<222> LOCATION: (33)..(33)
<223> OTHER INFORMATION: Xaa is didehydroalanine

<400> SEQUENCE: 38

Ile Xaa Ala Ile Xaa Leu Ala Xaa Pro Gly Ala Lys Xaa Gly Ala Leu
1               5                   10                  15

Met Gly Ala Asn Met Lys Xaa Ala Xaa Ala Asn Ala Ser Ile Asn Val
            20                  25                  30

Xaa Lys


<210> SEQ ID NO 39
<211> LENGTH: 12
<212> TYPE: PRT
<213> ORGANISM: Artificial Sequence
<220> FEATURE:
<223> OTHER INFORMATION: host defense peptide JK1

<400> SEQUENCE: 39

Val Phe Leu Arg Arg Ile Arg Val Ile Val Ile Arg
1               5                   10


<210> SEQ ID NO 40
<211> LENGTH: 12
<212> TYPE: PRT
<213> ORGANISM: Artificial Sequence
<220> FEATURE:
<223> OTHER INFORMATION: host defense peptide JK2

<400> SEQUENCE: 40

Val Phe Trp Arg Arg Ile Arg Val Trp Val Ile Arg
1               5                   10


<210> SEQ ID NO 41
```

<211> LENGTH: 12
<212> TYPE: PRT
<213> ORGANISM: Artificial Sequence
<220> FEATURE:
<223> OTHER INFORMATION: host defense peptide JK3

<400> SEQUENCE: 41

Val Gln Leu Arg Ala Ile Arg Val Arg Val Ile Arg
1 5 10

<210> SEQ ID NO 42
<211> LENGTH: 12
<212> TYPE: PRT
<213> ORGANISM: Artificial Sequence
<220> FEATURE:
<223> OTHER INFORMATION: host defense peptide JK4

<400> SEQUENCE: 42

Val Gln Leu Arg Arg Ile Arg Val Trp Val Ile Arg
1 5 10

<210> SEQ ID NO 43
<211> LENGTH: 12
<212> TYPE: PRT
<213> ORGANISM: Artificial Sequence
<220> FEATURE:
<223> OTHER INFORMATION: host defense peptide JK5

<400> SEQUENCE: 43

Val Gln Trp Arg Ala Ile Arg Val Arg Val Ile Arg
1 5 10

<210> SEQ ID NO 44
<211> LENGTH: 12
<212> TYPE: PRT
<213> ORGANISM: Artificial Sequence
<220> FEATURE:
<223> OTHER INFORMATION: host defense peptide JK6

<400> SEQUENCE: 44

Val Gln Trp Arg Arg Ile Arg Val Trp Val Ile Arg
1 5 10

<210> SEQ ID NO 45
<211> LENGTH: 20
<212> TYPE: DNA
<213> ORGANISM: Artificial Sequence
<220> FEATURE:
<223> OTHER INFORMATION: CpG ODN 1826, a Class B CpG, phosphorothioated

<400> SEQUENCE: 45
tccatgacgt tcctgacgtt 20

<210> SEQ ID NO 46
<211> LENGTH: 24
<212> TYPE: DNA
<213> ORGANISM: Artificial Sequence
<220> FEATURE:
<223> OTHER INFORMATION: CpG 7907 or 10103, a Class B CpG, phosphorothioated

<400> SEQUENCE: 46
tcgtcgtttt gtcgttttgt cgtt 24

<210> SEQ ID NO 47
<211> LENGTH: 21
<212> TYPE: DNA

-continued

<213> ORGANISM: Artificial Sequence
<220> FEATURE:
<223> OTHER INFORMATION: CpG 8954, a Class A CpG

<400> SEQUENCE: 47
ggggacgacg tcgtgggggg g 21

<210> SEQ ID NO 48
<211> LENGTH: 22
<212> TYPE: DNA
<213> ORGANISM: Artificial Sequence
<220> FEATURE:
<223> OTHER INFORMATION: CpG 2395 or CpG 10101, a Class C CpG, phosphorothioated

<400> SEQUENCE: 48
tcgtcgtttt cggcgcgcgc cg 22

<210> SEQ ID NO 49
<211> LENGTH: 32
<212> TYPE: DNA
<213> ORGANISM: Artificial Sequence
<220> FEATURE:
<223> OTHER INFORMATION: a non-CpG oligonucleotide

<400> SEQUENCE: 49
aaaaaaggta cctaaatagt atgtttctga aa 32

<210> SEQ ID NO 50
<211> LENGTH: 1608
<212> TYPE: DNA
<213> ORGANISM: Artificial Sequence
<220> FEATURE:
<223> OTHER INFORMATION: Nucleotide sequence encoding fusion between YP_004400127.1 and YP_004399790.1 shown in SEQ ID NO:51, modified for expression in E. coli

<400> SEQUENCE: 50
catatgaaaa cggacaatac caaccaaaaa atcaaagaaa aagacaacga aacgggcagt 60
aaagacaaag acaaaccgaa caataacctg aatagctctg aacaggatct gccgaaagac 120
caaccgatca ccaagaaaga aaaagatgaa aaaacggaca gctttgcaga taaactgaag 180
aaagatctga agaaaattct ggacaagaaa gaagatctga aaatccgtga atacagtacc 240
aaactgatct ccaaatactt ccagaaaagt tccgaaaaac aactgctgaa agattggttc 300
gacctggaaa agaaaattaa aaaatggttc gacgaaagcg aactgaacga aattaagaaa 360
gaaatcacca tcctgttttc cgaatcactg gataacaatt caaacaatca ggaatcgcgc 420
aaactgaaag atctgctgga caaagttacc aaagataaca aagaaggcat cctggaagaa 480
gtcaaaaacc tgtttggtca gaaaatctca aaagaactgg aagaaaaact gaaatcggaa 540
accgatggca tcaacaatct gctgagcaaa aaacaatacg aaaccatcaa aacgaaactg 600
ttcgatattg tggacaaaac ggccgaactg gagaaaaaca tcaaaggcgg tggcggtggc 660
ggtatgaaaa aactgctggc aatcctgggc accatggcta tttcatcgac gggtgcgagt 720
ctggttattg cctgcgacaa tccgaccaaa aacgattcca aaaaaccgga aacgaaaccg 780
gaaaccccga cgaattcggg tagcaacgaa acctcgaatc agggcagcaa cgaaggttct 840
aacaaagaaa aagataactc tgaaccgagt aaaccgacga aaccggtgaa accggcaagc 900
ggcaccgctt ccctggtttc aaaaacggac attagcgcgt ggagctctat ttttatggat 960
tctatcaccg gtgaagatat tcaagaccat tctgtggaag aaaaagaaaa agcggacaaa 1020

-continued

```
gccaaaaata aagaattcgt ggaagttctg gatgaaatca acaaactgac cccgacgctg   1080

gaaaatgaac tgaaacagct ggcacaaaaa ttcaaagaaa tcaaagaaaa actggctaaa   1140

gaaaaagaac tgaaagacca gaaaaacaac aaagaattcg tcgaagtgct ggacgaaatt   1200

aacaaactga gtgtcacctt tgaaaaagaa ctgaaagccc tgttcaagaa aattggcgaa   1260

aacgaactgg aaaaagaacg tctgtacaaa gaattcacca cgagttcctc aaatgcgacc   1320

aaatattact tcgaagccct ggataccaag aaagaagtga gcgaatggaa ctttgaacgt   1380

ggccgcctgg tcgaactgat ttcgagcatc gatcgccagg tgaaagaact gaaatctagt   1440

ggtaaagaca tcaaaagcgt tatcgatacc gtcaaatcta acctggaaaa ttacaaaaac   1500

agtatcaaag aacacaaaaa ttccaaagtt ttctggaaat acgaaatgtg gacgcactgg   1560

ctggaagatg ttctgaccaa cctgaaaaat caaaatcaat aaggatcc                1608
```

<210> SEQ ID NO 51
<211> LENGTH: 532
<212> TYPE: PRT
<213> ORGANISM: Artificial Sequence
<220> FEATURE:
<223> OTHER INFORMATION: Amino acid sequence of fusion between
      YP_004400127.1 and YP_004399790.1 from M. mycoides subsp. capri
      (Mmc), including a Gly6 linker

<400> SEQUENCE: 51

```
Met Lys Thr Asp Asn Thr Asn Gln Lys Ile Lys Glu Lys Asp Asn Glu
1               5                   10                  15

Thr Gly Ser Lys Asp Lys Asp Lys Pro Asn Asn Asn Leu Asn Ser Ser
            20                  25                  30

Glu Gln Asp Leu Pro Lys Asp Gln Pro Ile Thr Lys Lys Glu Lys Asp
        35                  40                  45

Glu Lys Thr Asp Ser Phe Ala Asp Lys Leu Lys Lys Asp Leu Lys Lys
    50                  55                  60

Ile Leu Asp Lys Lys Glu Asp Leu Lys Ile Arg Glu Tyr Ser Thr Lys
65                  70                  75                  80

Leu Ile Ser Lys Tyr Phe Gln Lys Ser Ser Glu Lys Gln Leu Leu Lys
                85                  90                  95

Asp Trp Phe Asp Leu Glu Lys Lys Ile Lys Lys Trp Phe Asp Glu Ser
            100                 105                 110

Glu Leu Asn Glu Ile Lys Lys Glu Ile Thr Ile Leu Phe Ser Glu Ser
        115                 120                 125

Leu Asp Asn Asn Ser Asn Asn Gln Glu Ser Arg Lys Leu Lys Asp Leu
    130                 135                 140

Leu Asp Lys Val Thr Lys Asp Asn Lys Glu Gly Ile Leu Glu Glu Val
145                 150                 155                 160

Lys Asn Leu Phe Gly Gln Lys Ile Ser Lys Glu Leu Glu Glu Lys Leu
                165                 170                 175

Lys Ser Glu Thr Asp Gly Ile Asn Asn Leu Leu Ser Lys Lys Gln Tyr
            180                 185                 190

Glu Thr Ile Lys Thr Lys Leu Phe Asp Ile Val Asp Lys Thr Ala Glu
        195                 200                 205

Leu Glu Lys Asn Ile Lys Gly Gly Gly Gly Gly Gly Met Lys Lys Leu
    210                 215                 220

Leu Ala Ile Leu Gly Thr Met Ala Ile Ser Ser Thr Gly Ala Ser Leu
225                 230                 235                 240

Val Ile Ala Cys Asp Asn Pro Thr Lys Asn Asp Ser Lys Lys Pro Glu
                245                 250                 255
```

```
Thr Lys Pro Glu Thr Pro Thr Asn Ser Gly Ser Asn Glu Thr Ser Asn
            260                 265                 270

Gln Gly Ser Asn Glu Gly Ser Asn Lys Glu Lys Asp Asn Ser Glu Pro
        275                 280                 285

Ser Lys Pro Thr Lys Pro Val Lys Pro Ala Ser Gly Thr Ala Ser Leu
    290                 295                 300

Val Ser Lys Thr Asp Ile Ser Ala Trp Ser Ser Ile Phe Met Asp Ser
305                 310                 315                 320

Ile Thr Gly Glu Asp Ile Gln Asp His Ser Val Glu Glu Lys Glu Lys
                325                 330                 335

Ala Asp Lys Ala Lys Asn Lys Glu Phe Val Glu Val Leu Asp Glu Ile
            340                 345                 350

Asn Lys Leu Thr Pro Thr Leu Glu Asn Glu Leu Lys Gln Leu Ala Gln
        355                 360                 365

Lys Phe Lys Glu Ile Lys Glu Lys Leu Ala Lys Glu Lys Glu Leu Lys
    370                 375                 380

Asp Gln Lys Asn Asn Lys Glu Phe Val Glu Val Leu Asp Glu Ile Asn
385                 390                 395                 400

Lys Leu Ser Val Thr Phe Glu Lys Glu Leu Lys Ala Leu Phe Lys Lys
                405                 410                 415

Ile Gly Glu Asn Glu Leu Glu Lys Glu Arg Leu Tyr Lys Glu Phe Thr
            420                 425                 430

Thr Ser Ser Ser Asn Ala Thr Lys Tyr Tyr Phe Glu Ala Leu Asp Thr
        435                 440                 445

Lys Lys Glu Val Ser Glu Trp Asn Phe Glu Arg Gly Arg Leu Val Glu
    450                 455                 460

Leu Ile Ser Ser Ile Asp Arg Gln Val Lys Glu Leu Lys Ser Ser Gly
465                 470                 475                 480

Lys Asp Ile Lys Ser Val Ile Asp Thr Val Lys Ser Asn Leu Glu Asn
                485                 490                 495

Tyr Lys Asn Ser Ile Lys Glu His Lys Asn Ser Lys Val Phe Trp Lys
            500                 505                 510

Tyr Glu Met Trp Thr His Trp Leu Glu Asp Val Leu Thr Asn Leu Lys
        515                 520                 525

Asn Gln Asn Gln
    530
```

<210> SEQ ID NO 52
<211> LENGTH: 1642
<212> TYPE: DNA
<213> ORGANISM: Artificial Sequence
<220> FEATURE:
<223> OTHER INFORMATION: Nucleotide sequence encoding fusion between YP_004400610.1 and YP_00400580.1 shown in SEQ ID NO:53, modified for expression in E. coli

<400> SEQUENCE: 52

```
catatgggcg accgtgcccc gtccgcaaaa tccgcagaaa aagtggaaaa taaagaaaaa      60

accaaaccga gtgaagcccc gaagaagggc gaaaagagtg aagaaaagga aaacgaaaag     120

gataaagaac tgaaagccgt cttttccaaa gtggaaggcc agaatattgg taacttccaa     180

ccgaacaaca aaaacatcgt ctcccagggc gatattaaga aagaactggc aaacaaactg     240

ggcgtgtcag aatcggacct gcaaggtctg aaactgaatt atgatgacaa aagcggcgaa     300

gtgacgctgc cgaaattcaa caacaaaaac ctgaaattca aattcaccac gttctaccag     360
```

```
ctgggtaaaa tcaaaaccag taaaatcgat aacgttctgt ttctgtccca actggacatt    420

aagaaagaac tggctaacaa actgaaagtc aaagaatcag atctgcagga actgaaaacg    480

gactcgacca acggtatcgg cgcgggtagc gtgcgttcta aaaccttcgt tggtattctg    540

gaattcaaat tcgaaatcga tgaaaacaaa ggcggtggcg gtggcagcat ttctacgccg    600

aaaattaacc cgaccatcaa caaaaacgaa aacaaactgt acaaaaacaa atacgtctca    660

gaactgctga acctgtatct gagtgactcc aaactgcgcg atagctacat caatgaccag    720

gaaaacgttt cagattcgaa attctctgaa ctgaaatatg gcctgacctt ttacccgatt    780

ttcatccatc gttcactgga ttatcatatt ggtcagcact accgcgtgat tatccaaaaa    840

tcgaaaaatg cgctggaaca gacgctgaaa aacgattggt attgggttct ggacaacatc    900

accaacttca aatacaactt caacccgtat ggcgatctgt acaacgattt cgacaaagat    960

gaaaacctgt ttaaccagct ggaaaaagac ctgggtagtc tgatcagctc tgttaaaaac   1020

aaaaacgtcc aaaaaatcat caaaatcaac ctggatgaag tggttaacga aaaaatcaaa   1080

gatgactacc tgaagaaaga agcgctgtac ctgatcttcg ataacaacaa agcaatcaaa   1140

atctggaaat acgaaaacca gaacaaaacc gaattcctga tgaccacgga cctgtttatc   1200

ttcaaagaca cgaacaatct ggaaaatcag attaaagaac tggaaaacac catcttcgaa   1260

aaacgtaaag tggaatacaa caacaacctg gaaaacatca acaaaaacat cgaagctacc   1320

aaaaaacgca aagaaaaagc gcagcaagaa atccaggatc tgaaagaaaa aatcaaaaaa   1380

ctggaaaaaa cgaataccac caccaccacc ccgctggccc tgaccagttc cgccattctg   1440

ctgtctgcac cgaaaaacga taaaaagaaa gaaccgacgc tggaagaact gaagaaagat   1500

ctggaaaaga aagaaaaaca gagccagcaa tttgacgaaa acgttaaaaa atacgagaaa   1560

aacatcgaag atctgccgca gaaatctaac gacaaaaaat tcctggaatt ccacgcgacc   1620

gatcaataca atgaacgtct ga                                            1642
```

<210> SEQ ID NO 53
<211> LENGTH: 557
<212> TYPE: PRT
<213> ORGANISM: Artificial Sequence
<220> FEATURE:
<223> OTHER INFORMATION: Amino acid sequence of fusion between YP_004400610.1 and YP_00400580.1 from M. mycoides subsp. capri (Mmc), the YP_00400580.1 sequence lacking the first 20 amino acids, and the fusion including a Gly5 linker

<400> SEQUENCE: 53

```
Met Gly Asp Arg Ala Pro Ser Ala Lys Ser Ala Glu Lys Val Glu Asn
1               5                   10                  15

Lys Glu Lys Thr Lys Pro Ser Glu Ala Pro Lys Lys Gly Glu Lys Ser
            20                  25                  30

Glu Glu Lys Glu Asn Glu Lys Asp Lys Glu Leu Lys Ala Val Phe Ser
        35                  40                  45

Lys Val Glu Gly Gln Asn Ile Gly Asn Phe Gln Pro Asn Asn Lys Asn
    50                  55                  60

Ile Val Ser Gln Gly Asp Ile Lys Lys Glu Leu Ala Asn Lys Leu Gly
65                  70                  75                  80

Val Ser Glu Ser Asp Leu Gln Gly Leu Lys Leu Asn Tyr Asp Asp Lys
                85                  90                  95

Ser Gly Glu Val Thr Leu Pro Lys Phe Asn Asn Lys Asn Leu Lys Phe
            100                 105                 110
```

```
Lys Phe Thr Thr Phe Tyr Gln Leu Gly Lys Ile Lys Thr Ser Lys Ile
        115                 120                 125

Asp Asn Val Leu Phe Leu Ser Gln Leu Asp Ile Lys Lys Glu Leu Ala
    130                 135                 140

Asn Lys Leu Lys Val Lys Glu Ser Asp Leu Gln Glu Leu Lys Thr Asp
145                 150                 155                 160

Ser Thr Asn Gly Ile Gly Ala Gly Ser Val Arg Ser Lys Thr Phe Val
                165                 170                 175

Gly Ile Leu Glu Phe Lys Phe Glu Ile Asp Glu Asn Lys Gly Gly Gly
            180                 185                 190

Gly Gly Ser Ile Ser Thr Pro Lys Ile Asn Pro Thr Ile Asn Lys Asn
        195                 200                 205

Glu Asn Lys Leu Tyr Lys Asn Lys Tyr Val Ser Glu Leu Leu Asn Leu
    210                 215                 220

Tyr Leu Ser Asp Ser Lys Leu Arg Asp Ser Tyr Ile Asn Asp Gln Glu
225                 230                 235                 240

Asn Val Ser Asp Ser Lys Phe Ser Glu Leu Lys Tyr Gly Leu Thr Phe
                245                 250                 255

Tyr Pro Ile Phe Ile His Arg Ser Leu Asp Tyr His Ile Gly Gln His
            260                 265                 270

Tyr Arg Val Ile Ile Gln Lys Ser Lys Asn Ala Leu Glu Gln Thr Leu
        275                 280                 285

Lys Asn Asp Trp Tyr Trp Val Leu Asp Asn Ile Thr Asn Phe Lys Tyr
    290                 295                 300

Asn Phe Asn Pro Tyr Gly Asp Leu Tyr Asn Asp Phe Asp Lys Asp Glu
305                 310                 315                 320

Asn Leu Phe Asn Gln Leu Glu Lys Asp Leu Gly Ser Leu Ile Ser Ser
                325                 330                 335

Val Lys Asn Lys Asn Val Gln Lys Ile Ile Lys Ile Asn Leu Asp Glu
            340                 345                 350

Val Val Asn Glu Lys Ile Lys Asp Asp Tyr Leu Lys Lys Glu Ala Leu
        355                 360                 365

Tyr Leu Ile Phe Asp Asn Asn Lys Ala Ile Lys Ile Trp Lys Tyr Glu
    370                 375                 380

Asn Gln Asn Lys Thr Glu Phe Leu Met Thr Thr Asp Leu Phe Ile Phe
385                 390                 395                 400

Lys Asp Thr Asn Asn Leu Glu Asn Gln Ile Lys Glu Leu Glu Asn Thr
                405                 410                 415

Ile Phe Glu Lys Arg Lys Val Glu Tyr Asn Asn Asn Leu Glu Asn Ile
            420                 425                 430

Asn Lys Asn Ile Glu Ala Thr Lys Lys Arg Lys Glu Lys Ala Gln Gln
        435                 440                 445

Glu Ile Gln Asp Leu Lys Glu Lys Ile Lys Lys Leu Glu Lys Thr Asn
    450                 455                 460

Thr Thr Thr Thr Thr Pro Leu Ala Leu Thr Ser Ser Ala Ile Leu Leu
465                 470                 475                 480

Ser Ala Pro Lys Asn Asp Lys Lys Lys Glu Pro Thr Leu Glu Glu Leu
                485                 490                 495

Lys Lys Asp Leu Glu Lys Lys Glu Lys Gln Ser Gln Gln Phe Asp Glu
            500                 505                 510

Asn Val Lys Lys Tyr Glu Lys Asn Ile Glu Asp Leu Pro Gln Lys Ser
        515                 520                 525
```

```
Asn Asp Lys Lys Phe Leu Glu Phe His Ala Thr Asp Gln Tyr Asn Glu
    530                 535                 540

Arg Leu Lys Glu Ser Leu Asn Glu Ile Asn Lys Asp Gly
545                 550                 555


<210> SEQ ID NO 54
<211> LENGTH: 4377
<212> TYPE: DNA
<213> ORGANISM: Artificial Sequence
<220> FEATURE:
<223> OTHER INFORMATION: pAA352-YP_004400127.1-YP_004399790.1 fusion DNA

<400> SEQUENCE: 54

atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tggcctgtg gctgctttaa ttgcttctac tgtttctctt    840

gcgattagcc cattagcatt tgccggtatt gccgataaat ttaatcatgc aaaaagttta    900

gagagttatg ccgaacgctt taaaaaatta ggctatgacg gagataattt attagcagaa    960

tatcagcggg gaacagggac tattgatgca tcggttactg caattaatac cgcattggcc   1020

gctattgctg gtggtgtgtc tgctgctgca gccggctcgg ttattgcttc accgattgcc   1080

ttattagtat ctgggattac cggtgtaatt tctacgattc tgcaatattc taaacaagca   1140

atgtttgagc acgttgcaaa taaaattcat aacaaaattg tagaatggga aaaaaataat   1200

cacggtaaga actactttga aaatggttac gatgcccgtt atcttgcgaa tttacaagat   1260

aatatgaaat tcttactgaa cttaaacaaa gagttacagg cagaacgtgt catcgctatt   1320

actcagcagc aatgggataa caacattggt gatttagctg gtattagccg tttaggtgaa   1380

aaagtcctta gtggtaaagc ctatgtggat gcgtttgaag aaggcaaaca cattaaagcc   1440

gataaattag tacagttgga ttcggcaaac ggtattattg atgtgagtaa ttcgggtaaa   1500

gcgaaaactc agcatatctt attcagaacg ccattattga cgccgggaac agagcatcgt   1560

gaacgcgtac aaacaggtaa atatgaatat attaccaagc tcaatattaa ccgtgtagat   1620

agctggaaaa ttacagatgg tgcagcaagt tctacctttg atttaactaa cgttgttcag   1680

cgtattggta ttgaattaga caatgctgga aatgtaacta aaaccaaaga aacaaaaatt   1740

attgccaaac ttggtgaagg tgatgacaac gtatttgttg gttctggtac gacggaaatt   1800

gatggcggtg aaggttacga ccgagttcac tatagccgtg gaaactatgg tgctttaact   1860

attgatgcaa ccaaagagac cgagcaaggt agttataccg taaatcgttt cgtagaaacc   1920
```

```
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccat gaaaacggac aataccaacc aaaaaatcaa agaaaaagac   2820
aacgaaacgg gcagtaaaga caaagacaaa ccgaacaata acctgaatag ctctgaacag   2880
gatctgccga aagaccaacc gatcaccaag aaagaaaaag atgaaaaaac ggacagcttt   2940
gcagataaac tgaagaaaga tctgaagaaa attctggaca agaaagaaga tctgaaaatc   3000
cgtgaataca gtaccaaact gatctccaaa tacttccaga aagttccgaa aaaacaactg   3060
ctgaaagatt ggttcgacct ggaaaagaaa attaaaaaat ggttcgacga aagcgaactg   3120
aacgaaatta agaaagaaat caccatcctg ttttccgaat cactggataa caattcaaac   3180
aatcaggaat cgcgcaaact gaaagatctg ctggacaaag ttaccaaaga taacaaagaa   3240
ggcatcctgg aagaagtcaa aaacctgttt ggtcagaaaa tctcaaaaga actggaagaa   3300
aaactgaaat cggaaaccga tggcatcaac aatctgctga gcaaaaaaca atacgaaacc   3360
atcaaaacga aactgttcga tattgtggac aaaacggccg aactggagaa aaacatcaaa   3420
ggcggtggcg gtggcggtat gaaaaaactg ctggcaatcc tgggcaccat ggctatttca   3480
tcgacgggtg cgagtctggt tattgcctgc gacaatccga ccaaaaaacga ttccaaaaaa   3540
ccggaaacga aaccggaaac cccgacgaat tcgggtagca acgaaacctc gaatcagggc   3600
agcaacgaag gttctaacaa agaaaaagat aactctgaac cgagtaaacc gacgaaaccg   3660
gtgaaaccgg caagcggcac cgcttccctg gtttcaaaaa cggacattag cgcgtggagc   3720
tctatttta tggattctat caccggtgaa gatattcaag accattctgt ggaagaaaaa   3780
gaaaaagcgg acaaagccaa aaataaagaa ttcgtggaag ttctggatga aatcaacaaa   3840
ctgaccccga cgctggaaaa tgaactgaaa cagctggcac aaaaattcaa agaaatcaaa   3900
gaaaaactgg ctaaagaaaa agaactgaaa gaccagaaaa acaacaaaga attcgtcgaa   3960
gtgctggacg aaattaacaa actgagtgtc acctttgaaa aagaactgaa agccctgttc   4020
aagaaaattg gcgaaaacga actggaaaaa gaacgtctgt acaaagaatt caccacgagt   4080
tcctcaaatg cgaccaaata ttacttcgaa gccctggata ccaagaaaga agtgagcgaa   4140
tggaactttg aacgtggccg cctggtcgaa ctgatttcga gcatcgatcg ccaggtgaaa   4200
gaactgaaat ctagtggtaa agacatcaaa agcgttatcg ataccgtcaa atctaacctg   4260
```

```
gaaaattaca aaaacagtat caaagaacac aaaaattcca aagttttctg gaaatacgaa   4320

atgtggacgc actggctgga agatgttctg accaacctga aaaatcaaaa tcaataa      4377


<210> SEQ ID NO 55
<211> LENGTH: 1458
<212> TYPE: PRT
<213> ORGANISM: Artificial Sequence
<220> FEATURE:
<223> OTHER INFORMATION: LtkA-YP_004400127.1-YP_004399790.1 fusion
      protein

<400> SEQUENCE: 55

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335
```

-continued

```
Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750
```

```
Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Met Lys
        915                 920                 925

Thr Asp Asn Thr Asn Gln Lys Ile Lys Glu Lys Asp Asn Glu Thr Gly
    930                 935                 940

Ser Lys Asp Lys Asp Lys Pro Asn Asn Asn Leu Asn Ser Ser Glu Gln
945                 950                 955                 960

Asp Leu Pro Lys Asp Gln Pro Ile Thr Lys Lys Glu Lys Asp Glu Lys
                965                 970                 975

Thr Asp Ser Phe Ala Asp Lys Leu Lys Lys Asp Leu Lys Lys Ile Leu
            980                 985                 990

Asp Lys Lys Glu Asp Leu Lys Ile  Arg Glu Tyr Ser Thr  Lys Leu Ile
        995                 1000                1005

Ser Lys  Tyr Phe Gln Lys Ser  Ser Glu Lys Gln Leu  Leu Lys Asp
    1010                1015                1020

Trp Phe  Asp Leu Glu Lys Lys  Ile Lys Lys Trp Phe  Asp Glu Ser
    1025                1030                1035

Glu Leu  Asn Glu Ile Lys Lys  Glu Ile Thr Ile Leu  Phe Ser Glu
    1040                1045                1050

Ser Leu  Asp Asn Asn Ser Asn  Asn Gln Glu Ser Arg  Lys Leu Lys
    1055                1060                1065

Asp Leu  Leu Asp Lys Val Thr  Lys Asp Asn Lys Glu  Gly Ile Leu
    1070                1075                1080

Glu Glu  Val Lys Asn Leu Phe  Gly Gln Lys Ile Ser  Lys Glu Leu
    1085                1090                1095

Glu Glu  Lys Leu Lys Ser Glu  Thr Asp Gly Ile Asn  Asn Leu Leu
    1100                1105                1110

Ser Lys  Lys Gln Tyr Glu Thr  Ile Lys Thr Lys Leu  Phe Asp Ile
    1115                1120                1125

Val Asp  Lys Thr Ala Glu Leu  Glu Lys Asn Ile Lys  Gly Gly Gly
    1130                1135                1140

Gly Gly  Gly Met Lys Lys Leu  Leu Ala Ile Leu Gly  Thr Met Ala
    1145                1150                1155
```

```
Ile Ser  Ser Thr Gly Ala Ser  Leu Val Ile Ala Cys  Asp Asn Pro
    1160                 1165                 1170

Thr Lys  Asn Asp Ser Lys Lys  Pro Glu Thr Lys Pro  Glu Thr Pro
    1175                 1180                 1185

Thr Asn  Ser Gly Ser Asn Glu  Thr Ser Asn Gln Gly  Ser Asn Glu
    1190                 1195                 1200

Gly Ser  Asn Lys Glu Lys Asp  Asn Ser Glu Pro Ser  Lys Pro Thr
    1205                 1210                 1215

Lys Pro  Val Lys Pro Ala Ser  Gly Thr Ala Ser Leu  Val Ser Lys
    1220                 1225                 1230

Thr Asp  Ile Ser Ala Trp Ser  Ser Ile Phe Met Asp  Ser Ile Thr
    1235                 1240                 1245

Gly Glu  Asp Ile Gln Asp His  Ser Val Glu Glu Lys  Glu Lys Ala
    1250                 1255                 1260

Asp Lys  Ala Lys Asn Lys Glu  Phe Val Glu Val Leu  Asp Glu Ile
    1265                 1270                 1275

Asn Lys  Leu Thr Pro Thr Leu  Glu Asn Glu Leu Lys  Gln Leu Ala
    1280                 1285                 1290

Gln Lys  Phe Lys Glu Ile Lys  Glu Lys Leu Ala Lys  Glu Lys Glu
    1295                 1300                 1305

Leu Lys  Asp Gln Lys Asn Asn  Lys Glu Phe Val Glu  Val Leu Asp
    1310                 1315                 1320

Glu Ile  Asn Lys Leu Ser Val  Thr Phe Glu Lys Glu  Leu Lys Ala
    1325                 1330                 1335

Leu Phe  Lys Lys Ile Gly Glu  Asn Glu Leu Glu Lys  Glu Arg Leu
    1340                 1345                 1350

Tyr Lys  Glu Phe Thr Thr Ser  Ser Ser Asn Ala Thr  Lys Tyr Tyr
    1355                 1360                 1365

Phe Glu  Ala Leu Asp Thr Lys  Lys Glu Val Ser Glu  Trp Asn Phe
    1370                 1375                 1380

Glu Arg  Gly Arg Leu Val Glu  Leu Ile Ser Ser Ile  Asp Arg Gln
    1385                 1390                 1395

Val Lys  Glu Leu Lys Ser Ser  Gly Lys Asp Ile Lys  Ser Val Ile
    1400                 1405                 1410

Asp Thr  Val Lys Ser Asn Leu  Glu Asn Tyr Lys Asn  Ser Ile Lys
    1415                 1420                 1425

Glu His  Lys Asn Ser Lys Val  Phe Trp Lys Tyr Glu  Met Trp Thr
    1430                 1435                 1440

His Trp  Leu Glu Asp Val Leu  Thr Asn Leu Lys Asn  Gln Asn Gln
    1445                 1450                 1455
```

<210> SEQ ID NO 56
<211> LENGTH: 4417
<212> TYPE: DNA
<213> ORGANISM: Artificial Sequence
<220> FEATURE:
<223> OTHER INFORMATION: pAA352-YP_004400610.1-YP_004400580.1 fusion DNA

<400> SEQUENCE: 56

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240
```

-continued

```
tccgctccac aaattgataa attgctacag aaaactaaag caggccaagc attaggttct    300
gccgaaagca ttgtacaaaa tgcaaataaa gccaaaactg tattatctgg cattcaatct    360
attttaggct cagtattggc tggaatggat ttagatgagg ccttacagaa taacagcaac    420
caacatgctc ttgctaaagc tggcttggag ctaacaaatt cattaattga aaatattgct    480
aattcagtaa aaacacttga cgaatttggt gagcaaatta gtcaatttgg ttcaaaacta    540
caaaatatca aaggcttagg gactttagga gacaaactca aaaatatcgg tggacttgat    600
aaagctggcc ttggtttaga tgttatctca gggctattat cgggcgcaac agctgcactt    660
gtacttgcag ataaaaatgc ttcaacagct aaaaaagtgg gtgcgggttt tgaattggca    720
aaccaagttg ttggtaatat taccaaagcc gtttcttctt acattttagc ccaacgtgtt    780
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
```

```
aatgtgacaa acagcttaga taagttaatc tcatctgtaa gtgcatttac ctcgtctaat   2700

gattcgagaa atgtattagt ggctccaact tcaatgttgg atcaaagttt atcttctctt   2760

caatttgcta ggggatccat gggcgaccgt gccccgtccg caaaatccgc agaaaaagtg   2820

gaaaataaag aaaaaaccaa accgagtgaa gccccgaaga agggcgaaaa gagtgaagaa   2880

aaggaaaacg aaaaggataa agaactgaaa gccgtctttt ccaaagtgga aggccagaat   2940

attggtaact tccaaccgaa caacaaaaac atcgtctccc agggcgatat taagaaagaa   3000

ctggcaaaca aactgggcgt gtcagaatcg gacctgcaag gtctgaaact gaattatgat   3060

gacaaaagcg gcgaagtgac gctgccgaaa ttcaacaaca aaaacctgaa attcaaattc   3120

accacgttct accagctggg taaaatcaaa accagtaaaa tcgataacgt tctgtttctg   3180

tcccaactgg acattaagaa agaactggct aacaaactga aagtcaaaga atcagatctg   3240

caggaactga aaacggactc gaccaacggt atcggcgcgg gtagcgtgcg ttctaaaacc   3300

ttcgttggta ttctggaatt caaattcgaa atcgatgaaa acaaaggcgg tggcggtggc   3360

agcatttcta cgccgaaaat taacccgacc atcaacaaaa acgaaaacaa actgtacaaa   3420

aacaaatacg tctcagaact gctgaacctg tatctgagtg actccaaact gcgcgatagc   3480

tacatcaatg accaggaaaa cgtttcagat tcgaaattct ctgaactgaa atatggcctg   3540

acctttacc cgattttcat ccatcgttca ctggattatc atattggtca gcactaccgc   3600

gtgattatcc aaaaatcgaa aaatgcgctg gaacagacgc tgaaaaacga ttggtattgg   3660

gttctggaca acatcaccaa cttcaaatac aacttcaacc cgtatggcga tctgtacaac   3720

gatttcgaca aagatgaaaa cctgtttaac cagctggaaa aagacctggg tagtctgatc   3780

agctctgtta aaaacaaaaa cgtccaaaaa atcatcaaaa tcaacctgga tgaagtggtt   3840

aacgaaaaaa tcaaagatga ctacctgaag aaagaagcgc tgtacctgat cttcgataac   3900

aacaaagcaa tcaaaatctg gaaatacgaa aaccagaaca aaaccgaatt cctgatgacc   3960

acggacctgt ttatcttcaa agacacgaac aatctggaaa atcagattaa agaactggaa   4020

aacaccatct tcgaaaaacg taaagtggaa tacaacaaca acctggaaaa catcaacaaa   4080

aacatcgaag ctaccaaaaa acgcaaagaa aaagcgcagc aagaaatcca ggatctgaaa   4140

gaaaaaatca aaaaactgga aaaaacgaat accaccacca ccaccccgct ggccctgacc   4200

agttccgcca ttctgctgtc tgcaccgaaa aacgataaaa agaaagaacc gacgctggaa   4260

gaactgaaga aagatctgga aaagaaagaa aaacagagcc agcaatttga cgaaaacgtt   4320

aaaaaatacg agaaaaacat cgaagatctg ccgcagaaat ctaacgacaa aaaattcctg   4380

gaattccacg cgaccgatca atacaatgaa cgtctga                             4417
```

<210> SEQ ID NO 57
<211> LENGTH: 1483
<212> TYPE: PRT
<213> ORGANISM: Artificial Sequence
<220> FEATURE:
<223> OTHER INFORMATION: LtkA-YP_004400610.1-YP_004400580.1 fusion protein

<400> SEQUENCE: 57

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30
```

```
Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445
```

-continued

```
Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860
```

```
Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Met Gly
        915                 920                 925

Asp Arg Ala Pro Ser Ala Lys Ser Ala Glu Lys Val Glu Asn Lys Glu
    930                 935                 940

Lys Thr Lys Pro Ser Glu Ala Pro Lys Lys Gly Glu Lys Ser Glu Glu
945                 950                 955                 960

Lys Glu Asn Glu Lys Asp Lys Glu Leu Lys Ala Val Phe Ser Lys Val
                965                 970                 975

Glu Gly Gln Asn Ile Gly Asn Phe Gln Pro Asn Asn Lys Asn Ile Val
            980                 985                 990

Ser Gln Gly Asp Ile Lys Lys Glu  Leu Ala Asn Lys Leu  Gly Val Ser
        995                 1000                1005

Glu Ser  Asp Leu Gln Gly Leu  Lys Leu Asn Tyr Asp  Asp Lys Ser
    1010                1015                1020

Gly Glu  Val Thr Leu Pro Lys  Phe Asn Asn Lys Asn  Leu Lys Phe
    1025                1030                1035

Lys Phe  Thr Thr Phe Tyr Gln  Leu Gly Lys Ile Lys  Thr Ser Lys
    1040                1045                1050

Ile Asp  Asn Val Leu Phe Leu  Ser Gln Leu Asp Ile  Lys Lys Glu
    1055                1060                1065

Leu Ala  Asn Lys Leu Lys Val  Lys Glu Ser Asp Leu  Gln Glu Leu
    1070                1075                1080

Lys Thr  Asp Ser Thr Asn Gly  Ile Gly Ala Gly Ser  Val Arg Ser
    1085                1090                1095

Lys Thr  Phe Val Gly Ile Leu  Glu Phe Lys Phe Glu  Ile Asp Glu
    1100                1105                1110

Asn Lys  Gly Gly Gly Gly Gly  Ser Ile Ser Thr Pro  Lys Ile Asn
    1115                1120                1125

Pro Thr  Ile Asn Lys Asn Glu  Asn Lys Leu Tyr Lys  Asn Lys Tyr
    1130                1135                1140

Val Ser  Glu Leu Leu Asn Leu  Tyr Leu Ser Asp Ser  Lys Leu Arg
    1145                1150                1155

Asp Ser  Tyr Ile Asn Asp Gln  Glu Asn Val Ser Asp  Ser Lys Phe
    1160                1165                1170

Ser Glu  Leu Lys Tyr Gly Leu  Thr Phe Tyr Pro Ile  Phe Ile His
    1175                1180                1185

Arg Ser  Leu Asp Tyr His Ile  Gly Gln His Tyr Arg  Val Ile Ile
    1190                1195                1200

Gln Lys  Ser Lys Asn Ala Leu  Glu Gln Thr Leu Lys  Asn Asp Trp
    1205                1210                1215

Tyr Trp  Val Leu Asp Asn Ile  Thr Asn Phe Lys Tyr  Asn Phe Asn
    1220                1225                1230

Pro Tyr  Gly Asp Leu Tyr Asn  Asp Phe Asp Lys Asp  Glu Asn Leu
    1235                1240                1245

Phe Asn  Gln Leu Glu Lys Asp  Leu Gly Ser Leu Ile  Ser Ser Val
    1250                1255                1260
```

```
Lys Asn Lys Asn Val Gln Lys Ile Ile Lys Ile Asn Leu Asp Glu
    1265                1270                1275

Val Val Asn Glu Lys Ile Lys Asp Asp Tyr Leu Lys Lys Glu Ala
    1280                1285                1290

Leu Tyr Leu Ile Phe Asp Asn Asn Lys Ala Ile Lys Ile Trp Lys
    1295                1300                1305

Tyr Glu Asn Gln Asn Lys Thr Glu Phe Leu Met Thr Thr Asp Leu
    1310                1315                1320

Phe Ile Phe Lys Asp Thr Asn Asn Leu Glu Asn Gln Ile Lys Glu
    1325                1330                1335

Leu Glu Asn Thr Ile Phe Glu Lys Arg Lys Val Glu Tyr Asn Asn
    1340                1345                1350

Asn Leu Glu Asn Ile Asn Lys Asn Ile Glu Ala Thr Lys Lys Arg
    1355                1360                1365

Lys Glu Lys Ala Gln Gln Glu Ile Gln Asp Leu Lys Glu Lys Ile
    1370                1375                1380

Lys Lys Leu Glu Lys Thr Asn Thr Thr Thr Thr Thr Pro Leu Ala
    1385                1390                1395

Leu Thr Ser Ser Ala Ile Leu Leu Ser Ala Pro Lys Asn Asp Lys
    1400                1405                1410

Lys Lys Glu Pro Thr Leu Glu Glu Leu Lys Lys Asp Leu Glu Lys
    1415                1420                1425

Lys Glu Lys Gln Ser Gln Gln Phe Asp Glu Asn Val Lys Lys Tyr
    1430                1435                1440

Glu Lys Asn Ile Glu Asp Leu Pro Gln Lys Ser Asn Asp Lys Lys
    1445                1450                1455

Phe Leu Glu Phe His Ala Thr Asp Gln Tyr Asn Glu Arg Leu Lys
    1460                1465                1470

Glu Ser Leu Asn Glu Ile Asn Lys Asp Gly
    1475                1480
```

<210> SEQ ID NO 58
<211> LENGTH: 3963
<212> TYPE: DNA
<213> ORGANISM: Artificial Sequence
<220> FEATURE:
<223> OTHER INFORMATION: pAA352-MSC_0160 fusion DNA

<400> SEQUENCE: 58

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720
```

-continued

```
aaccaagttg ttggtaatat taccaaagcc gtttcttctt acattttagc ccaacgtgtt    780
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccgc gaaagaacag tttgatcgta gcctgccgca tgtgaacatt   2820
ggcaccatcg gtcatgttga ccacggcaaa accacgctga ccgcggccat tacgaaagtt   2880
ctgtctgaac agggtaacgc agaattcaaa gattacgcaa acatcgacaa tgctccggaa   2940
gaacgtgaac gcggcattac catcaacacg gcgcatgtgg aatataaaac cgcgaatcgc   3000
cattacgccc acgtcgattg cccgggtcac gcagactacg tgaaaaacat gattacgggt   3060
gcagctcaga tggatggcgc tatcctggtg gttgcagcaa ccgacggtcc gatgccgcag   3120
```

```
acgcgtgaac acattctgct gtcccgccaa gtgggtgttc cgaaaatcgt cgtgtttctg   3180

aacaaatgtg atatggttga agatgacgaa atgattgatc tggtggaaat ggaaatccgt   3240

gacctgctga ccgaatatga tttcgacggc gaaggtgccc cggttattcg tggcagcgca   3300

ctgggtgctc tgaacggtga ttctaaatgg accggcgcga ttaatgaact gatggcagct   3360

gtggatgaat acatcccgac cccgcagcgt gatgccgaca aaacgtttct gatgccggtg   3420

gaagatgttt tcaccatcac gggtcgtggt accgttgcaa cgggtcgtgt cgaacgcggc   3480

accgtcaaag tgaacgaaga agttgaaatt atcggcctga aagaagaacc gaccaaaacg   3540

gttgtcacgg gtctggaaat gtttcgtaaa ctgctggatt tcgcggtggc cggtgacaat   3600

gttggtgcac tgctgcgtgg tgtcgatcgt cattcagtgg aacgcggtca ggttctggcc   3660

aaaccgggca ccattaaacc gcacacggtc ctgaaagcgt cggtgtatgc cctgacccag   3720

gaagaaggcg gtcgtcataa accgtttttc aacaaatatc gtccgcaatt ttacttccgc   3780

accacggatg tcaccggtga agtgacgctg ccggaaggca ccgatatggt tatgccgggt   3840

gacaatgtcg aaatggaaat tcaactgatc aaaccggttg cagtcgaaga aggtaccaaa   3900

tttagtattc gtgaaggcgg tcgtaccatc ggtgctggta cggtgatttc catcgaaaaa   3960

taa                                                                 3963
```

```
<210> SEQ ID NO 59
<211> LENGTH: 1320
<212> TYPE: PRT
<213> ORGANISM: Artificial Sequence
<220> FEATURE:
<223> OTHER INFORMATION: LtkA-MSC_0160 fusion protein

<400> SEQUENCE: 59

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205
```

-continued

Ile Ser Gly Leu Leu Ser Gly Ala Thr Ala Ala Leu Val Leu Ala Asp
210 215 220

Lys Asn Ala Ser Thr Ala Lys Lys Val Gly Ala Gly Phe Glu Leu Ala
225 230 235 240

Asn Gln Val Val Gly Asn Ile Thr Lys Ala Val Ser Ser Tyr Ile Leu
245 250 255

Ala Gln Arg Val Ala Ala Gly Leu Ser Ser Thr Gly Pro Val Ala Ala
260 265 270

Leu Ile Ala Ser Thr Val Ser Leu Ala Ile Ser Pro Leu Ala Phe Ala
275 280 285

Gly Ile Ala Asp Lys Phe Asn His Ala Lys Ser Leu Glu Ser Tyr Ala
290 295 300

Glu Arg Phe Lys Lys Leu Gly Tyr Asp Gly Asp Asn Leu Leu Ala Glu
305 310 315 320

Tyr Gln Arg Gly Thr Gly Thr Ile Asp Ala Ser Val Thr Ala Ile Asn
325 330 335

Thr Ala Leu Ala Ala Ile Ala Gly Gly Val Ser Ala Ala Ala Ala Gly
340 345 350

Ser Val Ile Ala Ser Pro Ile Ala Leu Leu Val Ser Gly Ile Thr Gly
355 360 365

Val Ile Ser Thr Ile Leu Gln Tyr Ser Lys Gln Ala Met Phe Glu His
370 375 380

Val Ala Asn Lys Ile His Asn Lys Ile Val Glu Trp Glu Lys Asn Asn
385 390 395 400

His Gly Lys Asn Tyr Phe Glu Asn Gly Tyr Asp Ala Arg Tyr Leu Ala
405 410 415

Asn Leu Gln Asp Asn Met Lys Phe Leu Leu Asn Leu Asn Lys Glu Leu
420 425 430

Gln Ala Glu Arg Val Ile Ala Ile Thr Gln Gln Gln Trp Asp Asn Asn
435 440 445

Ile Gly Asp Leu Ala Gly Ile Ser Arg Leu Gly Glu Lys Val Leu Ser
450 455 460

Gly Lys Ala Tyr Val Asp Ala Phe Glu Glu Gly Lys His Ile Lys Ala
465 470 475 480

Asp Lys Leu Val Gln Leu Asp Ser Ala Asn Gly Ile Ile Asp Val Ser
485 490 495

Asn Ser Gly Lys Ala Lys Thr Gln His Ile Leu Phe Arg Thr Pro Leu
500 505 510

Leu Thr Pro Gly Thr Glu His Arg Glu Arg Val Gln Thr Gly Lys Tyr
515 520 525

Glu Tyr Ile Thr Lys Leu Asn Ile Asn Arg Val Asp Ser Trp Lys Ile
530 535 540

Thr Asp Gly Ala Ala Ser Ser Thr Phe Asp Leu Thr Asn Val Val Gln
545 550 555 560

Arg Ile Gly Ile Glu Leu Asp Asn Ala Gly Asn Val Thr Lys Thr Lys
565 570 575

Glu Thr Lys Ile Ile Ala Lys Leu Gly Glu Gly Asp Asp Asn Val Phe
580 585 590

Val Gly Ser Gly Thr Thr Glu Ile Asp Gly Gly Glu Gly Tyr Asp Arg
595 600 605

Val His Tyr Ser Arg Gly Asn Tyr Gly Ala Leu Thr Ile Asp Ala Thr
610 615 620

-continued

```
Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Ala Lys
        915                 920                 925

Glu Gln Phe Asp Arg Ser Leu Pro His Val Asn Ile Gly Thr Ile Gly
    930                 935                 940

His Val Asp His Gly Lys Thr Thr Leu Thr Ala Ala Ile Thr Lys Val
945                 950                 955                 960

Leu Ser Glu Gln Gly Asn Ala Glu Phe Lys Asp Tyr Ala Asn Ile Asp
                965                 970                 975

Asn Ala Pro Glu Glu Arg Glu Arg Gly Ile Thr Ile Asn Thr Ala His
            980                 985                 990

Val Glu Tyr Lys Thr Ala Asn Arg  His Tyr Ala His Val  Asp Cys Pro
        995                 1000                 1005

Gly His  Ala Asp Tyr Val Lys  Asn Met Ile Thr Gly  Ala Ala Gln
    1010                 1015                 1020

Met Asp  Gly Ala Ile Leu Val  Val Ala Ala Thr Asp  Gly Pro Met
    1025                 1030                 1035
```

```
Pro Gln  Thr Arg Glu His Ile  Leu Leu Ser Arg Gln  Val Gly Val
    1040                 1045                 1050

Pro Lys  Ile Val Val Phe Leu  Asn Lys Cys Asp Met  Val Glu Asp
    1055                 1060                 1065

Asp Glu  Met Ile Asp Leu Val  Glu Met Glu Ile Arg  Asp Leu Leu
    1070                 1075                 1080

Thr Glu  Tyr Asp Phe Asp Gly  Glu Gly Ala Pro Val  Ile Arg Gly
    1085                 1090                 1095

Ser Ala  Leu Gly Ala Leu Asn  Gly Asp Ser Lys Trp  Thr Gly Ala
    1100                 1105                 1110

Ile Asn  Glu Leu Met Ala Ala  Val Asp Glu Tyr Ile  Pro Thr Pro
    1115                 1120                 1125

Gln Arg  Asp Ala Asp Lys Thr  Phe Leu Met Pro Val  Glu Asp Val
    1130                 1135                 1140

Phe Thr  Ile Thr Gly Arg Gly  Thr Val Ala Thr Gly  Arg Val Glu
    1145                 1150                 1155

Arg Gly  Thr Val Lys Val Asn  Glu Glu Val Glu Ile  Ile Gly Leu
    1160                 1165                 1170

Lys Glu  Glu Pro Thr Lys Thr  Val Val Thr Gly Leu  Glu Met Phe
    1175                 1180                 1185

Arg Lys  Leu Leu Asp Phe Ala  Val Ala Gly Asp Asn  Val Gly Ala
    1190                 1195                 1200

Leu Leu  Arg Gly Val Asp Arg  His Ser Val Glu Arg  Gly Gln Val
    1205                 1210                 1215

Leu Ala  Lys Pro Gly Thr Ile  Lys Pro His Thr Val  Leu Lys Ala
    1220                 1225                 1230

Ser Val  Tyr Ala Leu Thr Gln  Glu Glu Gly Gly Arg  His Lys Pro
    1235                 1240                 1245

Phe Phe  Asn Lys Tyr Arg Pro  Gln Phe Tyr Phe Arg  Thr Thr Asp
    1250                 1255                 1260

Val Thr  Gly Glu Val Thr Leu  Pro Glu Gly Thr Asp  Met Val Met
    1265                 1270                 1275

Pro Gly  Asp Asn Val Glu Met  Glu Ile Gln Leu Ile  Lys Pro Val
    1280                 1285                 1290

Ala Val  Glu Glu Gly Thr Lys  Phe Ser Ile Arg Glu  Gly Gly Arg
    1295                 1300                 1305

Thr Ile  Gly Ala Gly Thr Val  Ile Ser Ile Glu Lys
    1310                 1315                 1320
```

<210> SEQ ID NO 60
<211> LENGTH: 3675
<212> TYPE: DNA
<213> ORGANISM: Artificial Sequence
<220> FEATURE:
<223> OTHER INFORMATION: pAA352-MSC_0136 fusion DNA

<400> SEQUENCE: 60

```
atggctactg ttatagatct aagcttccca aaaactgggg caaaaaaaat tatcctctat      60

attccccaaa attaccaata tgatactgaa caaggtaatg gtttacagga tttagtcaaa     120

gcggccgaag agttggggat tgaggtacaa agagaagaac gcaataatat tgcaacagct     180

caaaccagtt taggcacgat tcaaaccgct attggcttaa ctgagcgtgg cattgtgtta     240

tccgctccac aaattgataa attgctacag aaaactaaag caggccaagc attaggttct     300

gccgaaagca ttgtacaaaa tgcaaataaa gccaaaactg tattatctgg cattcaatct     360
```

```
attttaggct cagtattggc tggaatggat ttagatgagg ccttacagaa taacagcaac    420
caacatgctc ttgctaaagc tggcttggag ctaacaaatt cattaattga aaatattgct    480
aattcagtaa aaacacttga cgaatttggt gagcaaatta gtcaatttgg ttcaaaacta    540
caaaatatca aaggcttagg gactttagga gacaaactca aaaatatcgg tggacttgat    600
aaagctggcc ttggtttaga tgttatctca gggctattat cgggcgcaac agctgcactt    660
gtacttgcag ataaaaatgc ttcaacagct aaaaaagtgg gtgcgggttt tgaattggca    720
aaccaagttg ttggtaatat taccaaagcc gtttcttctt acattttagc ccaacgtgtt    780
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
```

-continued

```
gattcgagaa atgtattagt ggctccaact tcaatgttgg atcaaagttt atcttctctt   2760

caatttgcta ggggatccaa aaacgaaaac catttcaaca tcaactacaa aatgaaaatg   2820

gaaatgaaaa cccagaaaac ggaacaaccg cacaaatata aagaaggcga tcgtaccgaa   2880

attgtgcaga tcggctttta caaacgcggt aacgaaatca cgatcaaaca aatcccgtac   2940

tacgttaaaa aagtcccgga taaactgccg gacgaaatcc agtccctgta tcgtgcattt   3000

gctcatcgct acaaagatca aaaccacccg accgtcacgg gcttcgaaaa atgggacacc   3060

agcaaaatca aaaacatgtc ttatgtgttt tacgataacc agctgatcga tgcggacctg   3120

tcagaatgga aaacctcgaa tgttacgaac atggacggca tgttcaaaaa cgccatcaaa   3180

ttcaacaaca aagaaaaacc gctgaaatgg aacaccgaaa aagtcgaaag tatggaatcc   3240

atgtttgatg gcgcagaatc ttttaaacag aacctgaaag attggaaagt ggacaaagtt   3300

accaaaaaca aaaacttctc acgtgcttcg ggtattttcg aacatatcga taaaaaaccg   3360

tcatggaaaa tcaccgaaca caacgacccg attatcaaaa aaccggaatc gacggaaccg   3420

aaagtgatta tccatccgag cccgtctcgc ccgaaacaga ccattccgct gacgaaactg   3480

atcaatccga ttatcaaaag caccccgaac tctaatcaaa acctgggcat cccgaaaacg   3540

aacctgagca ccacgccgca gcaaagtaaa aaactgtcca ccccggcaat tgttggcatc   3600

gtggttggta gtcaggtcgt gctgacgtcc ctggcagcag gtattccgta cctgatcaaa   3660

cgtttcaaaa aataa                                                    3675
```

<210> SEQ ID NO 61
<211> LENGTH: 1224
<212> TYPE: PRT
<213> ORGANISM: Artificial Sequence
<220> FEATURE:
<223> OTHER INFORMATION: LtkA-MSC_0136 fusion protein

<400> SEQUENCE: 61

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190
```

-continued

```
Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605
```

-continued

```
Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Lys Asn
        915                 920                 925

Glu Asn His Phe Asn Ile Asn Tyr Lys Met Lys Met Glu Met Lys Thr
    930                 935                 940

Gln Lys Thr Glu Gln Pro His Lys Tyr Lys Glu Gly Asp Arg Thr Glu
945                 950                 955                 960

Ile Val Gln Ile Gly Phe Tyr Lys Arg Gly Asn Glu Ile Thr Ile Lys
                965                 970                 975

Gln Ile Pro Tyr Tyr Val Lys Lys Val Pro Asp Lys Leu Pro Asp Glu
            980                 985                 990

Ile Gln Ser Leu Tyr Arg Ala Phe  Ala His Arg Tyr Lys  Asp Gln Asn
        995                 1000                1005

His Pro  Thr Val Thr Gly Phe  Glu Lys Trp Asp Thr  Ser Lys Ile
    1010                1015                1020
```

```
Lys Asn  Met Ser Tyr Val Phe  Tyr Asp Asn Gln Leu  Ile Asp Ala
    1025                 1030                 1035

Asp Leu  Ser Glu Trp Lys Thr  Ser Asn Val Thr Asn  Met Asp Gly
    1040                 1045                 1050

Met Phe  Lys Asn Ala Ile Lys  Phe Asn Asn Lys Glu  Lys Pro Leu
    1055                 1060                 1065

Lys Trp  Asn Thr Glu Lys Val  Glu Ser Met Glu Ser  Met Phe Asp
    1070                 1075                 1080

Gly Ala  Glu Ser Phe Lys Gln  Asn Leu Lys Asp Trp  Lys Val Asp
    1085                 1090                 1095

Lys Val  Thr Lys Asn Lys Asn  Phe Ser Arg Ala Ser  Gly Ile Phe
    1100                 1105                 1110

Glu His  Ile Asp Lys Lys Pro  Ser Trp Lys Ile Thr  Glu His Asn
    1115                 1120                 1125

Asp Pro  Ile Ile Lys Lys Pro  Glu Ser Thr Glu Pro  Lys Val Ile
    1130                 1135                 1140

Ile His  Pro Ser Pro Ser Arg  Pro Lys Gln Thr Ile  Pro Leu Thr
    1145                 1150                 1155

Lys Leu  Ile Asn Pro Ile Ile  Lys Ser Thr Pro Asn  Ser Asn Gln
    1160                 1165                 1170

Asn Leu  Gly Ile Pro Lys Thr  Asn Leu Ser Thr Thr  Pro Gln Gln
    1175                 1180                 1185

Ser Lys  Lys Leu Ser Thr Pro  Ala Ile Val Gly Ile  Val Val Gly
    1190                 1195                 1200

Ser Gln  Val Val Leu Thr Ser  Leu Ala Ala Gly Ile  Pro Tyr Leu
    1205                 1210                 1215

Ile Lys  Arg Phe Lys Lys
    1220
```

```
<210> SEQ ID NO 62
<211> LENGTH: 3771
<212> TYPE: DNA
<213> ORGANISM: Artificial Sequence
<220> FEATURE:
<223> OTHER INFORMATION: pAA352-MSC_0431 fusion DNA

<400> SEQUENCE: 62

atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780
```

-continued

```
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatcctg cgcaaacatc gaaatgtcaa aaaacaaaaa agataaagac   2820
aaagatctga aatcggacaa aaacaaagat cagaacaaca aattcgacaa aagcaaagat   2880
aaaaaccaaa actctaaacc gaacaacaac gatcagaata gtaaatccaa ccaagacaaa   2940
acctcaccga aagataatcc gtcgacgcag tcagaatcgg aaaaacagga aaactccaaa   3000
caatatgacc tggataaact gatcacgaac aaattcatca gcatcgacgg ctctggtacc   3060
ggcgatggta aactggctaa actgccgcag aacctgcaag aatatctgga tctgatcaaa   3120
aaacagaacc cgaaattcac cctgacgctg aataacgtca gtttcaatgt ggaagaaaat   3180
```

```
gataactccg gctacaaaaa agtcagcgtg tctacgaagg gtaactctaa aaacccggtt   3240

atcgtctact tctacaaaga ccgtcatgat accgtttatg aaggcgagaa aaaagaagtg   3300

gttaaagaaa tcggttggag taaatccacc tacagtacgg acatcctgca cttcgatgaa   3360

cagacgaaag aagtcccgga aaacctgccg ccgtttatca ccagcctgga aggcgcgttc   3420

cgcaacaaca tccaagaaac catcaaaaac ctggacaaat gggatacgag caacatcgaa   3480

ttcatgaacg aaaccttcta cgaagcgaaa aattttaacc aggatatctc tggttggaaa   3540

accaataacg ttagtaacat ggattccatg ttttatggcg ccagctcttt cgaccgtaat   3600

ctgagcggtt ggaacgtgga taaagttatt acctacatcg aattcaacaa agattcaaaa   3660

atctcggaac gtaacaaacc gaaattcaaa gaactgaaac gcattcatca gggccaaggt   3720

gcaaccaaaa tcctgcacaa tcgcggcttt ctgaataaaa tgaacctgta a            3771
```

<210> SEQ ID NO 63
<211> LENGTH: 1256
<212> TYPE: PRT
<213> ORGANISM: Artificial Sequence
<220> FEATURE:
<223> OTHER INFORMATION: LtkA-MSC_0431 fusion protein

<400> SEQUENCE: 63

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255
```

-continued

```
Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670
```

```
Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Cys Ala
        915                 920                 925

Asn Ile Glu Met Ser Lys Asn Lys Lys Asp Lys Asp Lys Asp Leu Lys
    930                 935                 940

Ser Asp Lys Asn Lys Asp Gln Asn Asn Lys Phe Asp Lys Ser Lys Asp
945                 950                 955                 960

Lys Asn Gln Asn Ser Lys Pro Asn Asn Asn Asp Gln Asn Ser Lys Ser
                965                 970                 975

Asn Gln Asp Lys Thr Ser Pro Lys Asp Asn Pro Ser Thr Gln Ser Glu
            980                 985                 990

Ser Glu Lys Gln Glu Asn Ser Lys  Gln Tyr Asp Leu Asp  Lys Leu Ile
        995                 1000                1005

Thr Asn  Lys Phe Ile Ser Ile  Asp Gly Ser Gly Thr  Gly Asp Gly
    1010                1015                1020

Lys Leu  Ala Lys Leu Pro Gln  Asn Leu Gln Glu Tyr  Leu Asp Leu
    1025                1030                1035

Ile Lys  Lys Gln Asn Pro Lys  Phe Thr Leu Thr Leu  Asn Asn Val
    1040                1045                1050

Ser Phe  Asn Val Glu Glu Asn  Asp Asn Ser Gly Tyr  Lys Lys Val
    1055                1060                1065

Ser Val  Ser Thr Lys Gly Asn  Ser Lys Asn Pro Val  Ile Val Tyr
    1070                1075                1080
```

```
Phe Tyr  Lys Asp Arg His Asp  Thr Val Tyr Glu Gly  Glu Lys Lys
    1085                 1090                 1095

Glu Val  Val Lys Glu Ile Gly  Trp Ser Lys Ser Thr  Tyr Ser Thr
    1100                 1105                 1110

Asp Ile  Leu His Phe Asp Glu  Gln Thr Lys Glu Val  Pro Glu Asn
    1115                 1120                 1125

Leu Pro  Pro Phe Ile Thr Ser  Leu Glu Gly Ala Phe  Arg Asn Asn
    1130                 1135                 1140

Ile Gln  Glu Thr Ile Lys Asn  Leu Asp Lys Trp Asp  Thr Ser Asn
    1145                 1150                 1155

Ile Glu  Phe Met Asn Glu Thr  Phe Tyr Glu Ala Lys  Asn Phe Asn
    1160                 1165                 1170

Gln Asp  Ile Ser Gly Trp Lys  Thr Asn Asn Val Ser  Asn Met Asp
    1175                 1180                 1185

Ser Met  Phe Tyr Gly Ala Ser  Ser Phe Asp Arg Asn  Leu Ser Gly
    1190                 1195                 1200

Trp Asn  Val Asp Lys Val Ile  Thr Tyr Ile Glu Phe  Asn Lys Asp
    1205                 1210                 1215

Ser Lys  Ile Ser Glu Arg Asn  Lys Pro Lys Phe Lys  Glu Leu Lys
    1220                 1225                 1230

Arg Ile  His Gln Gly Gln Gly  Ala Thr Lys Ile Leu  His Asn Arg
    1235                 1240                 1245

Gly Phe  Leu Asn Lys Met Asn  Leu
    1250                 1255
```

<210> SEQ ID NO 64
<211> LENGTH: 4863
<212> TYPE: DNA
<213> ORGANISM: Artificial Sequence
<220> FEATURE:
<223> OTHER INFORMATION: pAA352-MSC_0499 fusion DNA

<400> SEQUENCE: 64

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tgggcctgtg gctgctttaa ttgcttctac tgtttctctt    840

gcgattagcc cattagcatt tgccggtatt gccgataaat ttaatcatgc aaaaagttta    900

gagagttatg ccgaacgctt taaaaaatta ggctatgacg gagataattt attagcagaa    960

tatcagcggg gaacagggac tattgatgca tcggttactg caattaatac cgcattggcc   1020
```

-continued

```
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatcctg caccacgaaa aacgataaat tcaacaaacc gttcatcacc   2820
gacgaactgg cgcagaaaat tatctcaggt ctgaaactgt cggatgactt taatttcacc   2880
acgggcgaac gtttcagtaa actggattac aaatccctga ttctggacat gatcaacgaa   2940
atcatctcca aaaacaaata caccgataac tggaacaacc tgagcaaaaa atttggtctg   3000
gaaattgaac aggcgaaaga attcggcaac aaaaaagccg aaaacgttct gaaaaacctg   3060
agcaccatca aactgttcgc agattatacg tctaaacgcg cttttgaaga agatttcgac   3120
agtgtggatc tgagttattc cgaaaattac ccgctgaatc cgtataacct ggaaagcaaa   3180
aacggtcaga aagataaaac cgtttacgcg atctactaca aaaacaacaa cggcggtagc   3240
tctagtggtt cctcatcgaa tggcggtggc accaacggtg aagcaacgtg gctgcgttgg   3300
cagaccacgg gtgaatttga taatattgac aacccgatcc cgtcaacccc gcaactgccg   3360
```

aatatctcgc tgctgaccga tacgagctct aaaaacttcc gcattgccaa actgtccaaa 3420
ccgaaagatc aggaatatat caccaatacg gcaagtgtta aagaagacgg taaagctacc 3480
aataacggca ataacgaatt tgtcgaatgg tacaaaaaca gttccgacaa attcgaaacc 3540
gatggtcagg gcatcatgca ataccgtttc atgtaccatt tcaaaacgaa aatcgaagcg 3600
aaactgttta atgatctgct gggtcacgcc tatattgaca gcaacctgtt cgtggataaa 3660
aacgacaaca aatcagcatc gaacaagaaa attatcctga acaacgtcag taaactgatt 3720
tccgatatcc agagcaatta ttctcaagtg gacaaaacca ttagtaacgt gaaaatggtt 3780
tgggcattta gcctggataa acagaaagtc tctgaagtga acggtgctat caatcaatat 3840
gtcaacccgg atggcagcct gaccaatgaa gacaacaaga aaccctgaa aaacgtgttc 3900 gataaaatca aatacaaagc gaccaacgaa tcaaaacagg gtacggattc gctgctgagc 3960
atttctggtt tcaacggctt cgttaaaaac aaagataaca acatcgaaag tctgtccggc 4020
gacctgaaac tgaccgaaga agcgaaaaaa gcggtcgccc gcgtgaatgt tccgtctctg 4080
ctgacgaata acaataacgg ctttgccagt gaaaactcca ataacgtgga ttatgtcttt 4140
gtgctgccga tttacctgaa tgacctgttt agctcgaacg acatgcagat caaacgtgaa 4200
accgaaagct ctggtggcgc cggttcaaat ggctcgaact atgaactgaa tgttctggaa 4260
aacacctggg tcaacctgaa tgacaaattt agcctggata atcgctactt cgacaacctg 4320
acgatcaaaa aagtggaatc tcaaaataac ggtgaagcac tggtggctaa caacaacgat 4380
aaatggtacg ttagcctgaa aaacggcaat gacaacaaaa aagttgaagt cacctacagc 4440
gatgacagca agaaaattat cacgctgaaa aaagttgata aaaacaacat caaaaccctg 4500
gacttcacgt acaaactgtc acagtcggat ttcaacaaac agctgttcaa acaaaacccg 4560
accgcaaaca tcacgtatga tatcaacctg aaaaactacg ataacatcaa agacaaacag 4620
aacgatgctt atatctggaa aaacgatccg aaaaaatcta acgatatcca agacctgtcc 4680
gcggccaaaa aacaggtgct gctggatcaa ctggaagcga tcaccgccaa aaatccggac 4740
gttcagaacg cagctaaaac cgaactgtat tcggcatatc tgtacacgga tggtatctac 4800
tacaaatcac tgttcgacga aatcagcaaa tacatcgaat ctgaaaaacc gaccctggat 4860
taa 4863

<210> SEQ ID NO 65
<211> LENGTH: 1620
<212> TYPE: PRT
<213> ORGANISM: Artificial Sequence
<220> FEATURE:
<223> OTHER INFORMATION: LtkA-MSC_0499 fusion protein

<400> SEQUENCE: 65

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

-continued

```
Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510
```

-continued

```
Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Cys Thr
        915                 920                 925
```

-continued

```
Thr Lys Asn Asp Lys Phe Asn Lys Pro Phe Ile Thr Asp Glu Leu Ala
    930                 935                 940

Gln Lys Ile Ile Ser Gly Leu Lys Leu Ser Asp Asp Phe Asn Phe Thr
945                 950                 955                 960

Thr Gly Glu Arg Phe Ser Lys Leu Asp Tyr Lys Ser Leu Ile Leu Asp
                965                 970                 975

Met Ile Asn Glu Ile Ile Ser Lys Asn Lys Tyr Thr Asp Asn Trp Asn
            980                 985                 990

Asn Leu Ser Lys Lys Phe Gly Leu  Glu Ile Glu Gln Ala  Lys Glu Phe
        995                 1000                1005

Gly Asn  Lys Lys Ala Glu Asn  Val Leu Lys Asn Leu  Ser Thr Ile
    1010                1015                1020

Lys Leu  Phe Ala Asp Tyr Thr  Ser Lys Arg Ala Phe  Glu Glu Asp
    1025                1030                1035

Phe Asp  Ser Val Asp Leu Ser  Tyr Ser Glu Asn Tyr  Pro Leu Asn
    1040                1045                1050

Pro Tyr  Asn Leu Glu Ser Lys  Asn Gly Gln Lys Asp  Lys Thr Val
    1055                1060                1065

Tyr Ala  Ile Tyr Tyr Lys Asn  Asn Asn Gly Gly Ser  Ser Ser Gly
    1070                1075                1080

Ser Ser  Ser Asn Gly Gly Gly  Thr Asn Gly Glu Ala  Thr Trp Leu
    1085                1090                1095

Arg Trp  Gln Thr Thr Gly Glu  Phe Asp Asn Ile Asp  Asn Pro Ile
    1100                1105                1110

Pro Ser  Thr Pro Gln Leu Pro  Asn Ile Ser Leu Leu  Thr Asp Thr
    1115                1120                1125

Ser Ser  Lys Asn Phe Arg Ile  Ala Lys Leu Ser Lys  Pro Lys Asp
    1130                1135                1140

Gln Glu  Tyr Ile Thr Asn Thr  Ala Ser Val Lys Glu  Asp Gly Lys
    1145                1150                1155

Ala Thr  Asn Asn Gly Asn Asn  Glu Phe Val Glu Trp  Tyr Lys Asn
    1160                1165                1170

Ser Ser  Asp Lys Phe Glu Thr  Asp Gly Gln Gly Ile  Met Gln Tyr
    1175                1180                1185

Arg Phe  Met Tyr His Phe Lys  Thr Lys Ile Glu Ala  Lys Leu Phe
    1190                1195                1200

Asn Asp  Leu Leu Gly His Ala  Tyr Ile Asp Ser Asn  Leu Phe Val
    1205                1210                1215

Asp Lys  Asn Asp Asn Lys Ser  Ala Ser Asn Lys Lys  Ile Ile Leu
    1220                1225                1230

Asn Asn  Val Ser Lys Leu Ile  Ser Asp Ile Gln Ser  Asn Tyr Ser
    1235                1240                1245

Gln Val  Asp Lys Thr Ile Ser  Asn Val Lys Met Val  Trp Ala Phe
    1250                1255                1260

Ser Leu  Asp Lys Gln Lys Val  Ser Glu Val Asn Gly  Ala Ile Asn
    1265                1270                1275

Gln Tyr  Val Asn Pro Asp Gly  Ser Leu Thr Asn Glu  Asp Asn Lys
    1280                1285                1290

Lys Thr  Leu Lys Asn Val Phe  Asp Lys Ile Lys Tyr  Lys Ala Thr
    1295                1300                1305

Asn Glu  Ser Lys Gln Gly Thr  Asp Ser Leu Leu Ser  Ile Ser Gly
    1310                1315                1320
```

-continued

```
Phe Asn  Gly Phe Val Lys Asn  Lys Asp Asn Asn Ile  Glu Ser Leu
    1325                 1330                 1335

Ser Gly  Asp Leu Lys Leu Thr  Glu Glu Ala Lys Lys  Ala Val Ala
    1340                 1345                 1350

Arg Val  Asn Val Pro Ser Leu  Leu Thr Asn Asn Asn  Asn Gly Phe
    1355                 1360                 1365

Ala Ser  Glu Asn Ser Asn Asn  Val Asp Tyr Val Phe  Val Leu Pro
    1370                 1375                 1380

Ile Tyr  Leu Asn Asp Leu Phe  Ser Ser Asn Asp Met  Gln Ile Lys
    1385                 1390                 1395

Arg Glu  Thr Glu Ser Ser Gly  Gly Ala Gly Ser Asn  Gly Ser Asn
    1400                 1405                 1410

Tyr Glu  Leu Asn Val Leu Glu  Asn Thr Trp Val Asn  Leu Asn Asp
    1415                 1420                 1425

Lys Phe  Ser Leu Asp Asn Arg  Tyr Phe Asp Asn Leu  Thr Ile Lys
    1430                 1435                 1440

Lys Val  Glu Ser Gln Asn Asn  Gly Glu Ala Leu Val  Ala Asn Asn
    1445                 1450                 1455

Asn Asp  Lys Trp Tyr Val Ser  Leu Lys Asn Gly Asn  Asp Asn Lys
    1460                 1465                 1470

Lys Val  Glu Val Thr Tyr Ser  Asp Asp Ser Lys Lys  Ile Ile Thr
    1475                 1480                 1485

Leu Lys  Lys Val Asp Lys Asn  Asn Ile Lys Thr Leu  Asp Phe Thr
    1490                 1495                 1500

Tyr Lys  Leu Ser Gln Ser Asp  Phe Asn Lys Gln Leu  Phe Lys Gln
    1505                 1510                 1515

Asn Pro  Thr Ala Asn Ile Thr  Tyr Asp Ile Asn Leu  Lys Asn Tyr
    1520                 1525                 1530

Asp Asn  Ile Lys Asp Lys Gln  Asn Asp Ala Tyr Ile  Trp Lys Asn
    1535                 1540                 1545

Asp Pro  Lys Lys Ser Asn Asp  Ile Gln Asp Leu Ser  Ala Ala Lys
    1550                 1555                 1560

Lys Gln  Val Leu Leu Asp Gln  Leu Glu Ala Ile Thr  Ala Lys Asn
    1565                 1570                 1575

Pro Asp  Val Gln Asn Ala Ala  Lys Thr Glu Leu Tyr  Ser Ala Tyr
    1580                 1585                 1590

Leu Tyr  Thr Asp Gly Ile Tyr  Tyr Lys Ser Leu Phe  Asp Glu Ile
    1595                 1600                 1605

Ser Lys  Tyr Ile Glu Ser Glu  Lys Pro Thr Leu Asp
    1610                 1615                 1620
```

<210> SEQ ID NO 66
<211> LENGTH: 4827
<212> TYPE: DNA
<213> ORGANISM: Artificial Sequence
<220> FEATURE:
<223> OTHER INFORMATION: pAA352-MSC_0775 fusion DNA

<400> SEQUENCE: 66

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300
```

-continued

```
gccgaaagca ttgtacaaaa tgcaaataaa gccaaaactg tattatctgg cattcaatct    360
attttaggct cagtattggc tggaatggat ttagatgagg ccttacagaa taacagcaac    420
caacatgctc ttgctaaagc tggcttggag ctaacaaatt cattaattga aaatattgct    480
aattcagtaa aaacacttga cgaatttggt gagcaaatta gtcaatttgg ttcaaaacta    540
caaaatatca aaggcttagg gactttagga gacaaactca aaaatatcgg tggacttgat    600
aaagctggcc ttggtttaga tgttatctca gggctattat cgggcgcaac agctgcactt    660
gtacttgcag ataaaaatgc ttcaacagct aaaaaagtgg gtgcgggttt tgaattggca    720
aaccaagttg ttggtaatat taccaaagcc gtttcttctt acattttagc ccaacgtgtt    780
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
```

-continued

```
aatgtgacaa acagcttaga taagttaatc tcatctgtaa gtgcatttac ctcgtctaat   2700

gattcgagaa atgtattagt ggctccaact tcaatgttgg atcaaagttt atcttctctt   2760

caatttgcta ggggatccca aacggaaaaa gacaaacaag aatttgaaaa ctataatcag   2820

attaacatgc tgagcgaaat caatcaatac ttcaccaaac atgatcacaa caaagacctg   2880

gtgaaattta ccacggatgg cgcgtccggt gacaccgttg aattcaacaa catcatgaaa   2940

aacaactatg cctcaaaata catcaaattc gatcaggaca aattcaaaga aatcatcaaa   3000

aaagaattca atctgtcaga ttcgttcctg aaacgtctgg aattcgaagt cgactacaac   3060

aacatctcgc gcgattacgg caacaatttt gacgttattt tcccgatccg tgttaaactg   3120

ccgctggtca gccataacaa tttcaaatat cagcaaggcc tgtttattga acagaccttt   3180

aaattccgca tcaaaaacgt caaagcgagc ggttctgaaa aatcgatgt gtctaaaatc   3240

aaagacatct acaacgaact ggtgaaactg aaagataaaa acaacttcac ggccagtgtg   3300

aaaaccgtta cggaagaaac caaaaaactg gttgatgaat ggggtattca tgaactgaac   3360

agcacgcaac tgagctctat cttcgatatc aaaaccgaag aattcgataa cctgatcaaa   3420

gacaaaaaag aagtggaaca caaagttacc atcacggatg tggacctgag tgatccgtcc   3480

ctggcgatta acgaaggcct gctgaaactg cgtctgggcg ttaaaatcaa gggtaaagaa   3540

accgaaacgg gtgtcaacgt gtggatcaaa ttcaacttcg atcagaaaga caccttttgg   3600

aaagaactga aaatcagtga atccatcaaa gtcaacacgg tgaaattcag tgaaaccaat   3660

acggatttta ccaaactgat gaacgacaac ctgatcatca aatcaaaatc gaaattcatc   3720

aaaaacatca aactgagttc catcgataaa accacggact atcgtaattc cggcgtcctg   3780

ctggaagtgc tgaccaacga atcaaaagat aacgtgatca aactgcataa aaaaccgggc   3840

gttggtaaat ataccgatct gtactccgca gacttcacga aaaacaatat ccacgcgccg   3900

aattttgcca ccgaaaaact gacgcaggaa aacctgaaat ctatcaacaa agatttcttt   3960

cgccaatttg actcagaact gttctcgggc ggttatgctc gttcacgcgg cttctactcg   4020

gaaaaagtga aaagcccgaa attcatgcat atcggtgaag attacatcgc aaacgacttt   4080

caggctgttc tgatgccgta tgatggtgaa attatcgcgg cctacgaact gagcaccaat   4140

gtgccgttcg caggcgttgg tacggttctg gtcgctaaag tgccgatcac cagcctgccg   4200

tggtctccga aacagaaaga aatcgaactg aacgataaca aaacgcatat ctacatcagc   4260

tttctgcacc tggatgccca acgcaccctg aacaatgaca aactgggctg ggtggcagaa   4320

accgctaaac tgaaaaaaga taaaacggtt aaagtggtta aaagtgtcac cccgtccacg   4380

ccgaaaaaag tcagcaaagg taccgtgatc ggctatctgg gtgatcactc atcgaacggc   4440

ggttggatgt ctcatgcaca cattaatctg tacacgaacc gtccgaatta tctgagtgaa   4500

aactacttta gctctaaaac cattcgtgcg cagctggatg acaaacgcgc caaaggctat   4560

aaaagttccg tgtctaacaa tgatttcagt gccattggca atatcggtgt tgaacgcaaa   4620

attgatacga aaatctatca ggtcgacccg aaaaccggca ttgaagataa acaaaaagca   4680

atttcggacg aaatcccgct gtacttcaac ggcctgagca tgctgggttt tgaaaaaacc   4740

aaaggttatg ctaacccgaa tctgatgtac aaactgcgtg atgaacgcac cgtgagcttt   4800

tctgttaaag aagtcaataa actgtaa                                       4827
```

<210> SEQ ID NO 67
<211> LENGTH: 1608
<212> TYPE: PRT
<213> ORGANISM: Artificial Sequence
<220> FEATURE:
<223> OTHER INFORMATION: LtkA-MSC_0775 fusion protein

<400> SEQUENCE: 67

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400
```

```
His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815
```

-continued

```
Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Gln Thr
        915                 920                 925

Glu Lys Asp Lys Gln Glu Phe Glu Asn Tyr Asn Gln Ile Asn Met Leu
    930                 935                 940

Ser Glu Ile Asn Gln Tyr Phe Thr Lys His Asp His Asn Lys Asp Leu
945                 950                 955                 960

Val Lys Phe Thr Thr Asp Gly Ala Ser Gly Asp Thr Val Glu Phe Asn
                965                 970                 975

Asn Ile Met Lys Asn Asn Tyr Ala Ser Lys Tyr Ile Lys Phe Asp Gln
            980                 985                 990

Asp Lys Phe Lys Glu Ile Ile Lys  Lys Glu Phe Asn Leu  Ser Asp Ser
        995                 1000                 1005

Phe Leu  Lys Arg Leu Glu Phe  Glu Val Asp Tyr Asn  Asn Ile Ser
    1010                 1015                 1020

Arg Asp  Tyr Gly Asn Asn Phe  Asp Val Ile Phe Pro  Ile Arg Val
    1025                 1030                 1035

Lys Leu  Pro Leu Val Ser His  Asn Asn Phe Lys Tyr  Gln Gln Gly
    1040                 1045                 1050

Leu Phe  Ile Glu Gln Thr Phe  Lys Phe Arg Ile Lys  Asn Val Lys
    1055                 1060                 1065

Ala Ser  Gly Ser Glu Lys Ile  Asp Val Ser Lys Ile  Lys Asp Ile
    1070                 1075                 1080

Tyr Asn  Glu Leu Val Lys Leu  Lys Asp Lys Asn Asn  Phe Thr Ala
    1085                 1090                 1095

Ser Val  Lys Thr Val Thr Glu  Glu Thr Lys Lys Leu  Val Asp Glu
    1100                 1105                 1110

Trp Gly  Ile His Glu Leu Asn  Ser Thr Gln Leu Ser  Ser Ile Phe
    1115                 1120                 1125

Asp Ile  Lys Thr Glu Glu Phe  Asp Asn Leu Ile Lys  Asp Lys Lys
    1130                 1135                 1140

Glu Val  Glu His Lys Val Thr  Ile Thr Asp Val Asp  Leu Ser Asp
    1145                 1150                 1155

Pro Ser  Leu Ala Ile Asn Glu  Gly Leu Leu Lys Leu  Arg Leu Gly
    1160                 1165                 1170

Val Lys  Ile Lys Gly Lys Glu  Thr Glu Thr Gly Val  Asn Val Trp
    1175                 1180                 1185

Ile Lys  Phe Asn Phe Asp Gln  Lys Asp Thr Phe Trp  Lys Glu Leu
    1190                 1195                 1200

Lys Ile  Ser Glu Ser Ile Lys  Val Asn Thr Val Lys  Phe Ser Glu
    1205                 1210                 1215
```

-continued

```
Thr Asn  Thr Asp Phe Thr Lys  Leu Met Asn Asp Asn  Leu Ile Ile
    1220                 1225                 1230

Lys Ser  Lys Ser Lys Phe Ile  Lys Asn Ile Lys Leu  Ser Ser Ile
    1235                 1240                 1245

Asp Lys  Thr Thr Asp Tyr Arg  Asn Ser Gly Val Leu  Leu Glu Val
    1250                 1255                 1260

Leu Thr  Asn Glu Ser Lys Asp  Asn Val Ile Lys Leu  His Lys Lys
    1265                 1270                 1275

Pro Gly  Val Gly Lys Tyr Thr  Asp Leu Tyr Ser Ala  Asp Phe Thr
    1280                 1285                 1290

Lys Asn  Asn Ile His Ala Pro  Asn Phe Ala Thr Glu  Lys Leu Thr
    1295                 1300                 1305

Gln Glu  Asn Leu Lys Ser Ile  Asn Lys Asp Phe Phe  Arg Gln Phe
    1310                 1315                 1320

Asp Ser  Glu Leu Phe Ser Gly  Gly Tyr Ala Arg Ser  Arg Gly Phe
    1325                 1330                 1335

Tyr Ser  Glu Lys Val Lys Ser  Pro Lys Phe Met His  Ile Gly Glu
    1340                 1345                 1350

Asp Tyr  Ile Ala Asn Asp Phe  Gln Ala Val Leu Met  Pro Tyr Asp
    1355                 1360                 1365

Gly Glu  Ile Ile Ala Ala Tyr  Glu Leu Ser Thr Asn  Val Pro Phe
    1370                 1375                 1380

Ala Gly  Val Gly Thr Val Leu  Val Ala Lys Val Pro  Ile Thr Ser
    1385                 1390                 1395

Leu Pro  Trp Ser Pro Lys Gln  Lys Glu Ile Glu Leu  Asn Asp Asn
    1400                 1405                 1410

Lys Thr  His Ile Tyr Ile Ser  Phe Leu His Leu Asp  Ala Gln Arg
    1415                 1420                 1425

Thr Leu  Asn Asn Asp Lys Leu  Gly Trp Val Ala Glu  Thr Ala Lys
    1430                 1435                 1440

Leu Lys  Lys Asp Lys Thr Val  Lys Val Val Lys Ser  Val Thr Pro
    1445                 1450                 1455

Ser Thr  Pro Lys Lys Val Ser  Lys Gly Thr Val Ile  Gly Tyr Leu
    1460                 1465                 1470

Gly Asp  His Ser Ser Asn Gly  Gly Trp Met Ser His  Ala His Ile
    1475                 1480                 1485

Asn Leu  Tyr Thr Asn Arg Pro  Asn Tyr Leu Ser Glu  Asn Tyr Phe
    1490                 1495                 1500

Ser Ser  Lys Thr Ile Arg Ala  Gln Leu Asp Asp Lys  Arg Ala Lys
    1505                 1510                 1515

Gly Tyr  Lys Ser Ser Val Ser  Asn Asn Asp Phe Ser  Ala Ile Gly
    1520                 1525                 1530

Asn Ile  Gly Val Glu Arg Lys  Ile Asp Thr Lys Ile  Tyr Gln Val
    1535                 1540                 1545

Asp Pro  Lys Thr Gly Ile Glu  Asp Lys Gln Lys Ala  Ile Ser Asp
    1550                 1555                 1560

Glu Ile  Pro Leu Tyr Phe Asn  Gly Leu Ser Met Leu  Gly Phe Glu
    1565                 1570                 1575

Lys Thr  Lys Gly Tyr Ala Asn  Pro Asn Leu Met Tyr  Lys Leu Arg
    1580                 1585                 1590

Asp Glu  Arg Thr Val Ser Phe  Ser Val Lys Glu Val  Asn Lys Leu
    1595                 1600                 1605
```

<210> SEQ ID NO 68
<211> LENGTH: 5046
<212> TYPE: DNA
<213> ORGANISM: Artificial Sequence
<220> FEATURE:
<223> OTHER INFORMATION: pAA352-MSC_0776 fusion DNA

<400> SEQUENCE: 68
atggctactg ttatagatct aagcttccca aaaactgggg caaaaaaaat tatcctctat 60
attccccaaa attaccaata tgatactgaa caaggtaatg gtttacagga tttagtcaaa 120
gcggccgaag agttggggat tgaggtacaa agagaagaac gcaataatat tgcaacagct 180
caaaccagtt taggcacgat tcaaaccgct attggcttaa ctgagcgtgg cattgtgtta 240
tccgctccac aaattgataa attgctacag aaaactaaag caggccaagc attaggttct 300
gccgaaagca ttgtacaaaa tgcaaataaa gccaaaactg tattatctgg cattcaatct 360
attttaggct cagtattggc tggaatggat ttagatgagg ccttacagaa taacagcaac 420
caacatgctc ttgctaaagc tggcttggag ctaacaaatt cattaattga aaatattgct 480
aattcagtaa aaacacttga cgaatttggt gagcaaatta gtcaatttgg ttcaaaacta 540
caaaatatca aaggcttagg gactttagga gacaaactca aaaatatcgg tggacttgat 600
aaagctggcc ttggtttaga tgttatctca gggctattat cgggcgcaac agctgcactt 660
gtacttgcag ataaaaatgc ttcaacagct aaaaaagtgg gtgcgggttt tgaattggca 720
aaccaagttg ttggtaatat taccaaagcc gtttcttctt acattttagc ccaacgtgtt 780
gcagcaggtt tatcttcaac tgggcctgtg gctgctttaa ttgcttctac tgtttctctt 840
gcgattagcc cattagcatt tgccggtatt gccgataaat ttaatcatgc aaaaagttta 900
gagagttatg ccgaacgctt taaaaaatta ggctatgacg gagataattt attagcagaa 960
tatcagcggg gaacagggac tattgatgca tcggttactg caattaatac cgcattggcc 1020
gctattgctg gtggtgtgtc tgctgctgca gccggctcgg ttattgcttc accgattgcc 1080
ttattagtat ctgggattac cggtgtaatt tctacgattc tgcaatattc taaacaagca 1140
atgtttgagc acgttgcaaa taaaattcat aacaaaattg tagaatggga aaaaaataat 1200
cacggtaaga actactttga aaatggttac gatgcccgtt atcttgcgaa tttacaagat 1260
aatatgaaat tcttactgaa cttaaacaaa gagttacagg cagaacgtgt catcgctatt 1320
actcagcagc aatgggataa caacattggt gatttagctg gtattagccg tttaggtgaa 1380
aaagtcctta gtggtaaagc ctatgtggat gcgtttgaag aaggcaaaca cattaaagcc 1440
gataaattag tacagttgga ttcggcaaac ggtattattg atgtgagtaa ttcgggtaaa 1500
gcgaaaactc agcatatctt attcagaacg ccattattga cgccgggaac agagcatcgt 1560
gaacgcgtac aaacaggtaa atatgaatat attaccaagc tcaatattaa ccgtgtagat 1620
agctggaaaa ttacagatgg tgcagcaagt tctacctttg atttaactaa cgttgttcag 1680
cgtattggta ttgaattaga caatgctgga aatgtaacta aaaccaaaga aacaaaaatt 1740
attgccaaac ttggtgaagg tgatgacaac gtatttgttg gttctggtac gacggaaatt 1800
gatggcggtg aaggttacga ccgagttcac tatagccgtg gaaactatgg tgctttaact 1860
attgatgcaa ccaaagagac cgagcaaggt agttataccg taaatcgttt cgtagaaacc 1920
ggtaaagcac tacacgaagt gacttcaacc cataccgcat tagtgggcaa ccgtgaagaa 1980
aaaatagaat atcgtcatag caataaccag caccatgccg gttattacac caaagatacc 2040
ttgaaagctg ttgaagaaat tatcggtaca tcacataacg atatctttaa aggtagtaag 2100

-continued

```
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatcctg taaaacgacg caaaatcaac agggcatcta taaaattgtg   2820
gacttcgaaa aagaaaatca aatcaacatt ctgagcgaaa tcaaccagtt tttcgaaaaa   2880
catgatttca acgaacagct ggttcaattc gtcaacaaag atagccacaa ttatattacc   2940
ctggactctc tgatgaaaaa caattatgcg gccaaatacg tgaaatttga taaagacaaa   3000
ttcaaacaga tcatcaaaaa agaattcaac ctgagtgatg catacctgaa taaactggaa   3060
atcgaagttg actataccaa cattgatcgc gactactcca acaattttga tattgtcttc   3120
ccgattcgta tcaaacgcca gctggaaaat cataaaaaag cgagctatca accgggcctg   3180
tttacggaac agattatcaa attccgcctg aaaaacgtga aaagctctcc gtcggaagca   3240
tttttcgctg aagaactgaa agatgttttc aacaaactga aagaactgaa atacgataac   3300
ttcaccgcgc gtctgaaaac gaacatcagt aacgaactga aaaaacagat cgatcaatgg   3360
aacatcaacg aactggacag tacccaactg tccaacatct tcgaaatcaa catctccgaa   3420
ttcgatcagc tgaaaaccaa caatccgaat tttgtgttca aaagtacgat ctttggtgtt   3480
gatttctccg acaaaaacct ggcgctgaat gaaggctatc tgaaagtgcg ttttgccgtt   3540
aaagaaggtt tcgatagtaa agacaaaacc aaacagatca acctgatcaa caaagaaatc   3600
aacgaactga tcgtgaaaaa agaaaacctg gaaaaaacca acaactcaga ttcgaacaaa   3660
acggaaatcg acaaactgat ccagatcatc aaacaaaaaa gcgcgcagct gaccaaaatt   3720
aaacaaaaag ccctgccggc ggaagccggc atcacgaaac tgatcaaatt caaattcgat   3780
tggaacgacc agttttggaa aaacatcaaa ctgaacgaag tgatcaaaat cgataccatc   3840
aaatatggta tcagcaatac cgatttcctg tctctgacga aagacaacct gattgttaaa   3900
atcctgaaca aagatgtgcg taacgttgac attaagaaaa ttgaaaaaac caacgatttc   3960
cgcaacgcga aactggtcct ggatgtgctg ctgaaagaca acaaaaaact ggaactgaac   4020
aagaaaattg gcgtgggtaa atatagcctg ctgtacgaaa atgatttcat caaaaacaac   4080
atccaggccc cgtatttcac cacggaacgt ctgacccaag aaaacctgca gtctgttaat   4140
aaagatttct ttcgccagtt tgactcagaa ctgttctcgg gcggttatgc aagttcccgt   4200
ggcttttacg ctccgaaaat taccacgccg atcttcatgc acattggtga agattatatt   4260
gcgaatgact ttcaggccgt gctgatgccg tatgatggcg aaattatcgc agcttacgaa   4320
ctgagcacca acgtcccgtt cgcaggcgtg ggtacggtgg ttgtcgtgaa aattaaagtt   4380
tctgatctgg actggacccc gaaagaaaaa gaaatctatc tgaacaacaa caaagatcat   4440
```

```
atctacatgt catttctgca cctggacgca tcgcgcacgc tgaataacca gaaactgggt   4500

tggtcagctg aaaaagttgt cctgaataac aatcgtacca ttcaagtggt taaatcgctg   4560

acgccggaaa aaccgcagaa agtcgccaaa aataccatta tcggctatct gggtaacaat   4620

gcaagtaacg gcggttggat gtcccatgct cacgttaacc tgtacaccaa tcgcccgtca   4680

tatctgtcgg aaaactactt tagcacgaaa tctaatcaag gcctgagcga agatcgtatc   4740

aaacagtacc atcaaaacat caacggtaaa gaaacctggc gtcagtttgg caatattggt   4800

ctgcaccagt ctccgcaacg tccgccgtac accatcaacg aagttgatca aattacgggc   4860

gtcgaaaaac tggacgaaaa caaaaagaaa attgtcgtga aaaacgaaca ggcgctgttt   4920

ctgccgaacc tgagcatgtc tctgttcgaa aaacgcctgg gttatgccaa cccgaatctg   4980

gtctaccgtc tgcgcgataa taaaaccgtg agtttttccg ttaaagaagt caacaaactg   5040

acgtaa                                                                5046
```

<210> SEQ ID NO 69
<211> LENGTH: 1681
<212> TYPE: PRT
<213> ORGANISM: Artificial Sequence
<220> FEATURE:
<223> OTHER INFORMATION: LtkA-MSC_0776 fusion protein

<400> SEQUENCE: 69

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255
```

-continued

```
Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670
```

-continued

```
Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Cys Lys
        915                 920                 925

Thr Thr Gln Asn Gln Gln Gly Ile Tyr Lys Ile Val Asp Phe Glu Lys
    930                 935                 940

Glu Asn Gln Ile Asn Ile Leu Ser Glu Ile Asn Gln Phe Phe Glu Lys
945                 950                 955                 960

His Asp Phe Asn Glu Gln Leu Val Gln Phe Val Asn Lys Asp Ser His
                965                 970                 975

Asn Tyr Ile Thr Leu Asp Ser Leu Met Lys Asn Asn Tyr Ala Ala Lys
            980                 985                 990

Tyr Val Lys Phe Asp Lys Asp Lys  Phe Lys Gln Ile Ile  Lys Lys Glu
        995                 1000                 1005

Phe Asn  Leu Ser Asp Ala Tyr  Leu Asn Lys Leu Glu  Ile Glu Val
    1010                 1015                 1020

Asp Tyr  Thr Asn Ile Asp Arg  Asp Tyr Ser Asn Asn  Phe Asp Ile
    1025                 1030                 1035

Val Phe  Pro Ile Arg Ile Lys  Arg Gln Leu Glu Asn  His Lys Lys
    1040                 1045                 1050

Ala Ser  Tyr Gln Pro Gly Leu  Phe Thr Glu Gln Ile  Ile Lys Phe
    1055                 1060                 1065

Arg Leu  Lys Asn Val Lys Ser  Ser Pro Ser Glu Ala  Phe Phe Ala
    1070                 1075                 1080
```

-continued

Glu Glu Leu Lys Asp Val Phe Asn Lys Leu Lys Glu Leu Lys Tyr
1085 1090 1095

Asp Asn Phe Thr Ala Arg Leu Lys Thr Asn Ile Ser Asn Glu Leu
1100 1105 1110

Lys Lys Gln Ile Asp Gln Trp Asn Ile Asn Glu Leu Asp Ser Thr
1115 1120 1125

Gln Leu Ser Asn Ile Phe Glu Ile Asn Ile Ser Glu Phe Asp Gln
1130 1135 1140

Leu Lys Thr Asn Asn Pro Asn Phe Val Phe Lys Ser Thr Ile Phe
1145 1150 1155

Gly Val Asp Phe Ser Asp Lys Asn Leu Ala Leu Asn Glu Gly Tyr
1160 1165 1170

Leu Lys Val Arg Phe Ala Val Lys Glu Gly Phe Asp Ser Lys Asp
1175 1180 1185

Lys Thr Lys Gln Ile Asn Leu Ile Asn Lys Glu Ile Asn Glu Leu
1190 1195 1200

Ile Val Lys Lys Glu Asn Leu Glu Lys Thr Asn Asn Ser Asp Ser
1205 1210 1215

Asn Lys Thr Glu Ile Asp Lys Leu Ile Gln Ile Ile Lys Gln Lys
1220 1225 1230

Ser Ala Gln Leu Thr Lys Ile Lys Gln Lys Ala Leu Pro Ala Glu
1235 1240 1245

Ala Gly Ile Thr Lys Leu Ile Lys Phe Lys Phe Asp Trp Asn Asp
1250 1255 1260

Gln Phe Trp Lys Asn Ile Lys Leu Asn Glu Val Ile Lys Ile Asp
1265 1270 1275

Thr Ile Lys Tyr Gly Ile Ser Asn Thr Asp Phe Leu Ser Leu Thr
1280 1285 1290

Lys Asp Asn Leu Ile Val Lys Ile Leu Asn Lys Asp Val Arg Asn
1295 1300 1305

Val Asp Ile Lys Lys Ile Glu Lys Thr Asn Asp Phe Arg Asn Ala
1310 1315 1320

Lys Leu Val Leu Asp Val Leu Leu Lys Asp Asn Lys Lys Leu Glu
1325 1330 1335

Leu Asn Lys Lys Ile Gly Val Gly Lys Tyr Ser Leu Leu Tyr Glu
1340 1345 1350

Asn Asp Phe Ile Lys Asn Asn Ile Gln Ala Pro Tyr Phe Thr Thr
1355 1360 1365

Glu Arg Leu Thr Gln Glu Asn Leu Gln Ser Val Asn Lys Asp Phe
1370 1375 1380

Phe Arg Gln Phe Asp Ser Glu Leu Phe Ser Gly Gly Tyr Ala Ser
1385 1390 1395

Ser Arg Gly Phe Tyr Ala Pro Lys Ile Thr Thr Pro Ile Phe Met
1400 1405 1410

His Ile Gly Glu Asp Tyr Ile Ala Asn Asp Phe Gln Ala Val Leu
1415 1420 1425

Met Pro Tyr Asp Gly Glu Ile Ile Ala Ala Tyr Glu Leu Ser Thr
1430 1435 1440

Asn Val Pro Phe Ala Gly Val Gly Thr Val Val Val Val Lys Ile
1445 1450 1455

Lys Val Ser Asp Leu Asp Trp Thr Pro Lys Glu Lys Glu Ile Tyr
1460 1465 1470

-continued

```
Leu Asn  Asn Asn Lys Asp His  Ile Tyr Met Ser Phe  Leu His Leu
    1475                 1480                 1485

Asp Ala  Ser Arg Thr Leu Asn  Asn Gln Lys Leu Gly  Trp Ser Ala
    1490                 1495                 1500

Glu Lys  Val Val Leu Asn Asn  Asn Arg Thr Ile Gln  Val Val Lys
    1505                 1510                 1515

Ser Leu  Thr Pro Glu Lys Pro  Gln Lys Val Ala Lys  Asn Thr Ile
    1520                 1525                 1530

Ile Gly  Tyr Leu Gly Asn Asn  Ala Ser Asn Gly Gly  Trp Met Ser
    1535                 1540                 1545

His Ala  His Val Asn Leu Tyr  Thr Asn Arg Pro Ser  Tyr Leu Ser
    1550                 1555                 1560

Glu Asn  Tyr Phe Ser Thr Lys  Ser Asn Gln Gly Leu  Ser Glu Asp
    1565                 1570                 1575

Arg Ile  Lys Gln Tyr His Gln  Asn Ile Asn Gly Lys  Glu Thr Trp
    1580                 1585                 1590

Arg Gln  Phe Gly Asn Ile Gly  Leu His Gln Ser Pro  Gln Arg Pro
    1595                 1600                 1605

Pro Tyr  Thr Ile Asn Glu Val  Asp Gln Ile Thr Gly  Val Glu Lys
    1610                 1615                 1620

Leu Asp  Glu Asn Lys Lys Lys  Ile Val Val Lys Asn  Glu Gln Ala
    1625                 1630                 1635

Leu Phe  Leu Pro Asn Leu Ser  Met Ser Leu Phe Glu  Lys Arg Leu
    1640                 1645                 1650

Gly Tyr  Ala Asn Pro Asn Leu  Val Tyr Arg Leu Arg  Asp Asn Lys
    1655                 1660                 1665

Thr Val  Ser Phe Ser Val Lys  Glu Val Asn Lys Leu  Thr
    1670                 1675                 1680
```

<210> SEQ ID NO 70
<211> LENGTH: 3927
<212> TYPE: DNA
<213> ORGANISM: Artificial Sequence
<220> FEATURE:
<223> OTHER INFORMATION: pAA352-MSC_0816 fusion DNA

<400> SEQUENCE: 70

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tgggcctgtg gctgctttaa ttgcttctac tgtttctctt    840
```

gcgattagcc cattagcatt tgccggtatt gccgataaat ttaatcatgc aaaaagttta 900
gagagttatg ccgaacgctt taaaaaatta ggctatgacg gagataattt attagcagaa 960
tatcagcggg gaacagggac tattgatgca tcggttactg caattaatac cgcattggcc 1020
gctattgctg gtggtgtgtc tgctgctgca gccggctcgg ttattgcttc accgattgcc 1080
ttattagtat ctgggattac cggtgtaatt tctacgattc tgcaatattc taaacaagca 1140
atgtttgagc acgttgcaaa taaaattcat aacaaaattg tagaatggga aaaaaataat 1200
cacggtaaga actactttga aaatggttac gatgcccgtt atcttgcgaa tttacaagat 1260
aatatgaaat tcttactgaa cttaaacaaa gagttacagg cagaacgtgt catcgctatt 1320
actcagcagc aatgggataa caacattggt gatttagctg gtattagccg tttaggtgaa 1380
aaagtcctta gtggtaaagc ctatgtggat gcgtttgaag aaggcaaaca cattaaagcc 1440
gataaattag tacagttgga ttcggcaaac ggtattattg atgtgagtaa ttcgggtaaa 1500
gcgaaaactc agcatatctt attcagaacg ccattattga cgccgggaac agagcatcgt 1560
gaacgcgtac aaacaggtaa atatgaatat attaccaagc tcaatattaa ccgtgtagat 1620
agctggaaaa ttacagatgg tgcagcaagt tctacctttg atttaactaa cgttgttcag 1680
cgtattggta ttgaattaga caatgctgga aatgtaacta aaaccaaaga aacaaaaatt 1740
attgccaaac ttggtgaagg tgatgacaac gtatttgttg gttctggtac gacggaaatt 1800
gatggcggtg aaggttacga ccgagttcac tatagccgtg gaaactatgg tgctttaact 1860
attgatgcaa ccaaagagac cgagcaaggt agttataccg taaatcgttt cgtagaaacc 1920
ggtaaagcac tacacgaagt gacttcaacc cataccgcat tagtgggcaa ccgtgaagaa 1980
aaaatagaat atcgtcatag caataaccag caccatgccg gttattacac caaagatacc 2040
ttgaaagctg ttgaagaaat tatcggtaca tcacataacg atatctttaa aggtagtaag 2100
ttcaatgatg cctttaacgg tggtgatggt gtcgatacta ttgacggtaa cgacggcaat 2160
gaccgcttat ttggtggtaa aggcgatgat attctcgatg gtggaaatgg tgatgatttt 2220
atcgatggcg gtaaaggcaa cgacctatta cacggtggca agggcgatga tattttcgtt 2280
caccgtaaag gcgatggtaa tgatattatt accgattctg acggcaatga taaattatca 2340
ttctctgatt cgaacttaaa agatttaaca tttgaaaaag ttaaacataa tcttgtcatc 2400
acgaatagca aaaaagagaa agtgaccatt caaaactggt tccgagaggc tgattttgct 2460
aaagaagtgc ctaattataa agcaactaaa gatgagaaaa tcgaagaaat catcggtcaa 2520
aatggcgagc ggatcacctc aaagcaagtt gatgatctta tcgcaaaagg taacggcaaa 2580
attacccaag atgagctatc aaaagttgtt gataactatg aattgctcaa acatagcaaa 2640
aatgtgacaa acagcttaga taagttaatc tcatctgtaa gtgcatttac ctcgtctaat 2700
gattcgagaa atgtattagt ggctccaact tcaatgttgg atcaaagttt atcttctctt 2760
caatttgcta ggggatccgc aaacaaaaac tctgtcgaaa acaacatcta tatcagtaaa 2820
cagattcaac gcaaaccgca taaaatcgaa ggcgataaac tgattgaaat cggttattac 2880
tgggattctc acgaccgtca ggtgcgcatt atgcgtatcc cgccgaccgt gaaagttatc 2940
gcggcccagc tgccgccgat tatcacgagt ctgaaaggcg catttcaagc tcgcattaac 3000
gacgttatct ggcatgtccc gtgggatacc aaaaacatca cgaacatgaa cagcatgttc 3060
tacaacaata tttggttcaa cagctctagt atcctggaat gggatacctc caatgttacg 3120
gacatgggtg aaatgtttgg ccgtaccggt agcttcaacc aggatctgtc caaatgggac 3180

```
gtctcaaaag tgaaaaactt caagaaaatg ttctacaacg cgaaaaaata caacaacaac   3240

gataaaccgc tgaaatggaa cgacaaactg aaatctgcag tcaatatgga agatatgttt   3300

caaggcgcta gtgacttcaa acatagtctg tccgattgga aactggaaac cgaaatcaac   3360

aacaaaaact tcggtctgct ggaagatcgc cacccgaaat ggaaagaaaa actgattaaa   3420

ccgtcctcac cgatctcgag ctctaattcc ctgagttcca ataacatcaa tgatcgctca   3480

gatgacaacc agattaatcg taactcatcg accccgacga atagcaacac catctctacg   3540

aatccgagta acgatctgag ctctaatacc acgaataacg aaaacatttc ggaaagttcc   3600

atgagcaata acatgctgga aattccgatc aatagcgaaa acaaaccgga aaaccccgaaa   3660

aacaacgaaa acatcaacta caaaatcctg ccgaaagtgg acaaaaccaa aaaacagagc   3720

gaagcgaaaa acaaaatccc ggttgaaaaa ggcgaactgt cgaaagatga aaatcaaacc   3780

acgaaaacca gcaacgccat caaagacaaa gaaaactcat cgatcaaatc agattcgctg   3840

tacaaaattc cgccgaaacc gaacaccatt atcagcaaac tgagctctcc gaatgcgggc   3900

attatcacgg gtgccgtgtt tcgttaa                                       3927
```

<210> SEQ ID NO 71
<211> LENGTH: 1308
<212> TYPE: PRT
<213> ORGANISM: Artificial Sequence
<220> FEATURE:
<223> OTHER INFORMATION: LtkA-MSC_0816 fusion protein

<400> SEQUENCE: 71

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220
```

-continued

```
Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640
```

-continued

```
Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Ala Asn
        915                 920                 925

Lys Asn Ser Val Glu Asn Asn Ile Tyr Ile Ser Lys Gln Ile Gln Arg
    930                 935                 940

Lys Pro His Lys Ile Glu Gly Asp Lys Leu Ile Glu Ile Gly Tyr Tyr
945                 950                 955                 960

Trp Asp Ser His Asp Arg Gln Val Arg Ile Met Arg Ile Pro Pro Thr
                965                 970                 975

Val Lys Val Ile Ala Ala Gln Leu Pro Pro Ile Ile Thr Ser Leu Lys
            980                 985                 990

Gly Ala Phe Gln Ala Arg Ile Asn  Asp Val Ile Trp His  Val Pro Trp
        995                 1000                1005

Asp Thr  Lys Asn Ile Thr Asn  Met Asn Ser Met Phe  Tyr Asn Asn
    1010                1015                1020

Ile Trp  Phe Asn Ser Ser Ser  Ile Leu Glu Trp Asp  Thr Ser Asn
    1025                1030                1035

Val Thr  Asp Met Gly Glu Met  Phe Gly Arg Thr Gly  Ser Phe Asn
    1040                1045                1050
```

```
Gln Asp  Leu Ser Lys Trp Asp  Val Ser Lys Val Lys  Asn Phe Lys
    1055                 1060                 1065

Lys Met  Phe Tyr Asn Ala Lys  Lys Tyr Asn Asn Asn  Asp Lys Pro
    1070                 1075                 1080

Leu Lys  Trp Asn Asp Lys Leu  Lys Ser Ala Val Asn  Met Glu Asp
    1085                 1090                 1095

Met Phe  Gln Gly Ala Ser Asp  Phe Lys His Ser Leu  Ser Asp Trp
    1100                 1105                 1110

Lys Leu  Glu Thr Glu Ile Asn  Asn Lys Asn Phe Gly  Leu Leu Glu
    1115                 1120                 1125

Asp Arg  His Pro Lys Trp Lys  Glu Lys Leu Ile Lys  Pro Ser Ser
    1130                 1135                 1140

Pro Ile  Ser Ser Ser Asn Ser  Leu Ser Ser Asn Asn  Ile Asn Asp
    1145                 1150                 1155

Arg Ser  Asp Asp Asn Gln Ile  Asn Arg Asn Ser Ser  Thr Pro Thr
    1160                 1165                 1170

Asn Ser  Asn Thr Ile Ser Thr  Asn Pro Ser Asn Asp  Leu Ser Ser
    1175                 1180                 1185

Asn Thr  Thr Asn Asn Glu Asn  Ile Ser Glu Ser Ser  Met Ser Asn
    1190                 1195                 1200

Asn Met  Leu Glu Ile Pro Ile  Asn Ser Glu Asn Lys  Pro Glu Asn
    1205                 1210                 1215

Pro Lys  Asn Asn Glu Asn Ile  Asn Tyr Lys Ile Leu  Pro Lys Val
    1220                 1225                 1230

Asp Lys  Thr Lys Lys Gln Ser  Glu Ala Lys Asn Lys  Ile Pro Val
    1235                 1240                 1245

Glu Lys  Gly Glu Leu Ser Lys  Asp Glu Asn Gln Thr  Thr Lys Thr
    1250                 1255                 1260

Ser Asn  Ala Ile Lys Asp Lys  Glu Asn Ser Ser Ile  Lys Ser Asp
    1265                 1270                 1275

Ser Leu  Tyr Lys Ile Pro Pro  Lys Pro Asn Thr Ile  Ile Ser Lys
    1280                 1285                 1290

Leu Ser  Ser Pro Asn Ala Gly  Ile Ile Thr Gly Ala  Val Phe Arg
    1295                 1300                 1305
```

<210> SEQ ID NO 72
<211> LENGTH: 4011
<212> TYPE: DNA
<213> ORGANISM: Artificial Sequence
<220> FEATURE:
<223> OTHER INFORMATION: pAA352-MSC_0957 fusion DNA

<400> SEQUENCE: 72

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540
```

```
caaaatatca aaggcttagg gactttagga gacaaactca aaaatatcgg tggacttgat    600
aaagctggcc ttggtttaga tgttatctca gggctattat cgggcgcaac agctgcactt    660
gtacttgcag ataaaaatgc ttcaacagct aaaaaagtgg gtgcgggttt tgaattggca    720
aaccaagttg ttggtaatat taccaaagcc gtttcttctt acattttagc ccaacgtgtt    780
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatcctg cagtaccacg attacccata cgatcaaaac gtcctttaac   2820
gataacgtta aagtcgaaaa attcacctgg gacggcaata aatatacctc caaagaacag   2880
```

-continued tcaacgaaca ttcaagatat caccaatagc ctgaacggta ccacgaatgc atactctaaa 2940
accattacgg acgtgctgaa cctgtttacc cgtaatatcc aggaagttcg caacctgaaa 3000
gaaagctatg acctgtttcg tggcaaagca gaaaatacgt cggtggttgg ctattacacc 3060
ggtgctaaca gtcagcgcca aaaaatctcc cagcaagatt tctacaaaaa actggatgac 3120
agtgacaccc acatcagctc tctgaaaggt ctgctgcagc tgcgtgaatt cgttaacgat 3180
aacaaaaaca aaaccacggt cgaaccgtgg aaaaatagcc tgaaaacgga tgcggacgaa 3240
gttaaaaaat ggtctgatga attcaccaaa aatctggaca acattgtcaa cagttccatc 3300
gataacaaaa tcaaaaacat caaactggtg tctaaagtta gtaaaacgtc atcgagcttt 3360
gccaccttcg aacaggacgt gaaaaccagc ccgacgggct ctagtattaa cctgacggaa 3420
cgcaacaatg aaaccgtcgt gggcgatatc aaaaacctga aagaccataa tccgtatgtc 3480
tttggtacca gtccggtgaa tgatccgttc ggcatgaacg tgattggtga aaataaagat 3540
ccggacatta aaaacctgaa accgaccatc aaatattcca ccgaaaaact gacgaaaaaa 3600
gatgactcat acattaatct gtcgaacaat ggtaacaaca acaaccagtt cgtttacaac 3660
atcaaccaaa aatgggaact gtcctcagca cataatttct attacatgag caaagatccg 3720
gaaacgctgg aactgcagat tacccacagc atcgaaaaca aatcttttac cttctacgtc 3780
caatttggcg gtctgcgtaa aatttatacc ccgatcgtgg aatcttacac cccgaaaaat 3840
acgaactcag cggataaacg ttattcgttt gtgggctggg ccttcaattc gtaccgcttt 3900
agcgatgact tctctaaggg taactcgagc ccgtacaaat tcaaagatat tagtctgaaa 3960
atctcccaga acgctttcac cacgaatacc ggcagcgtta acggtaaata a 4011

<210> SEQ ID NO 73
<211> LENGTH: 1336
<212> TYPE: PRT
<213> ORGANISM: Artificial Sequence
<220> FEATURE:
<223> OTHER INFORMATION: LtkA-MSC_0957 fusion protein

<400> SEQUENCE: 73

Met Ala Thr Val Ile Asp Leu Ser Phe Pro Lys Thr Gly Ala Lys Lys
1 5 10 15

Ile Ile Leu Tyr Ile Pro Gln Asn Tyr Gln Tyr Asp Thr Glu Gln Gly
20 25 30

Asn Gly Leu Gln Asp Leu Val Lys Ala Ala Glu Glu Leu Gly Ile Glu
35 40 45

Val Gln Arg Glu Glu Arg Asn Asn Ile Ala Thr Ala Gln Thr Ser Leu
50 55 60

Gly Thr Ile Gln Thr Ala Ile Gly Leu Thr Glu Arg Gly Ile Val Leu
65 70 75 80

Ser Ala Pro Gln Ile Asp Lys Leu Leu Gln Lys Thr Lys Ala Gly Gln
85 90 95

Ala Leu Gly Ser Ala Glu Ser Ile Val Gln Asn Ala Asn Lys Ala Lys
100 105 110

Thr Val Leu Ser Gly Ile Gln Ser Ile Leu Gly Ser Val Leu Ala Gly
115 120 125

Met Asp Leu Asp Glu Ala Leu Gln Asn Asn Ser Asn Gln His Ala Leu
130 135 140

Ala Lys Ala Gly Leu Glu Leu Thr Asn Ser Leu Ile Glu Asn Ile Ala
145 150 155 160

```
Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575
```

```
Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Cys Ser
        915                 920                 925

Thr Thr Ile Thr His Thr Ile Lys Thr Ser Phe Asn Asp Asn Val Lys
    930                 935                 940

Val Glu Lys Phe Thr Trp Asp Gly Asn Lys Tyr Thr Ser Lys Glu Gln
945                 950                 955                 960

Ser Thr Asn Ile Gln Asp Ile Thr Asn Ser Leu Asn Gly Thr Thr Asn
                965                 970                 975

Ala Tyr Ser Lys Thr Ile Thr Asp Val Leu Asn Leu Phe Thr Arg Asn
            980                 985                 990
```

```
Ile Gln Glu Val Arg Asn Leu Lys  Glu Ser Tyr Asp Leu  Phe Arg Gly
        995                 1000                 1005

Lys Ala  Glu Asn Thr Ser Val  Val Gly Tyr Tyr Thr  Gly Ala Asn
    1010                 1015                 1020

Ser Gln  Arg Gln Lys Ile Ser  Gln Gln Asp Phe Tyr  Lys Lys Leu
    1025                 1030                 1035

Asp Asp  Ser Asp Thr His Ile  Ser Ser Leu Lys Gly  Leu Leu Gln
    1040                 1045                 1050

Leu Arg  Glu Phe Val Asn Asp  Asn Lys Asn Lys Thr  Thr Val Glu
    1055                 1060                 1065

Pro Trp  Lys Asn Ser Leu Lys  Thr Asp Ala Asp Glu  Val Lys Lys
    1070                 1075                 1080

Trp Ser  Asp Glu Phe Thr Lys  Asn Leu Asp Asn Ile  Val Asn Ser
    1085                 1090                 1095

Ser Ile  Asp Asn Lys Ile Lys  Asn Ile Lys Leu Val  Ser Lys Val
    1100                 1105                 1110

Ser Lys  Thr Ser Ser Ser Phe  Ala Thr Phe Glu Gln  Asp Val Lys
    1115                 1120                 1125

Thr Ser  Pro Thr Gly Ser Ser  Ile Asn Leu Thr Glu  Arg Asn Asn
    1130                 1135                 1140

Glu Thr  Val Val Gly Asp Ile  Lys Asn Leu Lys Asp  His Asn Pro
    1145                 1150                 1155

Tyr Val  Phe Gly Thr Ser Pro  Val Asn Asp Pro Phe  Gly Met Asn
    1160                 1165                 1170

Val Ile  Gly Glu Asn Lys Asp  Pro Asp Ile Lys Asn  Leu Lys Pro
    1175                 1180                 1185

Thr Ile  Lys Tyr Ser Thr Glu  Lys Leu Thr Lys Lys  Asp Asp Ser
    1190                 1195                 1200

Tyr Ile  Asn Leu Ser Asn Asn  Gly Asn Asn Asn Asn  Gln Phe Val
    1205                 1210                 1215

Tyr Asn  Ile Asn Gln Lys Trp  Glu Leu Ser Ser Ala  His Asn Phe
    1220                 1225                 1230

Tyr Tyr  Met Ser Lys Asp Pro  Glu Thr Leu Glu Leu  Gln Ile Thr
    1235                 1240                 1245

His Ser  Ile Glu Asn Lys Ser  Phe Thr Phe Tyr Val  Gln Phe Gly
    1250                 1255                 1260

Gly Leu  Arg Lys Ile Tyr Thr  Pro Ile Val Glu Ser  Tyr Thr Pro
    1265                 1270                 1275

Lys Asn  Thr Asn Ser Ala Asp  Lys Arg Tyr Ser Phe  Val Gly Trp
    1280                 1285                 1290

Ala Phe  Asn Ser Tyr Arg Phe  Ser Asp Asp Phe Ser  Lys Gly Asn
    1295                 1300                 1305

Ser Ser  Pro Tyr Lys Phe Lys  Asp Ile Ser Leu Lys  Ile Ser Gln
    1310                 1315                 1320

Asn Ala  Phe Thr Thr Asn Thr  Gly Ser Val Asn Gly  Lys
    1325                 1330                 1335
```

<210> SEQ ID NO 74
<211> LENGTH: 4377
<212> TYPE: DNA
<213> ORGANISM: Artificial Sequence
<220> FEATURE:
<223> OTHER INFORMATION: pAA352-MSC_0446-MSC_0117 fusion DNA

<400> SEQUENCE: 74

```
atggctactg ttatagatct aagcttccca aaaactgggg caaaaaaaat tatcctctat     60
attccccaaa attaccaata tgatactgaa caaggtaatg gtttacagga tttagtcaaa    120
gcggccgaag agttggggat tgaggtacaa agagaagaac gcaataatat tgcaacagct    180
caaaccagtt taggcacgat tcaaaccgct attggcttaa ctgagcgtgg cattgtgtta    240
tccgctccac aaattgataa attgctacag aaaactaaag caggccaagc attaggttct    300
gccgaaagca ttgtacaaaa tgcaaataaa gccaaaactg tattatctgg cattcaatct    360
attttaggct cagtattggc tggaatggat ttagatgagg ccttacagaa taacagcaac    420
caacatgctc ttgctaaagc tggcttggag ctaacaaatt cattaattga aaatattgct    480
aattcagtaa aaacacttga cgaatttggt gagcaaatta gtcaatttgg ttcaaaacta    540
caaaatatca aaggcttagg gactttagga gacaaactca aaaatatcgg tggacttgat    600
aaagctggcc ttggtttaga tgttatctca gggctattat cgggcgcaac agctgcactt    660
gtacttgcag ataaaaatgc ttcaacagct aaaaaagtgg gtgcgggttt tgaattggca    720
aaccaagttg ttggtaatat taccaaagcc gtttcttctt acattttagc ccaacgtgtt    780
gcagcaggtt tatcttcaac tggggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
```

-continued

```
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccct gctgttcctg gtgaagaaaa ccaccatcaa ccagattagc   2820
gacaacaaca acaacagcag caccaacaag caggacaaga acaaacaaga tcacagcaac   2880
aacgagaaaa tgggtgaaaa caccaaaaac gacagcgata agatcaacac cgagaaaacc   2940
ctggacaacg atcgtatgaa caaccagagc gaccaaccgc gtgaggaaag caccccgcgt   3000
aacaacgata gcaaagagaa cgtttggagc cgtggcatta agaaacgtat cctggaaagc   3060
ctgaacagca ccaacctgga ctacctgaag accctgagca acagcctgat ccaggagaag   3120
gaaaaaaccc tgattagcaa caacatcgac aagaaaaccc tggagtataa gaccaaactg   3180
accaagttca gcagcgaact gaagttcgat gagattaaga aagaactgat cagcagcctg   3240
gaggaaagca ttaagaaaaa caagaacaac cagcaccaac acaaactgct gctgcaccaa   3300
ttcaaggacc gtcagctgga gaaacaacac atcagcgaaa ttaccaagct gatcattgac   3360
atctaccgta gcaacctgct gaacgaactg tataaagagc tggatgaaaa aattcagaag   3420
gagaaccgtg aattcgagga aatcttcaag cgtaagaaca agaacgagat caagaacaag   3480
ctgtttgacc tggtggataa gatcgttgat ctgcaagaag cgctgaaaaa catgagcgtg   3540
ggtggcggta tgagcattaa aagcctgctg accatcctga gcagcctgat gattagcgcg   3600
agcggtgttg gcctggtggt tgcgtgcacc aagaccgaca gcacccaggc gccgagcacc   3660
aaccaaaaca aagacaagga taagaaagat ggtaacggca agagcgagga aaaaccgaag   3720
gtgatcagca aaagccagtg gagcgacgcg tttcgtgata gcattaccgg ttgggacatc   3780
gagaactacg atttcagcaa accgaacaac aaccagaacc tgccgaaatt tccgaagcaa   3840
aacatcgaag tgggcaccta tagcaagaaa caagttctgg acaacagcgc gctgcacagc   3900
agcattaaga aaaagatcga tgagatcctg aagatcgagg agaagagcct gaaggtggag   3960
aacgtttact tcgacgatga aagcggcaag gcgatcgtta aaagcaccaa gttcagcgac   4020
accctgaagg tgacctttct ggttaaagag aacctggaac tgggcgcgta taccaaggac   4080
cagatcctgg ataacagcaa gttccacagc accattaaaa agaaaattgc ggagatcctg   4140
aaggtggatg aaagcaccct gaccgtgctg gacgtttact atgaagataa aaccggcggt   4200
ggcgtggtta aaagcaccaa gctgccgaac gagattaagt tcatctttag cgttaaagaa   4260
aagtgaccat ggcatcacag tatcgtgatg acagaggcag ggagtgggac aaaattgaaa   4320
tcaaataatg attttatttt gactgatagt gacctgttcg ttgcaacaaa ttgataa      4377
```

<210> SEQ ID NO 75
<211> LENGTH: 1421
<212> TYPE: PRT
<213> ORGANISM: Artificial Sequence
<220> FEATURE:
<223> OTHER INFORMATION: LtkA- MSC_0446-MSC_0117 fusion protein

<400> SEQUENCE: 75

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400
```

His Gly Lys Asn Tyr Phe Glu Asn Gly Tyr Asp Ala Arg Tyr Leu Ala
405 410 415

Asn Leu Gln Asp Asn Met Lys Phe Leu Leu Asn Leu Asn Lys Glu Leu
420 425 430

Gln Ala Glu Arg Val Ile Ala Ile Thr Gln Gln Gln Trp Asp Asn Asn
435 440 445

Ile Gly Asp Leu Ala Gly Ile Ser Arg Leu Gly Glu Lys Val Leu Ser
450 455 460

Gly Lys Ala Tyr Val Asp Ala Phe Glu Glu Gly Lys His Ile Lys Ala
465 470 475 480

Asp Lys Leu Val Gln Leu Asp Ser Ala Asn Gly Ile Ile Asp Val Ser
485 490 495

Asn Ser Gly Lys Ala Lys Thr Gln His Ile Leu Phe Arg Thr Pro Leu
500 505 510

Leu Thr Pro Gly Thr Glu His Arg Glu Arg Val Gln Thr Gly Lys Tyr
515 520 525

Glu Tyr Ile Thr Lys Leu Asn Ile Asn Arg Val Asp Ser Trp Lys Ile
530 535 540

Thr Asp Gly Ala Ala Ser Ser Thr Phe Asp Leu Thr Asn Val Val Gln
545 550 555 560

Arg Ile Gly Ile Glu Leu Asp Asn Ala Gly Asn Val Thr Lys Thr Lys
565 570 575

Glu Thr Lys Ile Ile Ala Lys Leu Gly Glu Gly Asp Asp Asn Val Phe
580 585 590

Val Gly Ser Gly Thr Thr Glu Ile Asp Gly Gly Glu Gly Tyr Asp Arg
595 600 605

Val His Tyr Ser Arg Gly Asn Tyr Gly Ala Leu Thr Ile Asp Ala Thr
610 615 620

Lys Glu Thr Glu Gln Gly Ser Tyr Thr Val Asn Arg Phe Val Glu Thr
625 630 635 640

Gly Lys Ala Leu His Glu Val Thr Ser Thr His Thr Ala Leu Val Gly
645 650 655

Asn Arg Glu Glu Lys Ile Glu Tyr Arg His Ser Asn Asn Gln His His
660 665 670

Ala Gly Tyr Tyr Thr Lys Asp Thr Leu Lys Ala Val Glu Glu Ile Ile
675 680 685

Gly Thr Ser His Asn Asp Ile Phe Lys Gly Ser Lys Phe Asn Asp Ala
690 695 700

Phe Asn Gly Gly Asp Gly Val Asp Thr Ile Asp Gly Asn Asp Gly Asn
705 710 715 720

Asp Arg Leu Phe Gly Gly Lys Gly Asp Asp Ile Leu Asp Gly Gly Asn
725 730 735

Gly Asp Asp Phe Ile Asp Gly Gly Lys Gly Asn Asp Leu Leu His Gly
740 745 750

Gly Lys Gly Asp Asp Ile Phe Val His Arg Lys Gly Asp Gly Asn Asp
755 760 765

Ile Ile Thr Asp Ser Asp Gly Asn Asp Lys Leu Ser Phe Ser Asp Ser
770 775 780

Asn Leu Lys Asp Leu Thr Phe Glu Lys Val Lys His Asn Leu Val Ile
785 790 795 800

Thr Asn Ser Lys Lys Glu Lys Val Thr Ile Gln Asn Trp Phe Arg Glu
805 810 815

-continued

```
Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Leu Leu
        915                 920                 925

Phe Leu Val Lys Lys Thr Thr Ile Asn Gln Ile Ser Asp Asn Asn Asn
    930                 935                 940

Asn Ser Ser Thr Asn Lys Gln Asp Lys Asn Lys Gln Asp His Ser Asn
945                 950                 955                 960

Asn Glu Lys Met Gly Glu Asn Thr Lys Asn Asp Ser Asp Lys Ile Asn
                965                 970                 975

Thr Glu Lys Thr Leu Asp Asn Asp Arg Met Asn Asn Gln Ser Asp Gln
            980                 985                 990

Pro Arg Glu Glu Ser Thr Pro Arg  Asn Asn Asp Ser Lys  Glu Asn Val
        995                 1000                1005

Trp Ser  Arg Gly Ile Lys Lys  Arg Ile Leu Glu Ser  Leu Asn Ser
    1010                 1015                 1020

Thr Asn  Leu Asp Tyr Leu Lys  Thr Leu Ser Asn Ser  Leu Ile Gln
    1025                 1030                 1035

Glu Lys  Glu Lys Thr Leu Ile  Ser Asn Asn Ile Asp  Lys Lys Thr
    1040                 1045                 1050

Leu Glu  Tyr Lys Thr Lys Leu  Thr Lys Phe Ser Ser  Glu Leu Lys
    1055                 1060                 1065

Phe Asp  Glu Ile Lys Lys Glu  Leu Ile Ser Ser Leu  Glu Glu Ser
    1070                 1075                 1080

Ile Lys  Lys Asn Lys Asn Asn  Gln His Gln His Lys  Leu Leu Leu
    1085                 1090                 1095

His Gln  Phe Lys Asp Arg Gln  Leu Glu Lys Gln His  Ile Ser Glu
    1100                 1105                 1110

Ile Thr  Lys Leu Ile Ile Asp  Ile Tyr Arg Ser Asn  Leu Leu Asn
    1115                 1120                 1125

Glu Leu  Tyr Lys Glu Leu Asp  Glu Lys Ile Gln Lys  Glu Asn Arg
    1130                 1135                 1140

Glu Phe  Glu Glu Ile Phe Lys  Arg Lys Asn Lys Asn  Glu Ile Lys
    1145                 1150                 1155

Asn Lys  Leu Phe Asp Leu Val  Asp Lys Ile Val Asp  Leu Gln Glu
    1160                 1165                 1170

Ala Leu  Lys Asn Met Ser Val  Gly Gly Gly Met Ser  Ile Lys Ser
    1175                 1180                 1185

Leu Leu  Thr Ile Leu Ser Ser  Leu Met Ile Ser Ala  Ser Gly Val
    1190                 1195                 1200

Gly Leu  Val Val Ala Cys Thr  Lys Thr Asp Ser Thr  Gln Ala Pro
    1205                 1210                 1215
```

```
Ser Thr  Asn Gln Asn Lys Asp  Lys Asp Lys Lys Asp  Gly Asn Gly
    1220                 1225                 1230

Lys Ser  Glu Glu Lys Pro Lys  Val Ile Ser Lys Ser  Gln Trp Ser
    1235                 1240                 1245

Asp Ala  Phe Arg Asp Ser Ile  Thr Gly Trp Asp Ile  Glu Asn Tyr
    1250                 1255                 1260

Asp Phe  Ser Lys Pro Asn Asn  Asn Gln Asn Leu Pro  Lys Phe Pro
    1265                 1270                 1275

Lys Gln  Asn Ile Glu Val Gly  Thr Tyr Ser Lys Lys  Gln Val Leu
    1280                 1285                 1290

Asp Asn  Ser Ala Leu His Ser  Ser Ile Lys Lys Lys  Ile Asp Glu
    1295                 1300                 1305

Ile Leu  Lys Ile Glu Glu Lys  Ser Leu Lys Val Glu  Asn Val Tyr
    1310                 1315                 1320

Phe Asp  Asp Glu Ser Gly Lys  Ala Ile Val Lys Ser  Thr Lys Phe
    1325                 1330                 1335

Ser Asp  Thr Leu Lys Val Thr  Phe Leu Val Lys Glu  Asn Leu Glu
    1340                 1345                 1350

Leu Gly  Ala Tyr Thr Lys Asp  Gln Ile Leu Asp Asn  Ser Lys Phe
    1355                 1360                 1365

His Ser  Thr Ile Lys Lys Lys  Ile Ala Glu Ile Leu  Lys Val Asp
    1370                 1375                 1380

Glu Ser  Thr Leu Thr Val Leu  Asp Val Tyr Tyr Glu  Asp Lys Thr
    1385                 1390                 1395

Gly Gly  Gly Val Val Lys Ser  Thr Lys Leu Pro Asn  Glu Ile Lys
    1400                 1405                 1410

Phe Ile  Phe Ser Val Lys Glu  Lys
    1415                 1420
```

<210> SEQ ID NO 76
<211> LENGTH: 4518
<212> TYPE: DNA
<213> ORGANISM: Artificial Sequence
<220> FEATURE:
<223> OTHER INFORMATION: pAA352-MSC 0922-MSC_1058 fusion DNA

<400> SEQUENCE: 76

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780
```

-continued

```
gcagcaggtt tatcttcaac tgggcctgtg gctgctttaa ttgcttctac tgtttctctt    840
gcgattagcc cattagcatt tgccggtatt gccgataaat ttaatcatgc aaaaagttta    900
gagagttatg ccgaacgctt taaaaaatta ggctatgacg gagataattt attagcagaa    960
tatcagcggg gaacagggac tattgatgca tcggttactg caattaatac cgcattggcc   1020
gctattgctg gtggtgtgtc tgctgctgca gccggctcgg ttattgcttc accgattgcc   1080
ttattagtat ctgggattac cggtgtaatt tctacgattc tgcaatattc taaacaagca   1140
atgtttgagc acgttgcaaa taaaattcat aacaaaattg tagaatggga aaaaaataat   1200
cacggtaaga actactttga aaatggttac gatgcccgtt atcttgcgaa tttacaagat   1260
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccaa gaaactgctg atcggcttca gcagcatttt cgcgtttctg   2820
accgtgagct gcagcaccag caccccgaag gttaacccga ccatcaacaa gaacgagaac   2880
aaactgtaca aaaacaagta tgtgagcaag ctgctgaacc tgtacctgag cgacagcaaa   2940
ctgcgtgata gctatattaa cgaccaggag aacgttagcg atagcaagtt tagcgaactg   3000
aaatacggcc tgaccttcta tccgatcttt attcaccgta gcctggacta ctatgtgggt   3060
cagcactacc gtgttatcat tcaaaaagcg aagaacagcc tggagcaaac cctgcgtaac   3120
gattggtact gggtgctgga caacatcacc aacttcaagt ataactttaa cccgtacggc   3180
```

gatctgtata acgaattcaa caaagacgag gacctgttca agcaggttga aaaagacctg 3240
ggtagcctga tcagcagcat caagaacaag aacgtgcaaa acatcatccg tgttaacctg 3300
aacaacagca tcaacgagaa aattaaggac gattacctga agaaagaagc gctgtatctg 3360
gtgttcgata acaacaaagc gatcaagatc tggaagtacg aatacaagaa caagatcgag 3420
ttcctgatga ccagcgacct gttcgttttt aaggacgcga acaacctgga gaaccagatc 3480
gagcaactgg aaaacaccat tttcgaaaaa cgtaaaagcg agtacaacaa caacctggaa 3540
agcatcaaca aaagcattga gaccaccaag aaacgtaaag aaaagaccca gcaagagatc 3600
caggaactga aagagaagat tgaaaagctg gagaaagaaa ccaacaccac caccaccgcg 3660
ccgctggcgc tggcgctgga tacccgtacc attgcgccgg gcgtgctgaa gaacgacaag 3720
aaaaaggagc cgaccattga ggaactgaaa aaggatctgg agaaaaagga aaaacagctg 3780
gagcaattcg acgaaaacgt taaaaagtac gagaaggaca tcgaagatct gccgcagaaa 3840
agcaacgata aaaagttcct ggaatttcac gcgaagaacc aatataacga gcgtctgaaa 3900
gaaagcctga acgagatcaa caaggacggc tggaaaattg tgcgttttag catgcgtggt 3960
atctacgagc aggaaggtgg cggtaaaaag ctgctgacca ttctgggcag cgtgggtctg 4020
gttgcgacca ccagcgcggc ggttattgcg tgcggtgata agaccagcca aaaaaccccg 4080
gacaccaagc cgaccgagga aacccgtaaa gaggacaaag aggaaccgaa aaaggacgat 4140
gaaaaaacca ccgaggacaa aaagaaagag gaagcgttca gcaaggtgga aaaacagatc 4200
attggcaact ttagcccgaa caacaacaac gcggtgccgc agagcaacat caagaaaaag 4260
ctggcggagc tgctgaaggt tcaagagagc gaactgaccg acctgaacgt ggattatgaa 4320
aacaacaccg gtaccgttaa aatcaaggac agcagcaaag cgattgagtt caagtttagc 4380
gttaaagaga agaagatcaa caactgacca tggcatcaca gtatcgtgat gacagaggca 4440
gggagtggga caaaattgaa atcaaataat gattttattt tgactgatag tgacctgttc 4500
gttgcaacaa attgataa 4518

<210> SEQ ID NO 77
<211> LENGTH: 1468
<212> TYPE: PRT
<213> ORGANISM: Artificial Sequence
<220> FEATURE:
<223> OTHER INFORMATION: LtkA-MSC_0922-MSC_1058 fusion protein

<400> SEQUENCE: 77

Met Ala Thr Val Ile Asp Leu Ser Phe Pro Lys Thr Gly Ala Lys Lys
1 5 10 15

Ile Ile Leu Tyr Ile Pro Gln Asn Tyr Gln Tyr Asp Thr Glu Gln Gly
20 25 30

Asn Gly Leu Gln Asp Leu Val Lys Ala Ala Glu Glu Leu Gly Ile Glu
35 40 45

Val Gln Arg Glu Glu Arg Asn Asn Ile Ala Thr Ala Gln Thr Ser Leu
50 55 60

Gly Thr Ile Gln Thr Ala Ile Gly Leu Thr Glu Arg Gly Ile Val Leu
65 70 75 80

Ser Ala Pro Gln Ile Asp Lys Leu Leu Gln Lys Thr Lys Ala Gly Gln
85 90 95

Ala Leu Gly Ser Ala Glu Ser Ile Val Gln Asn Ala Asn Lys Ala Lys
100 105 110

```
Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525
```

-continued

```
Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Lys Lys
        915                 920                 925

Leu Leu Ile Gly Phe Ser Ser Ile Phe Ala Phe Leu Thr Val Ser Cys
    930                 935                 940
```

```
Ser Thr Ser Thr Pro Lys Val Asn Pro Thr Ile Asn Lys Asn Glu Asn
945                 950                 955                 960

Lys Leu Tyr Lys Asn Lys Tyr Val Ser Lys Leu Leu Asn Leu Tyr Leu
                965                 970                 975

Ser Asp Ser Lys Leu Arg Asp Ser Tyr Ile Asn Asp Gln Glu Asn Val
            980                 985                 990

Ser Asp Ser Lys Phe Ser Glu Leu  Lys Tyr Gly Leu Thr  Phe Tyr Pro
        995                 1000                 1005

Ile Phe  Ile His Arg Ser Leu  Asp Tyr Tyr Val Gly  Gln His Tyr
    1010                 1015                 1020

Arg Val  Ile Ile Gln Lys Ala  Lys Asn Ser Leu Glu  Gln Thr Leu
    1025                 1030                 1035

Arg Asn  Asp Trp Tyr Trp Val  Leu Asp Asn Ile Thr  Asn Phe Lys
    1040                 1045                 1050

Tyr Asn  Phe Asn Pro Tyr Gly  Asp Leu Tyr Asn Glu  Phe Asn Lys
    1055                 1060                 1065

Asp Glu  Asp Leu Phe Lys Gln  Val Glu Lys Asp Leu  Gly Ser Leu
    1070                 1075                 1080

Ile Ser  Ser Ile Lys Asn Lys  Asn Val Gln Asn Ile  Ile Arg Val
    1085                 1090                 1095

Asn Leu  Asn Asn Ser Ile Asn  Glu Lys Ile Lys Asp  Asp Tyr Leu
    1100                 1105                 1110

Lys Lys  Glu Ala Leu Tyr Leu  Val Phe Asp Asn Asn  Lys Ala Ile
    1115                 1120                 1125

Lys Ile  Trp Lys Tyr Glu Tyr  Lys Asn Lys Ile Glu  Phe Leu Met
    1130                 1135                 1140

Thr Ser  Asp Leu Phe Val Phe  Lys Asp Ala Asn Asn  Leu Glu Asn
    1145                 1150                 1155

Gln Ile  Glu Gln Leu Glu Asn  Thr Ile Phe Glu Lys  Arg Lys Ser
    1160                 1165                 1170

Glu Tyr  Asn Asn Asn Leu Glu  Ser Ile Asn Lys Ser  Ile Glu Thr
    1175                 1180                 1185

Thr Lys  Lys Arg Lys Glu Lys  Thr Gln Gln Glu Ile  Gln Glu Leu
    1190                 1195                 1200

Lys Glu  Lys Ile Glu Lys Leu  Glu Lys Glu Thr Asn  Thr Thr Thr
    1205                 1210                 1215

Thr Ala  Pro Leu Ala Leu Ala  Leu Asp Thr Arg Thr  Ile Ala Pro
    1220                 1225                 1230

Gly Val  Leu Lys Asn Asp Lys  Lys Lys Glu Pro Thr  Ile Glu Glu
    1235                 1240                 1245

Leu Lys  Lys Asp Leu Glu Lys  Lys Glu Lys Gln Leu  Glu Gln Phe
    1250                 1255                 1260

Asp Glu  Asn Val Lys Lys Tyr  Glu Lys Asp Ile Glu  Asp Leu Pro
    1265                 1270                 1275

Gln Lys  Ser Asn Asp Lys Lys  Phe Leu Glu Phe His  Ala Lys Asn
    1280                 1285                 1290

Gln Tyr  Asn Glu Arg Leu Lys  Glu Ser Leu Asn Glu  Ile Asn Lys
    1295                 1300                 1305

Asp Gly  Trp Lys Ile Val Arg  Phe Ser Met Arg Gly  Ile Tyr Glu
    1310                 1315                 1320

Gln Glu  Gly Gly Gly Lys Lys  Leu Leu Thr Ile Leu  Gly Ser Val
    1325                 1330                 1335
```

```
Gly Leu  Val Ala Thr Thr Ser  Ala Ala Val Ile Ala  Cys Gly Asp
    1340                 1345                 1350

Lys Thr  Ser Gln Lys Thr Pro  Asp Thr Lys Pro Thr  Glu Glu Thr
    1355                 1360                 1365

Arg Lys  Glu Asp Lys Glu Glu  Pro Lys Lys Asp Asp  Glu Lys Thr
    1370                 1375                 1380

Thr Glu  Asp Lys Lys Lys Glu  Glu Ala Phe Ser Lys  Val Glu Lys
    1385                 1390                 1395

Gln Ile  Ile Gly Asn Phe Ser  Pro Asn Asn Asn Asn  Ala Val Pro
    1400                 1405                 1410

Gln Ser  Asn Ile Lys Lys Lys  Leu Ala Glu Leu Leu  Lys Val Gln
    1415                 1420                 1425

Glu Ser  Glu Leu Thr Asp Leu  Asn Val Asp Tyr Glu  Asn Asn Thr
    1430                 1435                 1440

Gly Thr  Val Lys Ile Lys Asp  Ser Ser Lys Ala Ile  Glu Phe Lys
    1445                 1450                 1455

Phe Ser  Val Lys Glu Lys Lys  Ile Asn Asn
    1460                 1465
```

<210> SEQ ID NO 78
<211> LENGTH: 3822
<212> TYPE: DNA
<213> ORGANISM: Artificial Sequence
<220> FEATURE:
<223> OTHER INFORMATION: pAA352-YP_004399807.1 fusion DNA

<400> SEQUENCE: 78

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tgggcctgtg gctgctttaa ttgcttctac tgtttctctt    840

gcgattagcc cattagcatt tgccggtatt gccgataaat ttaatcatgc aaaaagttta    900

gagagttatg ccgaacgctt taaaaaatta ggctatgacg gagataattt attagcagaa    960

tatcagcggg gaacagggac tattgatgca tcggttactg caattaatac cgcattggcc   1020

gctattgctg gtggtgtgtc tgctgctgca gccggctcgg ttattgcttc accgattgcc   1080

ttattagtat ctgggattac cggtgtaatt tctacgattc tgcaatattc taaacaagca   1140

atgtttgagc acgttgcaaa taaaattcat aacaaaattg tagaatggga aaaaaataat   1200

cacggtaaga actactttga aaatggttac gatgcccgtt atcttgcgaa tttacaagat   1260
```

-continued

```
aatatgaaat tcttactgaa cttaaacaaa gagttacagg cagaacgtgt catcgctatt   1320
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccag cagcaaagtt caggttatca acaagttcga tgacattacg   2820
tccattaaaa acacgggtgc gttcaaaaac aatcaggcat tcatttcccg ttcagaactg   2880
aaagaaatcg tcagctctaa caataccacg atttctaata ccacgagttc caccgcagtg   2940
atgacctcga cgagcaccac gtctatcggc acccagacga acaataacaa tgacctgaag   3000
aacgcgagtg aacgcctgaa agccctggcg gccaacaact tcaccaagaa caagaagcag   3060
gcatgggatt ccctgcaaaa cgcttcaatg accttctata aaaaggtgca gccgaccgcg   3120
gtcaatgtgc tgggttacga acaaattacc aaagacaacg ttgaaaaact ggataaggaa   3180
ctgaaaaccg tttttctggt cttcaaggac aataccaaag aaacggaaaa gctggaagtg   3240
gaactgctgc cggaaattaa caatggcaac aaagttatcg acaatggtaa cctgtatctg   3300
gatctgctgg aaaaaccgga aaatctgaag ctggcgaacc agaaaagcat tatcgaagtg   3360
ctgcgtccgg aaattaccaa aatcaaggtg gttctgcaaa ataccaaaaa caataactcc   3420
acgaacaaag aagatatcaa gaacaccgaa gttttcaacc tgctgattaa acagctgagc   3480
atctatctgg caaatgctgt caaatacttt aactctgaaa gtggcattat caccacgaat   3540
ccgaccttct cgtataaaac gcgcagcaat caaatctacg actacatcgt taagaacaag   3600
aaggatgaac tgtacaagaa gctggaaacc gcgtttacgt cagaattcaa caagatcaac   3660
```

```
ttcatcgata tcttcaaaga cttccagttc gatgaaaaca acagtaacga taacaaaaag   3720

attatcacca agattatcaa atcatcgacg aatagctctg ccagttcctc aaactcgagc   3780

accacgacca cgaccgaact gtctagtacg accacgcgtt aa                      3822


<210> SEQ ID NO 79
<211> LENGTH: 1273
<212> TYPE: PRT
<213> ORGANISM: Artificial Sequence
<220> FEATURE:
<223> OTHER INFORMATION: LtkA-YP_004399807.1 fusion protein

<400> SEQUENCE: 79

Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335
```

```
Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750
```

-continued

```
Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Ser Ser
        915                 920                 925

Lys Val Gln Val Ile Asn Lys Phe Asp Asp Ile Thr Ser Ile Lys Asn
    930                 935                 940

Thr Gly Ala Phe Lys Asn Asn Gln Ala Phe Ile Ser Arg Ser Glu Leu
945                 950                 955                 960

Lys Glu Ile Val Ser Ser Asn Asn Thr Thr Ile Ser Asn Thr Thr Ser
                965                 970                 975

Ser Thr Ala Val Met Thr Ser Thr Ser Thr Thr Ser Ile Gly Thr Gln
            980                 985                 990

Thr Asn Asn Asn Asn Asp Leu Lys  Asn Ala Ser Glu Arg  Leu Lys Ala
        995                 1000                 1005

Leu Ala  Ala Asn Asn Phe Thr  Lys Asn Lys Lys Gln  Ala Trp Asp
    1010                 1015                 1020

Ser Leu  Gln Asn Ala Ser Met  Thr Phe Tyr Lys Lys  Val Gln Pro
    1025                 1030                 1035

Thr Ala  Val Asn Val Leu Gly  Tyr Glu Gln Ile Thr  Lys Asp Asn
    1040                 1045                 1050

Val Glu  Lys Leu Asp Lys Glu  Leu Lys Thr Val Phe  Leu Val Phe
    1055                 1060                 1065

Lys Asp  Asn Thr Lys Glu Thr  Glu Lys Leu Glu Val  Glu Leu Leu
    1070                 1075                 1080

Pro Glu  Ile Asn Asn Gly Asn  Lys Val Ile Asp Asn  Gly Asn Leu
    1085                 1090                 1095

Tyr Leu  Asp Leu Leu Glu Lys  Pro Glu Asn Leu Lys  Leu Ala Asn
    1100                 1105                 1110

Gln Lys  Ser Ile Ile Glu Val  Leu Arg Pro Glu Ile  Thr Lys Ile
    1115                 1120                 1125

Lys Val  Val Leu Gln Asn Thr  Lys Asn Asn Asn Ser  Thr Asn Lys
    1130                 1135                 1140

Glu Asp  Ile Lys Asn Thr Glu  Val Phe Asn Leu Leu  Ile Lys Gln
    1145                 1150                 1155
```

```
Leu Ser  Ile Tyr Leu Ala Asn  Ala Val Lys Tyr Phe  Asn Ser Glu
    1160                 1165                 1170

Ser Gly  Ile Ile Thr Thr Asn  Pro Thr Phe Ser Tyr  Lys Thr Arg
    1175                 1180                 1185

Ser Asn  Gln Ile Tyr Asp Tyr  Ile Val Lys Asn Lys  Lys Asp Glu
    1190                 1195                 1200

Leu Tyr  Lys Lys Leu Glu Thr  Ala Phe Thr Ser Glu  Phe Asn Lys
    1205                 1210                 1215

Ile Asn  Phe Ile Asp Ile Phe  Lys Asp Phe Gln Phe  Asp Glu Asn
    1220                 1225                 1230

Asn Ser  Asn Asp Asn Lys Lys  Ile Ile Thr Lys Ile  Ile Lys Ser
    1235                 1240                 1245

Ser Thr  Asn Ser Ser Ala Ser  Ser Ser Asn Ser Ser  Thr Thr Thr
    1250                 1255                 1260

Thr Thr  Glu Leu Ser Ser Thr  Thr Thr Arg
    1265                 1270


<210> SEQ ID NO 80
<211> LENGTH: 3186
<212> TYPE: DNA
<213> ORGANISM: Artificial Sequence
<220> FEATURE:
<223> OTHER INFORMATION: pAA352-YP_004400559.1 fusion DNA

<400> SEQUENCE: 80

atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tgggcctgtg gctgctttaa ttgcttctac tgtttctctt    840

gcgattagcc cattagcatt tgccggtatt gccgataaat ttaatcatgc aaaaagttta    900

gagagttatg ccgaacgctt taaaaaatta ggctatgacg gagataattt attagcagaa    960

tatcagcggg gaacagggac tattgatgca tcggttactg caattaatac cgcattggcc   1020

gctattgctg gtggtgtgtc tgctgctgca gccggctcgg ttattgcttc accgattgcc   1080

ttattagtat ctgggattac cggtgtaatt tctacgattc tgcaatattc taaacaagca   1140

atgtttgagc acgttgcaaa taaaattcat aacaaaattg tagaatggga aaaaaataat   1200

cacggtaaga actactttga aaatggttac gatgcccgtt atcttgcgaa tttacaagat   1260

aatatgaaat tcttactgaa cttaaacaaa gagttacagg cagaacgtgt catcgctatt   1320
```

```
actcagcagc aatgggataa caacattggt gatttagctg gtattagccg tttaggtgaa   1380
aaagtcctta gtggtaaagc ctatgtggat gcgtttgaag aaggcaaaca cattaaagcc   1440
gataaattag tacagttgga ttcggcaaac ggtattattg atgtgagtaa ttcgggtaaa   1500
gcgaaaactc agcatatctt attcagaacg ccattattga cgccgggaac agagcatcgt   1560
gaacgcgtac aaacaggtaa atatgaatat attaccaagc tcaatattaa ccgtgtagat   1620
agctggaaaa ttacagatgg tgcagcaagt tctacctttg atttaactaa cgttgttcag   1680
cgtattggta ttgaattaga caatgctgga aatgtaacta aaaccaaaga aacaaaaatt   1740
attgccaaac ttggtgaagg tgatgacaac gtatttgttg gttctggtac gacggaaatt   1800
gatggcggtg aaggttacga ccgagttcac tatagccgtg gaaactatgg tgctttaact   1860
attgatgcaa ccaaagagac cgagcaaggt agttataccg taaatcgttt cgtagaaacc   1920
ggtaaagcac tacacgaagt gacttcaacc cataccgcat tagtgggcaa ccgtgaagaa   1980
aaaatagaat atcgtcatag caataaccag caccatgccg gttattacac caaagatacc   2040
ttgaaagctg ttgaagaaat tatcggtaca tcacataacg atatctttaa aggtagtaag   2100
ttcaatgatg cctttaacgg tggtgatggt gtcgatacta ttgacggtaa cgacggcaat   2160
gaccgcttat ttggtggtaa aggcgatgat attctcgatg gtggaaatgg tgatgatttt   2220
atcgatggcg gtaaaggcaa cgacctatta cacggtggca agggcgatga tattttcgtt   2280
caccgtaaag gcgatggtaa tgatattatt accgattctg acggcaatga taaattatca   2340
ttctctgatt cgaacttaaa agatttaaca tttgaaaaag ttaaacataa tcttgtcatc   2400
acgaatagca aaaaagagaa agtgaccatt caaaactggt tccgagaggc tgattttgct   2460
aaagaagtgc ctaattataa agcaactaaa gatgagaaaa tcgaagaaat catcggtcaa   2520
aatggcgagc ggatcacctc aaagcaagtt gatgatctta tcgcaaaagg taacggcaaa   2580
attacccaag atgagctatc aaaagttgtt gataactatg aattgctcaa acatagcaaa   2640
aatgtgacaa acagcttaga taagttaatc tcatctgtaa gtgcatttac ctcgtctaat   2700
gattcgagaa atgtattagt ggctccaact tcaatgttgg atcaaagttt atcttctctt   2760
caatttgcta ggggatccag caacaacaac aaaaaagaag aaaagcaatc aaaggaaatg   2820
aataaaaatc aaacctctaa ctccacgagc accaatatga acaacacgca gggcagcaat   2880
agctctacca cgaccaacat tacctctaac ccgatcaata gtgtcacgtc catggcgacc   2940
caaccgaaaa acgaaacctt tttcaataag gaaccgctga tcttttcaga actggattat   3000
gtgtcggaat acttcaagcg taaggaacat attgcgcgca ccagcgaact gatcctggaa   3060
aactctgaag gcattaaacg tcgtatgcag aatagtacgg ttgaaacgac ccaccgtgat   3120
tccctggccg aaacccaaga cctgattctg gaaaacagca acggtgtggt taacttcaag   3180
aagtaa                                                              3186
```

<210> SEQ ID NO 81
<211> LENGTH: 1061
<212> TYPE: PRT
<213> ORGANISM: Artificial Sequence
<220> FEATURE:
<223> OTHER INFORMATION: LtkA-YP_004400559.1 fusion protein

<400> SEQUENCE: 81

```
Met Ala Thr Val Ile Asp Leu Ser Phe Pro Lys Thr Gly Ala Lys Lys
1               5                   10                  15

Ile Ile Leu Tyr Ile Pro Gln Asn Tyr Gln Tyr Asp Thr Glu Gln Gly
            20                  25                  30
```

```
Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175

Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445
```

-continued

```
Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860
```

```
Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser Ser Asn
        915                 920                 925

Asn Asn Lys Lys Glu Glu Lys Gln Ser Lys Glu Met Asn Lys Asn Gln
    930                 935                 940

Thr Ser Asn Ser Thr Ser Thr Asn Met Asn Asn Thr Gln Gly Ser Asn
945                 950                 955                 960

Ser Ser Thr Thr Thr Asn Ile Thr Ser Asn Pro Ile Asn Ser Val Thr
                965                 970                 975

Ser Met Ala Thr Gln Pro Lys Asn Glu Thr Phe Phe Asn Lys Glu Pro
            980                 985                 990

Leu Ile Phe Ser Glu Leu Asp Tyr  Val Ser Glu Tyr Phe  Lys Arg Lys
        995                 1000                1005

Glu His  Ile Ala Arg Thr Ser  Glu Leu Ile Leu Glu  Asn Ser Glu
    1010                1015                1020

Gly Ile  Lys Arg Arg Met Gln  Asn Ser Thr Val Glu  Thr Thr His
    1025                1030                1035

Arg Asp  Ser Leu Ala Glu Thr  Gln Asp Leu Ile Leu  Glu Asn Ser
    1040                1045                1050

Asn Gly  Val Val Asn Phe Lys  Lys
    1055                1060
```

<210> SEQ ID NO 82
<211> LENGTH: 2778
<212> TYPE: DNA
<213> ORGANISM: Artificial Sequence
<220> FEATURE:
<223> OTHER INFORMATION: nucleotide sequence encoding a representative
leukotoxin 352 from plasmid pAA352

<400> SEQUENCE: 82

```
atggctactg ttatagatct aagcttccca aaaactgggg caaaaaaaat tatcctctat     60

attccccaaa attaccaata tgatactgaa caaggtaatg gtttacagga tttagtcaaa    120

gcggccgaag agttggggat tgaggtacaa agagaagaac gcaataatat tgcaacagct    180

caaaccagtt taggcacgat tcaaaccgct attggcttaa ctgagcgtgg cattgtgtta    240

tccgctccac aaattgataa attgctacag aaaactaaag caggccaagc attaggttct    300

gccgaaagca ttgtacaaaa tgcaaataaa gccaaaactg tattatctgg cattcaatct    360

attttaggct cagtattggc tggaatggat ttagatgagg ccttacagaa taacagcaac    420

caacatgctc ttgctaaagc tggcttggag ctaacaaatt cattaattga aaatattgct    480

aattcagtaa aaacacttga cgaatttggt gagcaaatta gtcaatttgg ttcaaaacta    540

caaaatatca aaggcttagg gactttagga gacaaactca aaaatatcgg tggacttgat    600

aaagctggcc ttggtttaga tgttatctca gggctattat cgggcgcaac agctgcactt    660

gtacttgcag ataaaaatgc ttcaacagct aaaaaagtgg gtgcgggttt tgaattggca    720

aaccaagttg ttggtaatat taccaaagcc gtttcttctt acattttagc ccaacgtgtt    780

gcagcaggtt tatcttcaac tgggcctgtg gctgctttaa ttgcttctac tgtttctctt    840
```

-continued

```
gcgattagcc cattagcatt tgccggtatt gccgataaat ttaatcatgc aaaaagttta    900

gagagttatg ccgaacgctt taaaaaatta ggctatgacg gagataattt attagcagaa    960

tatcagcggg gaacagggac tattgatgca tcggttactg caattaatac cgcattggcc   1020

gctattgctg gtggtgtgtc tgctgctgca gccggctcgg ttattgcttc accgattgcc   1080

ttattagtat ctgggattac cggtgtaatt tctacgattc tgcaatattc taaacaagca   1140

atgtttgagc acgttgcaaa taaaattcat aacaaaattg tagaatggga aaaaaataat   1200

cacggtaaga actactttga aaatggttac gatgcccgtt atcttgcgaa tttacaagat   1260

aatatgaaat tcttactgaa cttaaacaaa gagttacagg cagaacgtgt catcgctatt   1320

actcagcagc aatgggataa caacattggt gatttagctg gtattagccg tttaggtgaa   1380

aaagtcctta gtggtaaagc ctatgtggat gcgtttgaag aaggcaaaca cattaaagcc   1440

gataaattag tacagttgga ttcggcaaac ggtattattg atgtgagtaa ttcgggtaaa   1500

gcgaaaactc agcatatctt attcagaacg ccattattga cgccgggaac agagcatcgt   1560

gaacgcgtac aaacaggtaa atatgaatat attaccaagc tcaatattaa ccgtgtagat   1620

agctggaaaa ttacagatgg tgcagcaagt tctacctttg atttaactaa cgttgttcag   1680

cgtattggta ttgaattaga caatgctgga aatgtaacta aaaccaaaga aacaaaaatt   1740

attgccaaac ttggtgaagg tgatgacaac gtatttgttg gttctggtac gacggaaatt   1800

gatggcggtg aaggttacga ccgagttcac tatagccgtg gaaactatgg tgctttaact   1860

attgatgcaa ccaaagagac cgagcaaggt agttataccg taaatcgttt cgtagaaacc   1920

ggtaaagcac tacacgaagt gacttcaacc cataccgcat tagtgggcaa ccgtgaagaa   1980

aaaatagaat atcgtcatag caataaccag caccatgccg gttattacac caaagatacc   2040

ttgaaagctg ttgaagaaat tatcggtaca tcacataacg atatctttaa aggtagtaag   2100

ttcaatgatg cctttaacgg tggtgatggt gtcgatacta ttgacggtaa cgacggcaat   2160

gaccgcttat ttggtggtaa aggcgatgat attctcgatg gtggaaatgg tgatgatttt   2220

atcgatggcg gtaaaggcaa cgacctatta cacggtggca agggcgatga tattttcgtt   2280

caccgtaaag gcgatggtaa tgatattatt accgattctg acggcaatga taaattatca   2340

ttctctgatt cgaacttaaa agatttaaca tttgaaaaag ttaaacataa tcttgtcatc   2400

acgaatagca aaaaagagaa agtgaccatt caaaactggt tccgagaggc tgattttgct   2460

aaagaagtgc ctaattataa agcaactaaa gatgagaaaa tcgaagaaat catcggtcaa   2520

aatggcgagc ggatcacctc aaagcaagtt gatgatctta tcgcaaaagg taacggcaaa   2580

attacccaag atgagctatc aaaagttgtt gataactatg aattgctcaa acatagcaaa   2640

aatgtgacaa acagcttaga taagttaatc tcatctgtaa gtgcatttac ctcgtctaat   2700

gattcgagaa atgtattagt ggctccaact tcaatgttgg atcaaagttt atcttctctt   2760

caatttgcta ggggatcc                                                 2778
```

<210> SEQ ID NO 83
<211> LENGTH: 926
<212> TYPE: PRT
<213> ORGANISM: Artificial Sequence
<220> FEATURE:
<223> OTHER INFORMATION: amino acid sequence of a representative leukotoxin 352 from plasmid pAA352 with flanking sequences from plasmid

<400> SEQUENCE: 83

Met Ala Thr Val Ile Asp Leu Ser Phe Pro Lys Thr Gly Ala Lys Lys
1 5 10 15

Ile Ile Leu Tyr Ile Pro Gln Asn Tyr Gln Tyr Asp Thr Glu Gln Gly
20 25 30

Asn Gly Leu Gln Asp Leu Val Lys Ala Ala Glu Glu Leu Gly Ile Glu
35 40 45

Val Gln Arg Glu Glu Arg Asn Asn Ile Ala Thr Ala Gln Thr Ser Leu
50 55 60

Gly Thr Ile Gln Thr Ala Ile Gly Leu Thr Glu Arg Gly Ile Val Leu
65 70 75 80

Ser Ala Pro Gln Ile Asp Lys Leu Leu Gln Lys Thr Lys Ala Gly Gln
85 90 95

Ala Leu Gly Ser Ala Glu Ser Ile Val Gln Asn Ala Asn Lys Ala Lys
100 105 110

Thr Val Leu Ser Gly Ile Gln Ser Ile Leu Gly Ser Val Leu Ala Gly
115 120 125

Met Asp Leu Asp Glu Ala Leu Gln Asn Asn Ser Asn Gln His Ala Leu
130 135 140

Ala Lys Ala Gly Leu Glu Leu Thr Asn Ser Leu Ile Glu Asn Ile Ala
145 150 155 160

Asn Ser Val Lys Thr Leu Asp Glu Phe Gly Glu Gln Ile Ser Gln Phe
165 170 175

Gly Ser Lys Leu Gln Asn Ile Lys Gly Leu Gly Thr Leu Gly Asp Lys
180 185 190

Leu Lys Asn Ile Gly Gly Leu Asp Lys Ala Gly Leu Gly Leu Asp Val
195 200 205

Ile Ser Gly Leu Leu Ser Gly Ala Thr Ala Ala Leu Val Leu Ala Asp
210 215 220

Lys Asn Ala Ser Thr Ala Lys Lys Val Gly Ala Gly Phe Glu Leu Ala
225 230 235 240

Asn Gln Val Val Gly Asn Ile Thr Lys Ala Val Ser Ser Tyr Ile Leu
245 250 255

Ala Gln Arg Val Ala Ala Gly Leu Ser Ser Thr Gly Pro Val Ala Ala
260 265 270

Leu Ile Ala Ser Thr Val Ser Leu Ala Ile Ser Pro Leu Ala Phe Ala
275 280 285

Gly Ile Ala Asp Lys Phe Asn His Ala Lys Ser Leu Glu Ser Tyr Ala
290 295 300

Glu Arg Phe Lys Lys Leu Gly Tyr Asp Gly Asp Asn Leu Leu Ala Glu
305 310 315 320

Tyr Gln Arg Gly Thr Gly Thr Ile Asp Ala Ser Val Thr Ala Ile Asn
325 330 335

Thr Ala Leu Ala Ala Ile Ala Gly Gly Val Ser Ala Ala Ala Ala Gly
340 345 350

Ser Val Ile Ala Ser Pro Ile Ala Leu Leu Val Ser Gly Ile Thr Gly
355 360 365

Val Ile Ser Thr Ile Leu Gln Tyr Ser Lys Gln Ala Met Phe Glu His
370 375 380

Val Ala Asn Lys Ile His Asn Lys Ile Val Glu Trp Glu Lys Asn Asn
385 390 395 400

-continued

```
His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Gly Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605

Val His Tyr Ser Arg Gly Asn Tyr Gly Ala Leu Thr Ile Asp Ala Thr
    610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
            660                 665                 670

Ala Gly Tyr Tyr Thr Lys Asp Thr Leu Lys Ala Val Glu Glu Ile Ile
        675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815
```

-continued

```
Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser
        915                 920                 925


<210> SEQ ID NO 84
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3, 5
<223> OTHER INFORMATION: Xaa = Lys, Asp, Val or Asn

<400> SEQUENCE: 84

Gly Gly Xaa Gly Xaa Ala
1               5
```